(12) United States Patent
Marcin et al.

(10) Patent No.: US 8,349,880 B2
(45) Date of Patent: Jan. 8, 2013

(54) BICYCLIC COMPOUNDS FOR THE REDUCTION OF BETA-AMYLOID PRODUCTION

(75) Inventors: Lawrence R. Marcin, Bethany, CT (US); Lorin A. Thompson, III, Higganum, CT (US); Kenneth M. Boy, Durham, CT (US); Jason M. Guernon, Moodus, CT (US); Mendi A. Higgins, Meriden, CT (US); Jianliang Shi, Madison, CT (US); Yong-Jin Wu, Madison, CT (US); Yunhui Zhang, Glastonbury, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 309 days.

(21) Appl. No.: 12/683,791

(22) Filed: Jan. 7, 2010

(65) Prior Publication Data
US 2011/0015175 A1   Jan. 20, 2011

Related U.S. Application Data

(60) Provisional application No. 61/145,319, filed on Jan. 16, 2009.

(51) Int. Cl.
| | | |
|---|---|---|
| *A61K 31/41* | (2006.01) | |
| *A61K 31/425* | (2006.01) | |
| *C07D 249/00* | (2006.01) | |
| *C07D 277/82* | (2006.01) | |

(52) U.S. Cl. ...... 514/371; 514/383; 548/161; 548/262.4
(58) Field of Classification Search .............. 514/371, 514/383; 548/161, 262.4
See application file for complete search history.

(56) References Cited

U.S. PATENT DOCUMENTS
2009/0062529 A1   3/2009 Kimura et al.

FOREIGN PATENT DOCUMENTS
| WO | WO 2007/102580 | 9/2007 |
| WO | WO 2008/138753 | 11/2008 |
| WO | WO 2009/028588 | 3/2009 |
| WO | WO 2009/087127 | 7/2009 |
| WO | WO 2009/103652 | 8/2009 |

OTHER PUBLICATIONS

Behrens MI, Lendon C, Roe CM. A common biological mechanism in cancer and Alzheimer's disease? Curr Alzheimer Res. Jun. 2009;6(3):196-204.*
Greenberg SA. Inclusion body myositis: review of recent literature. Curr Neurol Neurosci Rep. Jan. 2009;9(1):83-9.*
Herman AM, Khandelwal PJ, Stanczyk BB, Rebeck GW, Moussa CE. β-Amyloid triggers ALS-associated TDP-43 pathology in AD models. Brain Res. Apr. 22, 2011;1386:191-9.*
Johansen KK, White LR, Sando SB, Aasly JO. Biomarkers: Parkinson disease with dementia and dementia with Lewy bodies. Parkinsonism Relat Disord. Jun. 2010;16(5):307-15.*
Sanchez MM, Moghadam S, Naik P, Martin KJ, Salehi A. Hippocampal network alterations in Alzheimer's disease and Down syndrome: from structure to therapy. J Alzheimers Dis. 2011;26 Suppl 3:29-47.*
Shih IeM, Wang TL. Notch signaling, gamma-secretase inhibitors, and cancer therapy. Cancer Res. Mar. 1, 2007;67(5):1879-82.*
Weller RO, Massey A, Newman TA, Hutchings M, Kuo YM, Roher AE.Cerebral amyloid angiopathy: amyloid beta accumulates in putative interstitial fluid drainage pathways in Alzheimer's disease. Am J Pathol. Sep. 1998;153(3):725-33.*
Yoshida T, Ohno-Matsui K, Ichinose S, Sato T, Iwata N, Saido TC, Hisatomi T, Mochizuki M, Morita I. The potential role of amyloid beta in the pathogenesis of age-related macular degeneration. J Clin Invest. Oct. 2005;115(10):2793-800.*
U.S. Appl. No. 12/845,045, filed Jul. 28, 2010, Boy et al.

* cited by examiner

*Primary Examiner* — San-Ming Hui
*Assistant Examiner* — Paul Zarek
(74) *Attorney, Agent, or Firm* — John F. Levis; Pamela A. Mingo

(57) ABSTRACT

The present disclosure provides a series of compounds of the formula (I)

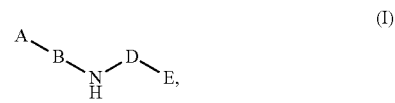

which reduce β-amyloid peptide (β-AP) production and are useful in the treatment of Alzheimer's Disease and other conditions affected by β-amyloid peptide (β-AP) production.

6 Claims, No Drawings

BICYCLIC COMPOUNDS FOR THE REDUCTION OF BETA-AMYLOID PRODUCTION

CROSS-REFERENCE TO RELATED APPLICATIONS

This application claims the benefit of U.S. Provisional Application Ser. No. 61/145,319 filed Jan. 16, 2009.

The present disclosure relates to methods of treating Alzheimer's Disease (AD) and other conditions related to β-amyloid production using compounds which are inhibitors of β-amyloid peptide (Aβ) production. The disclosure further relates to pharmaceutical compositions comprising these compounds.

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat. Neurosci.* (2005) 8: 79-84). Inhibitors of the enzymes that form Aβ42, such as γ-secretase, represent potential disease-modifying therapeutics for the treatment of AD.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, compounds that reduce Aβ levels could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

Based on the role of Notch signaling in tumorigenesis, compounds which inhibit γ-secretase may also be useful as therapeutic agents for the treatment of cancer (Shih, I.-M., et al., *Cancer Research* (2007) 67: 1879-1882).

A logical approach to reducing Aβ levels is to block the action of the secretases. A complementary approach is to selectively reduce production of Aβ1-42 by the action of certain compounds that serve to direct the γ-secretase-mediated cleavage of APP to instead produce shorter forms of Aβ. These shorter forms appear to aggregate less easily and solutions of the shorter forms of Aβ are less neurotoxic than solutions of Aβ1-42 (See Barten, Donna M.; Meredith, Jere E., Jr.; Zaczek, Robert; Houston, John G.; Albright, Charles F. *Drugs in R&D* (2006), 7(2), 87-97). Thus, compounds that selectively reduce Aβ1-42, production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

In its first aspect the present disclosure provides a compound of Formula (I)

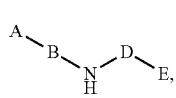
(I)

or a pharmaceutically acceptable salt thereof, wherein

A is a five- or six-membered heteroaromatic ring containing from one to three heteroatoms independently selected from nitrogen, oxygen, and sulfur; wherein said heteroaromatic ring is optionally substituted with one or two groups selected from halo, haloC$_{1-6}$alkyl, hydroxy, amino, C$_{1-6}$alkoxy, and C$_{1-6}$alkyl;

B is selected from phenyl and pyridinyl, wherein the phenyl and pyridinyl are optionally substituted with one or two substituents independently selected from C$_{1-6}$alkoxy, C$_{1-6}$alkyl, C$_{1-3}$alkylamino-C$_{1-6}$alkoxy, cyano, C$_{1-3}$dialkylamino-C$_{1-6}$alkoxy, halo, haloC$_{1-6}$alkoxy, haloC$_{1-6}$alkyl, hydroxy, methylamino, and amino;

D is selected from

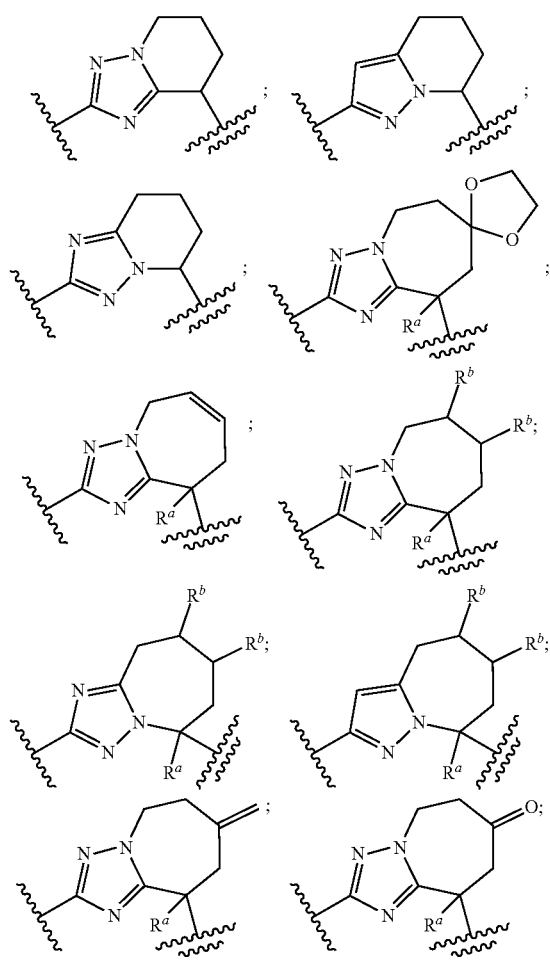

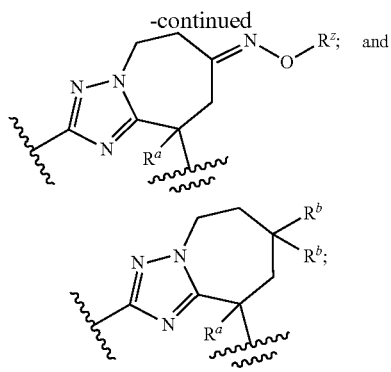

wherein "⸹" denotes the point of attachment to the nitrogen atom of the parent molecule and "⸺" denotes the point of attachment to the 'E' moiety;

R$^a$ is selected from hydrogen, C$_{1-6}$ alkyl, C$_{1-6}$ alkoxy, hydroxy, dimethylamino, amino, methylamino and benzylamino, wherein the phenyl part of the benzyl is optionally substituted with one, two, or three substituents independently selected from C$_{1-6}$ alkyl, C$_{1-6}$alkoxy, cyano, halo, haloC$_{1-6}$alkoxy, and haloC$_{1-6}$alkyl;

each R$^b$ is independently selected from hydrogen, C$_{1-6}$ alkoxy, C$_{1-6}$alkyl, C$_{1-6}$alkylamino, amino, C$_{1-6}$dialkylamino, halo, hydroxy; and

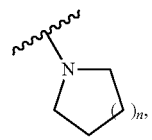

wherein n is 0 or 1 and "⸹" denotes the point of attachment to the ring;

R$^z$ is C$_{1-6}$alkyl; and

E is selected from C$_{1-6}$alkyl, C$_{4-6}$cycloalkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from C$_{1-6}$alkoxy, C$_{1-6}$ alkyl, C$_{1-6}$alkylsulfonyl, cyano, halo, haloC$_{1-6}$alkoxy, haloC$_{1-6}$alkylsulfonyl, haloC$_{1-6}$alkyl, and a five-membered heteroaromatic ring containing one, two, or three nitrogen atoms, wherein the heteroaromatic ring is optionally substituted with one C$_{1-6}$ alkyl group.

In a first embodiment of the first aspect the present disclosure provides a compound of Formula (I), or a pharmaceutically acceptable salt thereof, wherein A is selected from imidazolyl, isoxazolyl, oxadiazolyl, pyrazolyl, pyridazinyl, pyridinyl, and triazolyl; wherein each is optionally substituted with one group selected from halo, haloC$_{1-6}$alkyl, and C$_{1-6}$alkyl.

In a second embodiment of the first aspect the present disclosure provides a compound of Formula (I), or a pharmaceutically acceptable salt thereof, wherein B is selected from phenyl and pyridinyl, wherein the phenyl and pyridinyl are optionally substituted with one or two substituents independently selected from C$_{1-6}$alkoxy, cyano, and halo.

In a third embodiment of the first aspect the present disclosure provides a compound of Formula (I), or a pharmaceutically acceptable salt thereof, wherein D is selected from

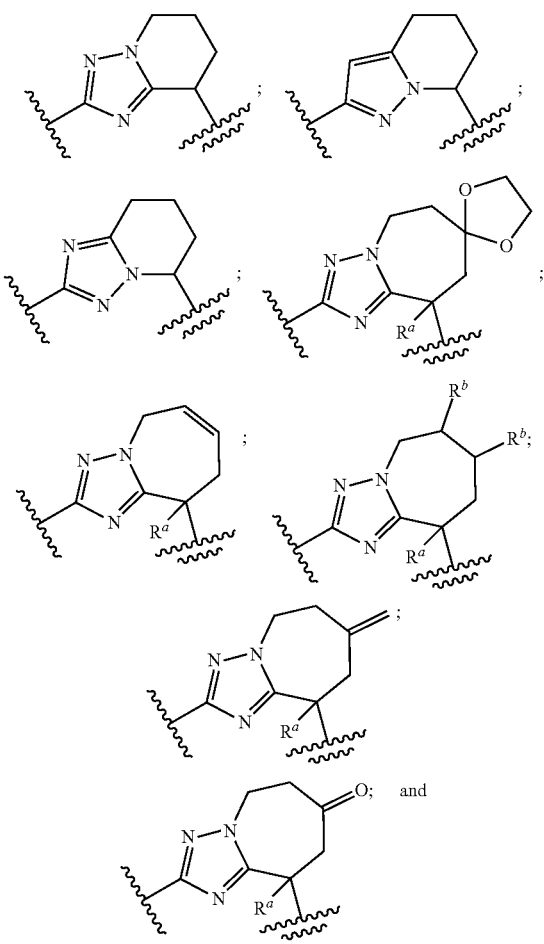

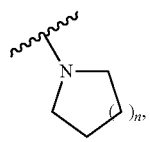

wherein n is 0 or 1 and "⌇" denotes the point of attachment to the ring; and $R^z$ is $C_{1-6}$alkyl.

In a fourth embodiment of the first aspect the present disclosure provides a compound of Formula (I), or a pharmaceutically acceptable salt thereof, wherein E is selected from $C_{1-6}$alkyl, benzyl, phenyl, pyrazolyl, pyridinyl, wherein the phenyl, the phenyl part of the benzyl, the pyrazolyl, and the pyridinyl are each optionally substituted with one, two, or three substituents independently selected from $C_{1-6}$alkoxy, $C_{1-6}$alkylsulfonyl, cyano, halo, halo$C_{1-6}$alkoxy, halo$C_{1-6}$alkylsulfonyl, imidazolyl, pyrazolyl, and triazolyl, wherein the imidazolyl, pyrazolyl, and triazolyl rings are optionally substituted with one $C_{1-6}$ alkyl group.

In a fifth embodiment of the first aspect the present disclosure provides a compound of Formula (I), or a pharmaceutically acceptable salt thereof, wherein A is selected from imidazolyl, isoxazolyl, oxadiazolyl, pyrazolyl, pyridazinyl, pyridinyl, and triazolyl; wherein each is optionally substituted with one group selected from halo, halo$C_{1-6}$alkyl, and $C_{1-6}$alkyl.

B is selected from phenyl and pyridinyl, wherein the phenyl and pyridinyl are optionally substituted with one or two substituents independently selected from $C_{1-6}$alkoxy, cyano, and halo;

D is selected from

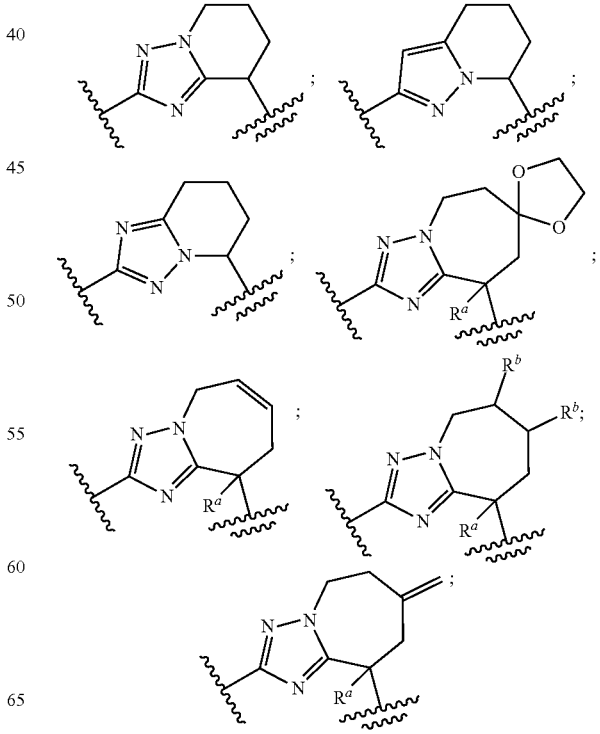

wherein "⌇" denotes the point of attachment to the nitrogen atom of the parent molecule and "⌇" denotes the point of attachment to the 'E' moiety;

$R^a$ is selected from hydrogen, $C_{1-6}$ alkyl, hydroxy, amino and benzylamino, wherein the phenyl part of the benzyl is optionally substituted with one halo group;

each $R^b$ is independently selected from hydrogen, $C_{1-6}$ alkoxy, $C_{1-6}$alkyl, $C_{1-6}$alkylamino, amino, $C_{1-6}$dialkylamino, halo, hydroxy; and

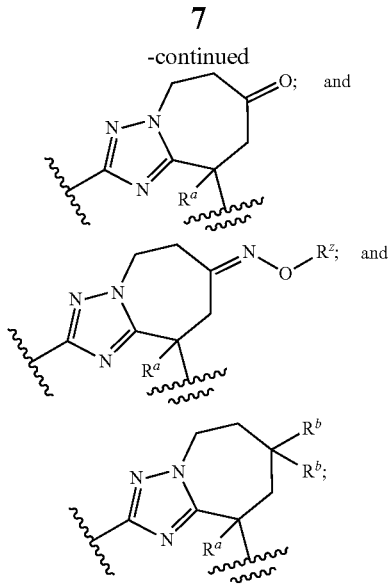

wherein "⸺" denotes the point of attachment to the nitrogen atom of the parent molecule and "⸺" denotes the point of attachment to the 'E' moiety;

$R^a$ is selected from hydrogen, $C_{1-6}$ alkyl, hydroxy, amino and benzylamino, wherein the phenyl part of the benzyl is optionally substituted with one halo group;

each $R^b$ is independently selected from hydrogen, $C_{1-6}$ alkoxy, $C_{1-6}$alkyl, $C_{1-6}$alkylamino, amino, $C_{1-6}$dialkylamino, halo, hydroxy; and

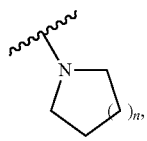

wherein n is 0 or 1 and "⸺" denotes the point of attachment to the ring;

$R^z$ is $C_{1-6}$alkyl; and

E is selected from $C_{1-6}$alkyl, benzyl, phenyl, pyrazolyl, pyridinyl, wherein the phenyl, the phenyl part of the benzyl, the pyrazolyl, and the pyridinyl are each optionally substituted with one, two, or three substituents independently selected from $C_{1-6}$alkoxy, $C_{1-6}$alkylsulfonyl, cyano, halo, halo$C_{1-6}$alkoxy, halo$C_{1-6}$alkylsulfonyl, imidazolyl, pyrazolyl, and triazolyl, wherein the imidazolyl, pyrazolyl, and triazolyl rings are optionally substituted with one $C_{1-6}$ alkyl group.

In a sixth embodiment the present disclosure provides a compound of Formula (I), or a pharmaceutically acceptable salt thereof, wherein A is selected from imidazolyl and triazolyl; wherein each is optionally substituted with one group selected from halo and $C_{1-6}$alkyl.

B is selected from phenyl and pyridinyl, wherein the phenyl and pyridinyl are optionally substituted with one or two substituents independently selected from $C_{1-6}$alkoxy, cyano, and halo;

D is selected from

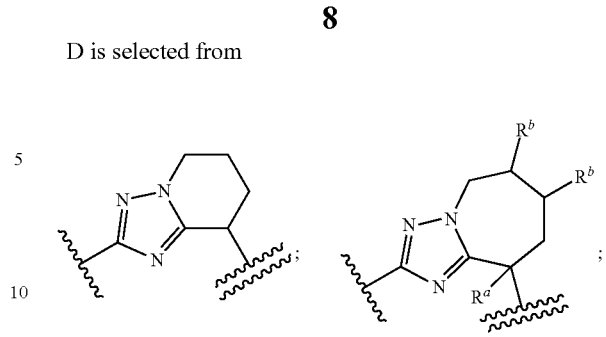

wherein "⸺" denotes the point of attachment to the nitrogen atom of the parent molecule and "⸺" denotes the point of attachment to the 'E' moiety;

$R^a$ is selected from hydrogen and $C_{1-6}$ alkyl;

each $R^b$ is independently selected from hydrogen, $C_{1-6}$ alkoxy, $C_{1-6}$alkyl, amino, $C_{1-6}$alkylamino, $C_{1-6}$dialkylamino, halo, hydroxy;

E is selected from phenyl, pyridyl, and pyrazole, wherein the phenyl and the heteroaromatic ring are each optionally substituted with one, two, or three substituents independently selected from $C_{1-6}$ alkyl, $C_{1-6}$alkoxy, cyano, halo, halo$C_{1-6}$alkoxy.

In a second aspect the present disclosure provides a compound of Formula (I)

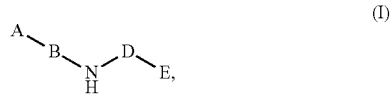

or a pharmaceutically acceptable salt thereof, wherein

A is a five- or six-membered heteroaromatic ring containing from one to three heteroatoms independently selected from nitrogen, oxygen, and sulfur; wherein said heteroaromatic ring is optionally substituted with one or two groups selected from halo, halo$C_{1-6}$alkyl, hydroxy, amino, $C_{1-6}$alkoxy, and $C_{1-6}$alkyl;

B is selected from phenyl and pyridinyl, wherein the phenyl and pyridinyl are optionally substituted with one or two substituents independently selected from $C_{1-6}$alkoxy, $C_{1-6}$alkyl, $C_{1-3}$alkylamino-$C_{1-6}$alkoxy, cyano, $C_{1-3}$dialkylamino-$C_{1-6}$alkoxy, halo, halo$C_{1-6}$alkoxy, hydroxy, methylamino, and amino;

D is selected from

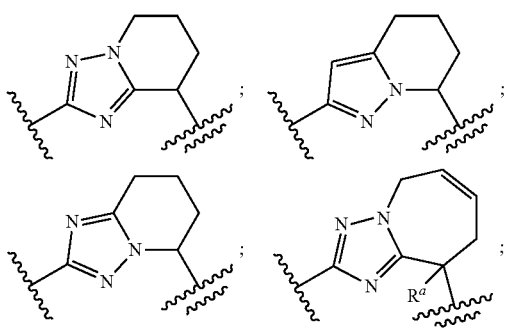

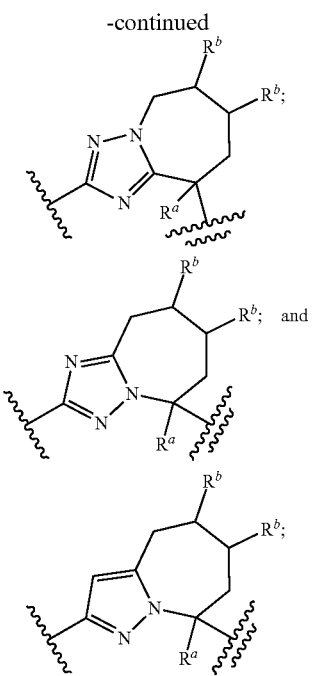

wherein "⸺" denotes the point of attachment to the nitrogen atom of the parent molecule;

"⸺" denotes the point of attachment to the 'E' moiety;

$R^a$ is selected from hydrogen, $C_{1-6}$ alkyl, $C_{1-6}$ alkoxy, hydroxy, dimethylamino, amino, methylamino and benzylamino, wherein the phenyl part of the benzyl is optionally substituted with one, two, or three substituents independently selected from $C_{1-6}$ alkyl, $C_{1-6}$alkoxy, cyano, halo, halo$C_{1-6}$alkoxy, and halo$C_{1-6}$alkyl;

$R^b$ is selected from hydrogen, $C_{1-6}$alkylamino, amino, $C_{1-6}$dialkylamino, halo, and hydroxy; and E is selected from $C_{1-6}$alkyl, $C_{4-6}$cycloalkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from $C_{1-6}$ alkyl, $C_{1-6}$alkoxy, cyano, halo, halo$C_{1-6}$alkoxy, and halo $C_{1-6}$alkyl.

In a third aspect the present disclosure provides a pharmaceutical composition for the treatment of disorders responsive to the reduction of β-amyloid peptide production comprising a therapeutically effective amount of a compound of formula (I), or a pharmaceutically acceptable salt thereof, in association with a pharmaceutically acceptable carrier or diluent.

In a fourth aspect the present disclosure provides a method for the treatment of disorders responsive to the reduction of β-amyloid peptide production in a mammal in need thereof, which comprises administering to said mammal a therapeutically effective amount of a compound of formula (I) or a pharmaceutically acceptable salt thereof. In a first embodiment of the fourth aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the fourth aspect said disorder is selected from Alzheimer's Disease and Down Syndrome. In a second embodiment of the third aspect said disorder is Alzheimer's Disease.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, in the compounds of the present disclosure where D is

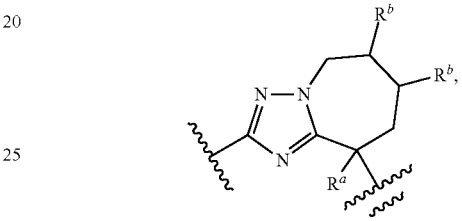

each of the two $R^b$ groups may be the same or different.

All patents, patent applications, and literature references cited in the specification are herein incorporated by reference in their entirety. In the case of inconsistencies, the present disclosure, including definitions, will prevail.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

In some instances, the number of carbon atoms in any particular group is denoted before the recitation of the group. For example, the term "halo$C_{1-6}$alkoxy" denotes a haloalkoxy group containing one to six carbon atoms. Where these designations exist they supercede all other definitions contained herein.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylsulfonyl," as used herein, refers to an alkyl group attached to the parent molecular moiety through a sulfonyl group.

The term "amino," as used herein, refers to —NH$_2$.

The term "benzylamino," as used herein, refers to —NHCH$_2$Ph.

The term "cyano," as used herein, refers to —CN.

The term "cycloalkyl," as used herein, refers to a saturated monocyclic hydrocarbon ring system having three to fourteen carbon atoms and zero heteroatoms.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dimethylamino," as used herein, refers to —N(CH$_3$)$_2$.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "haloalkylsulfonyl," as used herein, refers to a haloalkyl group attached to the parent molecular moiety through a sulfonyl group.

The term "hydroxy," as used herein, refers to —OH.

The term "methylamino," as used herein, refers to —NHCH$_3$.

The term "sulfonyl," as used herein, refers to —SO$_2$—.

It should be understood that the disclosure encompasses all stereochemical forms, or mixtures thereof, which possess the ability to reduce β-amyloid peptide production.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for tent-butoxycarbonyl, "DMSO" for dimethylsulfoxide; "h" or "hr" or "hrs" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; "TMOF" for trimethylorthoformate; MTBE for methyl tert-butyl ether; "EtOH" for ethanol; "DCM" for dichloromethane; and "TsOH" for p-toluenesulfonic acid.

Examples of methods useful for the production of compounds of this disclosure are illustrated in schemes 1-13. Schemes 1-3 outline different routes for the synthesis of substituted aniline fragments used in the preparation of the title compounds. As illustrated in Scheme 1, a variety of substituted heterocycles 1, including but not limited to 1H-imidazole, 4-methyl-1H-imidazole, 4-chloro-1H-imidazole, 4-(difluoromethyl)-1H-imidazole can be added to substituted chloro- or fluoronitroarenes 2, including but not limited to 2-chloro-4-nitroanisole, under basic conditions to provide heteroaryl substituted nitroarenes 3. Reduction of the compounds 3 using reagents including iron in acidic medium or catalytic hydrogenation, employing catalysts such as palladium on carbon or other catalysts know to one skilled in the art, affords substituted anilines 4. While Scheme 1 illustrates the preparation of 4-(1H-imidazol-1-yl)anilines 4, it should be recognized by one skilled in the art this method is widely applicable to the synthesis of other 4-heteroarylanilines, including but not limited to variously substituted 4-(1H-1,2,4-triazol-1-yl)anilines and 4-(1H-1,2,3-triazol-1-yl)anilines.

In addition, substituted nitropyridines can be used in place of the nitroarenes of formula 2 to ultimately provide amino-substituted pyridines.

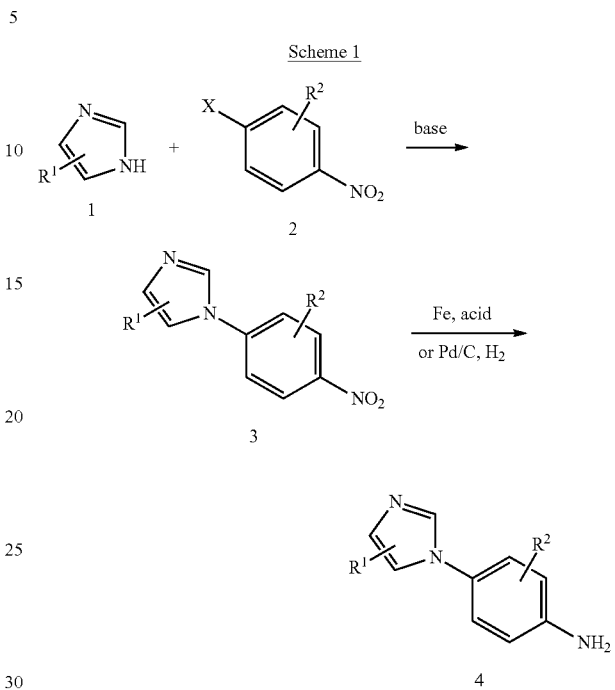

Scheme 1

X = F or Cl

Additional procedures for creating substituted anilines rely on the palladium-catalyzed coupling of aryl halides or heteroaryl halides to boronic acids (the Suzuki coupling reaction). As shown in Scheme 2, biaryl anilines 10 and 11, and their nitro precursors 8 and 9, can be created by the coupling of an aryl or heteroaryl boronic esters 5 and 7, respectively, to substituted aryl halides 6, including 1-bromo-2-methoxy-4-nitrobenzene. Alternatively, the coupling partners can be reversed as is shown in Scheme 3, where coupling of an aryl halide 12 or heteroaryl halide 14 to the boronic ester of the nitro arene 13 creates the substituted nitro arenes 8 and 9, respectively.

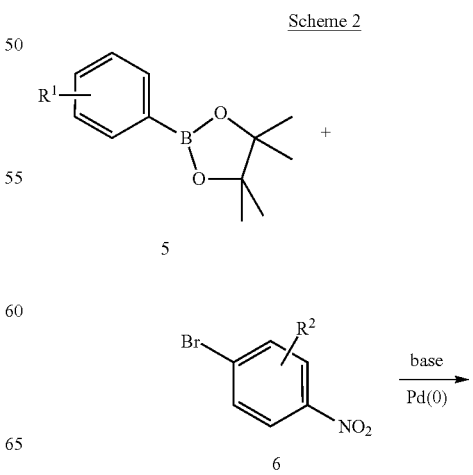

Scheme 2

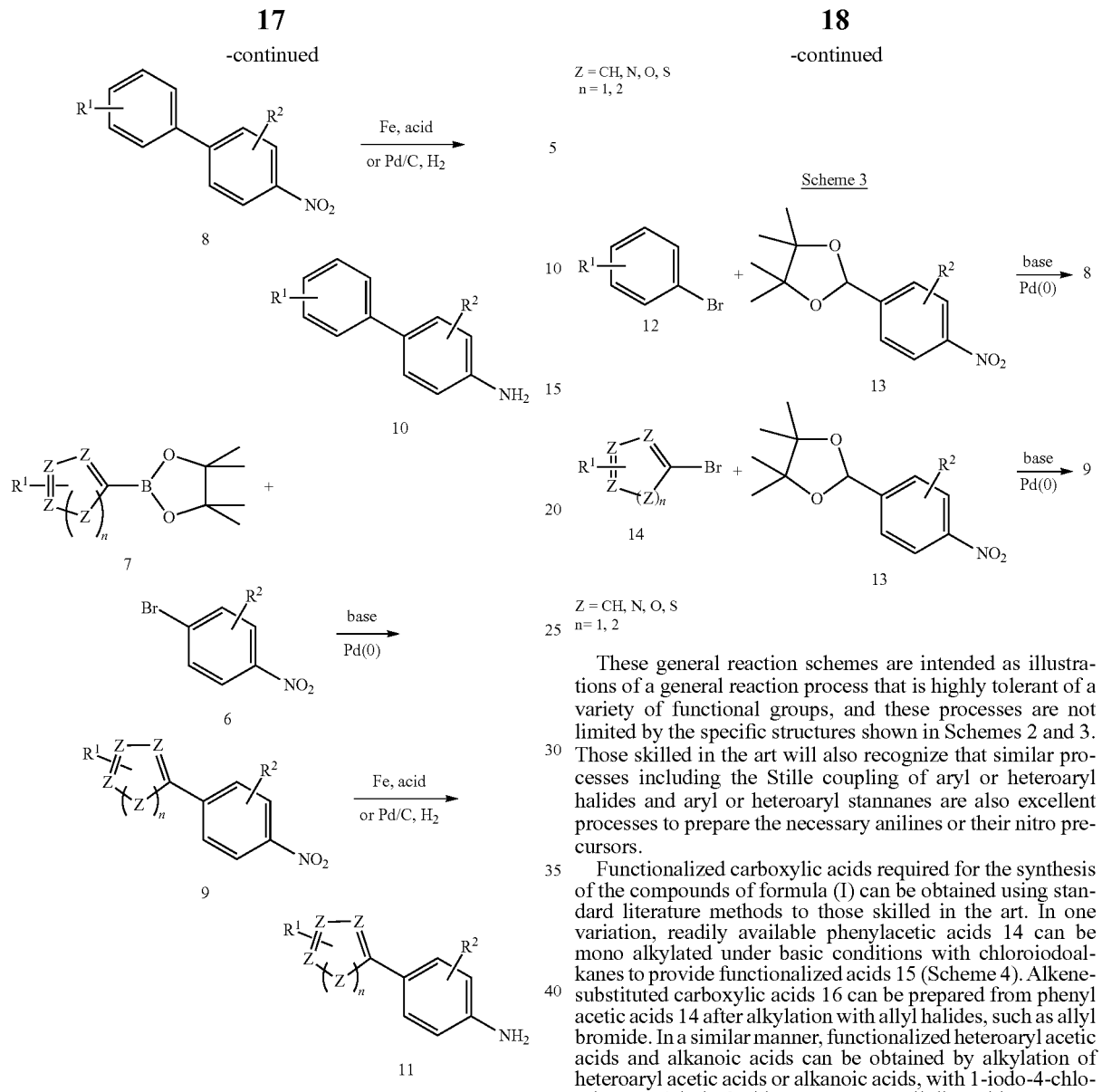

These general reaction schemes are intended as illustrations of a general reaction process that is highly tolerant of a variety of functional groups, and these processes are not limited by the specific structures shown in Schemes 2 and 3. Those skilled in the art will also recognize that similar processes including the Stille coupling of aryl or heteroaryl halides and aryl or heteroaryl stannanes are also excellent processes to prepare the necessary anilines or their nitro precursors.

Functionalized carboxylic acids required for the synthesis of the compounds of formula (I) can be obtained using standard literature methods to those skilled in the art. In one variation, readily available phenylacetic acids 14 can be mono alkylated under basic conditions with chloroiodoalkanes to provide functionalized acids 15 (Scheme 4). Alkene-substituted carboxylic acids 16 can be prepared from phenyl acetic acids 14 after alkylation with allyl halides, such as allyl bromide. In a similar manner, functionalized heteroaryl acetic acids and alkanoic acids can be obtained by alkylation of heteroaryl acetic acids or alkanoic acids, with 1-iodo-4-chlorobutane, 1-iodo-3-chloropropane, or allylbromide.

Scheme 4

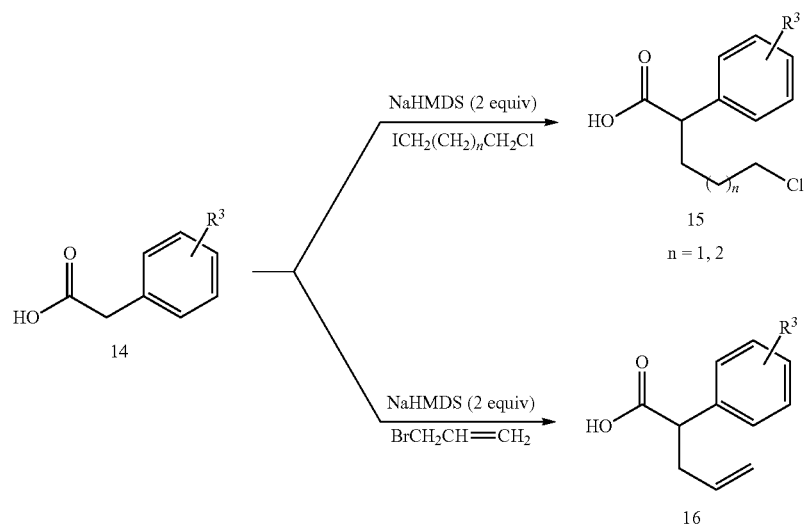

Substituted anilines and functionalized carboxylic acids can be coupled and further transformed into bicyclic compounds of formula (I) in a number of ways known to those skilled in the art. Scheme 5 outlines one such method wherein treatment of anilines 4 with 1,1'-thiocarbonyldipyridin-2 (1H)-one produces the isothiocyanates 17. Reaction of the isothiocyanates with methanolic ammonia then affords the corresponding thioureas 18. Alkylation of thiourea 18 with methyl iodide then provides the methyl isothioureas 19. The intermediates 19 are coupled, using standard methods, to functionalized carboxylic acids, such as acids 15, to afford the acylthioureas 20. Treatment of intermediates 20 with hydrazine provides triazoles of formula 21. Triazoles 21 undergo base-catalyzed intramolecular alkylation using diisopropylethylamine and sodium iodide in a solvent such as acetone or using an inorganic base, such as potassium or cesium carbonate, and potassium iodide in DMF to afford the bicyclic triazoles of formula Ia. It should be noted that other anilines, such as, but not limited to, those of formulas 10 and 11 can be used to prepare additional analogs of formula (I) using a variation of the same reaction process outlined in Scheme 5.

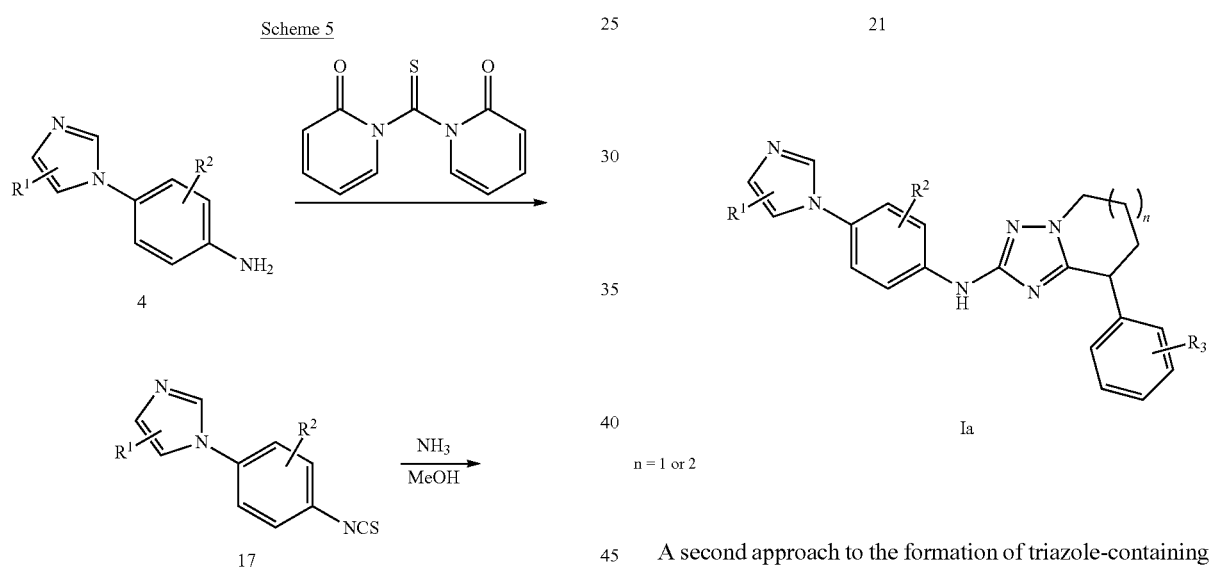

A second approach to the formation of triazole-containing bicyclic compounds of formula (I), is depicted in Scheme 6. The standard coupling of alkene bearing carboxylic acids of the formula 16 with thioureas 19 provides allyl-bearing acylthioureas 22. Substituted alkenyl hydrazines, including allylhydrazine, react with acylthioureas 22 to form the N-allyltriazoles 23. Ring closing metathesis, using the Hoyveda-Grubbs' second-generation catalyst or any other related catalyst useful for such transformations, affords unsaturated bicyclic triazoles of formula Ib.

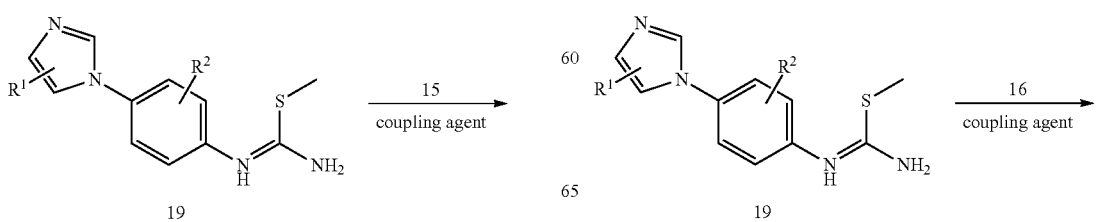

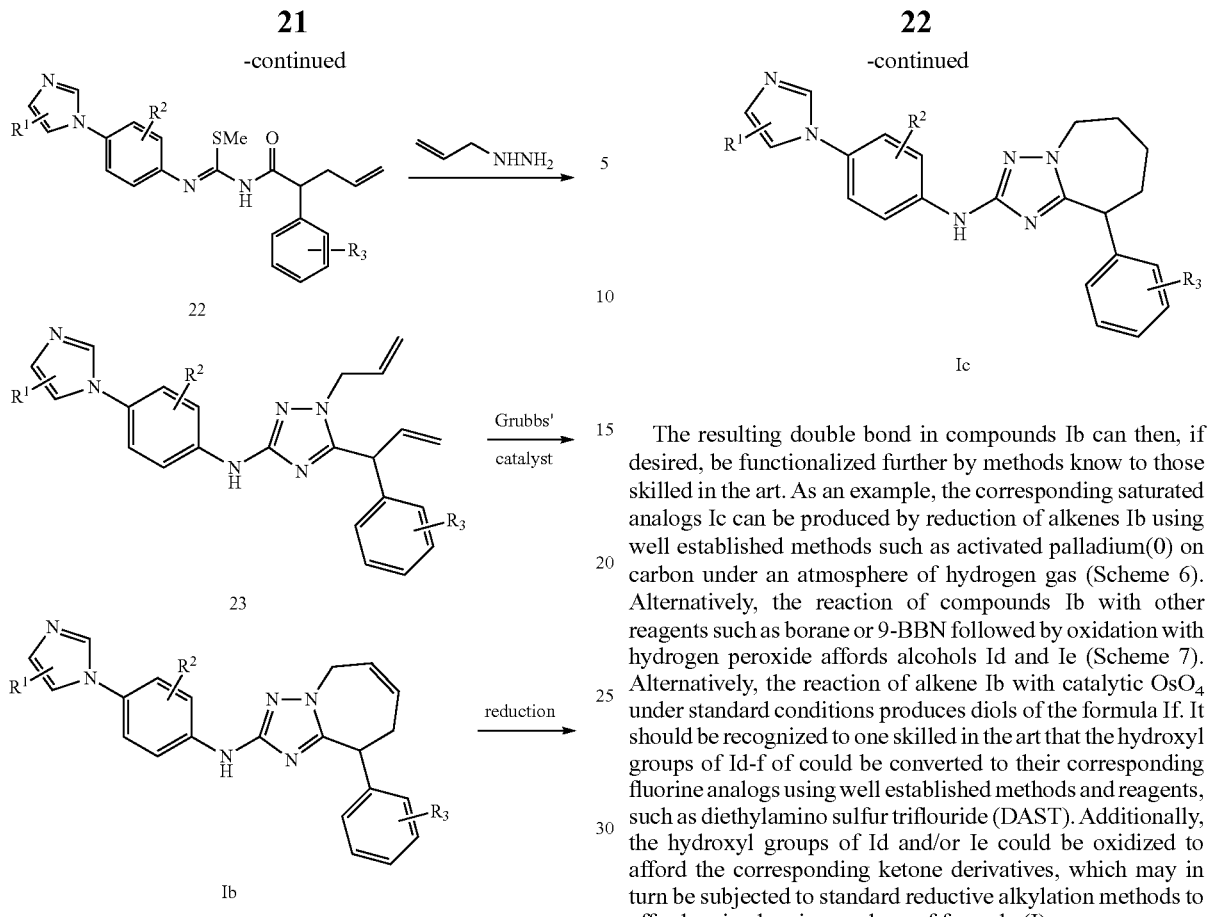

The resulting double bond in compounds Ib can then, if desired, be functionalized further by methods know to those skilled in the art. As an example, the corresponding saturated analogs Ic can be produced by reduction of alkenes Ib using well established methods such as activated palladium(0) on carbon under an atmosphere of hydrogen gas (Scheme 6). Alternatively, the reaction of compounds Ib with other reagents such as borane or 9-BBN followed by oxidation with hydrogen peroxide affords alcohols Id and Ie (Scheme 7). Alternatively, the reaction of alkene Ib with catalytic $OsO_4$ under standard conditions produces diols of the formula If. It should be recognized to one skilled in the art that the hydroxyl groups of Id-f of could be converted to their corresponding fluorine analogs using well established methods and reagents, such as diethylamino sulfur triflouride (DAST). Additionally, the hydroxyl groups of Id and/or Ie could be oxidized to afford the corresponding ketone derivatives, which may in turn be subjected to standard reductive alkylation methods to afford amine bearing analogs of formula (I).

Scheme 7

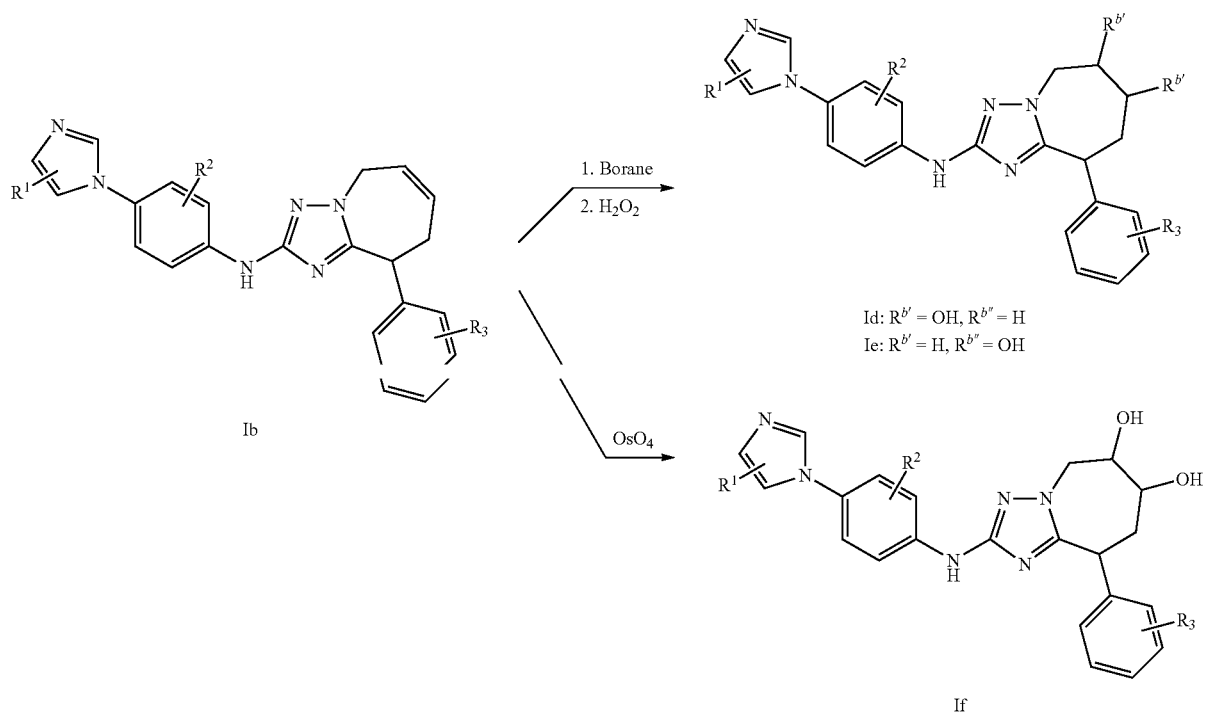

Thioureas of formula 19 can be utilized as components in the Hantzsch reaction with cyclic α-halo ketones 24 to provide, in one synthetic step, bicyclic thiazoles of formula Ig (Scheme 8). This procedure is useful for preparing both b- and 7-membered bicyclic compounds, and is tolerant of additional functionality on the rings. The precursor α-halo ketones 24 can be readily made by a number of methods known to one skilled in the art.

Scheme 8

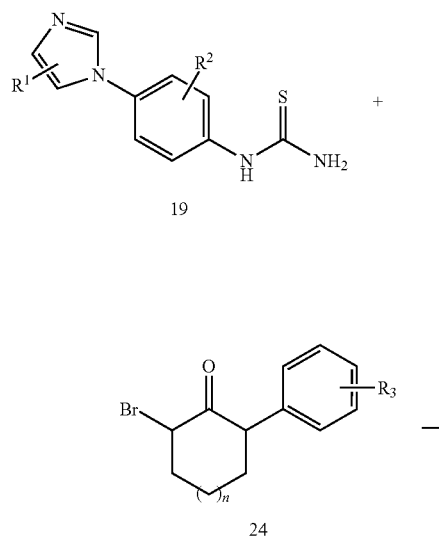

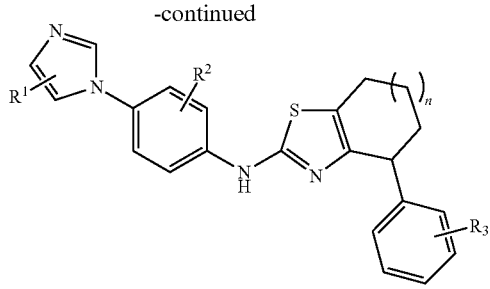

Ig n = 1 or 2

Palladium catalyzed α-arylation of ketones 25 with aryl halides is a useful and convenient method for the preparation of α-aryl ketones 26 (Fox, J. M. et al, *Journal of the American Chemical Society* 2000, 122, 1360-1370) (Scheme 9). Bromination of α-aryl ketones 26 using N-bromosuccinimide and benzoyl peroxide or using bromine in halogenated solvents produces the requisite α-halo ketones 24. Additional substitution can be installed on intermediates 26 by successive alkylation. In this case, the position of the substituent introduced by the second alkylation can be controlled by using principles known to those skilled in the art. Thus, alkylation of the anion of structures 26 under thermodynamic control will install the second substituent "Z" at the more substituted position delivering structures 27, which can be halogenated using the previously described conditions to afford intermediates 28. Elaborating the substituted ketones 28 into compounds of formula (I) can be accomplished in direct analogy to the preparation of analogs in scheme 8, using alpha-halo ketones 28 in place of ketones 24. It must be noted that α-aryl ketones 24 and 28 are prone to decomposition during purification and storage; however, crude reaction products are suitable for immediately use in the Hantzsch reaction.

Scheme 9

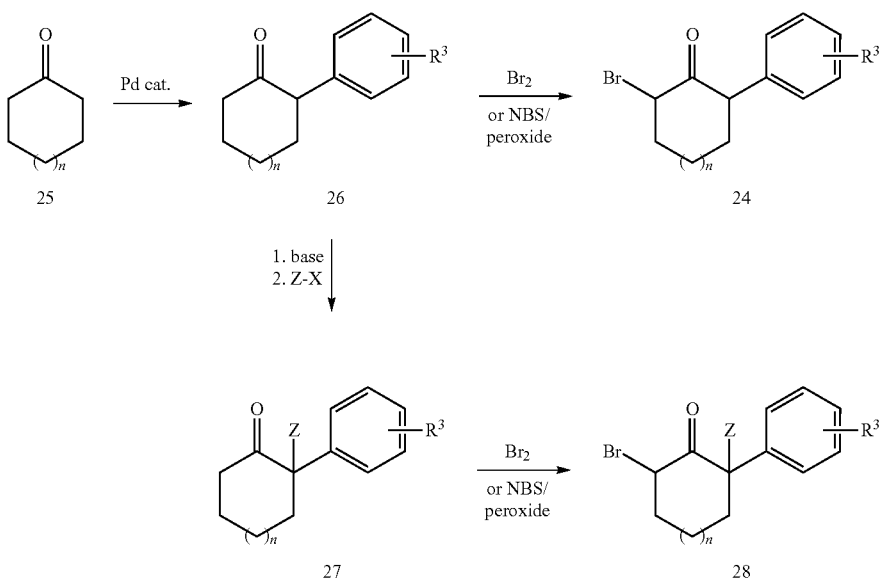

n = 1 or 2

Additional compounds of formula (I) can be prepared using the general process shown in Scheme 10. Condensation of thioureas 18 with bromodiketone 24a affords the thiazole ketones 29. Grignard addition with aryl- or alkylmagnesium halides provides the tertiary alcohols Ih. Azidation with sodium azide/trifluoroacetic acid produces the azides, which can be reduced using lithium aluminum hydride to the corresponding amines of formula Ii. The amine may be further functionalized using acylation, reductive alkylation, or other techniques know to those skilled in the art.

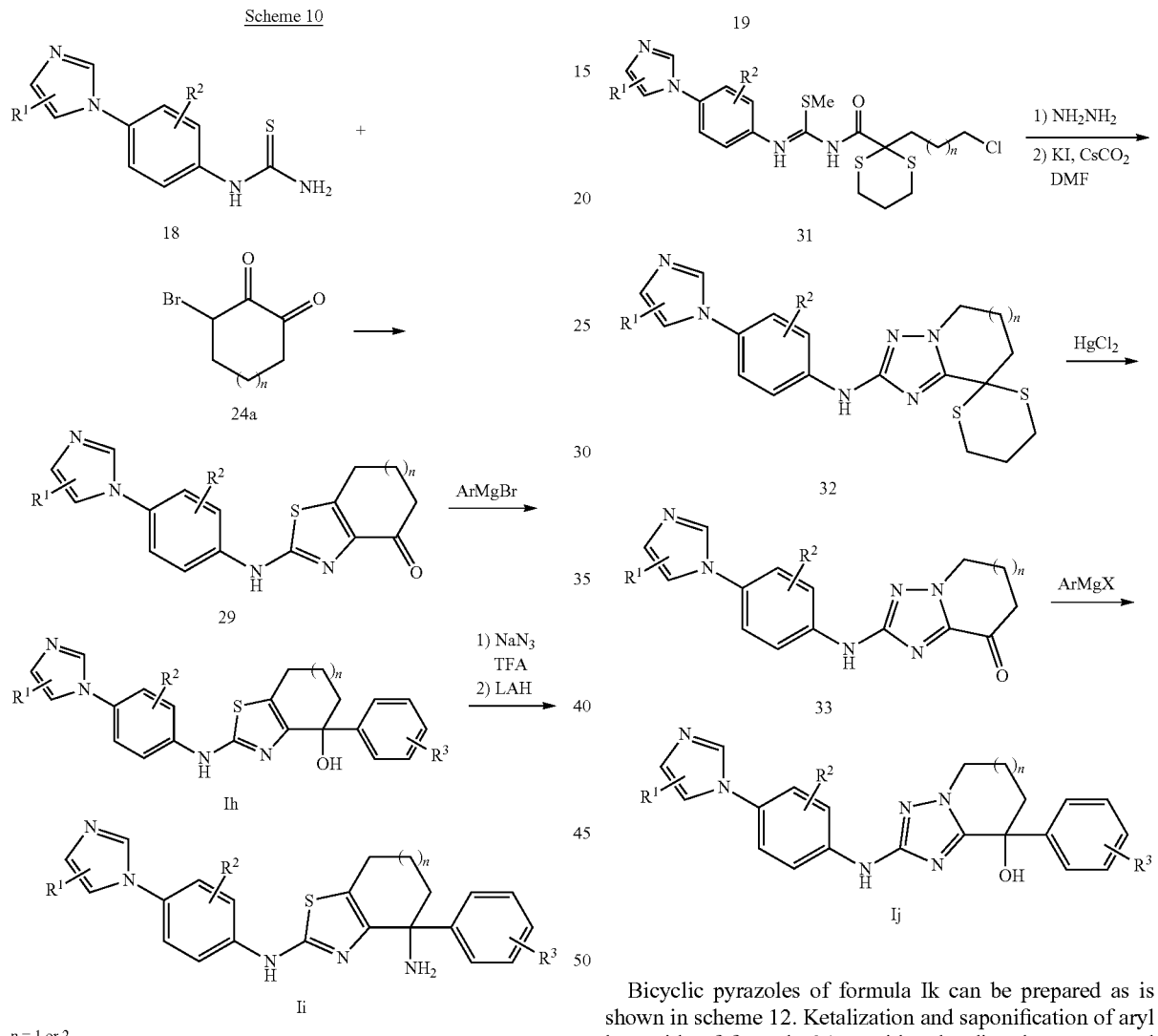

In another embodiment of the disclosure, tertiary alcohol and amine derivatives belonging to the bicyclic triazole scaffold can be prepared using the methods outlined in Scheme 11. The coupling of methyl thioureas 19 with suitably protected alpha-ketoacids, such as dithianes 30, provide the N-acylthioureas 31. Triazole formation and intramolecular alkylation affords dithiane protected triazoles of formula 32. Dithiane cleavage reveals the corresponding keto triazoles 33. Grignard addition with aryl- or alkylmagnesium halides provides the tertiary alcohols Ij. Preparation of the corresponding tertiary amines from Ij should proceed in analogous fashion to the methods previously outlined in Scheme 10.

Bicyclic pyrazoles of formula Ik can be prepared as is shown in scheme 12. Ketalization and saponification of aryl ketoacids of formula 34 provides the dioxolane protected intermediates 35. Conversion to the acid chlorides and reaction with the anion of 2,2-dimethyl-1,3-dioxane-4,6-dione acids affords intermediates of formula 36. The resulting compounds 37 can be reacted with aniline to provide the corresponding beta-keto amides, which upon treatment with hydrazine results in the formation of pyrazolones 37. Boron trichloride-mediated ring closure then produces the bicycles 38. Anilines 4 can be coupled under metal-mediated conditions with suitably acted derivatives of core 38, such as the triflate, nonaflate, or halide to afford compounds of formula 39. The olefin moiety of the products 39 can be hydrogenated to afford analogs of formula Ii, or further functionalized by methods known to those skilled in the art.

Scheme 12

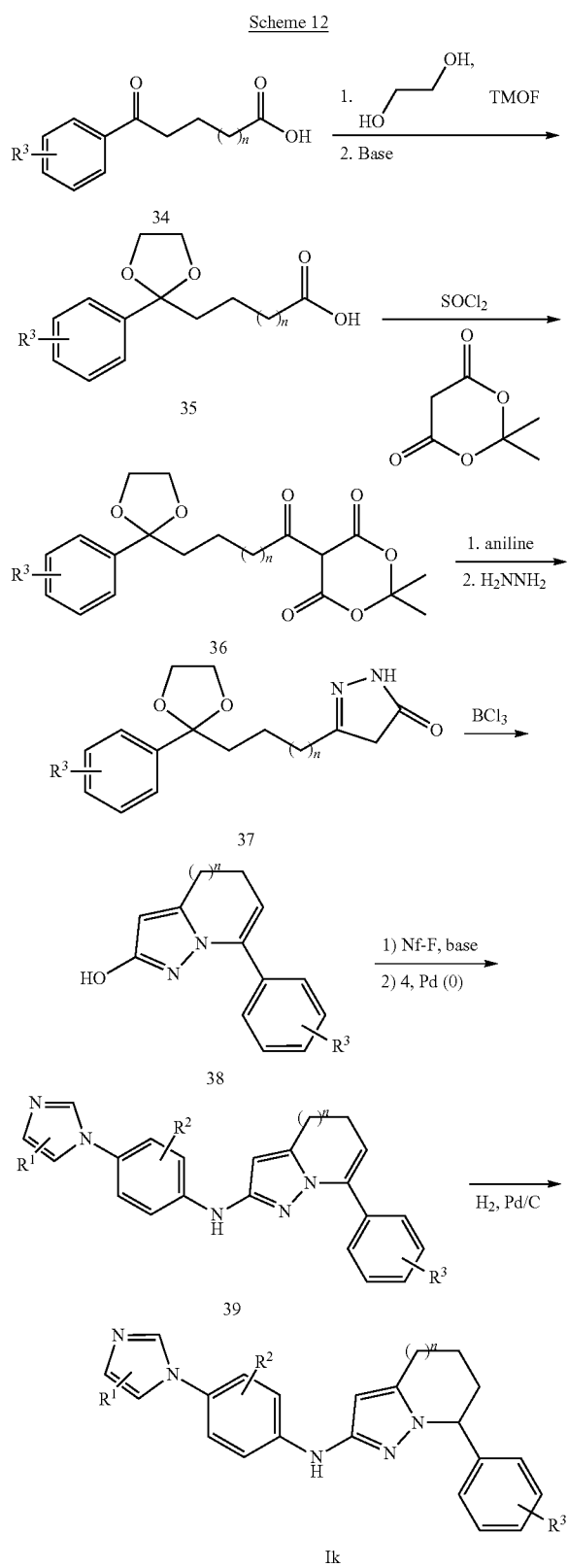

In an additional embodiment of the disclosure, reversed triazoles of the formula II can be prepared by the methods depicted in scheme 13. Substituted aryl ketoacids 34 react with t-butylcarbazide to afford BOC protected hydrazones 40. Intramolecular reductive alkylation using hydrogen and catalytic palladium can provide, after acidic deprotection, the corresponding 1-amino-piperidines 42. Subsequent reaction with methylthioureas 19 affords the reversed triazoles of formula Il.

Scheme 13

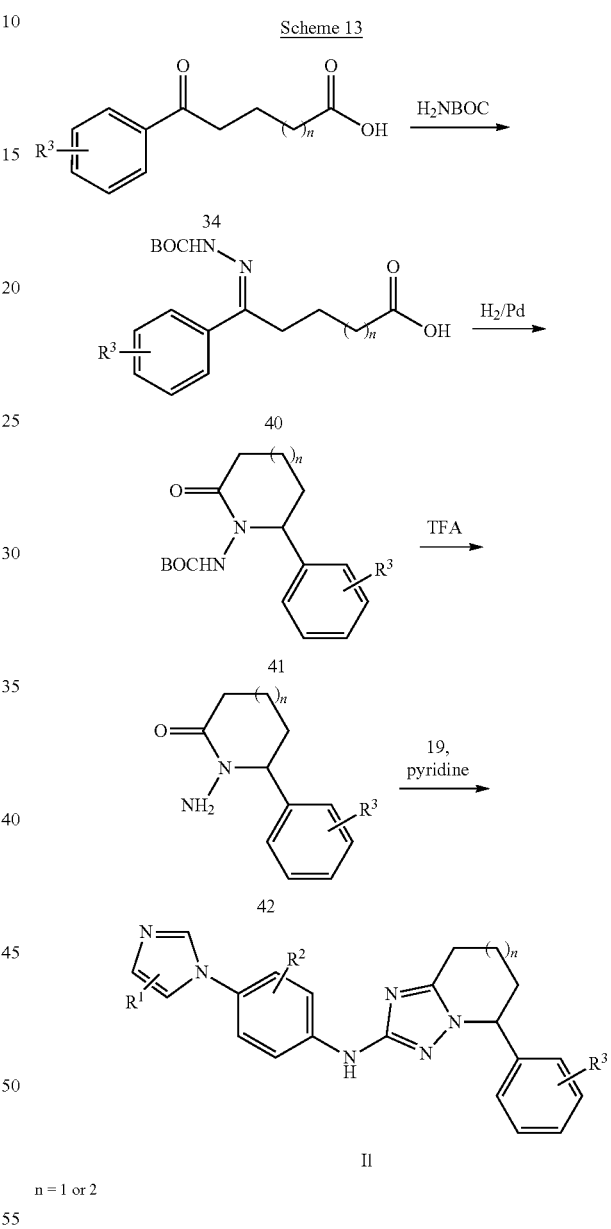

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/ruin. Reverse phase preparatory HPLC: When described as performed under "standard conditions", samples (approx. 20 mg) were dissolved in methanol (10 mg/mL) and purified on a 30 mm×100 mm Waters-Atlantis S5 column using a 10 minute gradient elution from 0% to 100% buffer B in buffer A (buffer A=10% MeOH/90% water/0.1% TFA and buffer B=90% MeOH/10% water/0.1% TFA). at 40 mL/minute.

Proton NMR spectra were obtained on a Bruker 400 or 500 spectrometer. Data were referred to the lock solvent.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation A

Methyl N'-4-(4-chloro-1H-imidazol-1-yl)-3-methoxyphenylcarbamimidothioate hydroiodide

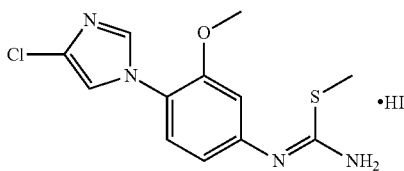

Step A (1): A mixture of 4-chloro-1H-imidazole (5.0 g, 48.8 mmol), 1-chloro-2-methoxy-4-nitrobenzene (9.15 g, 48.8 mmol), and potassium hydroxide flakes (2.74 g, 48.8 mmol) in anhydrous DMSO (50 mL) was heated at 80° C. for 20 h. The reaction mixture was allowed to cool to rt and was poured into 800 mL of water with vigorous stirring. The resulting yellow-orange precipitate was collected by vacuum filtration using a coarse sintered glass funnel. The crude wet solid was transferred to a 1 L Erlenmeyer flask. Absolute ethanol (250 mL) was added to the flask and the resulting suspension was heated until all of the solids dissolved. The clear solution was cooled to rt and the desired product slowly crystallized. After 2 h, the crystalline solid was collected by vacuum filtration and rinsed with 100 mL of fresh ethanol. The solid was dried under high vacuum to afford 4-chloro-1-(2-methoxy-4-nitrophenyl)-1H-imidazole (5.2 g, 42% yield) as an off-white crystalline solid. LC-MS (M+H)$^+$=254.0. $^1$H NMR (500 MHz, chloroform-d) δ ppm 7.94-8.01 (m, 2 H) 7.76 (d, J=1.53 Hz, 1 H) 7.45 (d, J=8.55 Hz, 1 H) 7.21 (d, J=1.53 Hz, 1 H) 4.02 (s, 3 H).

Step A (2): Iron powder-325 mesh (4.6 g, 82 mmol) was added to a 500 mL round bottom flask charged with a mixture of 4-chloro-1-(2-methoxy-4-nitrophenyl)-1H-imidazole (5.2 g, 20.5 mmol), absolute ethanol (100 mL), and glacial acetic acid (50 mL). A water-cooled reflux condenser was attached to the flask and the heterogeneous mixture was heated to 100° C. with vigorous stirring for 30 min. The reaction mixture allowed to cool to rt and was added to a chilled and stirred solution of 3 M NaOH (291 mL). The resulting mixture was poured into a separatory funnel and extracted with EtOAc (3×250 mL). The combined organic layers were dried over sodium sulfate, filtered, and concentrated in vacuo to afford 4-(4-chloro-1H-imidazol-1-yl)-3-methoxyaniline (4.57 g, 97% yield) as a solid. LC-MS (M+H)$^+$ 224.0. $^1$H NMR (500 MHz, chloroform-d) δ ppm 7.47 (d, J=1.22 Hz, 1 H) 7.00 (d, J=8.24 Hz, 1 H) 6.99 (d, J=1.53 Hz, 1 H) 6.32 (d, J=2.44 Hz, 1 H) 6.29 (dd, J=8.24, 2.14 Hz, 1 H) 3.88 (br. s., 2 H) 3.78 (s, 3 H).

Step A (3): Dichloromethane (125 mL) was added to a flask charged with 4-(4-chloro-1H-imidazol-1-yl)-3-methoxyaniline (4.55 g, 20.3 mmol) and 1,1'-thiocarbonyldipyridin-2(1H)-one (4.72 g, 20.3 mmol). The resulting mixture was stirred for 24 h at rt. The crude reaction mixture was concentrated and the crude products were purified using silica gel chromatography to afford 4-chloro-1-(4-isothiocyanato-2-methoxy-phenyl)-1H-imidazole (4.28 g, 79% yield) as a white solid. LC-MS (M+H)$^+$ 266.0. $^1$H NMR (500 MHz, chloroform-d) δ ppm 7.60 (d, J=1.53 Hz, 1 H) 7.24 (d, J=8.24 Hz, 1 H) 7.09 (d, J=1.83 Hz, 1 H) 6.93 (dd, J=8.24, 2.14 Hz, 1 H) 6.89 (d, J=2.14 Hz, 1 H) 3.88 (s, 3 H).

Step A (4): Methanolic ammonia (1.0 M, 100 mL, 100 mmol) was added to a flask charged with 4-chloro-1-(4-isothiocyanato-2-methoxy-phenyl)-1H-imidazole (4.27 g, 16.1 mmol) in a ice-water bath. After the addition was complete, the resulting slurry was stirred for 10 min and then allowed to warm to rt. After 24 h, the reaction mixture was concentrated to dryness in vacuo. The solid was suspended in ethanol (200 mL) and stirred for 2 hours. The solid was collected by vacuum filtration and dried under high vacuum for 24 h to afford 1-(4-(4-chloro-1H-imidazol-1-yl)-3-methoxyphenyl)thiourea (3.85 g, 83% yield) as a white solid. LC-MS (M+H)$^+$ 283.0.

Step A (5): Iodomethane (0.890 mL, 14.3 mmol) was added to a solution of 1-(4-(4-chloro-1H-imidazol-1-yl)-3-methoxyphenyl)thiourea (3.85 g, 13.6 mmol) in absolute ethanol (100 mL). The resulting mixture was heated at 70° C. for 3 h. After cooling to rt, the reaction was concentrated in vacuo. The residual volatiles were removed in vacuo to afford methyl 4-(4-chloro-1H-imidazol-1-yl)-3-methoxyphenylcarbamimidothioate, hydroiodide (6.32 g, 109% yield) as a white solid. LC-MS (M+H)$^+$ 297.1. $^1$H NMR (500 MHz, methanol-d$_4$) δ ppm 7.86 (d, J=1.22 Hz, 1 H) 7.55 (d, J=8.24 Hz, 1 H) 7.40 (d, J=1.22 Hz, 1 H) 7.28 (d, J=2.14 Hz, 1 H) 7.08 (dd, J=8.39, 2.29 Hz, 1 H) 3.94 (s, 3 H) 2.76 (s, 3 H).

Preparation B

Methyl N'-2-fluoro-5-methoxy-4-(3-methyl-1H-1,2,4-triazol-1-yl)phenylcarbamimidothioate hydroiodide

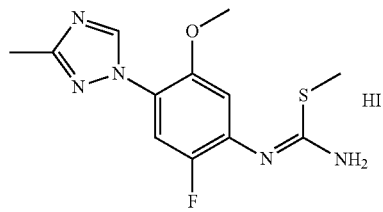

Step B (1): A mixture of 3-methyl-1H-1,2,4-triazole (2.20 g, 26.4 mmol), 1,5-difluoro-2-methoxy-4-nitrobenzene (5.00 g, 26.4 mmol), and potassium carbonate (3.65 g, 26.4 mmol) in anhydrous DMSO (50 mL) was heated at 80° C. for 24 h. The reaction mixture was allowed to cool to rt and was poured into 500 mL of water/10 mL brine solution. The aqueous mixture was extracted with EtOAc (2×250 mL). The combined organic extracts were washed with water (500 mL), dried over sodium sulfate, filtered, and concentrated in vacuo. The crude reaction mixture was purified using silica gel column chromatography (50% EtOAc/hexane) to afford 1-(5-fluoro-2-methoxy-4-nitrophenyl)-3-methyl-1H-1,2,4-triazole (1.24 g, 18% yield). LC-MS (M+H)$^+$=253.2. $^1$H NMR (500 MHz, chloroform-d) δ ppm 8.95 (s, 1 H) 8.00 (d, J=11.60 Hz, 1 H) 7.80 (d, J=6.10 Hz, 1 H) 4.09 (s, 3 H) 2.50 (s, 3 H).

Step B (2): 10% Palladium on carbon (0.523 g, 4.92 mmol) was added under an atmosphere of nitrogen to a chilled (ice-water bath) solution of 1-(5-fluoro-2-methoxy-4-nitrophenyl)-3-methyl-1H-1,2,4-triazole (1.24 g, 4.92 mmol) dissolved in methanol (100 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short diatomaceous earth (Celite®) plug. The reaction vessel and plug were rinsed with fresh methanol. The combined filtrates were concentrated in vacuo. The residue was dried on high vacuum overnight to afford 2-fluoro-5-methoxy-4-(3-methyl-1H-1,2,4-triazol-1-yl)aniline (1.05 g, 96% yield) as a gray solid. LC-MS (M+H)+ 223.1. ¹H NMR (500 MHz, chloroform-d) δ ppm 8.46 (s, 1 H) 7.39 (d, J=11.29 Hz, 1 H) 6.44 (d, J=7.63 Hz, 1 H) 3.89 (br. s., 2 H) 3.83 (s, 3 H) 2.47 (s, 3 H).

Step B (3): Dichloromethane (125 mL) was added to a flask charged with 2-fluoro-5-methoxy-4-(3-methyl-1H-1,2,4-triazol-1-yl)aniline (1.07 g, 4.82 mmol) and 1,1'-thiocarbonyldipyridin-2(1H)-one (1.12 g, 4.82 mmol). The resulting mixture was stirred for 24 h at rt and concentrated in vacuo. The crude residue was purified using silica gel chromatography (0-5% EtOAc/chloroform, linear gradient over 36 min, flow 25 mL/min) to afford 1-(5-fluoro-4-isothiocyanato-2-methoxyphenyl)-3-methyl-1H-1,2,4-triazole (950 mg, 75% yield) as a yellow solid. LC-MS (M+H)+ 265.1. ¹H NMR (500 MHz, chloroform-d) δ ppm 8.74 (s, 1 H) 7.75 (d, J=10.07 Hz, 1 H) 6.84 (d, J=6.41 Hz, 1 H) 3.94 (s, 3 H) 2.48 (s, 3 H).

Step B (4): Methanolic ammonia (1.0 M, 25 mL, 25 mmol) was added to a flask charged with 1-(5-fluoro-4-isothiocyanato-2-methoxyphenyl)-3-methyl-1H-1,2,4-triazole (870 mg, 3.29 mmol) in a ice-water bath. After the addition was complete, the resulting slurry was stirred for 10 min and then allowed to warm to rt. After 24 h, the reaction mixture was concentrated in vacuo. The resulting solid was dried under high vacuum to afford 1-(2-fluoro-5-methoxy-4-(3-methyl-1H-1,2,4-triazol-1-yl)phenyl)thiourea (930 mg, 100% yield). LC-MS (M+H)+ 282.1. ¹H NMR (500 MHz, DMSO-d₆) δ ppm 8.84 (s, 1 H) 7.88 (d, J=6.41 Hz, 1 H) 7.57 (d, J=10.99 Hz, 1 H) 3.86 (s, 3 H) 2.36 (s, 3 H).

Step B (5): Iodomethane (0.184 mL, 2.95 mmol) was added to a solution of 1-(2-fluoro-5-methoxy-4-(3-methyl-1H-1,2,4-triazol-1-yl)phenyl)thiourea (664 mg, 2.36 mmol) in absolute ethanol (100 mL). The resulting mixture was heated at 70° C. for 3 h. After cooling to rt, the reaction was concentrated in vacuo. The residual volatiles were removed under high vacuum to afford methyl 2-fluoro-5-methoxy-4-(3-methyl-1H-1,2,4-triazol-1-yl)phenylcarbamimidothioate, hydroiodide (1.05 g, 105% yield) as a white solid. LC-MS (M+H)+ 296.2. ¹H NMR (500 MHz, methanol-d₄) δ ppm 7.70 (s, 1 H) 6.57 (d, J=10.68 Hz, 1 H) 6.12 (d, J=6.41 Hz, 1 H) 2.74 (s, 3 H) 1.50 (s, 3 H) 1.17 (s, 3 H).

Preparation C

Methyl N'-3-fluoro-4-(5-methyl-1H-1,2,4-triazol-1-yl)phenylcarbamimidothioate hydroiodide

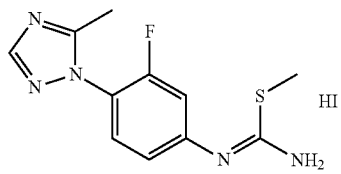

Step C (1): A mixture of 3-methyl-1H-1,2,4-triazole (15.0 g, 181 mmol), 1,2-difluoro-4-nitrobenzene (28.7 g, 181 mmol), and sodium bicarbonate (15.2 g, 181 mmol) in DMSO (100 mL) was heated at 80° C. for 48 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The crude reaction mixture was purified using silica gel chromatography (30-80% EtOAc/hexane, linear gradient) to afford two regioisomeric products. Pure fractions of the less polar regioisomer were combined and concentrated to afford 1-(2-fluoro-4-nitrophenyl)-3-methyl-1H-1,2,4-triazole (7.2 g, 30.8 mmol, 17% yield) as an off-white solid. Pure fractions of the more polar regioisomer were combined and concentrated to afford 1-(2-fluoro-4-nitrophenyl)-5-methyl-1H-1,2,4-triazole (6.23 g, 28.0 mmol, 15% yield) as an off-white solid.

Data for 1-(2-fluoro-4-nitrophenyl)-5-methyl-1H-1,2,4-triazole: LC-MS (M+H)+=223.1. ¹H NMR (500 MHz, chloroform-d) δ ppm 8.18-8.24 (m, 2 H) 8.04 (s, 1 H) 7.69-7.78 (m, 1 H) 2.47-2.53 (m, 3 H).

Data for 1-(2-fluoro-4-nitrophenyl)-3-methyl-1H-1,2,4-triazole: LC-MS (M+H)+=223.1. ¹H NMR (500 MHz, chloroform-d) δ ppm 8.73 (d, J=2.7 Hz, 1 H), 8.15-8.26 (m, 3 H), 2.53 (s, 3 H).

Step C (2): 10% Palladium on carbon (1.5 g, 14.1 mmol) was added under an atmosphere of nitrogen to a chilled (ice-water bath) solution of 1-(2-fluoro-4-nitrophenyl)-5-methyl-1H-1,2,4-triazole (3.7 g, 17 mmol) dissolved in methanol (200 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short plug of diatomaceous earth (Celite®). The reaction vessel and Celite® were rinsed with fresh methanol. The combined filtrates were concentrated in vacuo. The residue was dried under high vacuum to afford 3-fluoro-4-(5-methyl-1H-1,2,4-triazol-1-yl)aniline (3.14 g, 91% yield) as a blackish/grey solid. LC-MS (M+H)+ 193.1. ¹H NMR (500 MHz, chloroform-d) δ ppm 7.91 (s, 1 H) 7.14 (t, J=8.55 Hz, 1 H) 6.43-6.53 (m, 2 H) 4.04 (br. s., 2 H) 2.36 (s, 3 H).

Step C (3): Dichloromethane (125 mL) was added to a flask charged with 3-fluoro-4-(5-methyl-1H-1,2,4-triazol-1-yl)aniline (3.14 g, 16.3 mmol) and 1,1'-thiocarbonyldipyridin-2(1H)-one (3.79 g, 16.3 mmol). The resulting mixture was stirred for 24 h at rt and concentrated in vacuo. The crude residue was purified using silica gel chromatography (0-5% EtOAc/chloroform, linear gradient) to afford 1-(2-fluoro-4-isothiocyanatophenyl)-5-methyl-1H-1,2,4-triazole (3.18 g, 13.6 mmol, 83% yield) as a white solid. LC-MS (M+H)+ 235.0. ¹H NMR (500 MHz, chloroform-d) δ ppm 7.99 (s, 1 H) 7.47 (t, J=8.24 Hz, 1 H) 7.13-7.22 (m, 2 H) 2.43 (d, J=1.83 Hz, 3H).

Step C (4): Methanolic ammonia (1.0 M, 100 mL, 100 mmol) was added to a flask charged with 1-(2-fluoro-4-isothiocyanatophenyl)-5-methyl-1H-1,2,4-triazole (3.18 g, 13.6 mmol) in a ice-water bath. After the addition was complete, the resulting slurry was stirred for 10 min and then allowed to warm to rt. After 24 h, the reaction mixture was concentrated in vacuo. The resulting solid was dried under high vacuum to afford 1-(3-fluoro-4-(5-methyl-1H-1,2,4-triazol-1-yl)phenyl)thiourea (3.21 g, 94% yield) as an off-white solid. LC-MS (M+H)+ 252.1. ¹H NMR (500 MHz, DMSO-d$_6$) δ ppm 8.06 (s, 1 H), 7.93 (dd, J=12.8, 2.1 Hz, 1 H), 7.54 (t, J=8.7 Hz, 1 H), 7.37 (dd, J=8.5, 1.8 Hz, 1 H), 2.32 (s, 3 H)

Step C (5) [79643-051]: Iodomethane (0.835 mL, 13.4 mmol) was added to a solution of 1-(3-fluoro-4-(5-methyl-1H-1,2,4-triazol-1-yl)phenyl)thiourea (3.21 g, 12.8 mmol) in absolute ethanol (100 mL). The resulting mixture was heated at 70° C. for 3 h. After cooling to rt, the reaction was concentrated in vacuo. The residual volatiles were removed under high vacuum to afford methyl 3-fluoro-4-(5-methyl-1H-1,2,4-triazol-1-yl)phenylcarbamimidothioate, hydroiodide (4.82 g, 96% yield) as a white solid. LC-MS (M+H)$^+$ 266.0. $^1$H NMR (500 MHz, DMSO-d$_6$) δ ppm 8.12 (s, 1 H), 7.77 (t, J=8.5 Hz, 1 H), 7.64 (dd, J=11.0, 2.1 Hz, 1 H), 7.37 (dd, J=8.4, 1.4 Hz, 1 H), 2.72 (s, 3 H), 2.36 (s, 3 H).

Preparation D

Methyl N'-3-methoxy-4-(4-methyl-1H-imidazol-1-yl)phenylcarbamimidothioate hydroiodide

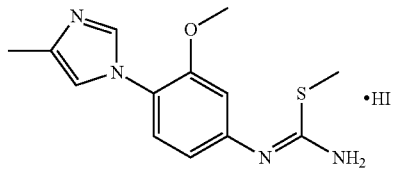

Step D (1): A mixture of 4-methyl-1H-imidazole (18.0 g, 53.5 mmol), 1-chloro-2-methoxy-4-nitrobenzene (10.0 g, 53.5 mmol), and potassium hydroxide (4.5 g, 80.3 mmol) in DMSO (50 mL) was heated at 110° C. for 24 h. The reaction mixture was allowed to cool to rt and was poured into 1000 mL of water. The aqueous mixture was extracted with dichloromethane (3×250 mL). The combined organic extracts were washed with brine, dried over sodium sulfate, filtered, and concentrated in vacuo. The crude reaction mixture was purified using silica gel chromatography (330 g silica cartridge, 0-2% MeOH/chloroform, linear gradient over 72 min, flow 25 mL/min) to afford 1-(2-methoxy-4-nitrophenyl)-4-methyl-1H-imidazole (2.56 g, 20% yield) as a yellow/orange solid. LC-MS (M+H)$^+$=234.1. $^1$H NMR (500 MHz, chloroform-d) δ ppm 7.97-8.00 (m, 1 H) 7.93-7.97 (m, 2 H) 7.45 (d, J=8.85 Hz, 1 H) 7.02 (s, 1 H) 4.02 (s, 3 H) 2.35 (s, 3 H).

Step D (2): 10% Palladium on carbon (250 mg) was added under an atmosphere of nitrogen to a chilled (ice-water bath) solution of 1-(2-methoxy-4-nitrophenyl)-4-methyl-1H-imidazole (2.56 g, 11.0 mmol) dissolved in methanol (150 mL). The flask was repeated evacuated and flushed with hydrogen gas (double balloon). The resulting mixture was allowed to warm to rt and left to stir for 18 h under the hydrogen atmosphere. Purged with nitrogen gas. Filtered the crude reaction mixture through a short diatomaceous earth (Celite®) plug. Rinsed reaction vessel and plug with methanol. Concentrated filtrate in vacuo. Dried residue on high vacuum overnight to afford 3-methoxy-4-(4-methyl-1H-imidazol-1-yl)aniline (2.25 g, 100% yield) as a blackish/grey waxy solid. LC-MS (M+H)$^+$ 204.1. $^1$H NMR (500 MHz, chloroform-d) δ ppm 7.69 (s, 1 H) 7.01 (d, J=8.55 Hz, 1 H) 6.82 (s, 1 H) 6.33 (d, J=2.14 Hz, 1 H) 6.30 (d, J=8.55 Hz, 1 H) 3.78 (s, 3 H) 2.33 (s, 3 H).

Step D (3): Dichloromethane (125 mL) was added to a flask charged with 3-fluoro-4-(3-methyl-1H-1,2,4-triazol-1-yl) aniline (3.14 g, 16.34 mmol) and 1,1'-thiocarbonyldipyridin-2(1H)-one (3.79 g, 16.34 mmol). The resulting mixture was stirred for 24 h at rt and concentrated in vacuo. The crude residue was purified using silica gel chromatography (10-66% EtOAc/hexane, linear gradient over 72 min, flow 25 mL/min) to afford 1-(4-isothiocyanato-2-methoxyphenyl)-4-methyl-1H-imidazole (0.798 g, 87% yield) as a yellow solid. LC-MS (M+H)$^+$ 246.0. $^1$H NMR (500 MHz, chloroform-d) δ ppm 7.73 (d, J=1.53 Hz, 1 H) 7.23 (d, J=8.24 Hz, 1 H) 6.86-6.94 (m, 3 H) 3.87 (s, 3 H) 2.31 (s, 3 H).

Step D (4): Methanolic ammonia (1.0 M, 100 mL, 100 mmol) was added to a flask charged with 1-(4-isothiocyanato-2-methoxyphenyl)-4-methyl-1H-imidazole (500 mg, 2.04 mmol) in a ice-water bath. After the addition was complete, the resulting slurry was stirred for 10 min and then allowed to warm to rt. After 24 h, the reaction mixture was concentrated to dryness in vacuo. The resulting solid was dried under high vacuum to afford 1-(3-methoxy-4-(4-methyl-1H-imidazol-1-yl)phenyl)thiourea (0.529 g, 100% yield) as a white solid. LC-MS (M+H)$^+$ 263.3.

Step D (5): Iodomethane (0.066 mL, 1.07 mmol) was added to a solution of 1-(3-methoxy-4-(4-methyl-1H-imidazol-1-yl)phenyl)thiourea (280 mg, 1.07 mmol) in absolute ethanol (5 mL). The resulting mixture was heated at 50° C. for 3 h. After cooling to rt, the reaction was concentrated in vacuo. The crude residue was purified using silica gel chromatography (0-10% MeOH/chloroform, linear gradient over 72 min, flow 25 mL/min) to afford 1-(4-isothiocyanato-2-methoxyphenyl)-4-methyl-1H-imidazole hydroiodide (135 mg, 46% yield) as a white solid. LC-MS (M+H)$^+$ 277.2.

Preparation E

Methyl N'-4-(3-chloro-1H-1,2,4-triazol-1-yl)-3-methoxyphenylcarbamimidothioate hydroiodide

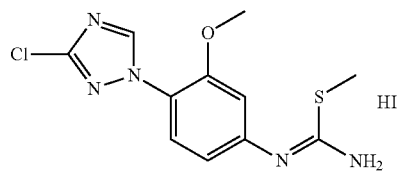

Step E (1): A mixture of 3-chloro-1H-1,2,4-triazole (2.76 g, 26.7 mmol), 1-chloro-2-methoxy-4-nitrobenzene (5.0 g, 26.7 mmol), potassium hydroxide flakes (1.496 g, 26.7 mmol), and DMSO (25 mL) was heated in a sealed reaction vessel 100° C. for 24 h. The reaction was allowed to cool to rt and additional portions of 3-chloro-1H-1,2,4-triazole (1.38 g, 0.5 equiv) and potassium hydroxide (0.75 g, 0.5 equiv) were added. The reaction vessel was resealed and heated to 110° C. for an additional 24 h. The resulting mixture was allowed to cool to rt and was poured into 500 mL of water. The aqueous mixture was extracted with EtOAc (3×100 mL). The combined organics were washed with brine, dried over Na$_2$SO$_4$, filtered and concentrated in vacuo. The crude residue was purified using silica gel chromatography (0-5% MeOH/chloroform, linear gradient over 144 min, flow 25 mL/min) to afford 2-(3-chloro-1H-1,2,4-triazol-1-yl)-5-nitrophenol (0.924 g, 3.84 mmol, 14.4% yield). LC-MS (M+H)$^+$=241.0. $^1$H NMR (500 MHz, chloroform-d) δ ppm 11.97 (br. s., 1 H) 9.24 (s, 1 H) 7.90-7.95 (m, 1 H) 7.89 (d, J=2.44 Hz, 1 H) 7.84 (dd, J=8.85, 2.44 Hz, 1 H).

Step E (2): Iodomethane (0.860 mL, 13.82 mmol) was added to a mixture of 2-(3-chloro-1H-1,2,4-triazol-1-yl)-5- nitrophenol (1.33 g, 5.53 mmol), potassium hydroxide (0.388 g, 6.91 mmol), and DMSO (25 mL). The mixture was left to stir at rt for 24 h. The reaction mixture was poured into water (250 mL) and extracted with EtOAc (3×100 mL). The combined extracts were washed with water, washed with brine, dried over sodium sulfate, filtered and concentrated in vacuo. The crude residue was purified using silica gel column chromatography (0-1% MeOH/chloroform, linear gradient over 72 min, flow 25 mL/min). The pure fractions were combined and concentrated to afford 3-chloro-1-(2-methoxy-4-nitrophenyl)-1H-1,2,4-triazole (0.924 g, 3.63 mmol, 65.6% yield) as a light yellow solid. LC-MS (M+H)$^+$=255.0. $^1$H NMR (500 MHz, chloroform-d) δ ppm 8.35 (s, 1 H) 7.36 (d, J=8.55 Hz, 1 H) 6.29-6.34 (m, 2 H) 3.80 (s, 3 H) 2.46 (s, 3 H).

Step E (3): Water (8 mL) and dioxane (8 mL) were added to a mixture of 3-chloro-1-(2-methoxy-4-nitrophenyl)-1H-1,2,4-triazole (0.900 g, 3.53 mmol) and sodium sulfide (1.379 g, 17.67 mmol) in a 20 mL vial. The vial was capped and heated at 70-80° C. for 24 hours. The mixture was cooled to rt, poured into water (300 mL) and extracted with EtOAc (2×150 mL). The combined organic layers were washed with brine, dried over sodium sulfate, filtered, and concentrated in vacuo to afford 4-(3-chloro-1H-1,2,4-triazol-1-yl)-3-methoxyaniline (577 mg, 73%) as a brown solid. LC-MS (M+H)$^+$ 225.1.

Step E (4): Dichloromethane (25 mL) was added to a flask charged with 4-(3-chloro-1H-1,2,4-triazol-1-yl)-3-methoxyaniline (0.577 g, 2.57 mmol) and 1,1'-thiocarbonyldi-2(1H)-pyridone (0.597 g, 2.57 mmol). The resulting mixture was stirred for 24 h at rt. The crude reaction mixture concentrated in vacuo and the crude product was purified using silica gel chromatography (0-5% EtOAc/chloroform, linear gradient) to afford 3-chloro-1-(4-isothiocyanato-2-methoxyphenyl)-1H-1,2,4-triazole (529 mg, 1.983 mmol, 77% yield) as a off-white solid. LC-MS (M+H)$^+$ 267.1. $^1$H NMR (500 MHz, chloroform-d) δ ppm 8.67 (s, 1 H) 7.79 (d, J=8.55 Hz, 1 H) 6.98 (dd, J=8.70, 1.98 Hz, 1 H) 6.91 (d, J=1.83 Hz, 1 H) 3.97 (s, 3 H).

Step E (5): Methanolic ammonia (1.0 M, 25 mL, 25 mmol) was added to a flask charged with 3-chloro-1-(4-isothiocyanato-2-methoxyphenyl)-1H-1,2,4-triazole 4-chloro-1-(4-isothiocyanato-2-methoxy-phenyl)-1H-imidazole (525 mg, 1.968 mmol) in a ice-water bath. After the addition was complete, the resulting slurry was stirred for 10 min and then allowed to warm to rt. After 24 h, the reaction mixture was concentrated to dryness in vacuo to afford 1-(4-(3-chloro-1H-1,2,4-triazol-1-yl)-3-methoxyphenyl)thiourea (560 mg, 100% yield) as a white solid. LC-MS (M+H)$^+$ 284.1.

Step E (6): Iodomethane (0.164 mL, 2.62 mmol) was added to a solution of 1-(4-(3-chloro-1H-1,2,4-triazol-1-yl)-3-methoxyphenyl) (550 mg, 1.938 mmol) in absolute ethanol (25 mL). The resulting mixture was heated at 70° C. for 3 h. After cooling to rt, the reaction was concentrated in vacuo. The residual volatiles were removed in high vacuo to afford methyl N'-4-(3-chloro-1H-1,2,4-triazol-1-yl)-3-methoxyphenylcarbamimidothioate, hydroiodide (865 mg, 100% yield) as a white solid, LC-MS (M+H)$^+$ 298.1.

Preparation F

Methyl N'-3-methoxy-4-(3-methyl-1H-1,2,4-triazol-1-yl)phenylcarbamimidothioate hydroiodide

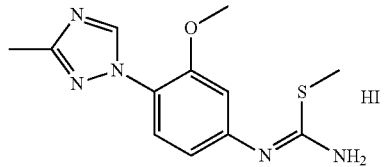

Step F (1): A mixture of 3-methyl-1H-1,2,4-triazole (5.0 g, 60.2 mmol), 1-chloro-2-methoxy-4-nitrobenzene (11.3 g, 60.2 mmol), and KOH flakes (3.4 g, 48.1 mmol) in anhydrous DMSO (50 mL) was heated at 80° C. for 6 h. The reaction mixture was allowed to cool to rt and was poured into 800 mL of water with vigorous stirring. The aqueous mixture was extracted with EtOAc (3×200 mL). The combined organics were washed with brine, dried over Na$_2$SO$_4$, filtered and concentrated in vacuo. The crude residue was purified using silica gel chromatography (0-2% MeOH/chloroform, linear gradient) to afford 1-(2-methoxy-4-nitrophenyl)-3-methyl-1H-1,2,4-triazole (3.7 g, 26% yield). LC-MS (M+H)$^+$=235.2.

Step F (2): 10% Palladium on carbon (1.2 g) was added under an atmosphere of nitrogen to a chilled (ice-water bath) solution of 1-(2-methoxy-4-nitrophenyl)-3-methyl-1H-1,2,4-triazole (3.7 g, 12.7 mmol) dissolved in methanol (250 mL). The flask was repeated evacuated and flushed with hydrogen gas (double balloon). The resulting mixture was allowed to warm to rt and left to stir for 18 h under the hydrogen atmosphere. Purged with nitrogen gas. Filtered the crude reaction mixture through a short diatomaceous earth (Celite®) plug. Rinsed reaction vessel and plug with methanol. Concentrated filtrate in vacuo. Dried residue on high vacuum overnight to afford 3-methoxy-4-(3-methyl-1H-1,2,4-triazol-1-yl)aniline (2.44 g, 94% yield) as a reddish solid. LC-MS (M+H)$^+$ 205.2. $^1$H NMR (500 MHz, chloroform-d) δ ppm 8.35 (s, 1 H) 7.36 (d, J=8.55 Hz, 1 H) 6.29-6.34 (m, 2 H) 3.80 (s, 3 H) 2.46 (s, 3 H).

Step F (3): Dichloromethane (125 mL) was added to a flask charged with 3-methoxy-4-(3-methyl-1H-1,2,4-triazol-1-yl)aniline (4.00 g, 19.59 mmol) and 1,1'-thiocarbonyldipyridin-2(1H)-one (4.55 g, 19.59 mmol). The resulting mixture was stirred for 24 h at rt. The crude reaction mixture was concentrated and the crude products were purified using silica gel chromatography (0-5% EtOAc/chloroform) linear gradient to afford 1-(4-isothiocyanato-2-methoxyphenyl)-3-methyl-1H-1,2,4-triazole (3.91 g, 15.88 mmol, 81% yield) as a white solid. LC-MS (M+H)$^+$ 247.0. $^1$H NMR (500 MHz, chloroform-d) δ ppm 8.64 (s, 1 H) 7.78 (d, J=8.55 Hz, 1 H) 6.96 (dd, J=8.55, 2.14 Hz, 1 H) 6.90 (d, J=2.14 Hz, 1 H) 3.94 (s, 3 H) 2.48 (s, 3 H).

Step F (4): Methanolic ammonia (1.0 M, 100 mL, 100 mmol) was added to a flask charged with 1-(4-isothiocyanato-2-methoxyphenyl)-3-methyl-1H-1,2,4-triazole (3.91 g, 15.88 mmol) in a ice-water bath. After the addition was complete, the resulting slurry was stirred for 10 min and then allowed to warm to rt. After 24 h, the reaction mixture was concentrated to dryness in vacuo to afford 1-(3-methoxy-4-(3-methyl-1H-1,2,4-triazol-1-yl)phenyl)thiourea (4.18 g, 13.81 mmol, 87% yield) as a white solid. LC-MS (M+H)$^+$ 264.0.

Step F (5): Iodomethane (1.04 mL, 16.67 mmol) was added to a solution of 1-(3-methoxy-4-(3-methyl-1H-1,2,4-triazol-1-yl)phenyl)thiourea (4.18 g, 15.87 mmol) in absolute ethanol (100 mL). The resulting mixture was heated at 70° C. for 3 h. After cooling to rt, the reaction was concentrated in vacuo. The residual volatiles were removed in high vacuo to afford methyl 3-methoxy-4-(3-methyl-1H-1,2,4-triazol-1-yl)phenylcarbamimidothioate, hydroiodide (6.52 g, 16.09 mmol, 101% yield) as a white solid. LC-MS (M+H)$^+$ 278.1.

Preparation G

Methyl N-3-cyano-4-(3-methyl-1H-1,2,4-triazol-1-yl)phenylcarbamimidothioate hydroiodide

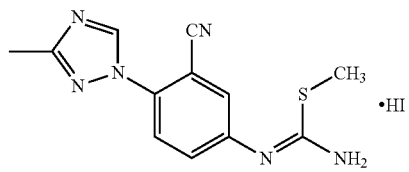

Step G (1): A mixture of 3-methyl-1H-1,2,4-triazole (6.83 g, 82 mmol), 2-chloro-5-nitrobenzonitrile (15 g, 82 mmol), and potassium carbonate (34.1 g, 246 mmol) in anhydrous acetonitrile (200 mL) was heated at 70° C. for 16 h. The dark brown reaction mixture was allowed to cool to rt and was poured into water (500 mL). The aqueous mixture was extracted with EtOAc (3×200 mL). The combined organic layers were washed with brine, dried over $Na_2SO_4$, filtered, and concentrated in vacuo. The crude residue was purified using silica gel chromatography (40-100% ethyl acetate/hexane, linear gradient) to afford 2-(3-methyl-1H-1,2,4-triazol-1-yl)-5-nitrobenzonitrile (10.9 g, 58% yield). LC-MS $(M+H)^+$=230.1. $^1$H NMR (500 MHz, chloroform-D) δ ppm 2.53 (s, 3 H) 8.10 (d, J=9.16 Hz, 1 H) 8.56 (dd, J=9.16, 2.44 Hz, 1 H) 8.68 (d, J=2.44 Hz, 1 H) 8.93 (s, 1 H).

Step G (2): 10% Palladium on carbon (5.06 g) was added under an atmosphere of nitrogen to a chilled (ice-water bath) solution of 2-(3-methyl-1H-1,2,4-triazol-1-yl)-5-nitrobenzonitrile (10.9 g, 47.6 mmol) dissolved in methanol (100 mL). The flask was repeated evacuated and flushed with hydrogen gas (double balloon). The resulting mixture was allowed to warm to rt and left to stir for 16 h under the hydrogen atmosphere. Purged with nitrogen gas. Filtered the crude reaction mixture through a short diatomaceous earth (Celite®) plug. Rinsed reaction vessel and plug with methanol. Concentrated filtrate in vacuo. Dried residue on high vacuum overnight to afford 5-amino-2-(3-methyl-1H-1,2,4-triazol-1-yl)benzonitrile (6.59 g, 70% yield) as a brown solid. LC-MS $(M+H)^+$ 200.0. $^1$H NMR (500 MHz, DMSO-$d_6$) δ ppm 2.29-2.37 (m, 3 H) 5.99 (s, 2 H) 6.94 (dd, J=8.85, 2.44 Hz, 1 H) 7.00 (d, J=2.44 Hz, 1 H) 7.37 (d, J=8.54 Hz, 1 H) 8.69-8.81 (m, 1 H).

Step G (3): Dichloromethane (100 mL) was added to a flask charged with 5-amino-2-(3-methyl-1H-1,2,4-triazol-1-yl)benzonitrile (6.59 g, 33.1 mmol) and 1,1'-thiocarbonyldipyridin-2(1H)-one (7.68 g, 33.1 mmol). The resulting mixture was stirred for 24 h at rt. The crude reaction mixture was concentrated and the crude products were purified using silica gel chromatography (0-5% EtOAc/chloroform) linear gradient to afford 5-isothiocyanato-2-(3-methyl-1H-1,2,4-triazol-1-yl)benzonitrile (5.19 g, 15.88 mmol, 56% yield) as a yellow solid. LC-MS $(M+H)^+$ 242.0.

Step G (4): Methanolic ammonia (1.0 M, 100 mL, 100 mmol) was added to a flask charged with 1-(4-isothiocyanato-2-methoxyphenyl)-3-methyl-1H-1,2,4-triazole (5.19 g, 21.5 mmol). After stirring at rt for 24 h, the reaction mixture was concentrated to dryness in vacuo to afford 1-(3-cyano-4-(3-methyl-1H-1,2,4-triazol-1-yl)phenyl)thiourea (5.56 g, 100% yield) as a off-white solid. $^1$H NMR (500 MHz, DMSO-$d_6$) δ ppm 2.39 (s, 3 H) 7.74 (d, J=8.85 Hz, 1 H) 7.91 (dd, J=8.85, 2.14 Hz, 1 H) 8.25 (d, J=2.14 Hz, 1 H) 8.98 (s, 1 H) 10.10 (s, 1 H).

Step G (5): Iodomethane (1.48 mL, 23.7 mmol) was added to a solution of 1-(3-cyano-4-(3-methyl-1H-1,2,4-triazol-1-yl)phenyl)thiourea (5.56 g, 21.5 mmol) in absolute ethanol (200 mL). The resulting mixture was heated at 70° C. for 3 h. After cooling to rt, the reaction was concentrated in vacuo. The residual volatiles were removed in high vacuo to afford 8.25 g (96% yield) of the titled compound. LC-MS $(M+H)^+$ 273.1.

Preparation H

Methyl N'-3-methoxy-4-(3-methylisoxazol-5-yl)phenylcarbamimidothioate hydroiodide

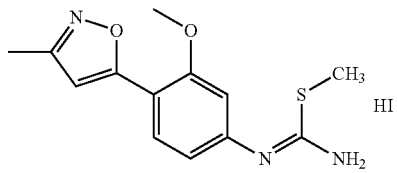

Step H (1): 3-Methyl-5-(tributylstannyl)isoxazole (2.4 g, 6.4 mmol, H. Yamanaka et. al *Tetrahedron*, 1991, 47, 5111) and dichlorobis(triphenylphosphine)palladium (II) (45 mg, 0.0643 mmol) were added to a degassed solution of 1-bromo-2-methoxy-4-nitrobenzene (1.26 g, 5.5 mmol) in dioxane (25 mL). The resulting mixture was heated to reflux (105° C. oil bath temperature) for 24 h. The reaction mixture was cooled to rt and concentrated in vacuo. The residue was dissolved in dichloromethane and washed with water. The organic layer was dried over sodium sulfate, filtered, and concentrated in vacuo. The crude product was purified using silica gel column chromatography to afford 5-(2-methoxy-4-nitrophenyl)-3-methylisoxazole (600 mg, 40% yield).

Step H (2): 5-(2-Methoxy-4-nitrophenyl)-3-methylisoxazole (750 mg, 3.2 mmol) was added portionwise (exotherm observed) to a stirred mixture of tin(II) chloride (3.0 g), concentrated hydrochloric acid (3.0 mL), methanol (3.8 mL), and THF (15 mL). The resulting mixture was stirred at rt for 3 h. The solvent was removed in vacuo. The residue diluted with water and extracted with MTBE. The aqueous layer was basified with 10% NaOH solution to pH 13. The basic solution was extracted with chloroform. The organic layer was dried over sodium sulfate, filtered, and concentrated to afford 3-methoxy-4-(3-methylisoxazol-5-yl)aniline (550 mg, 84% yield).

Step H (3): Dichloromethane (20 mL) was added to a flask charged with 3-methoxy-4-(3-methylisoxazol-5-yl)aniline (500 mg, 2.448 mmol) and 1,1'-thiocarbonyldipyridin-2(1H)-one (569 mg, 2.448 mmol). The resulting mixture was stirred for 24 h at rt. The crude reaction mixture was concentrated and the crude products were purified using silica gel chromatography (20-50% EtOAc/hexane) linear gradient to afford 5-(4-isothiocyanato-2-methoxyphenyl)-3-methylisoxazole (0.510 g, 84% yield). LC-MS $(M+H)^+$ 247.2. $^1$H NMR (400 MHz, methanol-$d_4$) δ ppm 7.86 (d, J=8.56 Hz, 1 H) 7.06 (d, J=2.01 Hz, 1 H) 6.99 (dd, J=8.44, 1.89 Hz, 1 H) 6.73 (s, 1 H) 3.97 (s, 3 H) 2.31 (s, 3 H).

Step H (4): Methanolic ammonia (1.3 mL, 9.28 mmol) was added to a flask charged with 5-(4-isothiocyanato-2-methoxyphenyl)-3-methylisoxazole (508 mg, 2.063 mmol) in MeOH (4.6 mL). After stirring at rt for 24 h, the reaction mixture was concentrated to dryness in vacuo to afford 1-(3-methoxy-4-(3-methylisoxazol-5-yl)phenyl)thiourea (540 mg, 2.051 mmol, 99% yield). LC-MS (M+H)⁺ 264.2. ¹H NMR (400 MHz, methanol-d₄) δ ppm 7.82 (d, J=8.56 Hz, 1 H) 7.49-7.54 (m, 1 H) 6.99 (dd, J=8.56, 2.01 Hz, 1 H) 6.67 (s, 1 H) 3.96 (s, 3 H) 2.30 (s, 3 H).

Step H (5): Iodomethane (128 μL, 2.05 mmol) was added to a solution of 1-(3-methoxy-4-(3-methylisoxazol-5-yl)phenyl)thiourea (540 mg, 2.051 mmol) in absolute ethanol (15 mL). The resulting mixture was heated at 50° C. for 24 h. After cooling to rt, the reaction was concentrated in vacuo. The residual volatiles were removed in high vacuo to afford 831 mg (100% yield) of the titled compound. LC-MS (M+H)⁺ 278.3. ¹H NMR (400 MHz, methanol-d₄) δ ppm 7.99 (d, J=8.31 Hz, 1 H) 7.18 (d, J=2.01 Hz, 1 H) 7.06 (dd, J=8.31, 2.01 Hz, 1 H) 6.78 (s, 1 H) 4.01 (s, 3 H) 2.74 (s, 3 H) 2.32 (s, 3 H).

Preparation I

Methyl N'-3-methoxy-4-(3-methyl-1,2,4-oxadiazol-5-yl)phenylcarbamimidothioate hydroiodide

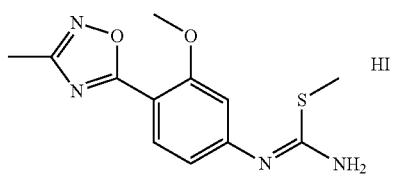

Step I (1): Dichloromethane (50 mL) was added to a flask charged with 3-methoxy-4-(3-methyl-1,2,4-oxadiazol-5-yl)aniline (1.2 g, 5.85 mmol, N. Smith et. al PCT Publication WO 2003/077918) and 1,1'-thiocarbonyldipyridin-2(1H)-one (1.36 g, 5.85 mmol). The resulting mixture was stirred for 24 h at rt. The crude reaction mixture was concentrated and the crude products were purified using silica gel chromatography (20-50% EtOAc/hexane) linear gradient to afford 5-(4-isothiocyanato-2-methoxyphenyl)-3-methyl-1,2,4-oxadiazole (1.28 g, 5.18 mmol, 89% yield). LC-MS (M+H)⁺ 248.2.

Step I (2): Methanolic ammonia (3.33 mL, 23.3 mmol) was added to a flask charged with 5-(4-isothiocyanato-2-methoxyphenyl)-3-methyl-1,2,4-oxadiazole (1.28 g, 5.18 mmol) in MeOH (12 mL). After stirring at rt for 24 h, the reaction mixture was concentrated to dryness in vacuo to afford 1-(3-methoxy-4-(3-methyl-1,2,4-oxadiazol-5-yl)phenyl)thiourea (1.368 g, 5.18 mmol, 100% yield). LC-MS (M+H)⁺ 265.2. ¹H NMR (400 MHz, methanol-d₄) δ ppm 7.94 (d, J=8.56 Hz, 1 H) 7.77 (d, J=2.01 Hz, 1 H) 7.06 (dd, J=8.31, 2.01 Hz, 1 H) 3.95 (s, 3 H) 2.40 (s, 3 H).

Step I (3): Iodomethane (0.170 mL, 2.72 mmol) was added to a solution of 1-(3-methoxy-4-(3-methyl-1,2,4-oxadiazol-5-yl)phenyl)thiourea (0.72 g, 2.72 mmol) in absolute ethanol (20 mL). The resulting mixture was heated at 50° C. for 24 h. After cooling to rt, the reaction was concentrated in vacuo. The residual volatiles were removed in high vacuo to afford 1.11 g (100% yield) of the titled compound. LC-MS (M+H)⁺ 279.2.

Preparation J

Methyl N'-4-(4-chloro-1H-imidazol-1-yl)-3,5-difluorophenylcarbamimidothioate hydroiodide

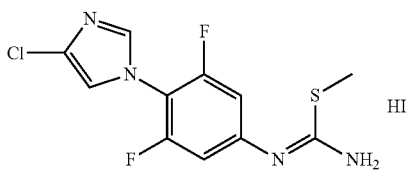

Step J (1): A mixture of 4-chloro-1H-imidazole (1.18 g, 11.5 mmol), 1,2,3-trifluoro-5-nitrobenzene (1.7 g, 9.60 mmol) and potassium carbonate (1.86 g, 13.4 mmol) in DMF (10 mL) was heated at 50° C. for 2 h. The reaction mixture was allowed to cool to rt and was stirred for 16 h. The reaction mixture was diluted with EtOAc (200 mL) and washed with water and brine. The organic layer was dried (Na₂SO₄), filtered, and concentrated in vacuo. The residue was purified using silica gel column chromatography (50% EtOAc/hexane) to afford 4-chloro-1-(2,6-difluoro-4-nitrophenyl)-1H-imidazole (2.0 g, 80% yield). LC-MS (M+H)⁺=260.1. ¹H NMR (500 MHz, chloroform-d) δ ppm 8.03-8.10 (m, 2 H) 7.71 (q, J=1.83 Hz, 1 H) 7.19 (q, J=1.93 Hz, 1 H).

Step J (2): 10% Palladium on carbon (0.500 g) was added under an atmosphere of nitrogen to a solution of 4-chloro-1-(2,6-difluoro-4-nitrophenyl)-1H-imidazole (1.9 g, 7.32 mmol) in EtOH (30 mL). The flask was repeated evacuated and flushed with hydrogen gas (double balloon). The resulting mixture was allowed to warm to rt and left to stir for 1.5 h under the hydrogen atmosphere. Purged with nitrogen gas. Filtered the crude reaction mixture through a short plug of diatomaceous earth (Celite®). Rinsed reaction vessel and plug with methanol. Concentrated filtrate in vacuo. Dried residue on high vacuum overnight to afford a 1:1 mixture of 4-(4-chloro-1H-imidazol-1-yl)-3,5-difluoroaniline and 3,5-difluoro-4-(1H-imidazol-1-yl)aniline (1.67 g, ~99% yield). LC-MS (M+H)⁺ 230.1 and 196.2.

Step J (3): Dichloromethane (15 mL) was added to a flask charged with a 1:1 mixture of 4-(4-chloro-1H-imidazol-1-yl)-3,5-difluoroaniline/3,5-difluoro-4-(1H-imidazol-1-yl)aniline (1.0 g, 4.36 mmol) and 1,1'-thiocarbonyldipyridin-2(1H)-one (1.012 g, 4.36 mmol). The resulting mixture was stirred for 16 h at rt. The crude reaction mixture was concentrated and the crude products were purified using silica gel chromatography (60% EtOAc/hexanes) to afford 4-chloro-1-(2,6-difluoro-4-isothiocyanatophenyl)-1H-imidazole (195 mg, 0.718 mmol, 17% yield). LC-MS (M+H)⁺ 272.0. ¹H NMR (500 MHz, chloroform-d) δ ppm 7.57 (d, J=1.83 Hz, 1 H) 7.07 (d, J=1.53 Hz, 1 H) 6.94-7.04 (m, 2 H).

Step J (4): Methanolic ammonia (2.0 M, 5 mL, 10 mmol) was added to a flask charged with 4-chloro-1-(2,6-difluoro-4-isothiocyanatophenyl)-1H-imidazole (195 mg, 0.718 mmol). After 3 h, the reaction mixture was concentrated to dryness in vacuo to afford 1-(4-(4-chloro-1H-imidazol-1-yl)-3,5-difluorophenyl)thiourea (207 mg, 100% yield) as a white solid. LC-MS (M+H)⁺ 289.2

Step J (5): Iodomethane (0.047 mL, 0.753 mmol) was added to a solution of 1-(4-(4-chloro-1H-imidazol-1-yl)-3,5- difluorophenyl)thiourea (207 mg, 0.717 mmol) in absolute ethanol (4 mL). The resulting mixture was heated at 60° C. for 16 h. After cooling to rt, the reaction was concentrated in vacuo. The residual volatiles were removed in high vacuo to afford methyl 4-(4-chloro-1H-imidazol-1-yl)-3,5-difluorophenylcarbamimidothioate hydroiodide (309 mg, 0.717 mmol, 100% yield). LC-MS (M+11)$^+$ 303.1.

Preparation K

Methyl N'-3-methoxy-4-(1-methyl-1H-pyrazol-4-yl) phenylcarbamimidothioate hydroiodide

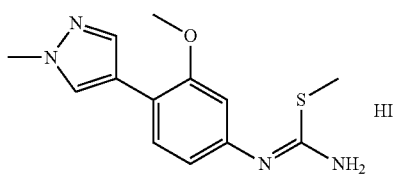

Step K (1): [1,1'-Bis(diphenylphosphino)ferrocene]-dichloropalladium(II) (1:1 complex with dichloromethane, 7.0 g, 8.62 mmol) was added to a degassed mixture of 1-bromo-2-methoxy-4-nitrobenzene (20 g, 86.2 mmol), 1-methyl-4-(4,4,5,5-tetramethyl-1,3,2-dioxaborolan-2-yl)-1H-pyrazole (23.3 g, 112 mmol), and potassium carbonate (23.6 g, 122 mmol) in DMF (200 mL). The mixture was heated at 150° C. for 18 h. The crude reaction mixture was cooled to rt and filtered through diatomaceous earth (Celite®). The reaction mixture was diluted with EtOAc (200 mL) and washed with water and then brine. The organic layer was dried over sodium sulfate, filtered, and concentrated in vacuo. The residue was purified using silica gel column chromatography (EtOAc/hexane) to afford 4-(2-methoxy-4-nitrophenyl)-1-methyl-1H-pyrazole (14 g, 70% yield).

Step K (2): 10% Palladium on carbon (1.0 g) was added under an atmosphere of nitrogen to a solution of 4-(2-methoxy-4-nitrophenyl)-1-methyl-1H-pyrazole (10.0 g, 42.9 mmol) in methanol (100 mL). The flask was repeated evacuated and flushed with hydrogen gas. The resulting mixture was allowed to stir at rt for 16 h under. The reaction vessel was purged with nitrogen gas. The crude reaction mixture was filtered through a short diatomaceous earth (Celite®) plug. Rinsed reaction vessel and plug with methanol. Concentrated filtrate in vacuo. Dried residue on high vacuum overnight to afford 3-methoxy-4-(1-methyl-1H-pyrazol-4-yl)aniline (6.8 g, 78% yield). LC-MS (M+H)$^+$ 204.2. $^1$H NMR (400 MHz, DMSO-$d_6$) δ ppm 7.84 (s, 1 H) 7.66 (s, 1 H) 7.19 (d, J=8.2 Hz, 1 H) 6.28 (s, 1 H), 6.18 (d, J=8.2 Hz, 1 H) 5.31 (br s, 1 H), 3.88 (s, 3 H), 3.74 (s, 3 H).

Step K (3): Dichloromethane (25 mL) was added to a flask charged with 3-methoxy-4-(1-methyl-1H-pyrazol-4-yl) aniline (1.5 g, 7.38 mmol) and 1,1'-thiocarbonyldipyridin-2 (1H)-one (2.57 g, 11.1 mmol). The resulting mixture was stirred for 16 h at rt. The reaction mixture was concentrated in vacuo. The crude products were purified using silica gel chromatography (30% EtOAc/dichloromethane). The fractions containing product were combined and concentrated. The resulting solid was recrystallized from hexane to afford 4-(4-isothiocyanato-2-methoxyphenyl)-1-methyl-1H-pyrazole (1.46 g, 5.95 mmol, 81% yield) as a light yellow solid. LC-MS (M+H)$^+$ 272.0. $^1$H NMR (500 MHz, chloroform-d) δ ppm 7.57 (d, J=1.83 Hz, 1 H) 7.07 (d, J=1.53 Hz, 1 H) 6.94-7.04 (m, 2 H).

Step K (4): Methanolic ammonia (2.0 M, 20 mL, 40 mmol) was added to a flask charged with 4-(4-isothiocyanato-2-methoxyphenyl)-1-methyl-1H-pyrazole (1.46 g, 5.95 mmol). After 3 h, the reaction mixture was concentrated in vacuo. The solid was triturated with diethyl ether. The solid was collected by vacuum filtration and dried under high vacuum to afford 1-(3-methoxy-4-(1-methyl-1H-pyrazol-4-yl)phenyl)thiourea (1.35 g, 86% yield). LC-MS (M+H)$^+$ 263.1.

Step K (5): Iodomethane (595 mg, 4.19 mmol) was added to a solution of 1-(3-methoxy-4-(1-methyl-1H-pyrazol-4-yl) phenyl)thiourea (1.00 g, 3.81 mmol) in absolute ethanol (10 mL). The resulting mixture was stirred at 75° C. 16 h. The reaction mixture was concentrated in vacuo. The residue was triturated with diethyl ether. The solid was collected by vacuum filtration and dried under high vacuum to afford residual volatiles were removed in high vacuo to afford 1.48 g (96% yield) of the titled compound. LC-MS (M+H)$^+$ 277.1.

Preparation L

Methyl N'-3-methoxy-4-(6-methylpyridazin-4-yl) phenylcarbamimidothioate hydroiodide

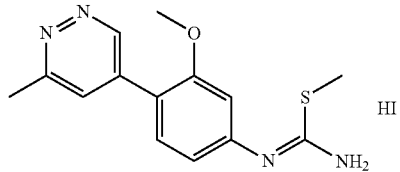

Step L (1): A high pressure bottle was charged with [1,1'-bis(diphenylphosphino)ferrocene]-dichloropalladium(II) (1:1 complex with dichloromethane, 1.56 g, 2.15 mmol), potassium acetate (5.25 g, 22.5 mmol), 1-promo-2-methoxy-4-nitrobenzene (5.0 g, 21.5 mmol), bis(pinacolato)diboron (6.6 g, 25 mmol), and 1,4-dioxane (100 mL). The mixture was degassed by bubbling nitrogen through the solution. The bottle was capped and heated at 80° C. for 5 h. The resulting mixture was diluted with EtOAc (500 mL) and washed with 1 N aqueous HCl (500 mL). The organic layer was washed with brine, dried over sodium sulfate, filtered, and concentrated in vacuo to afford 2-(2-methoxy-4-nitrophenyl)-4,4,5,5-tetramethyl-1,3,2-dioxaborolane (7.0 g, 100% yield) as a brown solid. The crude material was used for subsequent chemistry without purification.

Step L (2): A high pressure bottle was charged with 2-(2-methoxy-4-nitrophenyl)-4,4,5,5-tetramethyl-1,3,2-dioxaborolane (6.1 g, 13.8 mmol), [1,1'-bis(diphenylphosphino) ferrocene]-dichloropalladium(II) (1:1 complex with dichloromethane, 1.0 g, 1.1 mmol), 4-bromo-6-methylpyridazine 1-oxide (2.0 g, 11 mmol, B. Buettelmann et. al US Patent Application Publication 2004/0254179 A1), cesium carbonate (in 5 mL of water, 8.0 g, 21 mmol), and 1,4-dioxane (80 mL). The mixture was degassed by bubbling nitrogen through the solution. The bottle was capped and heated at 110° C. for 2 h. The resulting mixture was filtered through diatomaceous earth (Celite®). The filtrated was concentrated in vacuo. The crude product was purified using silica gel column chromatography (EtOAc/hexane) to afford 4-(2-methoxy-4-nitrophenyl)-6-methylpyridazine 1-oxide (1.4 g, 49% yield).

Step L (3): 10% Palladium on carbon (140 mg), followed by 5 drops of concentrated HCl, was added under an atmosphere of nitrogen to a solution of 4-(2-methoxy-4-nitrophenyl)-6-methylpyridazine 1-oxide (1.4 g, 53.6 mmol) in methanol (20 mL). The flask was repeatedly evacuated and flushed with hydrogen gas to 3 kg of hydrogen pressure. The resulting mixture was allowed to stir at rt for 4 h. The reaction vessel was purged with nitrogen gas. The crude reaction mixture was filtered through a short diatomaceous earth (Celite®) plug. Rinsed reaction vessel and plug with methanol. Concentrated filtrate in vacuo. The crude product was purified using silica gel column chromatography (EtOAc/hexane) to afford 3-methoxy-4-(6-methylpyridazin-4-yl)aniline hydrochloride (850 mg, 49% yield). LC-MS (M+H)$^+$ 216.2. $^1$H NMR (400 MHz, DMSO-d$_6$) δ ppm 9.54 (s, 1 H) 8.39 (s, 1 H) 7.68 (d, J=9.2 Hz, 1 H) 6.44 (m, 2 H) 3.85 (s, 3 H), 2.74 (s, 3 H).

Step L (4): Dichloromethane (20 mL) was added to a flask charged with 3-methoxy-4-(6-methylpyridazin-4-yl)aniline hydrochloride (900 mg, 3.58 mmol) and 1,1'-thiocarbonyldipyridin-2(1H)-one (913 mg, 3.93 mmol). The resulting mixture was stirred for 16 h at rt. The reaction mixture was concentrated in vacuo. The crude products were purified using silica gel chromatography (0-50% EtOAc/dichloromethane to afford 5-(4-isothiocyanato-2-methoxyphenyl)-3-methylpyridazine (650 mg, 2.53 mmol, 70.7% yield). LC-MS (M+H)$^+$ 258.0. $^1$H NMR (500 MHz, chloroform-d) δ ppm 9.18 (d, J=2.44 Hz, 1 H) 7.43 (d, J=2.14 Hz, 1 H) 7.32 (d, J=7.93 Hz, 1 H) 6.95 (dd, J=8.09, 1.98 Hz, 1 H) 6.83 (d, J=2.14 Hz, 1 H) 3.85 (s, 3 H) 2.75 (s, 3 H).

Step L (5): Methanolic ammonia (2.0 M, 20 mL, 40 mmol) was added to a flask charged with 5-(4-isothiocyanato-2-methoxyphenyl)-3-methylpyridazine (650 mg, 2.53 mmol). After 4 h, the reaction mixture was concentrated in vacuo to afford 1-(3-methoxy-4-(6-methylpyridazin-4-yl)phenyl)thiourea (690 mg, 100% yield). LC-MS (M+H)$^+$ 275.2.

Step L (6): Iodomethane (0.165 mL, 2.64 mmol) was added to a solution of 1-(3-methoxy-4-(6-methylpyridazin-4-yl)phenyl)thiourea (690 mg, 2.52 mmol) in absolute ethanol (15 mL). The resulting mixture was stirred at 55° C. 16 h. The reaction mixture was concentrated in vacuo to afford 1.04 g (99% yield) of the titled compound. LC-MS (M+H)$^+$ 289.2.

Preparation M

Methyl N'-4-(4-chloro-1H-imidazol-1-yl)-3-fluoro-5-methoxyphenylcarbamimidothioate hydroiodide

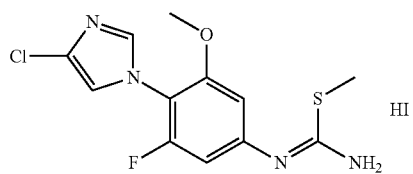

Step M (1): Ethyl chloroformate (16.6 g, 153 mmol) was added to a solution of 2,3-difluorophenol (20 g, 153 mmol) and triethylamine (20.7 mL, 146 mmol) in EtOAc (200 mL). The resulting mixture was stirred at rt for 2 h. The crude reaction was poured into 1 N HCl and extracted with EtOAc. The organic layer was washed with brine, dried over sodium sulfate, filtered, and concentrated in vacuo. The residue was purified using silica gel column chromatography (5% EtOAc/hexane) to afford 2,3-difluorophenyl ethyl carbonate (20 g, 64% yield).

Step M (2): A mixture of concentrated sulfuric acid and nitric acid (1:1 ratio, 60 mL total volume) was slowly and carefully added to a solution of 2,3-difluorophenyl ethyl carbonate (20 g, 98.9 mmol) in concentrated sulfuric acid (15 mL). The internal temperature was maintained at rt throughout the addition. After complete addition, the resulting mixture was stirred for 2 h. The mixture was poured onto ice and extracted with chloroform. The organic layer was washed with brine, dried over sodium sulfate, filtered, and concentrated in vacuo. The residue was purified using silica gel column chromatography (hexane) to afford 2,3-difluoro-5-nitrophenyl ethyl carbonate (1.5 g, 6% yield).

Step M (3): Aqueous ammonium hydroxide (5 mL) was added to a solution of 2,3-difluoro-5-nitrophenyl ethyl carbonate (250 mg, 1.0 mol) in EtOAc (4 mL). The reaction mixture was quenched with 1 N HCl. The mixture was diluted with water and extracted with EtOAc. The organic layer was washed with brine, dried over sodium sulfate, filtered, and concentrated in vacuo to afford 2,3-difluoro-5-nitrophenol (150 mg, 85% yield).

Step M (4): Sodium hydride (120 mg, 5 mmol) was added to a solution of 2,3-difluoro-5-nitrophenol (250 mg, 1.4 mmol) in DMF/THF (4 mL/4 mL). After 10 min, iodomethane (0.2 mL, 5 mmol) was added. The mixture was heated at 80° C. for 2 h. The reaction mixture was quenched with 1 N HCl. The mixture was diluted with water and extracted with EtOAc. The organic layer was washed with brine, dried over sodium sulfate, filtered, and concentrated in vacuo to afford 1,2-difluoro-3-methoxy-5-nitrobenzene (130 mg, 48% yield).

Step M (5): A mixture of 4-chloro-1H-imidazole (102 mg, 1.00 mmol), 1,2-difluoro-3-methoxy-5-nitrobenzene (200 mg, 1.00 mmol), and cesium carbonate (325 mg, 1 mmol) in acetonitrile (6 mL) was heated at 80° C. for 12 h. The reaction mixture was quenched with 1 N HCl. The organic layer was washed with brine, dried over sodium sulfate, filtered, and concentrated in vacuo. The residue was purified using silica gel column chromatography (20% EtOAc/hexane) to afford 4-chloro-1-(2-fluoro-6-methoxy-4-nitrophenyl)-1H-imidazole (60 mg, 22% yield).

Step M (6): A mixture of 4-chloro-1-(2-fluoro-6-methoxy-4-nitrophenyl)-1H-imidazole (60 mg, 0.22 mmol), zinc dust (70 mg, 1.1 mmol), ammonium chloride (58 mg, 1.1 mmol), and methanol (5 mL) was heated at 110° C. for 16 h. The reaction mixture was quenched with 1 N HCl. The organic layer was washed with brine, dried over sodium sulfate, filtered, and concentrated in vacuo. The residue was purified using silica gel column chromatography (15% EtOAc/hexane) to afford 4-(4-chloro-1H-imidazol-1-yl)-3-fluoro-5-methoxyaniline (20 mg, 38% yield). LC-MS (M+H)$^+$ 242.0. $^1$H NMR (400 MHz, DMSO-d$_6$) δ ppm 7.59 (s, 1 H) 7.28 (s, 1 H) 6.96 (s, 1 H), 6.08 (d, J=12.2 Hz, 1 H) 5.83 (s, 2 H) 3.67 (s, 3 H).

Step M (7): Dichloromethane (20 mL) was added to a flask charged with 4-(4-chloro-1H-imidazol-1-yl)-3-fluoro-5-methoxyaniline (290 mg, 1.200 mmol) and 1'-thiocarbonyldipyridin-2(1H)-one (307 mg, 1.320 mmol). The resulting mixture was stirred for 1 h at rt. The reaction mixture was concentrated in vacuo. The crude products were purified using silica gel chromatography (0-100% EtOAc/dichloromethane to afford 4-chloro-1-(2-fluoro-4-isothiocyanato-6-methoxyphenyl)-1H-imidazole (230 mg, 0.811 mmol, 67.6% yield). LC-MS (M+H)$^+$ 284.1. $^1$H NMR (500 MHz, chloroform-d) δ ppm 7.44-7.50 (m, 1 H) 6.97 (t, J=1.53 Hz, 1 H) 6.76 (dd, J=9.77, 2.14 Hz, 1 H) 6.68 (t, J=1.98 Hz, 1 H) 3.87 (s, 3 H).

Step M (8): Methanolic ammonia (2.0 M, 5 mL, 10 mmol) was added to a flask charged with 4-chloro-1-(2-fluoro-4-isothiocyanato-6-methoxyphenyl)-1H-imidazole (230 mg, 0.811 mmol). After 2 h, the reaction mixture was concentrated in vacuo to afford 1-(4-(4-chloro-1H-imidazol-1-yl)-3-fluoro-5-methoxyphenyl)thiourea (244 mg, 100% yield). LC-MS (M+H)$^+$ 301.1.

Step M (9): Iodomethane (0.061 mL, 0.972 mmol) was added to a solution of 1-(4-(4-chloro-1H-imidazol-1-yl)-3-fluoro-5-methoxyphenyl)thiourea (0.244 g, 0.81 mmol) in absolute ethanol (5 mL). The resulting mixture was stirred at 58° C. 3 h. The reaction mixture was concentrated in vacuo to afford 0.359 g (100% yield) of the titled compound. LC-MS (M+H)$^+$ 315.14. $^1$H NMR (500 MHz, methanol-d$_4$) δ ppm 7.74 (t, J=1.37 Hz, 1 H) 7.28 (t, J=1.37 Hz, 1 H) 7.13 (t, J=1.83 Hz, 1 H) 7.08 (dd, J=10.07, 2.14 Hz, 1 H) 3.94 (s, 3 H) 2.78 (s, 3 H).

Preparation N

Methyl N'-4-(4-(difluoromethyl)-1H-imidazol-1-yl)-3-methoxyphenylcarbamimidothioate, hydroiodide

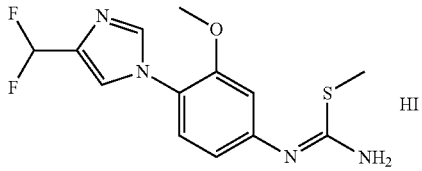

Step N (1): Followed the method of R. Roy et. al *Tetrahedron* 2007, 63, 4912. To a solution of N-(2-methoxy-4-nitrophenyl)formamide (4.0 g, 28 mmol, U. Mario et. al *General Pharmacology*, 1979, 10, 309) and N-formylglycine ethyl ester (16.6 g, 153 mmol) in dichloromethane (20 mL) were added triethylamine (28 mL, 72 mmol) and POCl$_3$ (8.0 mL, 200 mmol) dropwise at 0° C. The reaction was stirred at 0° C. for 2 h. The mixture was filtered over silica using dichloromethane/diethyl ether (4/1) and concentrated under reduced pressure. The crude residue was dissolved in THF (100 mL) to which Cu$_2$O (400 mg, 2.8 mmol) and L-proline (644 mg, 5.6 mmol) were added and the resulting solution stirred at rt for 4 h. A solution of aq EDTA (5%) was added to the reaction mixture, which was then extracted with EtOAc. The crude residue was purified using silica gel column chromatography (EtOAc/dichloromethane) to afford ethyl 1-(2-methoxy-4-nitrophenyl)-1H-imidazole-4-carboxylate (2.0 g, 24% yield).

Step N (2): Diisobutylaluminum hydride (1 M in toluene, 17.2 mL, 17.1 mmol) was added to a −78° C. solution of ethyl 1-(2-methoxy-4-nitrophenyl)-1H-imidazole-4-carboxylate (2.0 g, 6.9 mmol). After 30 min, the reaction mixture was quenched with 1 N HCl. The mixture was diluted with water and extracted with EtOAc. The organic layer was washed with brine, dried over sodium sulfate, filtered, and concentrated in vacuo. The crude residue was purified using silica gel column chromatography (EtOAc/hexane) to afford 1-(2-methoxy-4-nitrophenyl)-1H-imidazole-4-carbaldehyde (1.0 g, 59% yield).

Step N (3): (Diethylamino)sulfur trifluoride (2.4 mL, 16.1 mmol) was added to a 0° C. solution of 1-(2-methoxy-4-nitrophenyl)-1H-imidazole-4-carbaldehyde (2.4 g, 8.1 mop in dichloromethane (30 mL). The resulting mixture was stirred at rt overnight and then was concentrated in vacuo. The crude product was purified using silica gel column chromatography (EtOAc/hexane) to afford 4-(difluoromethyl)-1-(2-methoxy-4-nitrophenyl)-1H-imidazole (1.6 g, 73% yield).

Step N (4): 10% Palladium on carbon (250 mg) was added under an atmosphere of nitrogen to a solution of 4-(difluoromethyl)-1-(2-methoxy-4-nitrophenyl)-1H-imidazole (2.5 g, 92.9 mmol) in methanol (25 mL). The flask was repeatedly evacuated and flushed with hydrogen gas (double balloon). The resulting mixture was allowed to stir at rt for 2 h. The reaction vessel was purged with nitrogen gas. The crude reaction mixture was filtered through a short diatomaceous earth (Celite®) plug. Rinsed reaction vessel and plug with methanol. Concentrated filtrate in vacuo. The crude product was purified using silica gel column chromatography (EtOAc/hexane) to afford 4-(4-(difluoromethyl)-1H-imidazol-1-yl)-3-methoxyaniline (1.8 g, 81% yield). LC-MS (M+H)$^+$ 240.2. $^1$H NMR (400 MHz, DMSO-d$_6$) δ ppm 8.42 (s, 1 H) 7.93 (s, 1 H) 7.47 (d, J=8.4 Hz, 1 H) 7.19-6.88 (m, 3 H) 3.81 (s, 3 H).

Step N (5): Dichloromethane (100 mL) was added to a flask charged with 4-(4-(difluoromethyl)-1H-imidazol-1-yl)-3-methoxyaniline (2.5 g, 10.45 mmol) and 1,1'-thiocarbonyl-dipyridin-2(1H)-one (2.43 g, 10.5 mmol). The resulting mixture was stirred for 18 h at rt. The reaction mixture was concentrated in vacuo. The crude products were purified using silica gel chromatography (0-2% EtOAc/chloroform, linear gradient) to afford 4-(difluoromethyl)-1-(4-isothiocyanato-2-methoxyphenyl)-1H-imidazole (2.26 g, 77% yield). LC-MS (M+H)$^+$ 282.1.

Step N (6): Methanolic ammonia (2.0 M, 100 mL, 200 mmol) was added to a flask charged with 4-(difluoromethyl)-1-(4-isothiocyanato-2-methoxyphenyl)-1H-imidazole (2.26 g, 8.1 mmol). After 16 h, the reaction mixture was concentrated in vacuo to afford 1-(4-(4-(difluoromethyl)-1H-imidazol-1-yl)-3-methoxyphenyl)thiourea (2.08 g, 87% yield). LC-MS (M+H)$^+$ 299.1.

Step N (7): Iodomethane (0.440 mL, 7.04 mmol) was added to a solution of 1-(4-(4-(difluoromethyl)-1H-imidazol-1-yl)-3-methoxyphenyl)thiourea (2.00 g, 6.70 mmol) in absolute ethanol (75 mL). The resulting mixture was stirred at 70° C. for 3 h. The reaction mixture was concentrated in vacuo to afford 2.25 g (76% yield) of the titled compound. LC-MS (M+H)$^+$ 313.2.

Preparation O

Methyl N'-6-(4-chloro-1H-imidazol-1-yl)-5-methoxypyridin-3-ylcarbamimidothioate, hydroiodide

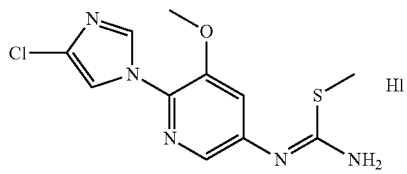 [SMILES: COc1cc(/N=C(/N)SC)cnc1-n1cnc(Cl)c1]

Step O (1): A mixture of 4-chloro-1H-imidazole (2.72 g, 26.5 mmol), 2-chloro-3-methoxy-5-nitropyridine (5.0 g, 26.5 mmol), and KOH flakes 1.488 g, 26.5 mmol) in anhydrous DMSO (25 mL) was heated at 80° C. for 5 h. The reaction mixture was allowed to cool to rt and was poured into 1.0 L of water with vigorous stirring. The mixture was stirred at rt for 16 h. The precipitate was collected by vacuum filtration using a coarse sintered glass funnel. The solid was dried under high vacuum for 24 h to provide 2-(4-chloro-1H-imidazol-1-yl)-3-methoxy-5-nitropyridine (5.22 g, 20.50 mmol, 77% yield) as a light brown solid. LC-MS (M+H)$^+$=255.0. $^1$H NMR (500

MHz, DMSO-d$_6$) δ ppm 8.94 (d, J=2.44 Hz, 1 H) 8.51 (d, J=1.83 Hz, 1 H) 8.42 (d, J=2.44 Hz, 1 H) 8.02 (d, J=1.83 Hz, 1 H) 4.12 (s, 3 H).

Step O (2): Iron powder-325 mesh (2.19 g, 39.3 mmol) was added to a flask charged with a mixture of 2-(4-chloro-1H-imidazol-1-yl)-3-methoxy-5-nitropyridine (5.0 g, 19.64 mmol), absolute ethanol (50 mL), and glacial acetic acid (20 mL). A water-cooled reflux condenser was attached to the flask and the heterogeneous mixture was heated to 100° C. with vigorous stirring for 30 min. The reaction mixture was allowed to cool to rt and was neutralized upon addition to a chilled and vigorously stirred solution of 5 M NaOH. The resulting mixture was poured into a reparatory funnel and extracted with EtOAc. The combined organic layers were dried over sodium sulfate, filtered, and concentrated in vacuo to afford 6-(4-chloro-1H-imidazol-1-yl)-5-methoxypyridin-3-amine (3.12 g, 71% yield). LC-MS (M+H)$^+$ 225.1. $^1$H NMR (500 MHz, chloroform-d) δ ppm 8.06 (d, J=1.83 Hz, 1 H) 7.53 (dd, J=13.28, 1.98 Hz, 2 H) 6.70 (d, J=2.44 Hz, 1 H) 3.90 (s, 3 H) 3.86 (br. s., 2 H).

Step O (3): Dichloromethane (100 mL) was added to a flask charged with 6-(4-chloro-1H-imidazol-1-yl)-5-methoxypyridin-3-amine (3.0 g, 13.35 mmol) and 1,1'-thiocarbonyldipyridin-2(1H)-one (3.10 g, 13.35 mmol). The resulting mixture was stirred for 18 h at rt. The reaction mixture was concentrated in vacuo. The crude products were purified using silica gel chromatography (0-5% EtOAc/chloroform, linear gradient) to afford 2-(4-chloro-1H-imidazol-1-yl)-5-isothiocyanato-3-methoxypyridine (2.89 g, 81% yield) as a yellow solid. LC-MS (M+H)$^+$ 267.1. $^1$H NMR (500 MHz, chloroform-d) δ ppm 8.30 (s, 1 H) 8.02 (s, 1 H) 7.72 (s, 1 H) 7.20 (s, 1 H) 4.00 (s, 3 H).

Step O (4): Methanolic ammonia (2.0 M, 25 mL, 50 mmol) was added to a flask charged with 2-(4-chloro-1H-imidazol-1-yl)-5-isothiocyanato-3-methoxypyridine (2.5 g, 9.37 mmol). After 16 h, the reaction mixture was concentrated in vacuo to afford 1-(6-(4-chloro-1H-imidazol-1-yl)-5-methoxypyridin-3-yl)thiourea (2.24 g, 7.89 mmol, 84% yield). LC-MS (M+H)$^+$ 283.9. $^1$H NMR (500 MHz, DMSO-d$_6$) δ ppm 8.24 (d, J=1.83 Hz, 1 H) 8.12 (d, J=2.14 Hz, 1 H) 8.09 (d, J=2.14 Hz, 1 H) 7.79-7.82 (m, 1 H) 3.90-3.95 (m, 3 H).

Step O (5): Iodomethane (0.543 mL, 8.68 mmol) was added to a solution of 1-(6-(4-chloro-1H-imidazol-1-yl)-5-methoxypyridin-3-yl)thiourea (2.24 g, 7.89 mmol) in absolute ethanol (150 mL). The resulting mixture was stirred at 80° C. for 3 h. The reaction mixture was concentrated in vacuo to afford 3.52 g (105% yield) of the titled compound. LC-MS (M+H)$^+$ 298.0.

Preparation P 1-(4-bromo-3-methoxyphenyl)thiourea

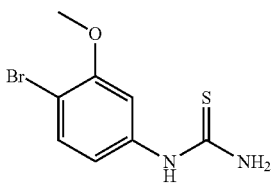

Step P (1): To a solution of 4-bromo-3-methoxyaniline (0.500 g, 2.48 mmol) in dichloromethane (10 mL) was added 1,1'-thiocarbonyldipyridin-2(1H)-one (0.575 g, 2.48 mmol). The resulting mixture was stirred at rt for 3 h. The crude reaction mixture was loaded onto silica gel and purified using silica gel chromatography (3-60% EtOAc/hexanes, linear gradient) to afford 1-bromo-4-isothiocyanato-2-methoxybenzene (0.48 g, 75% yield) as an off white solid. LC-MS (M+H)$^+$ 244.0. $^1$H NMR (400 MHz, methanol-d$_4$) δ ppm 7.53 (d, J=8.56 Hz, 1 H) 6.94 (d, J=2.27 Hz, 1 H) 6.79 (dd, J=8.56, 2.27 Hz, 1 H) 3.86 (s, 3 H).

Step P (2): To a solution of 1-bromo-4-isothiocyanato-2-methoxybenzene (0.46 g, 1.884 mmol) in methanol (5 mL) was added methanolic ammonia (2.0 M, 4.7). The resulting mixture was stirred at rt for 4 h. The crude mixture was concentrated in vacuo. The solid was dried under high vacuum to afford 0.49 g (100% yield) the titled compound as a white solid. LC-MS (M+H)$^+$ 263.0. $^1$H NMR (400 MHz, methanol-d$_4$) δ ppm 7.48 (d, J=8.31 Hz, 1 H) 7.21 (br. s., 1 H) 6.78 (dd, J=8.31, 2.27 Hz, 1 H) 3.85 (s, 3 H). The product was used for subsequent chemistry without purification.

Preparation Q

Methyl N'-3-fluoro-4-(3-methyl-1H-1,2,4-triazol-1-yl)phenylcarbamimidothioate hydroiodide

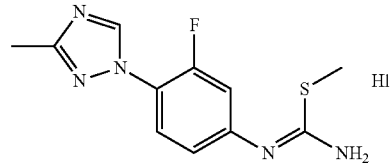

Step Q (1): 10% Palladium on carbon (2.50 g, 23.5 mmol) was added under an atmosphere of nitrogen to a chilled (ice-water bath) solution of 1-(2-fluoro-4-nitrophenyl)-5-methyl-1H-1,2,4-triazole (15.0 g, 67.5 mmol, from preparation C, step1) dissolved in methanol (400 mL). The flask was repeatedly evacuated and flushed with hydrogen gas (double balloon). The resulting mixture was allowed to warm to rt and left to stir for 72 h under the hydrogen atmosphere. The vessel was subsequently purged with nitrogen gas. The reaction vessel and it contents were chilled (ice-water bath) and an additional portion of 10% Palladium on carbon (2.50 g, 23.5 mmol) was added. The flask was repeatedly evacuated and flushed with hydrogen gas (double balloon). The resulting mixture was allowed to warm to rt and left to stir for 6 h under the hydrogen atmosphere. The vessel was subsequently purged with nitrogen gas. The crude reaction mixture was filtered through a short plug of diatomaceous earth (Celite®). The reaction vessel and the Celite® were rinsed with fresh methanol. The combined filtrates were concentrated in vacuo. The residue was dried under high vacuum overnight to afford 3-fluoro-4-(3-methyl-1H-1,2,4-triazol-1-yl)aniline (12.1 g, 63.0 mmol, 93% yield) as a blackish/grey solid. LC-MS (M+H)$^+$ 193.2. $^1$H NMR (500 MHz, chloroform-d) δ ppm 8.31 (d, J=2.4 Hz, 1 H), 7.47 (t, J=8.7 Hz, 1 H), 6.47-6.58 (m, 2 H), 3.97 (br. s., 2 H), 2.48 (s, 3 H).

Step Q (2): Dichloromethane (125 mL) was added to a flask charged with 3-fluoro-4-(3-methyl-1H-1,2,4-triazol-1-yl)aniline (5.00 g, 26.0 mmol) and 1,1'-thiocarbonyldipyridin-2(1H)-one (6.65 g, 28.6 mmol). The crude reaction was concentrated in vacuo. Methanolic ammonia (2.0 M, 150 mL, 300 mmol) was added at rt to the dark-red solid residue. A light brown precipitate resulted. After stirring for 30 min, the crude reaction mixture was chilled in a −20 C freezer for 1 h. The solid precipitate was collected using vacuum filtration.

The solid was rinsed with cold methanol and dried under high vacuum to afford 1-(3-fluoro-4-(3-methyl-1H-1,2,4-triazol-1-yl)phenyl)thiourea (5.48 g, 84% yield) as an off-white solid. LC-MS (M+H)+ 252.2. $^1$H NMR (500 MHz, DMSO-$d_6$) δ ppm 10.02 (br. s., 1 H), 8.80 (d, J=2.1 Hz, 1 H), 7.91 (dd, J=13.4, 2.1 Hz, 1 H), 7.66 (t, J=8.7 Hz, 1 H), 7.33 (dd, J=8.4, 2.0 Hz, 1 H), 2.36 (s, 3 H).

Step Q (3): Iodomethane (1.43 mL, 22.9 mmol) was added to a solution of 1-(3-fluoro-4-(3-methyl-1H-1,2,4-triazol-1-yl)phenyl)thiourea (5.48 g, 21.8 mmol) in absolute ethanol (200 mL). The resulting mixture was heated at 70° C. for 3 h. After cooling to rt, the reaction was chilled at −20° C. for 2 h. The precipitate was collected by vacuum filtration. The solid was dried under high vacuum to afford methyl 3-fluoro-4-(3-methyl-1H-1,2,4-triazol-1-yl)phenylcarbamimidothioate, hydroiodide (8.40 g, 21.4 mmol, 98% yield) as an off-white solid. LC-MS (M+H)+ 266.1. $^1$H NMR (500 MHz, DMSO-$d_6$) δ ppm 8.91 (d, J=2.4 Hz, 1 H), 7.91 (t, J=8.5 Hz, 1 H), 7.64 (dd, J=11.7, 2.0 Hz, 1 H), 7.35 (d, J=7.3 Hz, 1 H), 2.70 (s, 3 H), 2.38 (s, 3 H).

Preparation R

Methyl N'-3,5-difluoro-4-(3-methyl-1H-1,2,4-triazol-1-yl)phenylcarbamimidothioate hydroiodide

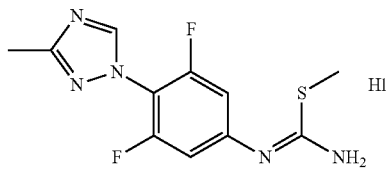

Step R (1): A mixture of 3-methyl-1H-1,2,4-triazole (8.12 g, 98 mmol), 1,2,3-trifluoro-5-nitrobenzene (17.3 g, 98 mmol), and sodium bicarbonate (8.21 g, 98 mmol) in DMSO (100 mL) was heated at 80° C. for 24 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The crude reaction mixture was purified using silica gel chromatography (30-80% EtOAc/hexane, linear gradient) to afford a 1.7:1.0 mixture of two regioisomeric products as an orange solid. The orange solid was recrystallized from EtOAc (hot-cold) to provide 4.25 g of 1-(2,6-difluoro-4-nitrophenyl)-3-methyl-1H-1,2,4-triazole as a white solid. The mother liquor was recrystallized from EtOAc/Hex (hot-rt) to afford 1.89 g of 1-(2,6-difluoro-4-nitrophenyl)-5-methyl-1H-1,2,4-triazole as a light yellow solid. The mother liquor was repeatly chromatographed under the previously stated conditions to provide two samples. One sample was partially enriched in the slightly less polar isomer, 1-(2,6-difluoro-4-nitrophenyl)-3-methyl-1H-1,2,4-triazole. The other sample was partially enriched in the slightly more polar isomer, 1-(2,6-difluoro-4-nitrophenyl)-5-methyl-1H-1,2,4-triazole. Both samples were independently recrystallized from EtOAc/Hex to provide an additional 1.9 g of 1-(2,6-difluoro-4-nitrophenyl)-3-methyl-1H-1,2,4-triazole and 1.37 g of 1-(2,6-difluoro-4-nitrophenyl)-5-methyl-1H-1,2,4-triazole. A combined total of 6.15 g (26% yield) of 1-(2,6-difluoro-4-nitrophenyl)-3-methyl-1H-1,2,4-triazole and 3.2 g (13% yield) of 1-(2,6-difluoro-4-nitrophenyl)-5-methyl-1H-1,2,4-triazole was obtained.

Data for 1-(2,6-difluoro-4-nitrophenyl)-3-methyl-1H-1,2,4-triazole: LC-MS (M+H)+=241.0. $^1$H NMR (500 MHz, CHLOROFORM-d) δ ppm 8.34 (s, 1 H), 8.01-8.10 (m, 2 H), 2.54 (s, 3 H).

Data for 1-(2,6-difluoro-4-nitrophenyl)-5-methyl-1H-1,2,4-triazole: LC-MS (M+H)+=241.0. $^1$H NMR (500 MHz, CHLOROFORM-d) δ ppm 8.08 (s, 1 H), 8.04-8.08 (m, 2 H), 2.45 (s, 3 H). An X-ray analysis of a single crystal grown from EtOAc/hexanes confirmed the regiochemical assignment of this isomer as the 5-methyl congener.

Step R (2): 10% Palladium on carbon (0.890 g, 0.830 mmol) was added under an atmosphere of nitrogen to a chilled (ice-water bath) solution of 1-(2,6-difluoro-4-nitrophenyl)-3-methyl-1H-1,2,4-triazole (2.00 g, 8.33 mmol dissolved in methanol (200 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short plug of diatomaceous earth (Celite®). The reaction vessel and Celite® were rinsed with fresh methanol. The combined filtrates were concentrated in vacuo. The residue was dried under high vacuum to afford 3,5-difluoro-4-(3-methyl-1H-1,2,4-triazol-1-yl)aniline (1.76 g, 8.37 mmol, quantitative yield) as a blackish/gray solid. LC-MS (M+H)+ 211.1. $^1$H NMR (500 MHz, CHLOROFORM-d) δ ppm 8.10 (1 H, s), 6.25-6.36 (2 H, m), 4.17 (2 H, br. s.), 2.49 (3 H, s).

Step R (3): Dichloromethane (50 mL) was added to a flask charged with 3,5-difluoro-4-(3-methyl-1H-1,2,4-triazol-1-yl)aniline (1.75 g, 8.33 mmol) and 1,1'-thiocarbonyldipyridin-2(1H)-one (2.90 g, 8.33 mmol). The resulting mixture was stirred for 24 h at rt and concentrated in vacuo. A solution of ammonia (2.0 M in methanol, 50 mL, 100 mmol) was added to the crude solid. The heterogeneous mixture was stirred at rt for 2 h, then evaporated to dryness under reduced pressure using a rotary evaporator. The solid residue was triturated with 40 mL of anhydrous ethanol and chilled to 0° C. for 1 h. The solid was collected by vacuum filtration and dried under high vacuum to afford 1-(3,5-difluoro-4-(3-methyl-1H-1,2,4-triazol-1-yl)phenyl)thiourea (1.76 g, 6.54 mmol, 79% yield) as a gray powdery solid. LC-MS (M+H)+ 270.0. $^1$H NMR (500 MHz, DMSO-$d_6$) d ppm 10.16 (1 H, br. s.), 8.77 (1 H, s), 7.64 (2 H, d, J=10.4 Hz), 2.35 (3 H, s).

Step R (4): Iodomethane (0.413 mL, 6.63 mmol) was added to a solution of 1-(3,5-difluoro-4-(3-methyl-1H-1,2,4-triazol-1-yl)phenyl)thiourea (1.7 g, 6.31 mmol) in absolute ethanol (50 mL). The resulting mixture was heated at 70° C. for 3 h. After cooling to rt, the reaction was concentrated in vacuo. The residual volatiles were removed under high vacuum to afford methyl 3,5-difluoro-4-(3-methyl-1H-1,2,4-triazol-1-yl)phenylcarbamimidothioate, hydroiodide (2.4 g, 5.84 mmol, 92% yield) as a grey solid. LC-MS (M+H)+ 284.0. $^1$H NMR (500 MHz, DMSO-$d_6$) δ ppm 8.86 (s, 1 H), 7.50 (d, J=8.9 Hz, 2 H), 2.71 (s, 3 H), 2.38 (s, 3 H).

Preparation S

Methyl N'-3-fluoro-5-methoxy-4-(3-methyl-1H-1,2,4-triazol-1-yl)phenylcarbamimidothioate hydroiodide

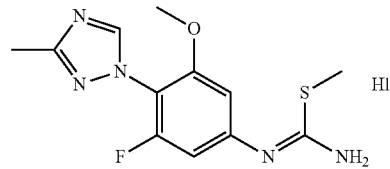

Step S (1): A solution of sodium methanolate (0.5 M in methanol, 17.5 mL, 8.74 mmol) was added to a round bottom flask charged with a solution of 1-(2,6-difluoro-4-nitrophenyl)-3-methyl-1H-1,2,4-triazole (2.1 g, 8.74 mmol, from preparation R, step R(1) in THF (25 mL). A slight pink color resulted. After 2 h, the reaction mixture was concentrated under reduced pressure. The white solid residue was triturated with ~50 mL of 1 N HCl. The solid was collected by vacuum filtration and dried under high vacuum for several hours to afford 1-(2-fluoro-6-methoxy-4-nitrophenyl)-3-methyl-1H-1,2,4-triazole (1.84 g, 7.15 mmol, 82% yield) as a white solid. LC-MS (M+H)' 253.1.0. $^1$H NMR (500 MHz, CHLOROFORM-d) δ ppm 8.22 (s, 1 H), 7.80 (dd, J=9.0, 2.3 Hz, 1 H), 7.76 (t, J=2.0 Hz, 1 H), 3.99 (s, 3 H), 2.52 (s, 3 H).

Step S (2): 10% Palladium on carbon (0.776 g, 0.730 mmol) was added under an atmosphere of nitrogen to a chilled (ice-water bath) solution of 1-(2-fluoro-6-methoxy-4-nitrophenyl)-3-methyl-1H-1,2,4-triazole (1.84 g, 7.30 mmol) dissolved in methanol (150 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short plug of diatomaceous earth (Celite®). The reaction vessel and the Celite® were rinsed with fresh methanol. The combined filtrates were concentrated in vacuo. The residue was dried under high vacuum overnight to afford 3-fluoro-5-methoxy-4-(3-methyl-1H-1,2,4-triazol-1-yl)aniline (2.17 g, quantitative % yield) as a blackish/gray solid. LC-MS (M+H)$^+$ 223.2. $^1$H NMR (500 MHz, CHLOROFORM-d) δ ppm 8.02 (s, 1 H), 6.11 (dd, J=11.1, 2.3 Hz, 1 H), 6.06 (d, J=1.5 Hz, 1 H), 4.04 (br. s., 2 H), 3.74 (s, 3 H), 2.48 (s, 3 H).

Step S (3): Dichloromethane (125 mL) was added to a flask charged with 3-fluoro-4-(3-methyl-1H-1,2,4-triazol-1-yl) aniline (5.00 g, 26.0 mmol) and 1,1'-thiocarbonyldipyridin-2 (1H)-one (6.65 g, 28.6 mmol). The crude reaction was concentrated in vacuo. Methanolic ammonia (2.0 M, 150 mL, 300 mmol) was added at rt to the dark-red solid residue. A light brown precipitate resulted. After stirring for 30 min, the crude reaction mixture was chilled in a –20° C. freezer for 1 h. The solid precipitate was collected using vacuum filtration. The solid was rinsed with cold methanol and dried under high vacuum to afford 1-(3-fluoro-4-(3-methyl-1H-1,2,4-triazol-1-yl)phenyl)thiourea (5.48 g, 84% yield) as an off-white solid. LC-MS (M+H)$^+$ 252.2. $^1$H NMR (500 MHz, DMSO-d$_6$) δ ppm 10.02 (br. s., 1 H), 8.80 (d, J=2.1 Hz, 1 H), 7.91 (dd, J=13.4, 2.1 Hz, 1 H), 7.66 (t, J=8.7 Hz, 1 H), 7.33 (dd, J=8.4, 2.0 Hz, 1 H), 2.36 (s, 3 H).

Step S (4): Iodomethane (0.179 mL, 2.88 mmol) was added to a solution of 1-(3-fluoro-5-methoxy-4-(3-methyl-1H-1,2,4-triazol-1-yl)phenyl)thiourea (0.772 g, 2.74 mmol) in absolute ethanol (50 mL). The resulting mixture was heated at 70° C. for 3 h. The crude reaction mixture was concentrated in vacuo. The residual solid was dried under high vacuum to afford methyl 3-fluoro-5-methoxy-4-(3-methyl-1H-1,2,4-triazol-1-yl)phenylcarbamimidothioate, hydroiodide (1.15 g, 2.72 mmol, 99% yield) as a yellow solid. LC-MS (M+H)$^+$ 296.1.

Preparation T

Methyl N'-4-(2,4-dimethyl-1H-imidazol-1-yl)-3,5-difluorophenylcarbamimidothioate hydroiodide

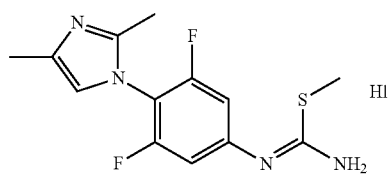

Step T (1): A mixture of 2,4-dimethyl-1H-imidazole (5.00 g, 52.0 mmol), 1,2-difluoro-4-nitrobenzene (8.27 g, 52.0 mmol), and sodium bicarbonate (4.37 g, 52.0 mmol) in DMSO (100 mL) was heated at 80° C. for 24 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The dark residue was dissolved in ethyl acetate (200 mL). Hexane (50 mL) was added to the solution. The resulting mixture was allowed to age for 72 h at rt. The resulting solid was collected by vacuum filtration. The solid was dried under high vacuum to afford 1-(2-fluoro-4-nitrophenyl)-2,4-dimethyl-1H-imidazole (6.68 g, 27.8 mmol, 54% yield) as a yellow crystalline solid. LC-MS (M+H)$^+$=236.1. $^1$H NMR (500 MHz, CHLOROFORM-d) δ ppm 8.13-8.22 (m, 2 H), 7.51 (dd, J=8.9, 7.3 Hz, 1 H), 6.72 (s, 1 H), 2.28-2.36 (m, 3 H), 2.22-2.28 (m, 3 H).

Step T (2): 10% Palladium on carbon (2.99 g, 2.81 mmol) was added under an atmosphere of nitrogen to a chilled (ice-water bath) solution of 1-(2-fluoro-4-nitrophenyl)-2,4-dimethyl-1H-imidazole (6.6 g, 28.1 mmol) dissolved in methanol (150 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short plug of diatomaceous earth (Celite®). The reaction vessel and Celite® were rinsed with fresh methanol. The combined filtrates were concentrated in vacuo. The residue was dried under high vacuum to afford 4-(2,4-dimethyl-1H-imidazol-1-yl)-3-fluoroaniline (6.02 g, quanitative yield) as a blackish/grey solid. LC-MS (M+H)$^+$ 206.2. $^1$H NMR (500 MHz, CHLOROFORM-d) δ ppm 7.00 (t, J=8.5 Hz, 1 H), 6.60 (s, 1 H), 6.43-6.53 (m, 2 H), 3.98 (br. s., 2 H), 2.16-2.28 (m, 6 H).

Step T (3): Dichloromethane (100 mL) was added to a flask charged with 4-(3,5-dimethyl-1H-1,2,4-triazol-1-yl)-3-fluoroaniline (1.67 g, 8.10 mmol and 1,1'-thiocarbonyldipyridin-2(1H)-one (1.88 g, 8.10 mmol). The resulting mixture was stirred for 24 h at rt and concentrated in vacuo. A solution of ammonia (2.0 M in methanol, 50 mL, 100 mmol) was added to the crude solid. The heterogeneous mixture was stirred at rt for 2 h, then evaporated to dryness under reduced pressure using a rotory evaporator. The solid residue was triturated with anhydrous ethanol and chilled to 0° C. for 1 h. The solid was collected by vacuum filtration and dried under high vacuum to afford 1-(4-(3,5-dimethyl-1H-1,2,4-triazol-1-yl)-3-fluorophenyl)thiourea (1.10 g, 4.06 mmol, 50% yield) as a white powdery solid. LC-MS (M+H)+ 266.3. ¹H NMR (500 MHz, DMSO-d₆) δ ppm 10.06 (s, 1 H), 7.91 (d, J=12.5 Hz, 1 H), 7.50 (t, J=8.5 Hz, 1 H), 7.35 (d, J=8.9 Hz, 1 H), 2.26 (s, 6 H).

Step T (4) [80456-011]: Iodomethane (0.281 mL, 4.51 mmol) was added to a solution of 1-(4-(3,5-dimethyl-1H-1,2,4-triazol-1-yl)-3-fluorophenyl)thiourea (1.14 g, 4.30 mmol) in absolute ethanol (50 mL). The resulting mixture was heated at 70° C. for 3 h. After cooling to rt, the reaction was concentrated in vacuo. The residual volatiles were removed under high vacuum to afford methyl 4-(3,5-dimethyl-1H-1,2,4-triazol-1-yl)-3-fluorophenylcarbamimidothioate, hydroiodide (1.76 g, 4.32 mmol, 101% yield) as a grey solid. LC-MS (M+H)+ 280.1.

Preparation U

Allyl N'-2-fluoro-5-methoxy-4-(3-methyl-1H-1,2,4-triazol-1-yl)phenylcarbamimidothioate hydrobromide

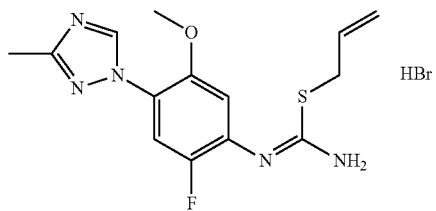 [SMILES: C=CCS/C(N)=N\c1cc(OC)c(-n2cnc(C)n2)cc1F ; Br]

Step U (1): Allyl bromide (0.308 mL, 3.55 mmol) was added to a solution of 1-(2-fluoro-5-methoxy-4-(3-methyl-1H-1,2,4-triazol-1-yl)phenyl)thiourea (1.0 g, 3.55 mmol, from Preparation B, Step B(4)) in absolute ethanol (25 mL). The resulting mixture was heated at 70° C. for 2 h. After cooling to rt, the reaction was concentrated in vacuo. The residual volatiles were removed under high vacuum to afford allyl 2-fluoro-5-methoxy-4-(3-methyl-1H-1,2,4-triazol-1-yl)phenylcarbamimidothioate, hydrobromide (1.45 g, 3.60 mmol, 101% yield) as an off-white solid. LC-MS (M+H)+ 322.0.

Preparation AA 2-(4-Fluorophenyl)pent-4-enoic acid

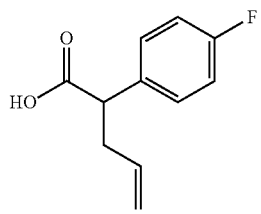

Step AA (1): NaHMDS (1.0 M in THF, 46.7 mL, 46.7 mmol) was added to a stirred solution of 2-(4-fluorophenyl)acetic acid (3.6 g, 23.4 mmol) in THF (50 mL) at 0° C. The resulting mixture was stirred for 20 min at 0° C. and neat 3-bromoprop-1-ene (2.02 mL, 23.4 mmol) was added. The mixture was allowed to warm to rt. After 16 hr, the reaction was quenched with water (3 mL). The crude mixture was concentrated in vacuo. Aqueous NaOH (1 M, 150 mL) was added to the residue and the resulting mixture was extracted with Et₂O (2×100 mL). The basic layer was acidified with aqueous HCl (1 M, 200 mL) and the resulting solution was extracted with Et₂O (2×100 mL). The combined organic layers from the acidic extraction were washed with mixture of brine/1N HCl/sodium sulfite, dried (MgSO₄), filtered, and concentrated in vacuo. The residue was dissolved in toluene (~50 mL) and left to sit at rt for 3 days. A white solid was collected by vacuum filtration. The solid was dried under high vacuum to afford 2-(4-fluorophenyl)pent-4-enoic acid (2.03 g, 10.1 mmol, 43% yield) as an off-white crystalline solid. ¹H NMR (500 MHz, chloroform-d) δ ppm 7.28-7.34 (m, 2 H) 6.99-7.07 (m, 2 H) 5.71 (dddd, J=17.09, 10.22, 6.87, 6.71 Hz, 1 H) 5.08 (dd, J=17.09, 1.53 Hz, 1 H) 5.01-5.05 (m, 1 H) 3.65 (t, J=7.63 Hz, 1 H) 2.75-2.87 (m, 1 H) 2.52 (dt, J=14.27, 7.06 Hz, 1 H).

Preparation AB 2-(2,4-Dichlorophenyl)pent-4-enoic acid

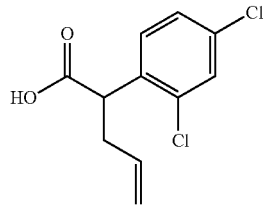

Step AB (1): 2-(2,4-Dichlorophenyl)acetic acid was deprotonated with NaHMDS and reacted with 3-bromoprop-1-ene using a procedure analogous to Step AA (1) to afford 2-(2,4-dichlorophenyl)pent-4-enoic acid as a clear viscous oil. LC-MS (M–H)– 243.1. ¹H NMR (500 MHz, chloroform-d) δ ppm 7.42 (d, J=2.14 Hz, 1 H) 7.31-7.36 (m, 1 H) 7.25 (dd, J=8.24, 2.14 Hz, 1 H) 5.67-5.77 (m, J=17.05, 10.19, 6.83, 6.83 Hz, 1 H) 5.07 (dd, J=17.09, 1.53 Hz, 1 H) 5.04 (d, J=10.38 Hz, 1 H) 4.26 (t, J=7.48 Hz, 1 H) 2.81 (dt, J=14.34, 7.17 Hz, 1 H) 2.55 (dt, J=14.57, 7.21 Hz, 1 H).

Preparation AC 2-(4-Fluorophenyl)pent-4-enoic acid

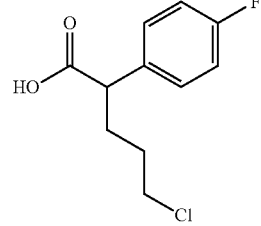

Step AC (1): NaHMDS (1.0 M in THF, 100 mL, 100 mmol) was added to a stirred solution of 2-(4-fluorophenyl)acetic acid (7.71 g, 50.0 mmol) in THF (100 mL) at 0° C. The resulting mixture was aged for 20 min at 0° C. and neat 1-chloro-3-iodopropane (5.27 mL, 50.0 mmol) was added. The mixture was allowed to warm to rt. After 16 hr, the reaction was quenched with water (3 mL). The crude mixture was concentrated in vacuo. Aqueous NaOH (1 M, 150 mL)

was added to the residue and the resulting mixture was extracted with Et₂O (2×100 mL). The basic layer was acidified with aqueous HCl (1 M, 200 mL) and the resulting solution was extracted with Et₂O (2×100 mL). The combined organic layers from the acidic extraction were washed with mixture of brine/1N HCl/sodium sulfite, dried (MgSO₄), filtered, and concentrated in vacuo. The crude product was purified using silica gel column chromatography (0-10% EtOAc/hexane, linear gradient). The pure fractions were combined and concentrated to afford 5-chloro-2-(4-fluorophenyl)pentanoic acid (7.59 g, 29.6 mmol, 59% yield) as a light brown solid. ¹H NMR (500 MHz, chloroform-d) δ ppm 7.30 (dd, J=8.55, 5.19 Hz, 2 H) 7.04 (t, J=8.70 Hz, 2 H) 3.58 (t, J=7.78 Hz, 1 H) 3.53 (t, J=5.80 Hz, 2 H) 2.21 (dddd, J=13.35, 10.45, 7.78, 5.34 Hz, 1 H) 1.90-2.01 (m, 1 H) 1.65-1.84 (m, 2 H).

Preparation AD

5-Chloro-2-(2,4-dichlorophenyl)pentanoic acid

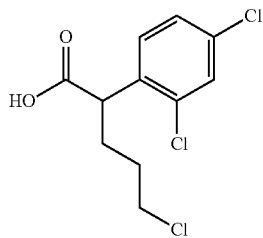 [SMILES: O=C(O)C(CCCCl)c1ccc(Cl)cc1Cl]

Step AD (1): 2-(2,4-Dichlorophenyl)acetic acid (10.25 g, 50.0 mmol) was deprotonated with NaHMDS (1.0 M in THF, 100 mL, 100 mmol) and reacted with 1-chloro-3-iodopropane (5.27 mL, 50.0 mmol) using a procedure analogous to Step AC (1) to afford, after purification by silica gel column chromatography, 5-chloro-2-(2,4-dichlorophenyl)pentanoic acid (8.15 g, 28.9 mmol, 58% yield) as a colorless oil. MS (M+H)⁺ 280.9. ¹H NMR (500 MHz, chloroform-d) δ ppm 7.47 (d, J=2.14 Hz, 1 H) 7.34-7.40 (m, 1 H) 7.28-7.33 (m, 1 H) 4.22 (t, J=7.48 Hz, 1 H) 3.57 (t, J=6.41 Hz, 2 H) 2.27 (dddd, J=13.08, 10.64, 7.55, 5.34 Hz, 1 H) 1.95-2.05 (m, 1 H) 1.82-1.92 (m, 1 H) 1.68-1.81 (m, 1 H).

Preparation AE

6-Chloro-2-(4-fluorophenyl)hexanoic acid

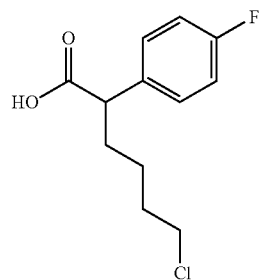 [SMILES: O=C(O)C(CCCCCl)c1ccc(F)cc1]

Step AE (1): NaHMDS (1.0 M in THF, 200 mL, 200 mmol) was added to a stirred solution of 2-(4-fluorophenyl)acetic acid (15.41 g, 100 mmol) in THF (200 mL) at 0° C. The resulting mixture was aged for 20 min at 0° C. and neat 1-chloro-4-iodobutane (21.85 g, 100 mmol) was added. The mixture was allowed to warm to rt. After 16 hr, the reaction was quenched with water (3 mL). The crude mixture was concentrated in vacuo. Aqueous NaOH (1 M, 150 mL) was added to the residue and the resulting mixture was extracted with Et₂O (2×250 mL). The basic layer was acidified with aqueous HCl (1 M, 200 mL) and the resulting solution was extracted with Et₂O (2×250 mL). The combined organic layers from the acidic extraction were washed with mixture of brine/1N HCl/sodium sulfite, dried (MgSO₄), filtered, and concentrated in vacuo to afford 6-chloro-2-(4-fluorophenyl)hexanoic acid (22.8 g, 84 mmol, 84% yield) as a viscous oil that slowly solidified upon standing to provide a light brown solid. LC-MS (M−H)⁻ 243.1. ¹H NMR (500 MHz, chloroform-d) δ ppm 7.29 (dd, J=8.70, 5.34 Hz, 2 H) 7.03 (t, J=8.70 Hz, 2 H) 3.56 (t, J=7.63 Hz, 1 H) 3.51 (t, J=6.56 Hz, 2 H) 2.06-2.14 (m, 1 H) 1.74-1.85 (m, 3 H) 1.33-1.51 (m, 2 H).

Preparation AF

6-Chloro-2-(2,4-dichlorophenyl)hexanoic acid

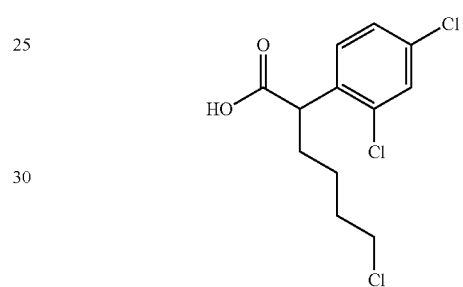

Step AF (1): 2-(2,4-Dichlorophenyl)acetic acid (2.5 g, 12.19 mmol) was deprotonated with NaHMDS (1.0 M in THF, 24.0 mL, 24.4 mmol) and reacted with 1-chloro-4-iodobutane (1.49 mL, 12.2 mmol) using a procedure analogous to Step AC (1) to afford, after purification by silica gel column chromatography, 6-chloro-2-(2,4-dichlorophenyl)hexanoic acid (2.17 g, 7.34 mmol, 60% yield) as a colorless oil. LC-MS (M−H)⁻ 295.1.

Preparation AG

6-Chloro-2-(3,4-difluorophenyl)hexanoic acid

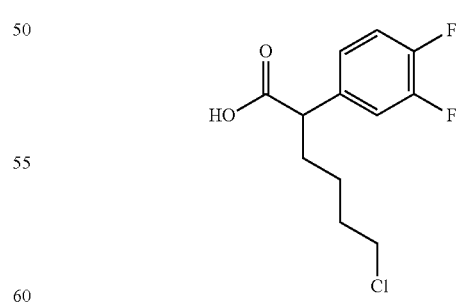

Step AG (1): 2-(3,4-Difluorophenyl)acetic acid (2.5 g, 14.52 mmol) was deprotonated with NaHMDS (1.0 M in THF, 29.0 mL, 29.0 mmol) and reacted with 1-chloro-4-iodobutane (1.78 mL, 14.5 mmol) using a procedure analogous to Step AC (1) to afford 6-chloro-2-(3,4-difluorophenyl)hexanoic acid (3.35 g, 88% yield). LC-MS (M−H)⁻ 261.1.

Preparation AH

6-Chloro-2-(4-chlorophenyl)hexanoic acid

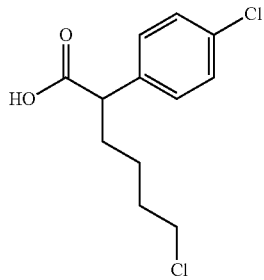 [SMILES: O=C(O)C(CCCCCl)c1ccc(Cl)cc1]

Step AH (1): 2-(4-Chlorophenyl)acetic acid (2.5 g, 14.65 mmol) was deprotonated with NaHMDS (1.0 M in THF, 29.3 mL, 29.3 mmol) and reacted with 1-chloro-4-iodobutane (1.80 mL, 14.7 mmol) using a procedure analogous to Step AC (1) to afford 6-chloro-2-(4-chlorophenyl)hexanoic acid (3.47 g, 59% yield). LC-MS (M–H)⁻ 259.1.

Preparation AI

6-Chloro-2-(4-(trifluoromethoxy)phenyl)hexanoic acid

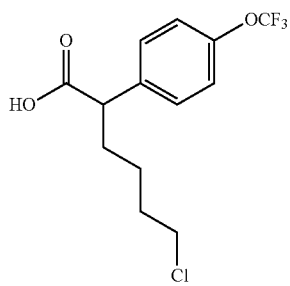 [SMILES: O=C(O)C(CCCCCl)c1ccc(OC(F)(F)F)cc1]

Step AI (1): 2-(4-(Trifluoromethoxy)phenyl)acetic acid (2.5 g, 11.36 mmol) was deprotonated with NaHMDS (1.0 M in THF, 23.0 mL, 22.7 mmol) and reacted with 1-chloro-4-iodobutane (1.39 mL, 11.4 mmol) using a procedure analogous to Step AC (1) to afford 6-chloro-2-(4-(trifluoromethoxy)phenyl)hexanoic acid (4.05 g, 69% yield). LC-MS (M–H)⁻ 309.1.

Preparation AJ

6-Chloro-2-(6-chloropyridin-3-yl)hexanoic acid

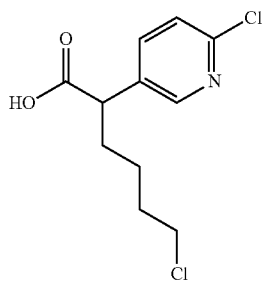 [SMILES: O=C(O)C(CCCCCl)c1ccc(Cl)nc1]

Step AJ (1): 2-(6-Chloropyridin-3-yl)acetic acid (2.5 g, 14.57 mmol) was deprotonated with NaHMDS (1.0 M in THF, 29.1 mL, 29.1 mmol) and reacted with 1-chloro-4-iodobutane (1.78 mL, 14.6 mmol) using a procedure analogous to Step AC (1) to afford 6-chloro-2-(6-chloropyridine-3-yl)hexanoic acid (1.95 g, 51% yield). LC-MS (M–H)⁻ 262.04.

Preparation AK

6-Chloro-2-(4-chloro-1H-pyrazol-1-yl)hexanoic acid

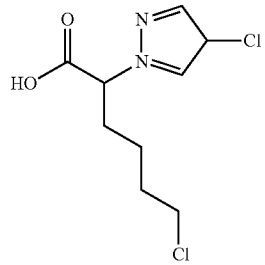

Step AK (1): 2-(4-Chloro-1H-pyrazol-1-yl)acetic acid (2.5 g, 15.57 mmol) was deprotonated with NaHMDS (1.0 M in THF, 31.0 mL, 31.0 mmol) and reacted with 1-chloro-4-iodobutane (1.91 mL, 15.6 mmol) using a procedure analogous to Step AC (1) to afford, after silica gel column chromatography (10-75% EtOAc/heanes), 6-chloro-2-(4-chloro-1H-pyrazol-1-yl)hexanoic acid (2.2 g, 56% yield). LC-MS (M–H)⁻ 249.1.

Preparation AL

6-Chloro-2-(3,5-difluorophenyl)hexanoic acid

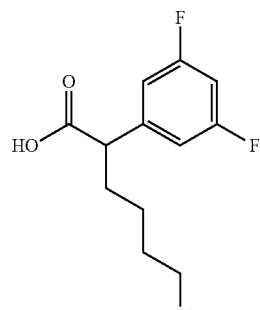

Step AL (1): 2-(3,5-Difluorophenyl)acetic acid (2.5 g, 14.5 mmol) was deprotonated with NaHMDS (1.0 M in THF, 29.0 mL, 29.0 mmol) and reacted with 1-chloro-4-iodobutane (1.78 mL, 14.5 mmol) using a procedure analogous to Step AC (1) to afford 6-chloro-2-(3,5-difluorophenyl)hexanoic acid (3.25 g, 85% yield). LC-MS (m-H)⁻ 261.1. The crude product was used for subsequent chemistry without purification.

Preparation AM

6-Chloro-2-(2,4-difluorophenyl)hexanoic acid

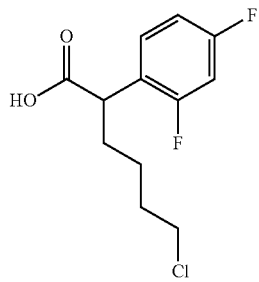 [SMILES: O=C(O)C(CCCCCl)c1ccc(F)cc1F]

Step AM (1): 2-(2,4-Difluorophenyl)acetic acid (2.5 g, 14.52 mmol) was deprotonated with NaHMDS (1.0 M in THF, 29.0 mL, 29.0 mmol) and reacted with 1-chloro-4-iodobutane (1.78 mL, 14.5 mmol) using a procedure analogous to Step AC (1) to afford 6-chloro-2-(2,4-difluorophenyl) hexanoic acid (3.39 g, 89% yield). LC-MS (M−H)⁻ 261.1. The crude product was used for subsequent chemistry without purification.

Preparation AN

6-Chloro-2-(3,4,5-trifluorophenyl)hexanoic acid

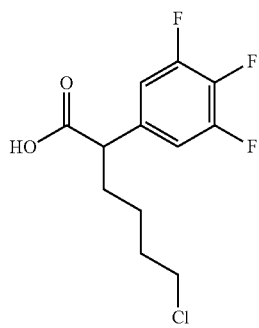 [SMILES: O=C(O)C(CCCCCl)c1cc(F)c(F)c(F)c1]

Step AN (1): 2-(3,4,5-Trifluorophenyl)acetic acid (10 g, 52.6 mmol) was deprotonated with NaHMDS (1.0 M in THF, 105 mL, 105 mmol) and reacted with 1-chloro-4-iodobutane (6.44 mL, 52.6 mmol) using a procedure analogous to Step AC (1) to afford 6-chloro-2-(2,4-difluorophenyl)hexanoic acid (1.56 g, 11% yield). LC-MS (M−H)⁻ 279.1. The crude product was used for subsequent chemistry without purification.

Preparation AO

6-Chloro-2-(3-fluorophenyl)hexanoic acid

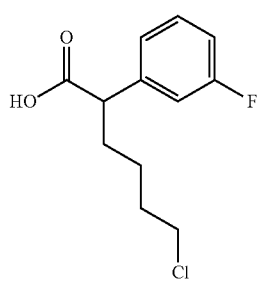 [SMILES: O=C(O)C(CCCCCl)c1cccc(F)c1]

Step AO (1): 2-(3-Fluorophenyl)acetic acid (5 g, 32.4 mmol) was deprotonated with NaHMDS (2.0 M in THF, 32.4 mL, 64.9 mmol) and reacted with 1-chloro-4-iodobutane (3.97 mL, 32.4 mmol) using a procedure analogous to Step AC (1) to afford 6-chloro-2-(3-fluorophenyl)hexanoic acid (7.26 g, 91% yield). LC-MS (M−H)⁻ 243.2. The crude product was used for subsequent chemistry without purification.

Preparation AP

6-Chloro-2-(3-chlorophenyl)hexanoic acid

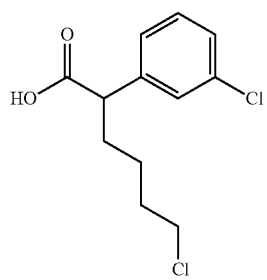 [SMILES: O=C(O)C(CCCCCl)c1cccc(Cl)c1]

Step AP (1): 2-(3-Chlorophenyl)acetic acid (5 g, 29.3 mmol) was deprotonated with NaHMDS (2.0 M in THF, 29.3 mL, 58.6 mmol) and reacted with 1-chloro-4-iodobutane (3.59 mL, 29.3 mmol) using a procedure analogous to Step AC (1) to afford 6-chloro-2-(3-chlorophenyl)hexanoic acid (7.47 g, 98% yield). LC-MS (M−H)⁻ 259.1. The crude product was used for subsequent chemistry without purification.

Preparation AQ

6-Chloro-2-(2-fluorophenyl)hexanoic acid

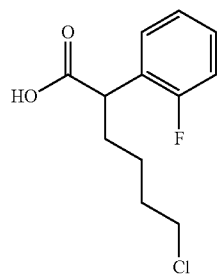 [SMILES: O=C(O)C(CCCCCl)c1ccccc1F]

Step AQ (1): 2-(2-Fluorophenyl)acetic acid (5 g, 32.4 mmol) was deprotonated with NaHMDS (2.0 M in THF, 32.4 mL, 64.9 mmol) and reacted with 1-chloro-4-iodobutane (3.97 mL, 32.4 mmol) using a procedure analogous to Step AC (1) to afford 6-chloro-2-(2-fluorophenyl)hexanoic acid (7.10 g, 89% yield). LC-MS (M−H)⁻ 243.1. The crude product was used for subsequent chemistry without purification.

Preparation AR

6-Chloro-2-(2-chlorophenyl)hexanoic acid

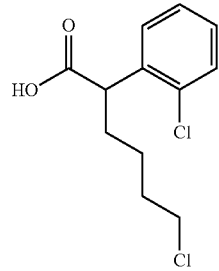 [SMILES: O=C(O)C(CCCCCl)c1ccccc1Cl]

Step AR (1): 2-(2-Chlorophenyl)acetic acid (5.0 g, 29.3 mmol) was deprotonated with NaHMDS (2.0 M in THF, 29.3 mL, 58.6 mmol) and reacted with 1-chloro-4-iodobutane (5.38 mL, 44.0 mmol) using a procedure analogous to Step AC (1) to afford 6-chloro-2-(2-chlorophenyl)hexanoic acid (7.47 g, 88% yield). LC-MS (M−H)⁻ 259.1. The crude product was used for subsequent chemistry without purification.

Preparation AS 2-(4-Chlorobutyl)-1,3-dithiane-2-carboxylic acid

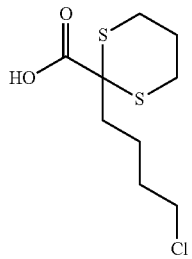 [SMILES: O=C(O)C1(CCCCCl)SCCCS1]

Step AS (1): To a solution of ethyl 1,3-dithiane-2-carboxylate (500 mg, 2.60 mmol) and 1-bromo-4-chlorobutane (1337 mg, 7.80 mmol) in DMF (10 mL) was added 60% NaH (dispersion in mineral oil, 125 mg, 3.12 mmol). The mixture was stirred at rt for 16 h. The reaction mixture was quenched with water (100 mL) and extracted with EtOAc (2×100 mL). The combined organic layers were washed with water (3×100 mL) and concentrated in vacuo. The residue was purified using silica gel column chromatography (10% EtOAc/hexanes) to give ethyl 2-(4-chlorobutyl)-1,3-dithiane-2-carboxylate (550 mg, 75% yield). LC-MS (M+H)⁺ 283.0.

Step AS (2): To a solution of ethyl 2-(4-chlorobutyl)-1,3-dithiane-2-carboxylate (550 mg, 1.94 mmol) in THF (5 mL) was added a solution of LiOH (233 mg, 9.72 mmol) in water (2 mL). Methanol (2 mL) was added and the resulting mixture was stirred at rt for 2 d. The solvents were removed in vacuo. Aqueous 1 N HCl (50 mL) was added. The mixture was extracted with EtOAc (80 mL). The organic layer was washed with water, dried over sodium sulfate, filter, and concentrated in vacuo to afford 2-(4-chlorobutyl)-1,3-dithiane-2-carboxylic acid (400 mg, 1.57 mmol, 81% yield). LC-MS (M+H)⁺ 253.0. The crude product was used for subsequent chemistry without purification.

Preparation AT 2-(4-Bromophenyl)-6-chlorohexanoic acid

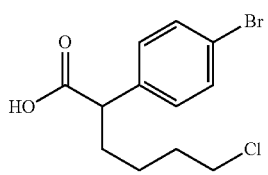 [SMILES: O=C(O)C(CCCCCl)c1ccc(Br)cc1]

Step AT (1): 2-(4-Bromophenyl)acetic acid (10.0 g, 46.5 mmol) was deprotonated with NaHMDS (2.0 M in THF, 70.0 mL, 140 mmol) and reacted with 1-chloro-4-iodobutane (15.2 g, 70.0 mmol) using a procedure analogous to Step AC (1) to afford 2-(4-bromophenyl)-6-chlorohexanoic (14.5 g, 98% yield) as a tan solid. LC-MS (M−H)⁻ 305.1. ¹H NMR (500 MHz, CHLOROFORM-d) δ ppm 7.46 (d, J=8.2 Hz, 2 H), 7.19 (d, J=8.2 Hz, 2 H), 3.45-3.57 (m, 3 H), 2.00-2.15 (m, 1 H), 1.70-1.85 (m, 3 H), 1.31-1.50 (m, 2 H).

Preparation AU

6-Chloro-2-(4-cyanophenyl)hexanoic acid

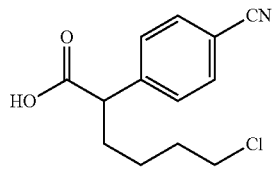 [SMILES: N#Cc1ccc(C(CCCCCl)C(=O)O)cc1]

Step AU (1): 2-(4-Cyanophenyl)acetic acid (5.0 g, 31.0 mmol) was deprotonated with NaHMDS (2.0 M in THF, 46.5 mL, 93 mmol) and reacted with 1-chloro-4-iodobutane (10.2 g, 46.5 mmol) using a procedure analogous to Step AC (1) to afford, after purification by silica gel column chromatography, 6-chloro-2-(4-cyanophenyl)hexanoic acid (5.59 g, 22.2 mmol, 72% yield) as a white solid.

Preparation AV

6-Chloro-2-(4-isopropoxyphenyl)hexanoic acid

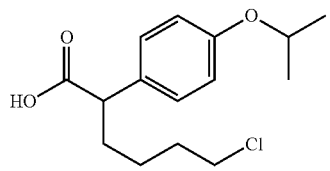 [SMILES: CC(C)Oc1ccc(C(CCCCCl)C(=O)O)cc1]

Step AV (1): 2-(4-Isopropoxyphenyl)acetic acid (7.7 g, 39.6 mmol, reference G. Solladie et al. Tetrahedron (2003), 59, 3315) was deprotonated with NaHMDS (2.0 M in THF, 39.5 mL, 79 mmol) and reacted with 1-chloro-4-iodobutane (10.8 g, 49.6 mmol) using a procedure analogous to Step AC (1) to afford 6-chloro-2-(4-isopropoxyphenyl)hexanoic acid (4.24 g, 37% yield) as a clear viscous oil. LC-MS (M–H)⁻ 193.0.

Preparation AW

6-Chloro-2-(4-(2,2,2-trifluoroethoxy)phenyl)hexanoic acid

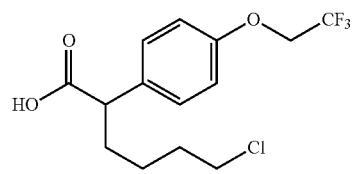 [SMILES: O=C(O)C(CCCCCl)c1ccc(OCC(F)(F)F)cc1]

Step AW (1): 2-(4-(2,2,2-Trifluoroethoxy)phenyl)acetic acid (6.00 g, 25.6 mmol, reference: D. Page, et al. Bioorganic Med. Chem. Lett. (2008), 18, 3695) was deprotonated with NaHMDS (2.0 M in THF, 38.4 mL, 77 mmol) and reacted with 1-chloro-4-iodobutane (8.40 g, 38.4 mmol) using a procedure analogous to Step AC (1) to afford 6-chloro-2-(4-(2,2,2-trifluoroethoxy)phenyl)hexanoic acid (4.32 g, 13.3 mmo, 52% yield) as a clear viscous oil that eventually formed a waxy solid. LC-MS (M–H)⁻ 323.1. $^1$H NMR (500 MHz, CHLOROFORM-d) δ ppm 7.24-7.27 (m, 2 H), 6.90 (d, J=8.5 Hz, 2 H), 4.32 (q, J=7.9 Hz, 2 H), 3.45-3.56 (m, 3 H), 2.00-2.12 (m, 1 H), 1.71-1.83 (m, 3 H), 1.29-1.49 (m, 2 H).

Preparation AX

6-Chloro-2-(4-(2,2-difluoroethoxy)phenyl)hexanoic acid

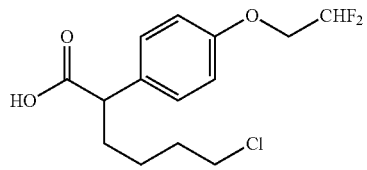 [SMILES: O=C(O)C(CCCCCl)c1ccc(OCC(F)F)cc1]

Step AX (1): Sodium hydride (60% in mineral oil, 1.70 g, 42.5 mmol) was carefully added portionwise to a solution of methyl 2-(4-hydroxyphenyl)acetate (7.06 g, 42.5 mmol) in THF (200 mL) maintained at 0° C. The cold bath was removed and the mixture was allowed to warm to rt and stir for 30 min. A solution of 2,2-difluoroethyl trifluoromethanesulfonate (10.0 g, 46.7 mmol) in THF (20 mL) was added and the resulting mixture was left to stir for 18 h. A solution of 2 N LiOH/water (40 mL, 80 mmol) was added to the crude reaction mixture and the resulting solution stirred at rt for 3 h. The reaction mixture was poured into 1 N HCl (250 mL) and extracted with Et₂O. The combined organic layers were washed with brine, dried (MgSO₄), filtered and concentrated. The residue was triturated with hexane. The crystalline solid was collected by vacuum filtration to afford 2-(4-(2,2-difluoroethoxy)phenyl)acetic acid (9.90 g, 45.8 mmol, 108% yield) as an off-white solid. LC-MS (M–H)⁻ 215.1. $^1$H NMR (500 MHz, CHLOROFORM-d) δ ppm 7.23 (d, J=8.5 Hz, 2 H), 6.89 (d, J=8.5 Hz, 2 H), 6.03-6.14 (m, 1 H), 4.18 (td, J=13.0, 4.1 Hz, 2 H), 3.61 (s, 2 H).

Step AX (2): 2-(4-(2,2-Difluoroethoxy)phenyl)acetic acid (6.00 g, 27.8 mmol) was deprotonated with NaHMDS (2.0 M in THF, 41.6 mL, 83 mmol) and reacted with 1-chloro-4-iodobutane (9.10 g, 41.6 mmol) using a procedure analogous to Step AC (1) to afford 6-chloro-2-(4-(2,2-difluoroethoxy)phenyl)hexanoic acid (6.94 g, 21.5 mmol, 77% yield) as a viscous oil that slowly solidified at rt to afford an off-white solid. LC-MS (M–H)⁻ 305.21. $^1$H NMR (500 MHz, CHLOROFORM-d) δ ppm 7.24 (d, J=8.9 Hz, 2 H), 6.87 (d, J=8.5 Hz, 2 H), 5.88-6.23 (m, 1 H), 4.15 (td, J=13.0, 4.1 Hz, 2 H), 3.44-3.53 (m, 3 H), 1.99-2.12 (m, 1 H), 1.70-1.86 (m, 3 H), 1.31-1.50 (m, 2 H).

Preparation AY

6-Chloro-2-(3-fluoro-4-(trifluoromethoxy)phenyl)hexanoic acid

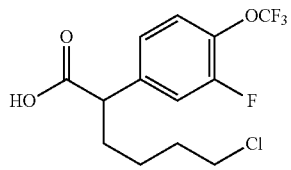 [SMILES: O=C(O)C(CCCCCl)c1ccc(OC(F)(F)F)c(F)c1]

Step AY (1): 2-(3-Fluoro-4-(trifluoroethoxy)phenyl)acetic acid (3.00 g, 12.6 mmol) was deprotonated with NaHMDS (2.0 M in THF, 12.6 mL, 25.2 mmol) and reacted with 1-chloro-4-iodobutane (1.54 g, 12.6 mmol) using a procedure analogous to Step AC (1) to afford 6-chloro-2-(3-fluoro-4-(trifluoromethoxy)phenyl)hexanoic acid (3.52 g, 85% yield) as a clear viscous oil. LC-MS (M–H)⁻ 327.1. $^1$H NMR (500 MHz, CHLOROFORM-d) δ ppm 7.22-7.28 (1 H, m), 7.19 (1 H, dd, J=10.7, 2.1 Hz), 7.09 (1 H, d, J=8.2 Hz), 3.55 (1 H, t, J=7.6 Hz), 3.50 (2 H, t, J=6.6 Hz), 2.04-2.13 (1 H, m), 1.75-1.81 (3 H, m), 1.33-1.52 (2 H, m).

Preparation AZ

6-Chloro-2-(4-(difluoromethoxy)phenyl)hexanoic acid

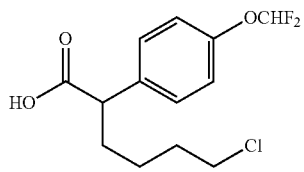

Step AZ (1): 2-(4-(Difluoromethoxy)phenyl)acetic acid (5.0 g, 24.8 mmol) was deprotonated with NaHMDS (2.0 M in THF, 24.7 mL, 49.5 mmol) and reacted with 1-chloro-4-iodobutane (3.03 g, 24.7 mmol) using a procedure analogous to Step AC (1) to afford after purification by silica gel column chromatography (0-70% EtOAc/hexane), 6-chloro-2-(4-(difluoromethoxy)phenyl)hexanoic acid (1.13 g, 3.86 mmol, 15.61% yield) as a pale-yellow oil. LC-MS (M–H)⁻ 291.1. $^1$H NMR (500 MHz, CHLOROFORM-d) δ ppm 7.30 (d, J=8.9 Hz, 2 H), 7.08 (d, J=8.5 Hz, 2 H), 6.29-6.66 (m, 1 H), 3.54 (t, J=7.6 Hz, 1 H), 3.49 (t, J=6.6 Hz, 2 H), 2.04-2.13 (m, 1 H), 1.72-1.82 (m, 3 H), 1.32-1.51 (m, 2 H).

Preparation AAA

2-Bromo-6-phenylcyclohexanone

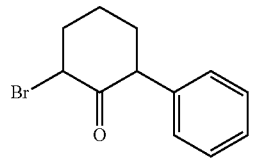 [SMILES: O=C1C(Br)CCCC1c1ccccc1]

Step AAA (1): Followed the procedure of B. Miller and H.-S. Wong *Tetrahedron* 1972, 28, 2369. A solution of bromine (0.348 mL, 6.75 mmol) in $CCl_4$ (5 mL) was added dropwise to a solution of 2-phenylcyclohexanone (1.12 g, 6.43 mmol) in $CCl_4$ (11 mL) at 0° C. The nearly colorless solution was evaporated in vacuo to afford 2-bromo-6-phenylcyclohexanone. The crude product, which is prone to decomposition, was used for subsequent chemistry without purification or characterization.

Preparation AAB 6-bromo-2-methyl-2-phenylcyclohexanone

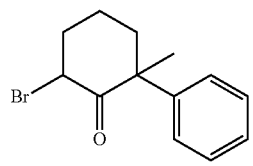

Step AAB (1): A solution of bromine (0.068 ml, 1.328 mmol) in $CCl_4$ (2 mL) was added dropwise, over a period of 10 min, to a solution of 2-methyl-2-phenylcyclohexanone (250 mg, 1.328 mmol) in $CCl_4$ (8 mL) at 0° C. The resulting solution was allowed to warm to rt and stir for 2 hr. The reaction mixture was concentrated in vacuo to afford 6-bromo-2-methyl-2-phenylcyclohexanone. The crude product was used for subsequent chemistry without purification or characterization.

Preparation AAC 7-bromo-9-(4-fluorophenyl)-1,4-dioxaspiro[4.5]decan-8-one

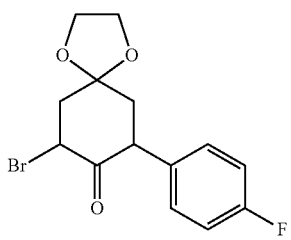 [SMILES: O=C1C(Br)CC2(CC1c1ccc(F)cc1)OCCO2]

Step AAC (1): Followed a method described by A. de Meijer et. al *Chem. Eur. J.* 2007, 13, 3739. Lithium diisopropylamide (1.8 M in THF, 1.26 mL, 2.26 mmol) was added to a −78° C. solution of 7-(4-fluorophenyl)-1,4-dioxaspiro[4.5]decan-8-one (515 mg, 2.06 mmol, O. Dirat et. al *Tetrahedron Lett.* 2006, 47, 1295) in THF (7 mL). The resulting mixture was allowed to stir for 1 hr. Trimethylsilane (0.289 mL, 2.264 mmol) was added and the mixture was allowed to warm to rt and stir for 30 min. The crude reaction was diluted with EtOAc and washed with saturated sodium bicarbonate solution. The organic layer was concentrated in vacuo to afford (9-(4-fluorophenyl)-1,4-dioxaspiro[4.5]dec-7-en-8-yloxy)trimethylsilane (696 mg, 100% yield) as a yellow solid. The crude product was used for subsequent chemistry without purification or characterization.

Step AAC (2): Followed a method described by A. de Meijer et. al *Chem. Eur. J.* 2007, 13, 3739. N-bromosuccinimide (52 mg, 0.29 mmol) was added to a solution of (9-(4-fluorophenyl)-1,4-dioxaspiro[4.5]dec-7-en-8-yloxy)trimethylsilane (89 mg, 276 mmol) in THF/water (1:1, 1.4 mL). The resulting mixture was allowed to stir for 2 hr. The crude reaction was diluted with EtOAc and washed with water. The organic layer was concentrated in vacuo to afford 7-bromo-9-(4-fluorophenyl)-1,4-dioxaspiro[4.5]decan-8-on (230 mg, 253%) yield). The crude product was used for subsequent chemistry without purification or characterization.

Preparation AAD 2-benzyl-6-bromocyclohexanone

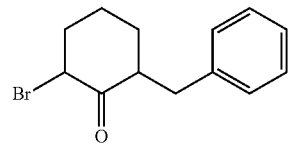 [SMILES: O=C1C(Br)CCCC1Cc1ccccc1]

Step AAD (1): Followed the method of B. Miller and H.-S. Wong *Tetrahedron* 1972, 28, 2369. Bromine (0.082 mL, 1.59 mmol) in was added dropwise over a period of 15 min to a solution of 2-benzylcyclohexanone (300 mg, 1.593 mmol) in chloroform (5 mL). The reaction mixture was stirred at rt for 2 h, then concentrated in vacuo to afford 2-benzyl-6-bromocyclohexanone. The crude product, which is prone to decomposition, was used for subsequent chemistry without purification or characterization.

Preparation AAE 3-bromocyclohexane-1,2-dione

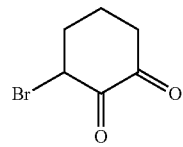

Step AAE (1): Followed the method of B. Miller and H.-S. Wong *Tetrahedron* 1972, 28, 2369. Bromine (0.651 mL, 12.6 mmol) in was added dropwise to a solution of cyclohexane-1,2-dione (1.35 g, 12.0 mmol) in $CCl_4$ (30 mL) at 0° C. The reaction mixture was allowed to warm to rt. The resulting solution was concentrated in vacuo to afford 3-bromocyclohexane-1,2-dione. The crude product, which is prone to decomposition, was used for subsequent chemistry without purification or characterization.

Preparation AAF 2-bromo-7-(4-fluorophenyl)cycloheptanone

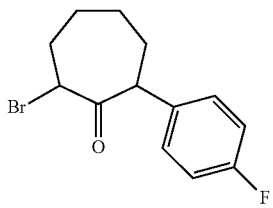 [SMILES: O=C1C(Br)CCCCC1c1ccc(F)cc1]

Step AAF (1): A mixture of cycloheptanone (1.0 g, 8.92 mmol), 1-bromo-4-fluorobenzene (0.874 g, 4.99 mmol), 4,5-bis(diphenylphosphino)-9,9-dimethylxanthene (0.067 g, 0.116 mmol), sodium tert-butoxide (1.157 g, 11.68 mmol) and tris(dibenzylideneacetone)dipalladium (0) (0.049 g, 0.053 mmol) in THF (10 mL) was heated at 80° C. overnight. The crude product was purified by Prep-HPLC (Solvent A=10% MeOH-90% water-0.1% TFA, Solvent B=90% MeOH-10% water-0.1% TFA. Column: Phenomenex Luna 30×100 mm, S10, Flow rate: 40 ml/min, 45-100% B, 30 min) to obtain 2-(4-fluorophenyl)cycloheptanone (400 mg, 1.94 mmol, 22% yield). LC-MS (M+H)$^+$=207.2. $^1$H NMR (400 MHz, methanol-d$_4$) δ ppm 7.13-7.31 (m, 2 H) 6.91-7.08 (m, 2 H) 3.68-3.86 (m, 1 H) 2.58-2.76 (m, 1 H) 2.42-2.57 (m, 1 H) 1.85-2.13 (m, 5 H) 1.57-1.75 (m, 1 H) 1.35-1.57 (m, 2 H).

Step AAF (2): Bromine (0.037 ml, 0.727 mmol) was added dropwise to a solution of cyclohexane-1,2-dione (1.35 g, 12.0 mmol) in CCl$_4$ (2.0 mL) at 0° C. The reaction mixture was allowed to warm to rt. The resulting solution was concentrated in vacuo to afford 2-bromo-7-(4-fluorophenyl)cycloheptanone. The crude product, which is prone to decomposition, was used for subsequent chemistry without purification or characterization.

Preparation AAG 1-amino-6-(4-fluorophenyl)piperidin-2-one

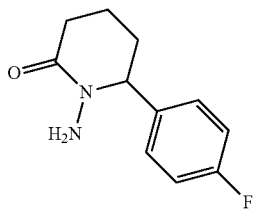 [SMILES: NN1C(=O)CCCC1c1ccc(F)cc1]

Step AAG (1): A mixture of tert-butyl hydrazinecarboxylate (1.45 g, 11.0 mmol) and 5-(4-fluorophenyl)-5-oxopentanoic acid (2.1 g, 10 mmol) in THF (20 mL) was stirred at 50° C. for 16 h. The reaction mixture was concentrated in vacuo to afford 5-(2-(tert-butoxycarbonyl)hydrazono)-5-(4-fluorophenyl)pentanoic acid (3.2 g, 9.87 mmol, 99% yield). LC-MS (M+H)$^+$ 325.24. The crude product was used for subsequent chemistry without purification.

Step AAG (2): 10% Palladium on carbon (0.5 g) was carefully added to a solution of 5-(2-(tert-Butoxycarbonyl)hydrazono)-5-(4-fluorophenyl)pentanoic acid (2.3 g, 7.09 mmol) in MeOH (30 mL) in a Parr hydrogenation bottle under nitrogen. The bottle was repeatedly evacuated and flushed with H$_2$ gas (50 psi). The mixture was shaken for 5 h. The vessel was flushed with nitrogen. The reaction contents were filtered through diatomaceous earth (Celite®). The plug and vessel were washed with fresh methanol. The filtrates were combined and concentrated in vacuo. The crude product was purified using silica gel column chromatography (10-80, EtOAc/chloroform, linear gradient) to afford tert-butyl 2-(4-fluorophenyl)-6-oxopiperidin-1-ylcarbamate (1.2 g, 55% yield). $^1$H NMR (500 MHz, chloroform-d) δ ppm 7.13-7.20 (an, 2 H) 7.06 (t, J=8.55 Hz, 2 H) 6.40 (br. s., 1 H) 4.91 (br. s., 1 H) 2.52-2.75 (m, 2 H) 2.20-2.40 (m, 1 H) 1.77-1.93 (m, 3 H) 1.44 (s, 9 H).

Step AAG (3): To a soln of tert-butyl 2-(4-fluorophenyl)-6-oxopiperidin-1-ylcarbamate (330 mg, 1.07 mmol) in CH$_2$Cl$_2$ (5 mL) was added TFA (1.00 mL, 13.0 mmol). The mixture was stirred at for 2 hrs. The solvent was removed in vacuo. The crude reaction was diluted with EtOAc (100 mL). The organic layer was separated and washed with saturated aqueous NaHCO$_3$ solution, dried over Na$_2$SO$_4$, filtered, and concentrated in vacuo to afford 1-amino-6-(4-fluorophenyl)piperidin-2-one (200 mg, 90% yield). LC-MS (M+H)$^+$ 209.26.

Preparation AAH 7-phenyl-4,5-dihydropyrazolo[1,5-a]pyridin-2-yl 1,1,2,2,3,3,4,4,4-nonafluorobutane-1-sulfonate

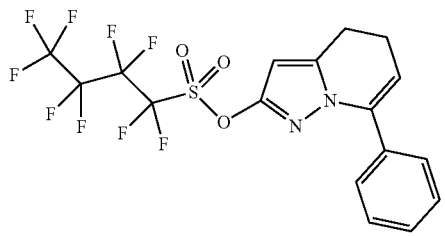 [SMILES: O=S(=O)(Oc1cc2n(n1)C(c1ccccc1)=CCC2)C(F)(F)C(F)(F)C(F)(F)C(F)(F)F]

Step AAH (1): Concentrated sulfuric acid (0.200 mL, 3.75 mmol) was added to a mixture of 5-oxo-5-phenylpentanoic acid (4.0 g, 20.81 mmol), ethylene glycol (6.96 mL, 125 mmol), and trimethylorthoformate (6.90 mL, 62.4 mmol) in dichloromethane (40 mL) at it under nitrogen. The mixture was stirred at it for 16 h. Solid NaHCO$_3$ (2.0 g) was carefully added. The resulting mixture was concentrated in vacuo. The residue was taken up in methanol (50 mL) and the vessel was placed in a it water bath. Aqueous 50% NaOH (5 mL) was slowly added and the mixture was stirred at for 16 h. The mixture was concentrated in vacuo (to remove methanol) and the resulting aqueous layer was neutralized to pH 2. The aqueous layer was extracted with EtOAc. The organic layer was dried over Na$_2$SO$_4$, filtered and concentrated in vacuo. The residue was crystallized from diethyl ether to afford 4-(2-phenyl-1,3-dioxolan-2-yl)butanoic acid (850 mg, 17% yield) which was contained with a significant portion of 5-oxo-5-phenylpentanoic acid. LC-MS (M+H)$^+$ 235.1.

Step AAH (2): To a solution of 4-(2-phenyl-1,3-dioxolan-2-yl)butanoic acid (490 mg, 2.07 mmol) in anhydrous Et$_2$O (10 mL) was added oxalyl dichloride (526 mg, 4.15 mmol). Anhydrous DMF (2 drops) was added and the resulting mixture stirred at rt for 1 h. The crude reaction was concentrated in vacuo. The residue was diluted with toluene (10 mL) and reconcentrated to afford 4-(2-phenyl-1,3-dioxolan-2-yl)butanoyl chloride (2.07 mmol).

Step AAH (3): To a soln of 2,2-dimethyl-1,3-dioxane-4,6-dione (329 mg, 2.281 mmol) in dichloromethane (10 mL) was added DMAP (405 mg, 3.32 mmol). After stirring for 10 min, a solution of 4-(2-phenyl-1,3-dioxolan-2-yl)butanoyl chloride (2.07 mmol) in dichloromethane was added at 0° C. under nitrogen. The mixture was stirred at rt for 3 hrs. The crude reaction mixture was concentrated in vacuo. The residue was dissolved in EtOAc. The organic layer was sequentially washed with 1.0 N aqueous HCl, 1.0 N aqueous NaOH, and water. The organic layer was dried over $Na_2SO_4$, filtered and concentrated in vacuo to 2,2-dimethyl-5-(4-(2-phenyl-1,3-dioxolan-2-yl)butanoyl)-1,3-dioxane-4,6-dione (700 mg, 1.93 mmol, 93% yield).

Step AAH (4): To a solution of 2,2-dimethyl-5-(4-(2-phenyl-1,3-dioxolan-2-yl)butanoyl)-1,3-dioxane-4,6-dione (4.0 g, 11.04 mmol) in xylene (30 mL) was added aniline (1.21 mL, 13.3 mmol). The rxn was stirred at 140° C. for 2 h. The crude reaction contents were directly loaded onto silica gel and purified by silica gel column chromatography (60% EtOAc/hexanes) to afford 3-oxo-N-phenyl-6-(2-phenyl-1,3-dioxolan-2-yl)hexanamide (3.0 g, 77% yield). $^1$H NMR (500 MHz, chloroform-d) δ ppm 9.16 (br. s., 1 H) 7.54 (d, J=7.63 Hz, 2 H) 7.44 (d, J=7.02 Hz, 2 H) 7.28-7.39 (m, 5 H) 7.12 (t, J=7.48 Hz, 1 H) 3.97-4.07 (m, 2 H) 3.72-3.82 (m, 2 H) 3.53 (s, 2 H) 2.60 (t, J=7.32 Hz, 2 H) 1.89-1.97 (m, 2 H) 1.67-1.79 (m, 2 H).

Step AAH (5): To a soln of 3-oxo-N-phenyl-6-(2-phenyl-1,3-dioxolan-2-yl)hexanamide (444 mg, 1.256 mmol) in THF (1 mL) was added hydrazine (0.059 mL, 1.88 mmol). The mixture was stirred at rt for 2 h, then at 65° C. for 2 h. The reaction mixture was concentrated in vacuo. Dichloromethane (10 mL) was added to the crude residue. After cooling to 0° C., the product crystallized out. The solid was collected by vacuum filtration and dried under high vacuum to afford 3-(3-(2-phenyl-1,3-dioxolan-2-yl)propyl)-1H-pyrazol-5(4H)-one (250 mg, 73% yield). LC-MS (M+H)$^+$ 275.1.

Step AAH (6): To a soln of 3-(3-(2-phenyl-1,3-dioxolan-2-yl)propyl)-1H-pyrazol-5(4H)-one (1.1 g, 4.01 mmol) in acetonitrile (15 mL) was added trichloroborane (1.0 M in $CH_2Cl_2$, 10.02 mL, 10.02 mmol) at −10° C. under nitrogen. The mixture was allowed to warm to rt, and stirred at rt for 6 h. The reaction was quenched with 50 mL of aqueous 0.1 N HCl (50 mL). The mixture was extracted with dichloromethane (3×80 mL). The organic layer was washed with brine, dried over $Na_2SO_4$, filtered and concentrated in vacuo. The product was purified using silica gel column chromatography (60% EtOAc/hexanes) to afford 7-phenyl-4,5-dihydropyrazolo[1,5-a]pyridin-2-ol (510 mg, 60% yield) as a solid. LC-MS (M+H)$^+$ 213.06. $^1$H NMR (500 MHz, methanol-$d_4$) δ ppm 7.42-7.53 (m, 2 H) 7.29-7.40 (m, 3 H) 5.55 (s, 1 H) 5.50 (t, J=4.88 Hz, 1 H) 2.86 (t, J=7.63 Hz, 2 H) 2.35-2.45 (m, 2 H).

Step AAH (7): To a soln of 7-phenyl-4,5-dihydropyrazolo[1,5-a]pyridin-2-ol (500 mg, 2.356 mmol) in THF (15 mL) was added NaHMDS (1.0 M in THF, 2.94 mL, 2.94 mmol) at −78° C. under nitrogen. After stirring for 10 min, 1,1,2,2,3,3,4,4,4-nonafluorobutane-1-sulfonyl fluoride (1281 mg, 4.24 mmol) was added. The mixture was allowed to warm from −78° C. to rt over 3 h. The reaction was diluted with EtOAc (200 mL) and washed sequentially with 0.1 N aqueous sodium hydroxide, water, and brine. The organic layer was dried over $Na_2SO_4$, filtered, and concentrated in vacuo. The residue was purified using silica gel column chromatography (30% EtOAc/hexanes) to afford 7-phenyl-4,5-dihydropyrazolo[1,5-a]pyridin-2-yl 1,1,2,2,3,3,4,4,4-nonafluorobutane-1-sulfonate (1.0 g, 86% yield). LC-MS (M+H)$^+$ 495.12.

Preparation AAI 5-(chloromethyl)-2-(4-fluorophenyl)hex-5-enoic acid

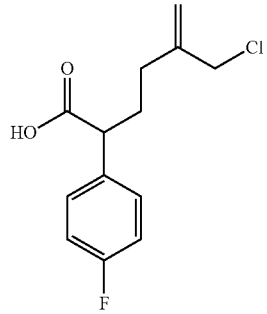 [SMILES: C=C(CCl)CCC(C(=O)O)c1ccc(F)cc1]

Step AAI (1): A 500 mL round bottom flask was charged with ethyl 3-chloropropanoate (10.0 g, 73.2 mmol), titanium (IV) isopropoxide (2.19 mL, 7.32 mmol) in ethyl ether (50 mL), and cooled to 0° C. A solution of ethyl magnesiumbromide (73.2 mL, 220 mmol) was added dropwise over 2 h to the stirred solution. The reaction was stirred at 0° C. for an additional 2 h. The reaction mixture was quenched slowly with 10% $H_2SO_4$ (100 mL). The organic layer was washed with $H_2O$ (100 mL), aq sat. $NaHCO_3$ solution (100 mL), brine (100 mL), dried over sodium sulfate and concentrated in vacuo. The crude product was used for subsequent chemistry without purification. $^1$H NMR (400 MHz, CHLOROFORM-d) δ ppm 3.80 (2 H, t, J=6.9 Hz), 2.16 (1 H, br. s.), 1.28 (2 H, t, J=7.2 Hz), 0.80-0.89 (2 H, m), 0.52-0.63 (2 H, m).

Step AAI (2): A 500 mL round bottom flask was charged with 1-(2-chloroethyl)cyclopropanol (8.83 g, 73.2 mmol), triethylamine (14.3 mL, 103 mmol) in DCM (100 mL), and cooled to 0° C. A solution of methanesulfonyl chloride (6.52 mL, 84.0 mmol) was added dropwise over 30 min to the stirred solution. After an additional 30 min, the reaction mixture was quenched with $H_2O$. The organic layer was collected and was sequentially washed with 10% $H_2SO_4$, sat $NaHCO_3$, and brine. The organic layer was dried over sodium sulfate, and concentrated in vacuo. The crude product was used for subsequent chemistry without purification. $^1$H NMR (500 MHz, CHLOROFORM-d) δ ppm 0.85 (t, 2 H) 1.35 (t, 2 H) 2.33 (t, J=6.87 Hz, 2 H) 2.94-3.09 (m, 3 H) 3.81 (t, J=6.87 Hz, 2 H).

Step AAI (3): A solution of 1-(2-chloroethyl)cyclopropyl methanesulfonate (12.0 g, 60.4 mmol) in diethyl ether (100 mL) was added dropwise with stirring to a solution of magnesium bromide (22.2 g, 121 mmol) in diethyl ether (200 mL). The mixture was heated to 35° C. for 16 h. The reaction mixture was cooled and was treated with sat'd ammonium chloride. The organic layer was separated and then washed with water, brine, and dried over sodium sulfate. The mixture was concentrated in vacuo to afford 2-(bromomethyl)-4-chlorobut-1-ene (10 g, 54.5 mmol, 90% yield). $^1$H NMR (500 MHz, CHLOROFORM-d) δ ppm 5.34 (1 H, s), 5.10 (1 H, s), 4.01 (2 H, s), 3.62-3.78 (2 H, m), 2.72 (2 H, t, J=6.9 Hz).

Step AAI (4): NaHMDS 2.0 M in THF (11.0 mL, 21.9 mmol) was added to a solution of 2-(4-fluorophenyl)acetic acid (1.50 g, 9.73 mmol) in THF (19.5 mL) at 0° C. The resulting mixture was stirred for 20 min at 0° C., then neat 2-(bromomethyl)-4-chlorobut-1-ene (1.96 g, 10.7 mmol) was added. After 10 min, the mixture was quenched with a water (5 mL) and concentrated in vacuo. The mixture was diluted with EtOAc and the organic layer was washed with 1N HCl, then brine, dried over sodium sulfate, and concentrated in vacuo to afford 5-(chloromethyl)-2-(4-fluorophenyl)hex-5-enoic acid. The titled product was used for subsequent chemistry without further purification. LC-MS (M–H)⁻ 255.1. ¹H NMR (500 MHz, CHLOROFORM-d) δ ppm 7.24-7.41 (2 H, m), 6.96-7.11 (2 H, m), 4.91 (2 H, d, J=3.1 Hz), 3.82 (1 H, dd, J=8.7, 6.9 Hz), 3.60 (2 H, t, J=7.2 Hz), 2.84 (1 H, dd, J=15.0, 8.9 Hz), 2.39-2.55 (3 H, m).

Preparation AAJ 5-(chloromethyl)-2-(4-(trifluoromethoxy)phenyl)hex-5-enoic acid

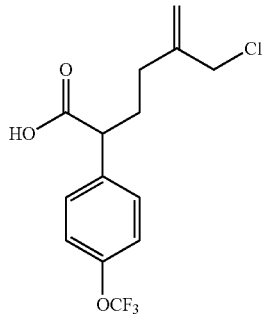 [SMILES: C=C(CCl)CCC(C(=O)O)c1ccc(OC(F)(F)F)cc1]

Step AAJ (1): NaHMDS 2.0 M in THF (10.2 mL, 20.4 mmol) was added to a solution of 2-(4-(trifluoromethoxy)phenyl)acetic acid (2.00 g, 9.08 mmol) in THF (18.2 mL) at 0° C. The resulting mixture was stirred for 20 min at 0° C., then neat 2-(bromomethyl)-4-chlorobut-1-ene (1.83 g, 9.99 mmol, from Step AAI (3)) was added. The mixture was quenched at 0° C. after 10 min with water (5 mL) and concentrated in vacuo. The mixture was diluted with EtOAc and the organic layer was extracted with 1N HCl, then brine, dried over sodium sulfate, and concentrated in vacuo to afford after purification by silica gel column chromatography (60-100% EtOAc/chloroform), 6-chloro-4-methylene-2-(4-(trifluoromethoxy)phenyl)hexanoic acid (2.21 g, 6.85 mmol, 75% yield) as a pale-yellow oil. LC-MS (M–H)⁻ 321.1. 1H NMR (500 MHz, CHLOROFORM-d) δ ppm 7.35-7.44 (2 H, m), 7.20 (2 H, d, J=8.5 Hz), 4.89-4.97 (2 H, m), 3.81-3.93 (1 H, m), 3.55-3.66 (2 H, m), 2.86 (1 H, dd, J=15.3, 8.9 Hz), 2.39-2.57 (3 H, m).

Preparation AAK 5-chloro-2-(4-(trifluoromethoxy)phenyl)pentanoic acid

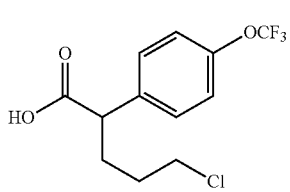 [SMILES: O=C(O)C(CCCCl)c1ccc(OC(F)(F)F)cc1]

Step AAK (1): 2-(4-(Trifluoromethoxy)phenyl)acetic acid (3.54 g, 16.1 mmol) was deprotonated with NaHMDS (2.0 M in THF, 18.1 mL, 36.2 mmol) and reacted with 1-chloro-3-iodopropane (3.62 g, 17.7 mmol) using a procedure analogous to Step AC (1) to afford after purification by silica gel column chromatography (25-50% EtOAc/hexane), 5-chloro-2-(4-(trifluoromethoxy)phenyl)pentanoic acid (0.48 g, 1.62 mmol, 10% yield) as a pale-yellow oil. LC-MS (M–H)⁻ 295.2.

Preparation AAL 6-chloro-2-(4-(methylsulfonyl)phenyl)hexanoic acid

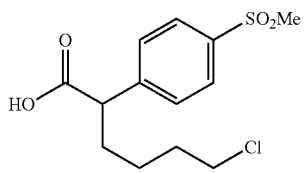 [SMILES: CS(=O)(=O)c1ccc(C(CCCCCl)C(=O)O)cc1]

Step AAL (1): 2-(4-(Methylthio)phenyl)acetic acid (1.00 g, 5.49 mmol) was deprotonated with NaHMDS 2.0 M in THF (5.49 mL, 11.0 mmol) and reacted with 1-chloro-4-iodobutane (0.672 mL, 5.49 mmol) using a procedure analogous to Step AC (1) to afford 6-chloro-2-(4-(methylthio)phenyl)hexanoic acid (1.36 g, 4.99 mmol, 91% yield) as a pale-yellow oil. LC-MS (M–H)⁻ 271.1. ¹H NMR (500 MHz, CHLOROFORM-d) δ ppm 8.95 (1 H, br. s.), 7.12-7.28 (4 H, m), 3.39-3.55 (3 H, m), 2.39-2.50 (3 H, m), 1.97-2.19 (1 H, m), 1.59-1.86 (3 H, m), 1.28-1.51 (2 H, m).

Step AAL (2): A solution of 6-chloro-2-(4-(methylthio)phenyl)hexanoic acid (1.10 g, 4.03 mmol) in DCM (25 mL) was cooled in an ice bath and a solution of 3-chloroperoxybenzoic acid (2.10 g, 12.2 mmol) in DCM (10 mL) was added dropwise. After warming to rt and stirring for 5 h, the reaction mixture was taken up into Et₂O and washed with 1N HCl and extracted with Et₂O (3×). The combined organic extracts were washed with brine, dried over sodium sulfate, and concentrated in vacuo. Silica gel column chromatography (0-10% MeOH/chloroform) afforded 6-chloro-2-(4-(methylsulfonyl)phenyl)hexanoic acid (700 mg, 2.30 mmol, 57% yield) as a white solid. LC-MS (2M–H)⁻ 607.1. ¹H NMR (500 MHz, CHLOROFORM-d) δ ppm 7.91 (2 H, d, J=7.3 Hz), 7.42-7.59 (2 H, m), 3.66 (1 H, br. s.), 3.52 (2 H, t, J=6.6 Hz), 3.07 (3 H, s), 2.12 (1 H, br. s.), 1.80 (3 H, br. s.), 1.47 (2 H, br. s.).

Preparation AAM 6-chloro-2-(4-(trifluoromethylsulfonyl)phenyl)hexanoic acid

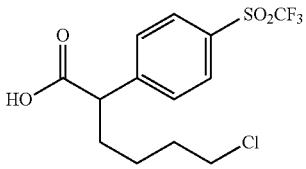

Step AAM (1): 2-(4-(Trifluoromethylthio)phenyl)acetic acid (4.7 g, 19.9 mmol) was deprotonated with NaHMDS 2.0 M in THF (19.9 mL, 39.8 mmol) and reacted with 1-chloro-4-iodobutane (2.44 mL, 19.9 mmol) using a procedure analogous to Step AC (1) to afford 6-chloro-2-(4-(trifluoromethylthio)-phenyl)hexanoic acid (3.07 g, 9.40 mmol, 47% yield) as a pale-yellow oil. LC-MS (M−H)⁻ 325.2. ¹H NMR (500 MHz, CHLOROFORM-d) δ ppm 1.32-1.51 (m, 2 H) 1.69-1.87 (m, 3 H) 2.01-2.17 (m, 1 H) 3.49 (t, J=6.56 Hz, 2 H) 3.59 (t, J=7.63 Hz, 1 H) 7.36 (d, J=8.24 Hz, 2 H) 7.61 (d, J=8.24 Hz, 2 H).

Step AAM (2): A solution of 6-chloro-2-(4-(trifluoromethylthio)-phenyl)hexanoic acid (1.5 g, 4.59 mmol) in DCM (25 mL) was cooled in an ice bath and a solution of 3-chloroperoxybenzoic acid (2.10 g, 12.2 mmol) in DCM (10 mL) was added dropwise. After warming to rt and stirring for 5 h, the reaction mixture was taken up into Et₂O and washed with 1N HCl and extracted with Et₂O (3×). The combined organic extracts were washed with brine, dried over sodium sulfate, and concentrated in vacuo. Silica gel column chromatography (30-100% EtOAc/hexanes) afforded 6-chloro-2-(4-(trifluoromethylsulfonyl)phenyl)hexanoic acid (420 mg, 1.17 mmol, 26% yield). LC-MS (2M−H)⁻ 715.0.

Preparation AAN 6-chloro-2-(4-ethoxyphenyl)hexanoic acid

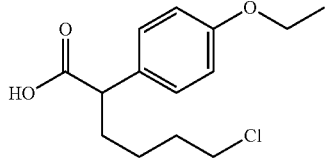 [SMILES: CCOc1ccc(C(CCCCCl)C(=O)O)cc1]

Step AAN (1): 2-(4-Ethoxyphenyl)acetic acid (2.00 g, 11.1 mmol) was deprotonated with NaHMDS 2.0 M in THF (12.5 mL, 25.0 mmol) and reacted with 1-chloro-4-iodobutane (1.49 mL, 12.2 mmol) using a procedure analogous to Step AC (1) and after silica gel column chromatography (30-80% EtOAc/hexanes) afforded 6-chloro-2-(4-ethoxyphenyl)hexanoic acid (1.10 g, 4.06 mmol, 37% yield) as a pale-yellow oil. LC-MS (M+Na)⁺ 293.1.

Preparation AAO 6-chloro-2-phenylhexanoic acid

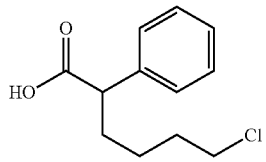 [SMILES: O=C(O)C(CCCCCl)c1ccccc1]

Step AAO (1): 2-Phenylacetic acid (2.19 g, 16.1 mmol) was deprotonated with NaHMDS 2.0 M in THF (18.1 mL, 36.2 mmol) and reacted with 1-chloro-4-iodobutane (3.87 g, 17.7 mmol) using a procedure analogous to Step AC (1) to afford 6-chloro-2-phenylhexanoic acid (3.57 g, quantitative yield) as a pale yellow oil. LC-MS (M−H)⁻ 225.1. ¹H NMR (500 MHz, CHLOROFORM-d) δ ppm 7.25-7.39 (5 H, m), 3.58 (1 H, t, J=7.6 Hz), 3.52 (2 H, t, J=6.7 Hz), 2.12 (1 H, dddd, J=13.4, 10.5, 7.8, 5.5 Hz), 1.73-1.90 (3 H, m), 1.34-1.54 (2 H, m).

EXAMPLE 1

(Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine

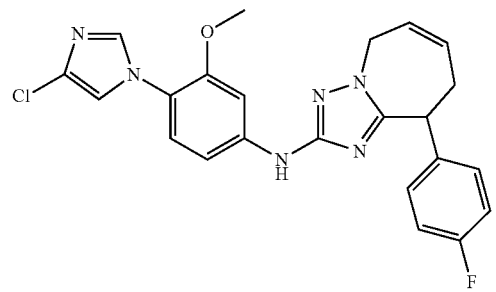 [SMILES: COc1cc(Nc2nc3n(n2)CC=CCC3c2ccc(F)cc2)ccc1-n1cnc(Cl)c1]

Step A: A solution of N-ethyldiisopropylamine (4.41 mL, 25.3 mmol) in DMF (10 mL) was added to a 50 mL round bottom flask charged with a mixture of methyl 4-(4-chloro-1H-imidazol-1-yl)-3-methoxyphenylcarbamimidothioate, hydroiodide (1.5 g, 3.53 mmol) from preparation A, 2-(4-fluorophenyl)pent-4-enoic acid (1.47 g, 7.58 mmol) from preparation AA, 1-hydroxybenzotriazole hydrate (1.55 g, 10.1 mmol), and 1-ethyl-3-(3-dimethylaminopropyl)carbodiimide hydrochloride (1.94 g, 10.1 mmol). The resulting mixture was magnetically stirred under nitrogen for 18 h at rt. The crude reaction mixture was poured into water (250 mL) and extracted with EtOAc (3×150 mL). Hexane (~5% total volume) was added to the combined organics. The organic layer was washed with brine, dried over sodium sulfate and concentrated in vacuo. The crude product was purified using silica gel column chromatography (0-5% EtOAc/chloroform, linear gradient) to afford methyl N-4-(4-chloro-1H-imidazol-1-yl)-3-methoxyphenyl-N'-(2-(4-fluorophenyl)pent-4-enoyl)carbamimidothioate (1.03 g, 60% yield) as clear yellow viscous residue. LC-MS (M+H)⁺=473.1.

Step B: A solution of allylhydrazine (70% solution in water) (0.55 mL, 5.29 mmol) was added to a flask charged with a solution of methyl N-4-(4-chloro-1H-imidazol-1-yl)-3-methoxyphenyl-N'-(2-(4-fluorophenyl)pent-4-enoyl)carbamimidothioate (500 mg, 1.057 mmol) in ethanol (10 mL). The flask was stoppered and heated at 80° C. for 3 hr. After cooling to rt, the reaction mixture was concentrated in vacuo. The crude product was purified using silica gel column chromatography (0-5% EtOAc/chloroform, linear gradient) to afford 1-allyl-N-(4-(4-chloro-1H-imidazol-1-yl)-3-methoxyphenyl)-5-(1-(4-fluorophenyl)but-3-enyl)-1H-1,2,4-triazol-3-amine (350 mg, 0.730 mmol, 69% yield) as a clear residue. LC-MS (M+H)⁺ 479.2. ¹H NMR (500 MHz, chloroform-d) δ ppm 7.51-7.56 (m, 2 H) 7.22-7.27 (m, 2 H) 7.13 (d, J=8.55 Hz, 1 H) 6.99-7.06 (m, 3 H) 6.89 (dd, J=8.55, 2.44 Hz, 1 H) 6.72 (s, 1 H) 5.68-5.84 (m, 2 H) 5.20 (d, J=10.38 Hz, 1 H) 5.06 (d, J=17.09 Hz, 2 H) 5.02 (d, J=10.07 Hz, 1 H) 4.44-4.60 (m, 2 H) 3.99 (t, J=7.63 Hz, H) 3.85 (s, 3 H) 3.00 (dt, J=14.34, 7.17 Hz, 1 H) 2.72 (dt, J=14.11, 7.13 Hz, 1 H).

Step C: Hoveyda-Grubbs Catalyst 2nd Generation (109 mg, 0.173 mmol) was added to a solution of 1-allyl-N-(4-(4-chloro-1H-imidazol-1-yl)-3-methoxyphenyl)-5-(1-(4-fluorophenyl)but-3-enyl)-1H-1,2,4-triazol-3-amine, TFA (410 mg, 0.691 mmol) in DCE (50.0 mL). The flask was flushed with nitrogen, sealed, and heated at 70° C. for 72 h. The reaction mixture was cooled to rt and an additional portion of Hoveyda-Grubbs Catalyst 2nd Generation (109 mg, 0.173 mmol) was added. The mixture was flushed with nitrogen, sealed, and heated at 70° C. for an additional 24 h. The crude reaction contents were directly loaded onto silica gel and the product was purified using silica gel column chromatography (10-75% EtOAc/chloroform, linear gradient) to afford (Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine (40 mg, 13% yield) as a solid. LC-MS (M+H)$^+$ 451.1. $^1$H NMR (500 MHz, chloroform-d) δ ppm 7.52 (d, J=1.53 Hz, 1 H) 7.40 (d, J=2.14 Hz, 1 H) 7.24 (dd, J=8.55, 5.19 Hz, 2 H) 7.09 (d, J=8.55 Hz, 1 H) 7.01-7.07 (m, 3 H) 6.86 (dd, J=8.39, 2.29 Hz, 1 H) 6.78 (s, 1 H) 5.94-6.05 (m, 1 H) 5.84-5.94 (m, 1 H) 4.84 (dt, J=17.70, 2.14 Hz, 1 H) 4.57-4.66 (m, 1 H) 4.50 (dd, J=8.39, 3.51 Hz, 1 H) 3.80 (s, 3 H) 2.82-2.95 (m, 1 H) 2.71-2.82 (m, 1 H).

EXAMPLE 2 AND EXAMPLE 3

(S,Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine and (R,Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine

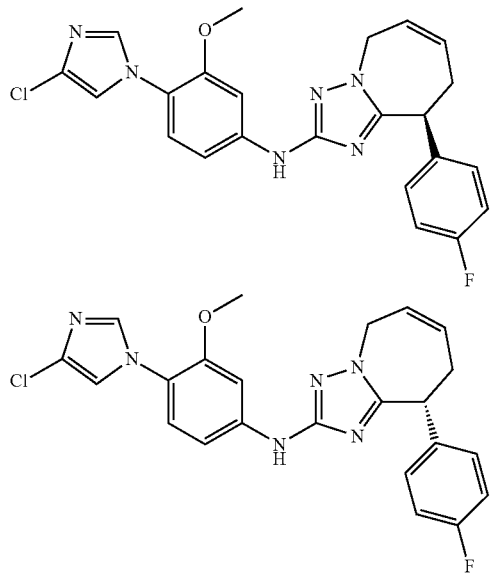

Step A: A racemic mixture of (Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine (40 mg from Example 1) was purified using chiral supercritical fluid chromatography (SFC) to afford 15.7 mg of peak A (example 2) and 17.3 mg of peak B (example 3). SFC Method: Chiralpak AD-H (30×250 mm, 5 uM), 35% methanol (0.1% diethylamine) in CO$_2$, 35° C., 70 mL/min, absorbance 220 nm, t$_R$ (peak A) 28.6 min, t$_R$ (peak B) 41.5 min. The absolute stereochemistry of individual enantiomers (examples 2 and 3) was not determined. LC-MS and $^1$H NMR analytical data for the separated enantiomers was identical to the racemic mixture (example 1).

EXAMPLE 4

(Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine

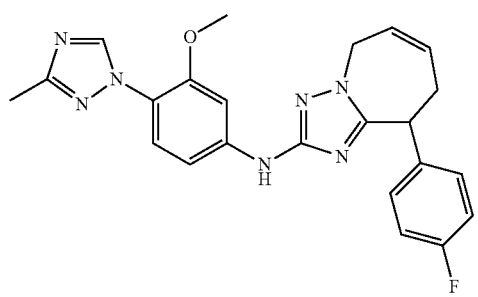 [SMILES: COc1cc(Nc2nc3n(n2)CC=CCC3c2ccc(F)cc2)ccc1-n1cnc(C)n1]

Step A: Methyl 3-methoxy-4-(3-methyl-1H-1,2,4-triazol-1-yl)phenylcarbamimidothioate, hydroiodide, (1.928 g, 6.95 mmol, from preparation F) and 2-(4-fluorophenyl)pent-4-enoic acid (1.62 g, 8.34 mmol, from preparation AA) were coupled using a procedure analogous to Step A of Example 1 to afford methyl N'-2-(4-fluorophenyl)pent-4-enoyl-N-(3-methoxy-4-(3-methyl-1H-1,2,4-triazol-1-yl)phenyl)carbamimidothioate (1.62 g, 3.57 mmol, 64% yield) as a white solid. LC-MS (M+H)$^+$=454.2.

Step B: Methyl N'-2-(4-fluorophenyl)pent-4-enoyl-N-(3-methoxy-4-(3-methyl-1H-1,2,4-triazol-1-yl)phenyl)carbamimidothioate (0.62 g, 1.367 mmol) was reacted with allylhydrazine (70% solution in water, 0.55 mL, 5.47 mmol) using a procedure analogous to Step B of Example 1 to provide 1-allyl-5-(1-(4-fluorophenyl)but-3-enyl)-N-(3-methoxy-4-(3-methyl-1H-1,2,4-triazol-1-yl)phenyl)-1H-1,2,4-triazol-3-amine. The purified product was dissolved in 0.1% TFA/dichloromethane and reconcentrated to afford 1-allyl-5-(1-(4-fluorophenyl)but-3-enyl)-N-(3-methoxy-4-(3-methyl-1H-1,2,4-triazol-1-yl)phenyl)-1H-1,2,4-triazol-3-amine, TFA salt (446 mg, 0.692 mmol, 51% yield) as a clear solid residue. LC-MS (M+H)$^+$=560.3.

Step C: 1-Allyl-5-(1-(4-fluorophenyl)but-3-enyl)-N-(3-methoxy-4-(3-methyl-1H-1,2,4-triazol-1-yl)phenyl)-1H-1,2,4-triazol-3-amine, TFA salt (446 mg, 0.971 mmol) was subject to a ring closing metathesis procedure analogous to Step C of Example 1 (120° C., 3 hr, 25 mol % Hoveyda-Grubbs Catalyst 2nd Generation) to afford (Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine (26 mg, 0.059 mmol, 6.08% yield) as a clear residue. LC-MS (M+H)$^+$=432.2. $^1$H NMR (500 MHz, chloroform-d) δ ppm 9.27 (br. s., 1 H) 8.90 (br. s., 1 H) 7.64 (dd, J=8.85, 3.05 Hz, 1 H) 7.40 (d, J=2.44 Hz, 1 H) 7.19-7.24 (m, 2 H) 7.06-7.14 (m, 3 H) 6.08 (d, J=6.10 Hz, 1 H) 5.94 (dd, J=10.38, 4.27

Hz, 1 H) 4.89 (d, J=17.70 Hz, 1 H) 4.58-4.65 (m, 2 H) 3.95 (s, 3 H) 2.94-3.05 (m, 1 H) 2.80-2.94 (m, 2 H) 2.57 (s, 3 H).

EXAMPLE 5 AND EXAMPLE 6

(S,Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine and (R,Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine

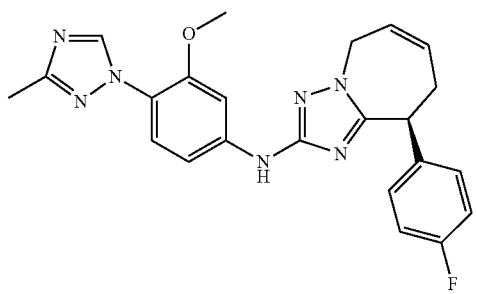

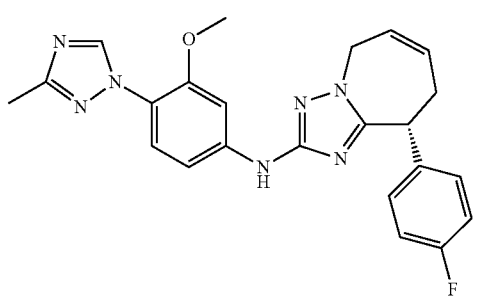

Step A: A racemic mixture of (Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine (26 mg from Example 4) was purified using chiral supercritical fluid chromatography (SFC) to afford 12 mg of peak A (example 5) and 12 mg of peak B (example 6). SFC Method: Chiralpak OJ-H (30×250 mm, 5 uM), 20% methanol (0.1% diethylamine) in $CO_2$, 35° C., 70 mL/min, absorbance 268 nm, $t_R$ (peak A) 8.2 min, $t_R$ (peak B) 11.7 min. The absolute stereochemistry of individual enantiomers (examples 5 and 6) was not determined. LC-MS and $^1$H NMR analytical data for the separated enantiomers was identical. LC-MS (M+H)$^+$=432.2. $^1$H NMR (500 MHz, chloroform-d) δ ppm 8.44 (s, 1 H) 7.51 (d, J=8.55 Hz, 1 H) 7.48 (d, J=2.14 Hz, 1 H) 7.25 (dd, J=8.70, 5.34 Hz, 2 H) 7.04 (t, J=8.55 Hz, 2 H) 6.84 (dd, J=8.55, 2.14 Hz, 1 H) 6.72 (s, 1 H) 5.94-6.03 (m, 1 H) 5.83-5.94 (m, 1 H) 4.84 (ddd, J=17.78, 4.35, 1.98 Hz, 1 H) 4.61 (ddd, J=17.78, 4.96, 1.68 Hz, 1 H) 4.50 (dd, J=8.24, 3.66 Hz, 1 H) 3.86 (s, 3 H) 2.70-2.90 (m, 2 H) 2.48 (s, 3 H).

EXAMPLE 7

9-(4-fluorophenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine 2,2,2-trifluoroacetate

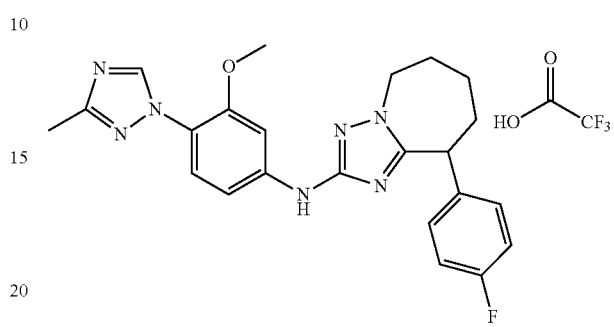

Step A: 10% Palladium-Carbon (2 mg, 0.019 mmol) was added to a solution of (Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine (11 mg, 0.025 mmol) in methanol (10 mL) under an atmosphere of dry nitrogen. The flask was then flushed with hydrogen from a balloon, and left to stir for 16 h under the hydrogen balloon. The crude reaction contents were filtered through diatomaceous earth (Celite®). The filtrate was concentrated filtrate in vacuo. The crude product was purified using reverse phase preparatory-HPLC (MeOH/water/TFA) to afford 9-(4-fluorophenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine, TFA (5.4 mg, 9.86 μmol, 39% yield). LC-MS (M+H)$^+$ 434.2. $^1$H NMR (500 MHz, chloroform-d) δ ppm 9.96 (br. s., 1 H) 8.95 (br. s., 1 H) 7.64 (d, J=8.85 Hz, 1 H) 7.38 (d, J=2.14 Hz, 1 H) 7.14 (dd, J=8.85, 2.14 Hz, 1 H) 7.01-7.12 (m, 4 H) 4.50 (d, J=6.10 Hz, 1 H) 4.30-4.45 (m, 1 H) 4.15-4.30 (m, 1 H) 3.94 (s, 3 H) 2.55 (s, 3 H) 2.36 (d, J=7.32 Hz, 1 H) 2.13 (d, J=14.65 Hz, 1 H) 1.94 (br. s., 4 H).

EXAMPLE 8

(Z)—N-(4-(4-chloro-1H-imidazol-1-yl)-3-methoxyphenyl)-9-(2,4-dichlorophenyl)-8,9-dihydro-5H-[1,2,4]triazolo[1,5-a]azepin-2-amine

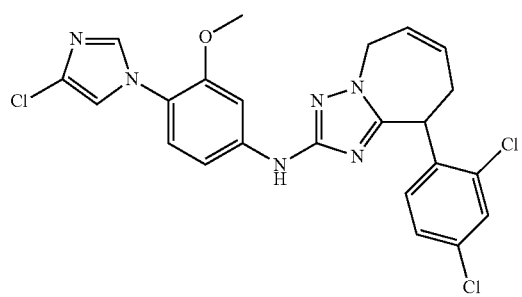 [SMILES: COc1cc(Nc2nc3n(n2)CC=CCC3c2ccc(Cl)cc2Cl)ccc1-n1cnc(Cl)c1]

Step A: Methyl 3-methoxy-4-(3-methyl-1H-1,2,4-triazol-1-yl)phenylcarbamimidothioate, hydroiodide, (800 mg, 2.70 mmol, from preparation F) and 2-(2,4-dichlorophenyl)pent-4-enoic acid (661 mg, 2.70 mmol, from preparation AB) were coupled using a procedure analogous to Step A of Example 1 to afford (Z)-methyl N'-4-(4-chloro-1H-imidazol-1-yl)-3-methoxyphenyl-N-(2-(2,4-dichlorophenyl)pent-4-enoyl)carbamimidothioate (1.4 g, 100% yield) as a dark yellow residue. LC-MS (M+H)+ 522.99.

Step B: Methyl N-4-(4-chloro-1H-imidazol-1-yl)-3-methoxyphenyl-N-(2-(2,4-dichlorophenyl)pent-4-enoyl)carbamimidothioate (1.5 g, 2.86 mmol) was reacted with allylhydrazine (70% solution in water, 3.83 g, 37.2 mmol) using a procedure analogous to Step B of Example 1 to provide 1-allyl-N-(4-(4-chloro-1H-imidazol-1-yl)-3-methoxyphenyl)-5-(1-(2,4-dichlorophenyl)but-3-enyl)-1H-1,2,4-triazol-3-amine (450 mg, 26% yield) as a clear solid residue. LC-MS (M+H)+=531.1.

Step C: 1-Allyl-N-(4-(4-chloro-1H-imidazol-1-yl)-3-methoxyphenyl)-5-(1-(2,4-dichlorophenyl)but-3-enyl)-1H-1,2,4-triazol-3-amine (450 mg, 0.094 mmol) was subjected to a ring closing metathesis procedure analogous to Step C of Example 1 (160° C., 15 min, 25 mol % Hoveyda-Grubbs Catalyst 2nd Generation) to afford (Z)—N-(4-(4-chloro-1H-imidazol-1-yl)-3-methoxyphenyl)-9-(2,4-dichlorophenyl)-8,9-dihydro-5H-[1,2,4]triazolo[1,5-a]azepin-2-amine (64.5 mg, 15% yield) as a dark brown solid. LC-MS (M+H)+=501.1. 1H NMR (500 MHz, chloroform-d) δ ppm 7.51 (d, J=1.53 Hz, 1 H) 7.45 (d, J=2.14 Hz, 1 H) 7.39 (d, J=2.14 Hz, 1 H) 7.25-7.30 (m, 1 H) 7.21-7.25 (m, 1 H) 7.09 (d, J=−8.55 Hz, 1 H) 7.02 (d, J=1.53 Hz, 1 H) 6.80 (dd, J=8.39, 2.29 Hz, 1 H) 6.63 (s, 1 H) 5.99-6.10 (m, 2 H) 4.81-5.01 (m, 3 H) 3.79 (s, 3 H) 2.78-2.97 (m, 1 H) 2.58-2.78 (m, 1 H).

EXAMPLE 9

(Z)—N-(4-(4-chloro-1H-imidazol-1-yl)-3-methoxyphenyl)-9,9-dimethyl-8,9-dihydro-5H-[1,2,4]triazolo[1,5-a]azepin-2-amine 2,2,2-trifluoroacetate

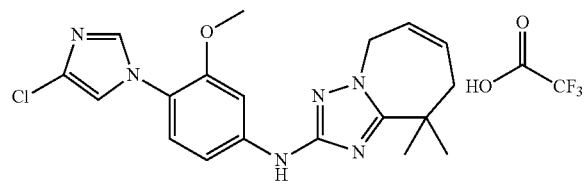

Step A: Methyl 3-methoxy-4-(3-methyl-1H-1,2,4-triazol-1-yl)phenylcarbamimidothioate, hydroiodide, (183 mg, 0.618 mmol, from preparation A) and 2,2-dimethylpent-4-enoic acid (79 mg, 0.618 mmol) were coupled using a procedure analogous to Step A of Example 1 to afford methyl N-4-(4-chloro-1H-imidazol-1-yl)-3-methoxyphenyl-N'-(2,2-dimethylpent-4-enoyl)carbamimidothioatemethyl (251 mg, 100% yield) as a dark yellow residue. The crude product was used without purification. LC-MS (M+H)+ 407.13.

Step B: Methyl N-4-(4-chloro-1H-imidazol-1-yl)-3-methoxyphenyl-N'-(2,2-dimethylpent-4-enoyl)carbamimidothioate (251 mg, 0.617 mmol) was reacted with allylhydrazine (70% solution in water, 578 mg, 8.02 mmol) using a procedure analogous to Step B of Example 1. The crude product was purified using reverse phase preparatory HPLC (MeOH, water, TFA) to provide 1-allyl-N-(4-(4-chloro-1H-imidazol-1-yl)-3-methoxyphenyl)-5-(2-methylpent-4-en-2-yl)-1H-1,2,4-triazol-3-amine, TFA (35 mg, 11% yield) as a clear solid residue. LC-MS (M+H)+=413.07.

Step C: 1-Allyl-N-(4-(4-chloro-1H-imidazol-1-yl)-3-methoxyphenyl)-5-(2-methylpent-4-en-2-yl)-1H-1,2,4-triazol-3-amine (82 mg, 0.199 mmol was subjected to a ring closing metathesis procedure analogous to Step C of Example 1 (160° C., 30 min, 35 mol % Hoveyda-Grubbs Catalyst 2nd Generation) to afford 19 mg (16% yield) of the titled compound as a dark brown solid. LC-MS (M+H)+=385.10. 1H NMR (500 MHz, chloroform-d) δ ppm 1.32-1.62 (m, 6 H) 2.55 (d, J=6.41 Hz, 2 H) 3.79-3.92 (m, 3 H) 4.90 (d, J=5.19 Hz, 2 H) 6.11-6.18 (m, 1 H) 6.18-6.26 (m, 1 H) 7.08 (s, 1 H) 7.14-7.21 (m, 2 H) 7.28 (d, J=1.83 Hz, 1 H) 7.91 (s, 1 H) 11.14 (s, 1 H).

EXAMPLE 10

N-(4-(4-chloro-1H-imidazol-1-yl)-3-methoxyphenyl)-8-(4-fluorophenyl)-5,6,7,8-tetrahydro-[1,2,4]triazolo[1,5-a]pyridin-2-amine 2,2,2-trifluoroacetate

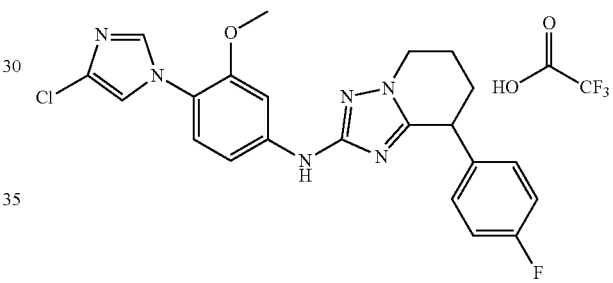

Step A: Methyl 4-(4-chloro-1H-imidazol-1-yl)-3-methoxyphenylcarbamimidothioate, hydroiodide (500 mg, 1.685 mmol, from preparation A) and 5-chloro-2-(4-fluorophenyl)pentanoic acid (583 mg, 2.53 mmol) from preparation AC) were coupled using a procedure analogous to Step A of Example 1 to afford methyl N-4-(4-chloro-1H-imidazol-1-yl)-3-methoxyphenyl-N'-(5-chloro-2-(4-fluorophenyl)pentanoyl)carbamimidothioate (390 mg, 43% yield) as a white solid. LC-MS (M+H)+ 509.2.

Step B: Hydrazine (1.53 mL, 0.766 mmol) was added to a high pressure reaction vessel charged with a solution of methyl N-4-(4-chloro-1H-imidazol-1-yl)-3-methoxyphenyl-N'-(5-chloro-2-(4-fluorophenyl)pentanoyl)carbamimidothioate (195 mg, 0.383 mmol) in absolute ethanol (5 mL). The vessel was sealed and heated in an oil bath at 80° C. for 18 h. The reaction mixture was concentrated in vacuo. The crude product was purified using reverse phase preparatory-HPLC (MeOH/water/TFA) to afford N-(4-(4-chloro-1H-imidazol-1-yl)-3-methoxyphenyl)-8-(4-fluorophenyl)-5,6,7,8-tetrahydro-[1,2,4]triazolo[1,5-a]pyridin-2-amine 2,2,2-trifluoroacetate (16 mg, 7% yield). LC-MS (M+H)+ 439.1. 1H NMR (500 MHz, chloroform-d) δ ppm 10.11 (br. s., 1 H) 8.01 (s, 1 H) 7.31 (s, 1 H) 7.19 (s, 2 H) 7.05-7.17 (m, 5 H) 4.25-4.37 (m, 3 H) 3.89 (s, 3 H) 2.39-2.51 (m, 1 H) 2.28-2.39 (m, 1 H) 2.15-2.26 (m, 1 H) 2.04-2.15 (m, 1 H).

EXAMPLE 11

2-(4-chloro-1H-imidazol-1-yl)-5-(8-(4-fluorophenyl)-5,6,7,8-tetrahydro-[1,2,4]triazolo[1,5-a]pyridin-2-ylamino)benzonitrile 2,2,2-trifluoroacetate

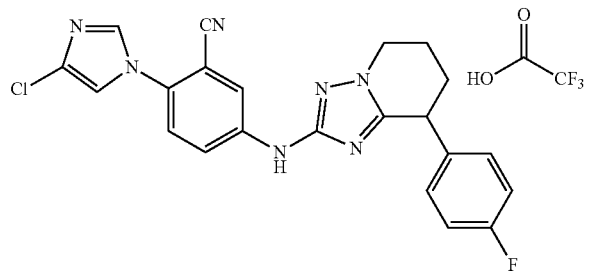

Step A: Methyl 3-cyano-4-(3-methyl-1H-1,2,4-triazol-1-yl)phenylcarbamimidothioate, hydroiodide (500 mg, 1.249 mmol, from preparation G) and 5-chloro-2-(4-fluorophenyl)pentanoic acid (432 mg, 1.874 mmol, from preparation AC) were coupled using a procedure analogous to Step A of Example 1 to afford methyl N'-5-chloro-2-(4-fluorophenyl)pentanoyl-N-(3-cyano-4-(3-methyl-1H-1,2,4-triazol-1-yl)phenyl)carbamimidothioate (606 mg, 100% yield) as a white solid. LC-MS (M+H)+ 485.2.

Step B: Methyl N'-5-chloro-2-(4-fluorophenyl)pentanoyl-N-(3-cyano-4-(3-methyl-1H-1,2,4-triazol-1-yl)phenyl)carbamimidothioate (606 mg, 1.250 mmol) was reacted with hydrazine (5.00 mL, 2.499 mmol) using a procedure analogous to Step B of Example 9 to afford 5-(8-(4-fluorophenyl)-5,6,7,8-tetrahydro-[1,2,4]triazolo[1,5-a]pyridin-2-ylamino)-2-(3-methyl-1H-1,2,4-triazol-1-yl)benzonitrile, TFA (36 mg, 0.062 mmol, 4.96% yield) as a beige solid. LC-MS (M+H)+ 415.17. $^1$H NMR (500 MHz, chloroform-d) δ ppm 10.17 (s, 1 H) 8.66 (s, 1 H) 8.20 (d, J=2.44 Hz, 1 H) 7.60-7.67 (m, 1 H) 7.54-7.60 (m, 1 H) 7.11-7.19 (m, 2 H) 7.08 (t, J=8.55 Hz, 2 H) 4.20-4.38 (m, 3 H) 2.54 (s, 3 H) 2.39-2.48 (m, 1 H) 2.28-2.39 (m, 1 H) 2.14-2.25 (m, 1 H) 2.03-2.13 (m, 1 H).

EXAMPLE 12

N-(4-(4-chloro-1H-imidazol-1-yl)-3-methoxyphenyl)-8-(2,4-dichlorophenyl)-5,6,7,8-tetrahydro-[1,2,4]triazolo[1,5-a]pyridin-2-amine

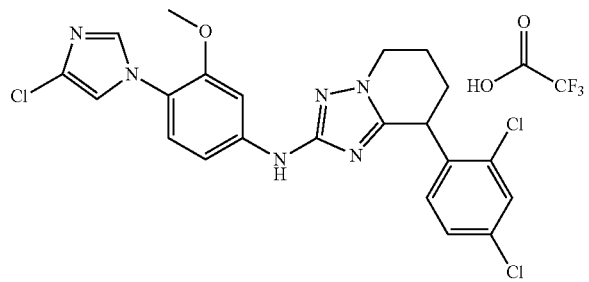

Step A: Methyl 4-(4-chloro-1H-imidazol-1-yl)-3-methoxyphenylcarbamimidothioate (150 mg, 0.353 mmol, from preparation X) and 5-chloro-2-(2,4-dichlorophenyl)pentanoic acid (99 mg, 0.353 mmol, from preparation X) were coupled using a procedure analogous to Step A of Example 1 to afford methyl N-4-(4-chloro-1H-imidazol-1-yl)-3-methoxyphenyl-N'-(5-chloro-2-(2,4-dichlorophenyl)pentanoyl)carbamimidothioate (198 mg, 100% yield) as a dark yellow residue. LC-MS (M+H)+ 561.03.

Step B: Methyl N-4-(4-chloro-1H-imidazol-1-yl)-3-methoxyphenyl-N'-(5-chloro-2-(2,4-dichlorophenyl)pentanoyl)carbamimidothioate (198 mg, 0.353 mmol) was reacted with hydrazine (1.413 mL, 0.707 mmol) using a procedure analogous to Step B of Example 9 to afford N-(4-(4-chloro-1H-imidazol-1-yl)-3-methoxyphenyl)-8-(2,4-dichlorophenyl)-5,6,7,8-tetrahydro-[1,2,4]triazolo[1,5-a]pyridin-2-amine 2,2,2-trifluoroacetate (26 mg, 0.050 mmol, 14% yield) as a white solid. LC-MS (M+H)+ 490.9. $^1$H NMR (500 MHz, chloroform-d) δ ppm 7.43 (s, 1 H) 7.34 (s, 1 H) 7.19 (d, J=8.55 Hz, 1 H) 7.07-7.13 (m, 1 H) 7.01 (s, 1 H) 6.85-6.97 (m, 2 H) 6.66 (s, 1 H) 4.58 (t, J=6.87 Hz, 1 H) 4.14-4.26 (m, 2 H) 3.76-3.84 (m, 3 H) 2.34 (d, J=9.46 Hz, 1 H) 2.07-2.23 (m, 2 H) 1.93-2.05 (m, 1 H) 1.56 (s, 1 H).

EXAMPLE 13

N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine

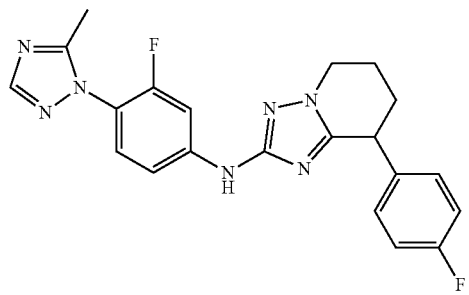 [SMILES: Cc1ncnn1-c1ccc(Nc2nc3n(n2)CCCC3c2ccc(F)cc2)cc1F]

Step A: A solution of N-ethyldiisopropylamine (1.29 mL, 7.39 mmol) in DMF (15 mL) was added to a 50 mL round bottom flask charged with a mixture of methyl 3-fluoro-4-(5-methyl-1H-1,2,4-triazol-1-yl)phenylcarbamimidothioate hydroiodide (1.16 g, 2.96 mmol, from preparation Q), 2-(4-fluorophenyl)pent-4-enoic acid (0.750 g, 3.25 mmol, from preparation AC), 1-hydroxybenzotriazole hydrate (0.905 g, 5.91 mmol), and 1-ethyl-3-(3-dimethylaminopropyl)carbodiimide hydrochloride (1.133 g, 5.91 mmol). The resulting mixture was magnetically stirred under nitrogen for 18 h at rt. Hydrazine (0372 mL, 11.84 mmol) was added to the reaction solution and the mixture was heated at 70° C. for 2 hr. The crude reaction mixture was poured into water (250 mL) and extracted with ethyl acetate (2×150 mL). The organic layer was washed with brine (50 mL), dried over sodium sulfate, filtered, and concentrated in vacuo to afford 5-(4-chloro-1-(4-fluorophenyl)butyl)-N-(3-fluoro-4-(5-methyl-1H-1,2,4-triazol-1-yl)phenyl)-1H-1,2,4-triazol-3-amine (1.02 g, 2.298 mmol, 78% yield). LC-MS (M+H)+ 443.3, ~50% purity by UV integration. Used crude isolate in the next step without purification.

Step B: A solution of 5-(4-chloro-1-(4-fluorophenyl)butyl)-N-(3-fluoro-4-(5-methyl-1H-1,2,4-triazol-1-yl)phenyl)-1H-1,2,4-triazol-3-amine (1.02 g, 2.30 mmol), sodium iodide (1.38 g, 9.19 mmol), and diisoproplylethylamine (0.40 mL, 2.30 mmol) in acetone (10 mL) was heated in a sealed vessel at 100° C. for 4 h. The reaction was concentrated in vacuo. The crude product was purified using silica gel column chromatography (0-80% EtOAc/chloroform, linear gradient). Fractions containing product were combined and concentrated to afford 365 mg of solid. The solid was recrystallized from ethanol and dried under vacuum to afford 220 mg (23% yield) of the titled compound as a white crystalline solid. LC-MS (M+H)+ 408.3. $^1$H NMR (500 MHz, chloroform-d) δ ppm 7.96 (s, 1H) 7.68 (dd, J=12.51, 2.44 Hz, 1H) 7.27-7.31 (m, 1H) 7.15 (dd, J=8.55, 5.49 Hz, 2H) 7.01-7.10 (m, 3H) 6.89 (s, 1H) 4.19-4.29 (m, 3H) 2.40 (s, 3H) 2.31-2.38 (m, 1H) 2.18-2.28 (m, 1H) 2.06-2.17 (m, 1H) 1.94-2.06 (m, 1H).

EXAMPLE 14 AND EXAMPLE 15

(S)—N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine and (R)—N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine

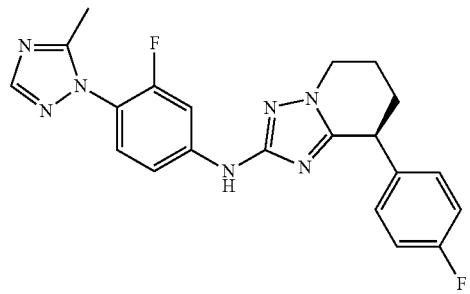

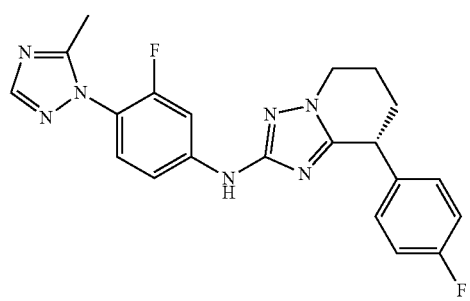

Step A: A racemic mixture of N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine (185 mg, from example 13) was purified using chiral supercritical fluid chromatography (SFC) to afford 87 mg of peak A (example 14) and 87 mg of peak B (example 15). SFC Method: Chiralpak OJ-H (30×250 mm, 5 uM), 15% methanol (0.1% diethylamine) in $CO_2$, 35° C., 70 mL/min, absorbance 268 nm, $t_R$ (peak A) 7.0 min, $t_R$ (peak B) 11.8 min. The absolute stereochemistry of individual enantiomers (examples 14 and 15) was not determined. LC-MS and $^1$H NMR analytical data for the separated enantiomers was identical to the racemate (example 13).

EXAMPLE 16

N-(4-(4-Chloro-1H-imidazol-1-yl)-3-methoxyphenyl)-9-(4-fluorophenyl)-6,7,8,9-tetrahydro-5H-[1,2,4]triazolo[1,5-a]azepin-2-amine

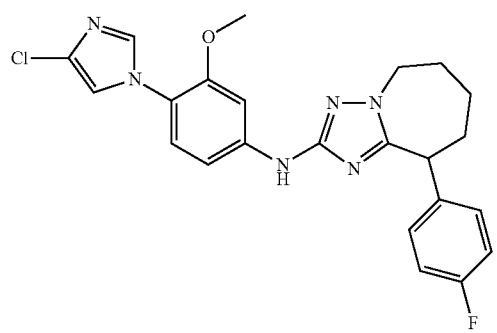 [SMILES: COc1cc(Nc2nc3n(n2)CCCCC3c2ccc(F)cc2)ccc1-n1cnc(Cl)c1]

Step A: Methyl 4-(4-chloro-1H-imidazol-1-yl)-3-methoxyphenylcarbamimidothioate, hydroiodide (4.0 g, 13.48 mmol, from preparation A) and 6-chloro-2-(4-fluorophenyl)hexanoic acid (3.63 g, 14.83 mmol, from preparation AC) were coupled and then reacted with hydrazine (1.69 mL, 53.9 mmol) using a procedure analogous to Step A of Example 13 to afford 5-(5-chloro-1-(4-fluorophenyl)pentyl)-N-(4-(4-chloro-1H-imidazol-1-yl)-3-methoxyphenyl)-1H-1,2,4-triazol-3-amine (5.2 g, 10.63 mmol, 79% yield) as a reddish foam solid. LC-MS (M+H)+ 489.1. Used the crude isolate in the next step without purification.

Step B: A solution of 5-(5-chloro-1-(4-fluorophenyl)pentyl)-N-(4-(4-chloro-1H-imidazol-1-yl)-3-methoxyphenyl)-1H-1,2,4-triazol-3-amine (5.2 g, 10.63 mmol, sodium iodide (7.96 g, 53.1 mmol), and diisoproplylethylamine (1.86 mL, 10.6 mmol) in acetone (100 mL) was heated in a sealed vessel at 100° C. for 4 h. The reaction was concentrated in vacuo. The crude product was purified using silica gel column chromatography (0-80% EtOAc/chloroform, linear gradient). Fractions containing product were combined and concentrated to afford 1.9 g of a pink foam solid. The solid was recrystallized from ethyl acetate/hexane and dried under vacuum to afford 710 mg (15% yield) of the titled compound as a white crystalline solid. The mother liquor was reconcentrated and crystallized from ethanol to afford an additional 230 mg (5% yield) of the titled compound as a white crystalline solid. LC-MS (M+H)+ 453.3. $^1$H NMR (500 MHz, chloroform-d) δ ppm 7.51 (d, J=1.53 Hz, 1 H) 7.42 (d, J=2.44 Hz, 1 H) 7.16 (dd, J=8.70, 5.34 Hz, 2 H) 7.03-7.11 (m, 3H) 7.02 (d, J=1.53 Hz, 1 H) 6.83 (dd, J=8.55, 2.14 Hz, 1 H) 6.75 (s, 1 H) 4.20-4.30 (m, 3 H) 3.79 (s, 3 H) 2.16-2.28 (m, 1 H) 2.06-2.15 (m, 1 H) 1.99-2.06 (m, 1 H) 1.92-1.99 (m, 1H) 1.79-1.92 (m, 2 H).

EXAMPLE 17 AND EXAMPLE 18

(S)—N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine

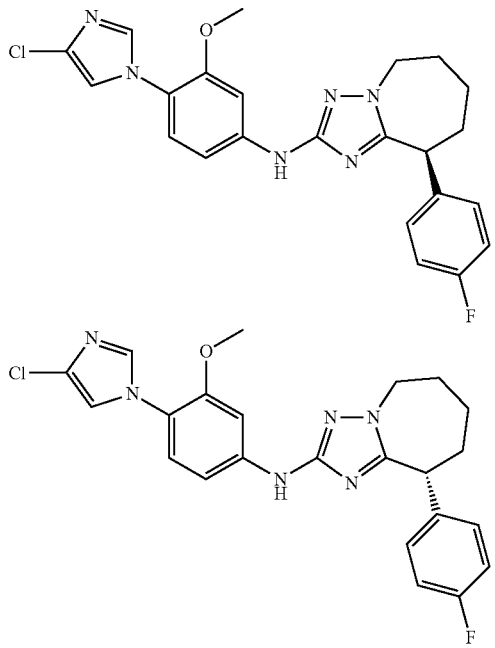

Step A: A racemic mixture of N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine (116 mg from Example 16) was purified using chiral supercritical fluid chromatography (SFC) to afford 36 mg of peak A (example 17) and 37 mg of peak B (example 18). SFC Method: Chiralpak OJ-H (30×250 mm, 5 uM), 25% methanol (0.1% diethylamine) in CO$_2$, 35° C., 70 mL/min, absorbance 220 nm, $t_R$ (peak A) 8.7 min, $t_R$ (peak B) 13.7 min. The absolute stereochemistry of individual enantiomers (examples 17 and 18) was not determined. LC-MS and $^1$H NMR analytical data for the separated enantiomers was identical to the racemate (see example 16).

EXAMPLE 19

N-(4-(4-chloro-1H-imidazol-1-yl)-3-methoxyphenyl)-9-(2,4-dichlorophenyl)-6,7,8,9-tetrahydro-5H-[1,2,4]triazolo azepin-2-amine 2,2,2-trifluoroacetate

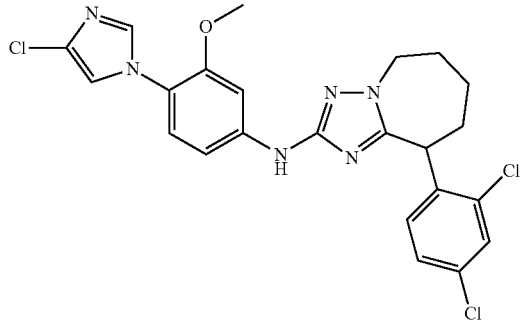

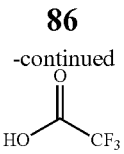

Step A: Methyl 4-(4-chloro-1H-imidazol-1-yl)-3-methoxyphenylcarbamimidothioate, hydroiodide (500 mg, 1.685 mmol, from preparation A) and 6-chloro-2-(2,4-dichlorophenyl)hexanoic acid (498 mg, 1.685 mmol, from preparation AG) were coupled and then reacted with hydrazine (0.212 mL, 6.74 mmol) using a procedure analogous to Step A of Example 13. The crude products were purified using silica gel chromatography (40-100% ethyl acetate/chloroform) to afford 5-(5-chloro-1-(2,4-dichlorophenyl)pentyl)-N-(4-(4-chloro-1H-imidazol-1-yl)-3-methoxyphenyl)-1H-1,2,4-triazol-3-amine (173 mg, 0.272 mmol, 16% yield) as a pink foamy solid. LC-MS (M+H)$^+$ 539.0.

Step B: A solution of 5-(5-chloro-1-(2,4-dichlorophenyl)pentyl)-N-(4-(4-chloro-1H-imidazol-1-yl)-3-methoxyphenyl)-1H-1,2,4-triazol-3-amine (173 mg, 0.320 mmol), sodium iodide (240 mg, 1.60 mmol), and diisoproplylethylamine (0.112 mL, 0.640 mmol) in acetone (4 mL) was heated in a sealed vessel at 100° C. for 4 h. The reaction was concentrated in vacuo. The crude product was purified using reverse phase preparatory HPLC (MeOH, water, TFA) to afford 58 mg (29% yield) of the titled compound as a white solid. LC-MS (M+H)$^+$ 505.1. $^1$H NMR (500 MHz, chloroform-d) δ ppm $^1$H NMR (500 MHz, chloroform-d) δ ppm 9.47 (br. s., 1 H) 7.79 (s, 1 H) 7.47 (d, J=2.14 Hz, 1 H) 7.34 (dd, J=8.24, 2.14 Hz, 1 H) 7.29 (d, J=2.14 Hz, 1 H) 7.23 (d, J=8.24 Hz, 1 H) 7.12 (d, J=8.55 Hz, 1 H) 7.04-7.07 (m, 2 H) 4.49-4.61 (m, 2 H) 4.29 (dd, J=14.04, 10.38 Hz, 1H) 3.82 (s, 3 H) 2.25-2.31 (m, 1 H) 2.11-2.24 (m, 3 H) 1.80-1.98 (m, 2 H).

EXAMPLE 20 AND EXAMPLE 21

(S)—N-(4-(4-chloro-1H-imidazol-1-yl)-3-methoxyphenyl)-9-(2,4-dichlorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(2,4-dichlorophenyl)-6,7,8,9-tetrahydro-5H-[1,2,4]triazolo[1,5-a]azepin-2-amine

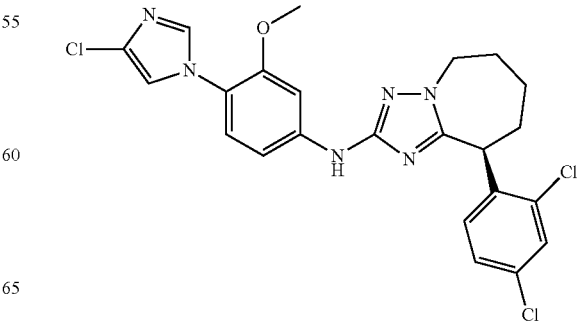

-continued

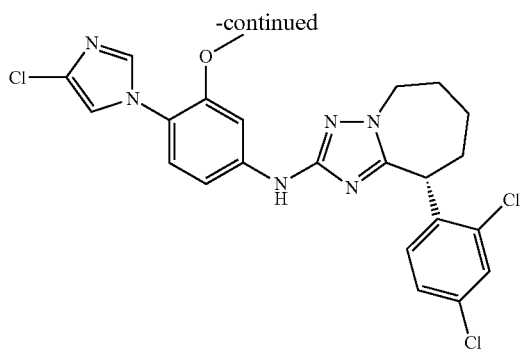

Step A: A racemic mixture of N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine (83 mg from Example 19) was purified using chiral supercritical fluid chromatography (SFC) to afford 25 mg of peak A (example 20) and 33 mg of peak B (example 21). SFC Method: Chiralpak OJ-H (30×250 mm, 5 uM), 20% methanol (0.1% diethylamine) in $CO_2$, 35° C., 70 mL/min, absorbance 268 nm, $t_R$ (peak A) 14.5 min, $t_R$ (peak B) 19.4 min. The absolute stereochemistry of individual enantiomers (examples 20 and 21) was not determined. LC-MS and $^1$H NMR analytical data for the separated enantiomers was identical. LC-MS (M+H)$^+$ 505.1. $^1$H NMR (500 MHz, chloroform-d) δ ppm 7.50 (d, J=1.53 Hz, 1H) 7.44 (d, J=1.83 Hz, 1 H) 7.42 (d, J=2.14 Hz, 1 H) 7.29-7.36 (m, 2 H) 7.08 (d, J=8.55 Hz, 1 H) 7.01 (d, J=1.53 Hz, 1 H) 6.75 (dd, J=8.55, 2.14 Hz, 1 H) 6.58 (s, 1 H) 4.54 (dd, J=10.38, 2.44 Hz, 1 H) 4.49 (dd, J=14.04, 5.19 Hz, 1 H) 4.20 (dd, J=14.04, 10.38 Hz, 1 H) 3.75 (s, 3 H) 2.17-2.29 (m, 1 H) 2.00-2.17 (m, 3 H) 1.75-1.94 (m, 2 H).

EXAMPLE 22

N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine 2,2,2-trifluoroacetate

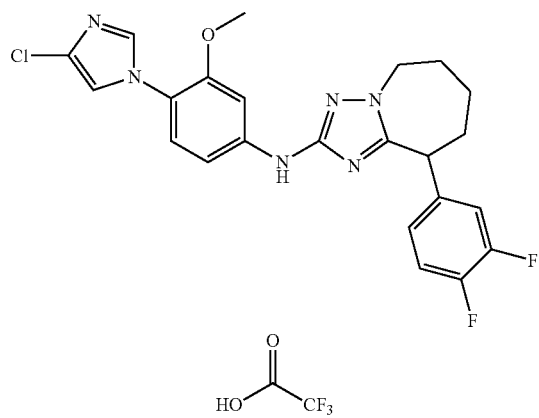

Step A: Methyl 4-(4-chloro-1H-imidazol-1-yl)-3-methoxyphenylcarbamimidothioate, hydroiodide (500 mg, 1.69 mmol, from preparation A) and 6-chloro-2-(3,4-difluorophenyl)hexanoic acid (443 mg, 1.69 mmol, from preparation AG) were coupled and then reacted with hydrazine (0.211 mL, 6.74 mmol) using a procedure analogous to Step A of Example 13. The crude products were purified using silica gel chromatography (40-100% ethyl acetate/chloroform) to afford 5-(5-chloro-1-(3,4-difluorophenyl)pentyl)-N-(4-(4-chloro-1H-imidazol-1-yl)-3-methoxyphenyl)-1H-1,2,4-triazol-3-amine (100 mg, 0.197 mmol, 12% yield) as a yellow residue. LC-MS (M+H)$^+$ 507.1.

Step B: A solution of 5-(5-chloro-1-(3,4-difluorophenyl)pentyl)-N-(4-(4-chloro-1H-imidazol-1-yl)-3-methoxyphenyl)-1H-1,2,4-triazol-3-amine (100 mg, 0.197 mmol), sodium iodide (148 mg, 0.985 mmol), and diisoproplylethylamine (0.069 mL, 0.394 mmol) in acetone (4 mL) was heated in a sealed vessel at 100° C. for 4 h. The reaction was concentrated in vacuo. The crude product was purified using reverse phase preparatory HPLC (MeOH, water, TFA) to afford 65 mg (54% yield) of the titled compound as a yellow solid. LC-MS (M+H)$^+$ 471.2. $^1$H NMR (500 MHz, chloroform-d) δ ppm 10.24 (s, 1 H) 8.15 (s, 1 H) 7.31 (s, 1 H) 7.16-7.26 (m, 3 H) 7.14 (s, 1 H) 6.93-7.03 (m, 1 H) 6.84 (d, J=8.55 Hz, 1 H) 4.46 (d, J=6.71 Hz, 1 H) 4.36-4.43 (m, 1 H) 4.27-4.36 (m, 1 H) 3.90 (s, 3 H) 2.26-2.43 (m, 1 H) 2.14-2.26 (m, 1 H) 1.90-2.10 (m, 4 H).

EXAMPLE 23 AND EXAMPLE 24

S)—N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine

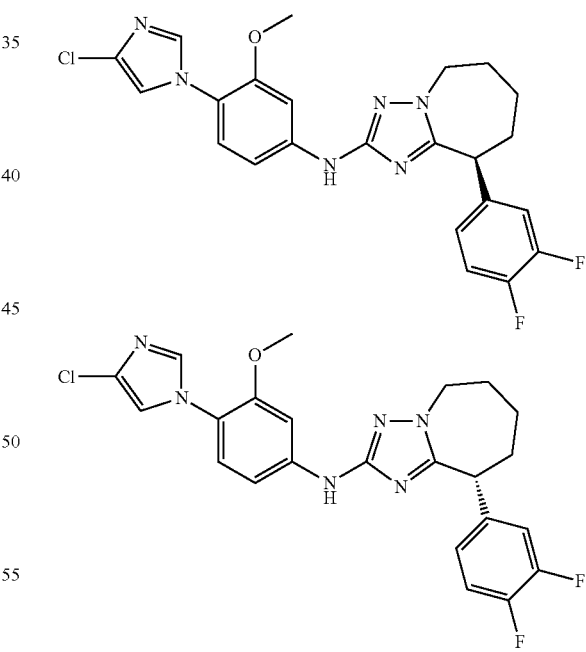

Step A: A racemic mixture of N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine 2,2,2-trifluoroacetate (415 mg from Example 22) was purified using chiral supercritical fluid chromatography (SFC) to afford 191 mg of peak A (example 23) and 188 mg of peak B (example 24). SFC Method: Chiralpak OJ-H (30×250 mm, 5 uM), 20% methanol (0.1% diethylamine) in $CO_2$, 35° C., 70 mL/min, absorbance 268 nm, $t_R$ (peak A) 11.7 min, $t_R$ (peak B) 16.4 min. The absolute stereochemistry of individual enantiomers (examples 23 and 24) was not determined. LC-MS and $^1$H NMR analytical data for the separated enantiomers was identical. LC-MS (M+H)$^+$ 471.3. $^1$H NMR (500 MHz, chloroform-d) δ ppm 7.52 (d, J=1.53 Hz, 1 H) 7.40 (d, J=2.44 Hz, 1 H) 7.12-7.20 (m, 1 H) 7.10 (d, J=8.24 Hz, 1 H) 7.03-7.09 (m, 1 H) 7.02 (d, J=1.53 Hz, 1 H) 6.88-6.95 (m, 1 H) 6.84 (dd, J=8.55, 2.14 Hz, 1 H) 6.59 (s, 1 H) 4.17-4.31 (m, 3 H) 3.81 (s, 3 H) 2.09-2.18 (m, 2 H) 2.02-2.08 (m, 1 H) 1.94-2.00 (m, 1 H) 1.80-1.92 (m, 2 H).

EXAMPLE 25

N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine

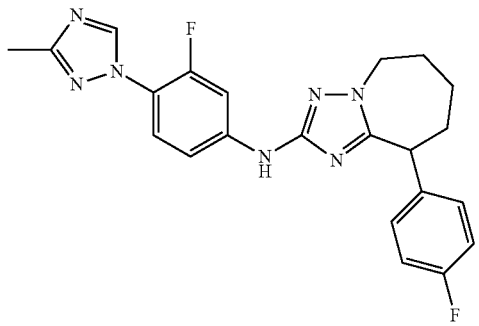 [SMILES: Cc1ncn(-c2ccc(Nc3nc4n(n3)CCCCC4c3ccc(F)cc3)cc2F)n1]

Step A: Methyl 3-fluoro-4-(3-methyl-1H-1,2,4-triazol-1-yl)phenylcarbamimidothioate, hydroiodide (1.50 g, 3.81 mmol, from preparation Q) and 6-chloro-2-(3,4-difluorophenyl)hexanoic acid (1.03 g, 4.20 mmol, from preparation AE) were coupled [N-methylmorpholine (2.10 mL, 19.1 mmol) was substituted for N,N-diisopropylethylamine] and then reacted with hydrazine (0.600 mL, 19.1 mmol) using a procedure analogous to Step A of Example 13. After an aqueous workup, the crude product was used in the next step without purification. LC-MS (M+H)$^+$ 458.2.

Step B: A solution of 5-(5-chloro-1-(4-fluorophenyl)pentyl)-N-(3-fluoro-4-(3-methyl-1H-1,2,4-triazol-1-yl)phenyl)-1H-1,2,4-triazol-3-amine (1.75 g, 3.81 mmol), sodium iodide (2.86 g, 19.1 mmol), and diisoproplylethylamine (3.33 mL, 19.1 mmol) in acetone (50 mL) was heated in a sealed vessel at 100° C. for 4 h. The reaction was concentrated in vacuo. Water (250 mL) was added and the mixture was extracted with EtOAc (2×250 mL). The combined organic layers were washed with brine (50 mL), dried (MgSO$_4$), filtered, and concentrated in vacuo. Ethanol (50 mL) was added to the residue. The mixture was stirred at rt for 30 min. The solid was collected by vacuum filtration to afford 720 mg (43% yield) of the titled compound as an off-white solid. LC-MS (M+H)$^+$ 422.5. $^1$H NMR (500 MHz, CHLOROFORM-d) δ ppm 8.39 (d, J=2.4 Hz, 1H), 7.68 (dd, J=13.9, 2.3 Hz, 1H), 7.59 (t, J=8.5 Hz, 1H), 7.14 (dd, J=8.5, 5.2 Hz, 2H), 6.97-7.11 (m, 3H), 6.90 (s, 1H), 4.19-4.39 (m, 3H), 2.49 (s, 3H), 2.16-2.32 (m, 1H), 2.06-2.15 (m, 1H), 1.84-2.03 (m, 4H).

EXAMPLE 26 AND EXAMPLE 27

(S)—N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine and (R)—N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine

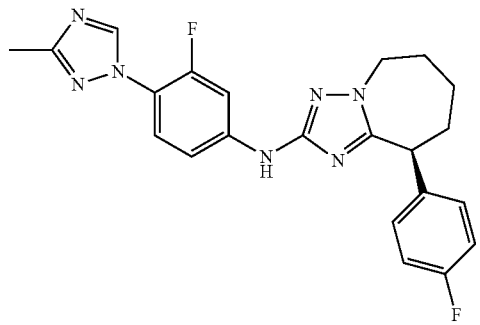

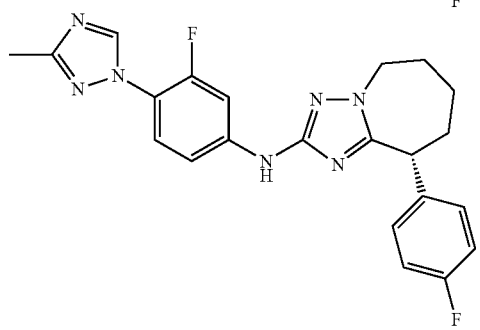

Step A: A racemic mixture of N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine (350 mg from Example 25) was purified using chiral supercritical fluid chromatography (SFC) to afford 145 mg of peak A (first to elute, example 26) and 146 mg of peak B (second to elute, example 27). SFC Method: Chiralpak OJ-H (30×150 mm, 5 uM), 15% methanol (0.1% diethylamine) in CO$_2$, 85 mL/min, absorbance 268 nm. The absolute stereochemistry of individual enantiomers (examples 26 and 27) was not determined. LC-MS and $^1$H NMR analytical data for the separated enantiomers was identical to the racemate (see Example 25).

EXAMPLE 28

N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine 2,2,2-trifluoroacetate

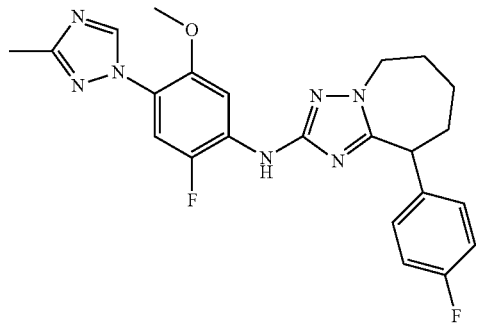

-continued

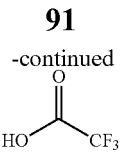

Step A: Methyl 2-fluoro-5-methoxy-4-(3-methyl-1H-1,2,4-triazol-1-yl)phenylcarbamimidothioate, hydroiodide (0.485 g, 1.642 mmol, from preparation B) and 6-chloro-2-(4-fluorophenyl)hexanoic acid (0.442 g, 1.806 mmol, from preparation AE) were coupled and then reacted with hydrazine (0.206 mL, 6.56 mmol) using a procedure analogous to Step A of Example 13. The crude products were purified using silica gel chromatography (0-95% ethyl acetate/chloroform) to afford 5-(5-chloro-1-(4-fluorophenyl)pentyl)-N-(2-fluoro-5-methoxy-4-(3-methyl-1H-1,2,4-triazol-1-yl)phenyl)-1H-1,2,4-triazol-3-amine (97 mg, 0.20 mmol, 12% yield). LC-MS (M+H)+ 488.2.

Step B: A solution of 5-(5-chloro-1-(4-fluorophenyl)pentyl)-N-(2-fluoro-5-methoxy-4-(3-methyl-1H-1,2,4-triazol-1-yl)phenyl)-1H-1,2,4-triazol-3-amine (97 mg, 0.199 mmol), sodium iodide (149 mg, 0.994 mmol), and diisoproplylethylamine (0.035 mL, 0.199 mmol) in acetone (5 mL) was heated in a sealed vessel at 100° C. for 4 h. The reaction was concentrated in vacuo. The crude product was purified using reverse phase preparatory-HPLC (MeOH/water/TFA) to afford 45 mg (38% yield) of the titled compound as a white solid. LC-MS (M+H)+ 452.2. 1H NMR (500 MHz, chloroform-d) δ ppm 9.41 (s, 1 H) 9.22 (br. s., 1 H) 8.11 (d, J=7.32 Hz, 1 H) 7.64 (d, J=10.99 Hz, 1H) 7.09 (d, J=2.75 Hz, 2 H) 7.08 (s, 2 H) 4.46-4.53 (m, 1 H) 4.39 (d, J=14.34 Hz, 1 H) 4.19-4.32 (m, 1 H) 3.98 (s, 3 H) 2.62 (s, 3 H) 2.26-2.44 (m, 1 H) 2.16 (d, J=13.73 Hz, 1H) 1.97 (br. s., 4H).

EXAMPLE 29 AND EXAMPLE 30

(S)—N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine and (R)—N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine

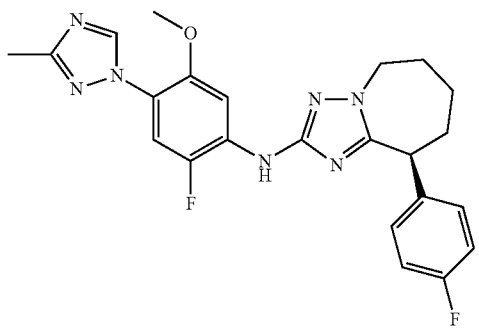

-continued

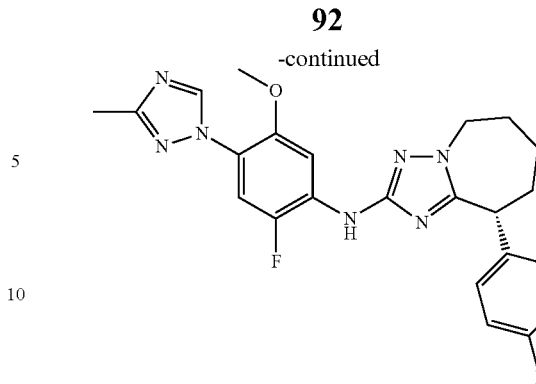

Step A: A racemic mixture of N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine (130 mg, 0.288 mmol, from Example 28) was purified using chiral supercritical fluid chromatography (SFC) to afford 60 mg of peak A (example 29) and 60 mg of peak B (example 30). SFC Method: Chiralpak AD-H (30×250 mm, 5 uM), 20% methanol (0.1% diethylamine) in CO2, 35° C., 70 mL/min, absorbance 268 nm, $t_R$ (peak A) 12 min, $t_R$ (peak B) 16 min. The absolute stereochemistry of example 29 was determined to be 9-(S) by single crystal X-ray analysis using the anomalous dispersion technique. The absolute stereochemistry of example 30 was assigned to be 9-(R) by default. LC-MS and 1H NMR analytical data for the separated enantiomers was identical. LC-MS (M+H)+ 452.1. 1H NMR (500 MHz, chloroform-d) δ ppm 8.55 (s, 1 H) 8.10 (d, J=7.81 Hz, 1 H) 7.47 (d, J=11.58 Hz, 1 H) 7.14-7.23 (m, 2 H) 7.02-7.12 (m, 2 H) 6.86 (d, J=3.27 Hz, 1 H) 4.15-4.35 (m, 3H) 3.82 (s, 3 H) 2.47 (s, 3 H) 1.95-2.15 (m, 4 H) 1.81-1.92 (m, 2 H).

EXAMPLE 31

N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine 2,2,2-trifluoroacetate

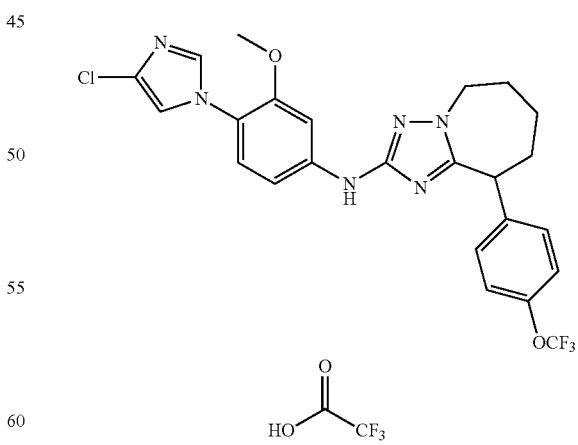

Step A: Methyl 4-(4-chloro-1H-imidazol-1-yl)-3-methoxyphenylcarbamimidothioate, hydroiodide (500 mg, 1.69 mmol, from preparation B) and 6-chloro-2-(4-(trifluoromethoxy)phenyl)hexanoic acid (523 mg, 1.685 mmol, from preparation AI) were coupled and then reacted with hydrazine (0.211 mL, 6.74 mmol) using a procedure analogous to Step A of Example 13. The crude products were purified using silica gel chromatography (40-100% ethyl acetate/chloroform) to afford 5-(5-chloro-1-(4-(trifluoromethoxy)phenyl)pentyl)-N-(4-(4-chloro-1H-imidazol-1-yl)-3-methoxyphenyl)-1H-1,2,4-triazol-3-amine (80 mg, 0.14 mmol, 9.0% yield) as a yellow residue. LC-MS (M+H)$^+$ 555.1.

Step B: A solution of 5-(5-chloro-1-(4-(trifluoromethoxy)phenyl)pentyl)-N-(4-(4-chloro-1H-imidazol-1-yl)-3-methoxyphenyl)-1H-1,2,4-triazol-3-amine (80 mg, 0.144 mmol), sodium iodide, and diisoproplylethylamine in acetone (2 mL) was heated in a sealed vessel at 100° C. for 4 h. The reaction was concentrated in vacuo. The crude product was purified using reverse phase preparatory-HPLC (MeOH/water/TFA) to afford 34 mg of the titled compound as a beige solid. LC-MS (M+H)$^+$ 519.2. $^1$H NMR (500 MHz, chloroform-d) δ ppm 7.32 (s, 1 H) 7.23 (s, 2 H) 7.14 (d, J=8.24 Hz, 3 H) 7.05 (d, J=7.93 Hz, 1 H) 4.15-4.28 (m, 3 H) 3.83 (s, 3 H) 2.27-2.41 (m, 1 H) 2.07-2.24 (m, 1 H) 1.85-2.03 (m, 4 H).

EXAMPLE 32

N-(4-(4-chloro-1H-imidazol-1-yl)-3-methoxyphenyl)-9-(4-chlorophenyl)-6,7,8,9-tetrahydro-5H-[1,2,4]triazolo[1,5-a]azepin-2-amine 2,2,2-trifluoroacetate

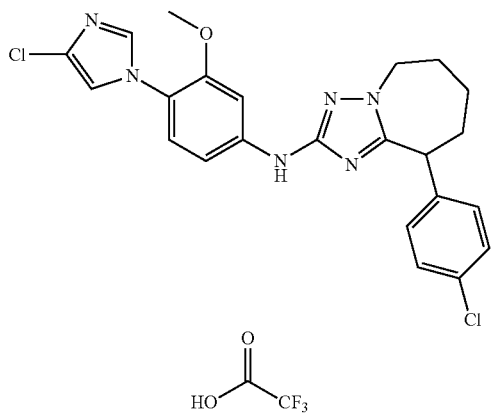

Step A: Methyl 4-(4-chloro-1H-imidazol-1-yl)-3-methoxyphenylcarbamimidothioate, hydroiodide (500 mg, 1.69 mmol, from preparation B) and 6-chloro-2-(4-chlorophenyl)hexanoic acid (440 mg, 1.685 mmol, from preparation AH) were coupled and then reacted with hydrazine (0.212 mL, 6.74 mmol) using a procedure analogous to Step A of Example 13. The crude products were purified using silica gel chromatography (40-100% ethyl acetate/chloroform) to afford 5-(5-chloro-1-(4-chlorophenyl)pentyl)-N-(4-(4-chloro-1H-imidazol-1-yl)-3-methoxyphenyl)-1H-1,2,4-triazol-3-amine (180 mg, 0.356 mmol, 21% yield) as a colorless residue. LC-MS (M+H)$^+$ 505.1.

Step B: A solution of 5-(5-chloro-1-(4-chlorophenyl)pentyl)-N-(4-(4-chloro-1H-imidazol-1-yl)-3-methoxyphenyl)-1H-1,2,4-triazol-3-amine (180 mg, 0.356 mmol), sodium iodide (267 mg, 1.78 mmol), and diisoproplylethylamine (0.12 mL, 0.71 mmol) in acetone (4 mL) was heated in a sealed vessel at 100° C. for 4 h. The reaction was concentrated in vacuo. The crude product was purified using reverse phase preparatory-HPLC (MeOH/water/TFA) to afford 53 mg of the titled compound as a off-white solid. LC-MS (M+H)$^+$ 469.2. $^1$H NMR (500 MHz, chloroform-d) δ ppm 10.24 (s, 1 H) 7.98 (d, J=1.53 Hz, 1 H) 7.40 (m, J=8.55 Hz, 2H) 7.31 (d, J=1.22 Hz, 1H) 7.16-7.21 (m, 2H) 7.11 (d, J=1.53 Hz, 1 H) 7.02 (m, J=8.55 Hz, 2 H) 4.55 (dd, J=7.17, 2.59 Hz, 1 H) 4.42 (dd, J=14.95, 6.41 Hz, 1 H) 4.22 (dd, J=14.34, 9.16 Hz, 1 H) 3.89 (s, 3 H) 2.43 (ddd, J=14.80, 7.32, 7.17 Hz, 1 H) 2.09-2.22 (m, 1 H) 1.87-2.04 (m, 4 H).

EXAMPLE 33

N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine 2,2,2-trifluoroacetate

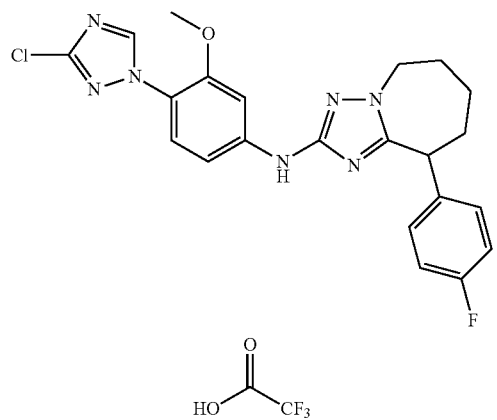

Step A: Methyl 4-(3-chloro-1H-1,2,4-triazol-1-yl)-3-methoxyphenylcarbamimidothioate, hydroiodide (0.362 g, 1.22 mmol, from preparation E) and 6-chloro-2-(4-fluorophenyl)hexanoic acid (0.327 g, 1.337 mmol, from preparation AE) were coupled and then reacted with hydrazine (0.153 mL, 4.88 mmol) using a procedure analogous to Step A of Example 13. The crude reaction mixture was poured into water (250 mL) and extracted with ethyl acetate (2×150 mL). Hexane (30 mL) was added to organic layer and the resulting solution was repeatedly washed with water (2×250 mL) to remove DMF. The organic layer was washed with brine (50 mL) and dried over sodium sulfate, filtered, and concentrated in vacuo to afford a yellow residue. The crude reaction product was used the in the next step without purification.

Step B: A solution of 5-(5-chloro-1-(4-fluorophenyl)pentyl)-N-(4-(3-chloro-1H-1,2,4-triazol-1-yl)-3-methoxyphenyl)-1H-1,2,4-triazol-3-amine (598 mg, 1.22 mmol), sodium iodide (731 mg, 4.88 mmol), and diisoproplylethylamine (0.213 mL, 1.22 mmol) in acetone (10 mL) was heated in a sealed vessel at 100° C. for 4 h. The crude product was purified using silica gel column chromatography (0-70% EtOAc/chloroform, linear gradient). Fractions containing product were combined and concentrated. The product was further purified using reverse phase preparatory-HPLC (MeOH/water/TFA) to afford 27 mg of the titled compound as an off-white solid. LC-MS (M+H)$^+$ 454.3. $^1$H NMR (500 MHz, chloroform-d) δ ppm 8.52 (s, 1H) 7.60 (d, J=8.85 Hz, 1H) 7.37 (d, J=2.14 Hz, 1H) 7.10 (d, J=6.71 Hz, 5H) 4.46 (dd, J=7.93, 2.14 Hz, 1 H) 4.30-4.42 (m, 1 H) 4.17-4.30 (m, 1 H) 3.92 (s, 3 H) 2.27-2.43 (m, 1 H) 2.07-2.24 (m, 1 H) 1.86-2.02 (m, 4 H).

EXAMPLE 34

9-(4-chlorophenyl)-N-(3-methoxy-4-(1-methyl-1H-pyrazol-4-yl)phenyl)-6,7,8,9-tetrahydro-5H-[1,2,4]triazolo[1,5-a]azepin-2-amine 2,2,2-trifluoroacetate

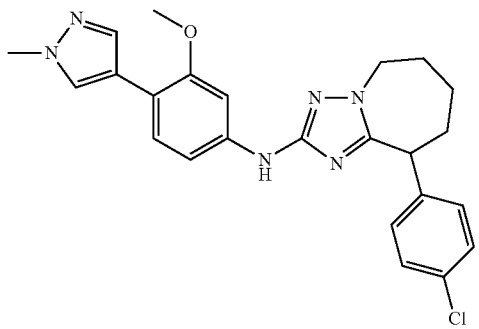

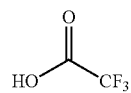

Step A: Methyl N'-3-methoxy-4-(1-methyl-1H-pyrazol-4-yl)phenylcarbamimidothioate hydroiodide (700 mg, 1.73 mmol) and 6-chloro-2-(4-fluorophenyl)hexanoic acid (424 mg, 1.73 mmol) were coupled using procedures and purification methods analogous to Step A of Example 1 to afford methyl N-6-chloro-2-(4-fluorophenyl)hexanoyl-N'-(3-methoxy-4-(1-methyl-1H-pyrazol-4-yl)phenyl)carbamimidothioate (103 mg, 0.205 mmol, 11% yield). LC-MS (M+H)$^+$ 503.3.

Step B: Methyl N-6-chloro-2-(4-fluorophenyl)hexanoyl-N'-(3-methoxy-4-(1-methyl-1H-pyrazol-4-yl)phenyl)carbamimidothioate (100 mg, 0.199 mmol) was reacted with hydrazine using procedures analogous to Step B of example 10 to afford 5-(5-chloro-1-(4-fluorophenyl)pentyl)-N-(3-methoxy-4-(1-methyl-1H-pyrazol-4-yl)phenyl)-1H-1,2,4-triazol-3-amine (39 mg, 0.83 mmol, 42% yield). LC-MS (M+H)$^+$ 469.2.

Step C: A solution of 5-(5-chloro-1-(4-fluorophenyl)pentyl)-N-(3-methoxy-4-(1-methyl-1H-pyrazol-4-yl)phenyl)-1H-1,2,4-triazol-3-amine (39 mg, 0.083 mmol), sodium iodide (50 mg, 0.33 mmol), diisoproplylethylamine (21 mg, 0.17 mmol) in acetone (3 mL) was heated in a sealed vessel at 100° C. for 3 h. The crude product was purified using reverse phase preparatory-HPLC (MeOH/water/TFA) to afford 21 mg (57% yield) of the titled compound. LC-MS (M+H)$^+$ 469.3. $^1$H NMR (500 MHz, chloroform-d) δ ppm 7.77 (s, 1 H) 7.39 (dd, J=8.24, 5.19 Hz, 2 H) 7.34 (s, 1 H) 7.22 (d, J=7.93 Hz, 1 H) 7.07 (t, J=8.55 Hz, 3 H) 6.69-6.84 (m, 2 H) 4.08 (t, J=7.93 Hz, 1 H) 3.93 (s, 3 H) 3.81 (s, 3 H) 3.54 (t, J=6.56 Hz, 2 H) 2.19-2.36 (m, J=14.73, 7.63, 7.44, 7.44 Hz, 1 H) 2.03-2.19 (m, 1 H) 1.77-1.91 (m, 2 H) 1.41-1.56 (m, 2H).

EXAMPLE 35

N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine 2,2,2-trifluoroacetate

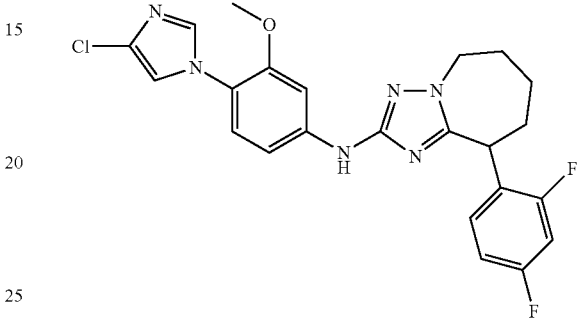

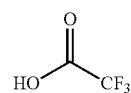

Step A: Methyl 4-(4-chloro-1H-imidazol-1-yl)-3-methoxyphenylcarbamimidothioate, hydroiodide (500 mg, 1.685 mmol, from preparation A) and 6-chloro-2-(2,4-difluorophenyl)hexanoic acid (443 mg, 1.69 mmol, from preparation AG) were coupled and then reacted with hydrazine (0.211 mL, 6.74 mmol) using a procedure analogous to Step A of Example 13. The crude product, 5-(5-chloro-1-(2,4-difluorophenyl)pentyl)-N-(4-(4-chloro-1H-imidazol-1-yl)-3-methoxyphenyl)-1H-1,2,4-triazol-3-amine (1.03 g, 100% yield), was used in the subsequent step without purification. LC-MS (M+H)$^+$ 507.3.

Step B: A solution of 5-(5-chloro-1-(2,4-difluorophenyl)pentyl)-N-(4-(4-chloro-1H-imidazol-1-yl)-3-methoxyphenyl)-1H-1,2,4-triazol-3-amine (855 mg, 1.685 mmol), sodium iodide (1.26 g, 8.43 mmol), and diisoproplylethylamine (0.589 mL, 3.37 mmol) in acetone (20 mL) was heated in a sealed vessel at 100° C. for 4 h. The reaction mixture was concentrated in vacuo. The crude product was purified using reverse phase preparatory-HPLC (MeOH/water/TFA) to afford 87 mg (9% yield) of the titled compound as a pale yellow solid. LC-MS (M+H)$^+$ 471.3. $^1$H NMR (500 MHz, chloroform-d) δ ppm 9.44 (br. s., 1 H) 7.75 (d, J=1.22 Hz, 1 H) 7.31 (d, J=2.14 Hz, 1 H) 7.10-7.22 (m, 2 H) 7.01-7.07 (m, 2 H) 6.95 (td, J=8.24, 2.14 Hz, 1 H) 6.90 (ddd, J=10.61, 8.47, 2.59 Hz, 1 H) 4.47-4.57 (m, 1 H) 4.44 (d, J=9.46 Hz, 1H) 4.23-4.37 (m, 1 H) 3.84 (s, 3H) 2.07-2.15 (m, 4 H) 1.82-2.01 (m, 2 H).

EXAMPLE 36 AND EXAMPLE 37

(S)—N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine

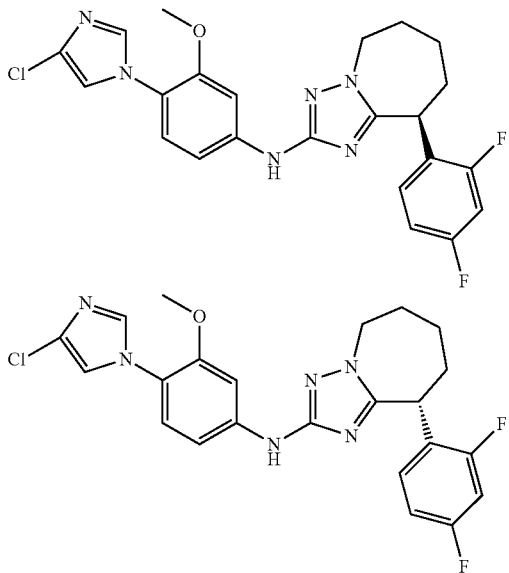

Step A: A racemic mixture of N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine (78 mg, 0.133 mmol, from Example 35) was purified using chiral supercritical fluid chromatography (SFC) to afford 16 mg of peak A (example 36) and 18 mg of peak B (example 37). SFC Method: Chiralcel OJ-H (30×250 mm, 5 uM), 15% methanol (0.1% diethylamine) in $CO_2$, 35° C., 70 mL/min, absorbance 268 nm, $t_R$ (peak A) 14.4 min, $t_R$ (peak B) 17.8 min. The absolute stereochemistry of individual enantiomers (examples 36 and 37) was not determined. LC-MS and $^1$H NMR analytical data for the separated enantiomers was identical. LC-MS (M+H)$^+$ 471.2. $^1$H NMR (500 MHz, chloroform-d) δ ppm 7.51 (d, J=1.53 Hz, 1 H) 7.41 (d, J=2.44 Hz, 1 H) 7.20-7.26 (m, 1 H) 7.08 (d, J=8.24 Hz, 1 H) 7.01 (d, J=1.53 Hz, 1H) 6.82-6.96 (m, 2 H) 6.79 (dd, J=8.55, 2.44 Hz, 1 H) 6.57 (s, 1 H) 4.40-4.51 (m, 1 H) 4.35 (dd, J=9.77, 2.75 Hz, 1 H) 4.10-4.25 (m, 1 H) 3.77 (s, 3 H) 2.00-2.13 (m, 4H) 1.75-1.95 (m, 2 H).

EXAMPLE 38

N-(4-(4-chloro-1H-imidazol-1-yl)-3-methoxyphenyl)-9-(3,5-difluorophenyl)-6,7,8,9-tetrahydro-5H-[1,2,4]triazolo[1,5-a]azepin-2-amine

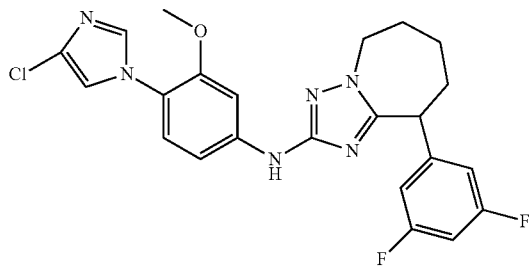 [SMILES: COc1cc(Nc2nc3n(n2)CCCCC3c2cc(F)cc(F)c2)ccc1-n1cnc(Cl)c1]

Step A: Methyl 4-(4-chloro-1H-imidazol-1-yl)-3-methoxyphenylcarbamimidothioate, hydroiodide (500 mg, 1.69 mmol, from preparation A) and 6-chloro-2-(3,5-difluorophenyl)hexanoic acid (443 mg, 1.69 mmol, from preparation AL) were coupled and then reacted with hydrazine (0.211 mL, 6.74 mmol) using a procedure analogous to Step A of Example 13. The crude product, 5-(5-chloro-1-(2,4-difluorophenyl)pentyl)-N-(4-(4-chloro-1H-imidazol-1-yl)-3-methoxyphenyl)-1H-1,2,4-triazol-3-amine (0.888 g, 100% yield), was used in the subsequent step without purification. LC-MS (M+H)$^+$ 507.2.

Step B: A solution of 5-(5-chloro-1-(3,5-difluorophenyl)pentyl)-N-(4-(4-chloro-1H-imidazol-1-yl)-3-methoxyphenyl)-1H-1,2,4-triazol-3-amine (855 mg, 1.685 mmol), sodium iodide (1.26 g, 8.43 mmol), and diisoproplylethylamine (0.589 mL, 3.37 mmol) in acetone (20 mL) was heated in a sealed vessel at 100° C. for 4 h. The reaction was concentrated in vacuo. The crude product was purified using reverse phase preparatory-HPLC (MeOH/water/TFA). The purified material was crystallized from methanol to afford 34 mg (4% yield) of the titled compound as a white solid. LC-MS (M+H)$^+$ 471.3. $^1$H NMR (500 MHz, chloroform-d) δ ppm 7.52 (d, J=1.53 Hz, 1 H) 7.42 (d, J=2.44 Hz, 1 H) 7.10 (d, J=8.55 Hz, 1 H) 7.03 (d, J=1.53 Hz, 1 H) 6.84 (dd, J=8.55, 2.44 Hz, 1 H) 6.70-6.80 (m, 3 H) 6.65 (s, 1 H) 4.18-4.32 (m, 3 H) 3.81 (s, 3 H) 2.06-2.25 (m, 2 H) 1.84-2.03 (m, 4 H).

EXAMPLE 39 AND EXAMPLE 40

(S)—N-(4-(4-chloro-1H-imidazol-1-yl)-3-methoxyphenyl)-9-(3,5-difluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(3,5-difluorophenyl)-6,7,8,9-tetrahydro-5H-[1,2,4]triazolo[1,5-a]azepin-2-amine

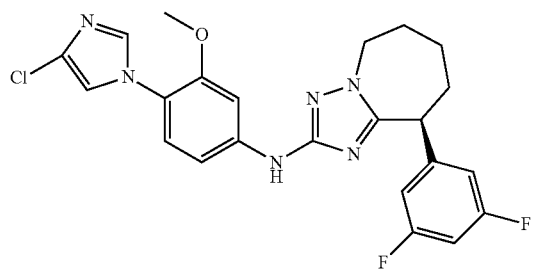

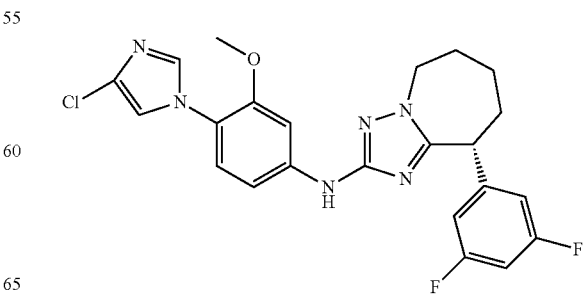

Step A: A racemic mixture of N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine (78 mg, 0.133 mmol, from Example 35) was purified using chiral supercritical fluid chromatography (SFC) to afford 16 mg of peak A (example 36) and 18 mg of peak B (example 37). SFC Method: Chiralpak AD-H (30×250 mm, 5 uM), 30% methanol (0.1% diethylamine) in $CO_2$, 35° C., 70 mL/min, absorbance 268 nm, $t_R$ (peak A) 21.8 min, t (peak B) 28.9 min. The absolute stereochemistry of individual enantiomers (Examples 39 and 40) was not determined. LC-MS and $^1$H NMR analytical data for the separated enantiomers was identical to the racemate (Example 37).

EXAMPLE 41

N-(4-(4-chloro-1H-imidazol-1-yl)-3-methoxyphenyl)-9-(6-chloropyridin-3-yl)-6,7,8,9-tetrahydro-5H-[1,2,4]thiazolo[1,5-a]azepin-2-amine 2,2,2-trifluoroacetate

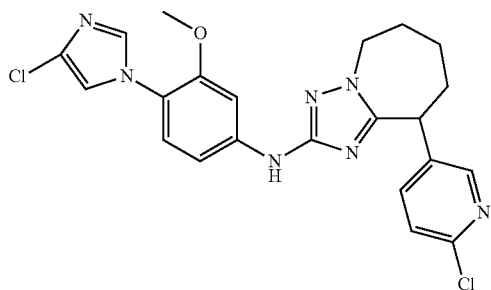

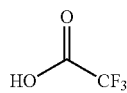

Step A: Methyl 4-(4-chloro-1H-imidazol-1-yl)-3-methoxyphenylcarbamimidothioate, hydroiodide (500 mg, 1.69 mmol, from preparation A) and 6-chloro-2-(6-chloropyridin-3-yl)hexanoic acid (442 mg, 1.69 mmol, from preparation AJ) were coupled and then reacted with hydrazine (0.211 mL, 6.74 mmol) using a procedure analogous to Step A of Example 13. The crude products were purified using silica gel chromatography (40-100% ethyl acetate/chloroform) to afford 5-(5-chloro-1-(6-chloropyridin-3-yl)pentyl)-N-(4-(4-chloro-1H-imidazol-1-yl)-3-methoxyphenyl)-1H-1,2,4-triazol-3-amine (190 mg, 0.375 mmol, 23% yield) as a pink foam. LC-MS (M+H)$^+$ 508.1.

Step B: A solution of 5-(5-chloro-1-(6-chloropyridin-3-yl)pentyl)-N-(4-(4-chloro-1H-imidazol-1-yl)-3-methoxyphenyl)-1H-1,2,4-triazol-3-amine (190 mg, 0.375 mmol), sodium iodide (281 mg, 1.874 mmol), and diisoproplylethylamine (0.065 mL, 0.375 mmol) in acetone (4 mL) was heated in a sealed vessel at 100° C. for 4 h. The reaction was concentrated in vacuo. The crude product was purified using reverse phase preparatory-HPLC (MeOH/water/TFA) to afford 94 mg (42% yield) of the titled compound as an off-white solid. LC-MS (M+H)$^+$ 470.1. $^1$H NMR (500 MHz, chloroform-d) δ ppm 9.20 (br. s., 1H) 8.27 (br. s., 1H) 7.88 (br. s., 1 H) 7.47-7.57 (m, 1 H) 7.36-7.47 (m, 1 H) 7.28-7.34 (m, 1 H) 7.25-7.27 (m, 1 H) 7.11-7.20 (m, 1 H) 7.06-7.11 (m, 1 H) 7.01-7.06 (m, 2 H) 4.25-4.44 (m, 3H) 3.85 (s, 3 H) 2.10-2.23 (m, 4 H) 1.85-2.02 (m, 2 H).

EXAMPLE 42

N-(4-(4-chloro-1H-imidazol-1-yl)-3-methoxyphenyl)-9-(4-chloro-1H-pyrazol-1-yl)-6,7,8,9-tetrahydro-5H-[1,2,4]triazolo[1,5-a]azepin-2-amine 2,2,2-trifluoroacetate

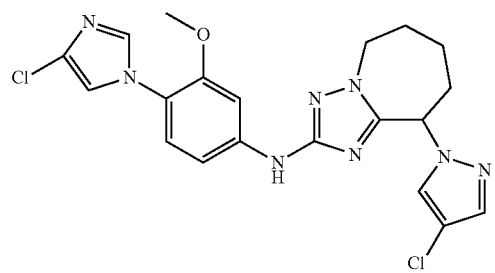

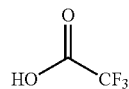

Step A: Methyl 4-(4-chloro-1H-imidazol-1-yl)-3-methoxyphenylcarbamimidothioate, hydroiodide (500 mg, 1.69 mmol, from preparation A) and 6-chloro-2-(4-chloro-1H-pyrazol-1-yl)hexanoic acid (423 mg, 1.685 mmol, from preparation AK) were coupled and then reacted with hydrazine (0.212 mL, 6.74 mmol) using a procedure analogous to Step A of Example 13 to afford 5-(5-chloro-1-(4-chloro-1H-pyrazol-1-yl)pentyl)-N-(4-(4-chloro-1H-imidazol-1-yl)-3-methoxyphenyl)-1H-1,2,4-triazol-3-amine (956 mg, 1.93 mmol, 100% yield). LC-MS (M+H)$^+$ 497.2. The crude products were used in the subsequent step without purification.

Step B: A solution of 5-(5-chloro-1-(4-chloro-1H-pyrazol-1-yl)pentyl)-N-(4-(4-chloro-1H-imidazol-1-yl)-3-methoxyphenyl)-1H-1,2,4-triazol-3-amine (836 mg, 1.686 mmol), sodium iodide (1.26 g, 8.43 mmol), and diisoproplylethylamine (0.589 mL, 3.37 mmol) in acetone (20 mL) was heated in a sealed vessel at 100° C. for 4 h. The reaction was concentrated in vacuo. The crude product was purified using reverse phase preparatory-HPLC (MeOH/water/TFA) to afford 55 mg (42% yield) of the titled compound. LC-MS (M+H)$^+$ 459.3. $^1$H NMR (500 MHz, chloroform-d) δ ppm 8.04 (br. s., 1H) 7.78 (d, J=1.53 Hz, 1 H) 7.49 (d, J=6.10 Hz, 2 H) 7.36 (d, J=2.14 Hz, 1 H) 7.15 (d, J=8.55 Hz, 1 H) 7.07 (d, J=1.53 Hz, 1 H) 7.00 (dd, J=8.55, 2.44 Hz, 1 H) 5.68 (dd, J=7.17, 2.59 Hz, 1 H) 4.50-4.52 (m, 1 H) 4.35-4.40 (m, 1H) 3.87 (s, 3H) 2.46-2.58 (m, 1 H) 2.12-2.25 (m, 1H) 1.88-2.08 (m, 4 H).

EXAMPLE 43

N-(4-(4-(difluoromethyl)-1H-imidazol-1-yl)-3-methoxyphenyl)-9-(4-fluorophenyl)-6,7,8,9-tetrahydro-5H-[1,2,4]triazolo[1,5-a]azepin-2-amine 2,2,2-trifluoroacetate

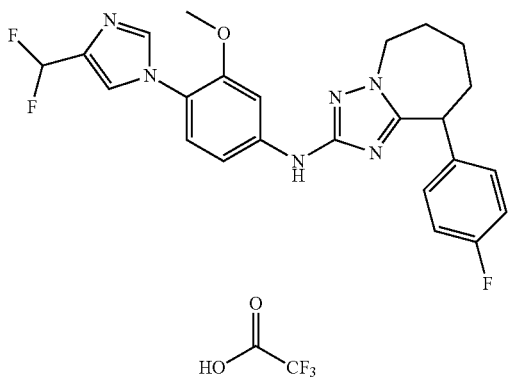

Step A: Methyl 4-(4-(difluoromethyl)-1H-imidazol-1-yl)-3-methoxyphenylcarbamimidothioate hydroiodide (500 mg, 1.601 mmol, from preparation N) and 6-chloro-2-(4-fluorophenyl)hexanoic acid (392 mg, 1.601 mmol, from preparation AH) were coupled and then reacted with hydrazine (0.201 mL, 6.40 mmol) using a procedure analogous to Step A of Example 13 to afford 5-(5-chloro-1-(4-fluorophenyl)pentyl)-N-(4-(4-(difluoromethyl)-1H-imidazol-1-yl)-3-methoxyphenyl)-1H-1,2,4-triazol-3-amine (821 mg, 100% yield). LC-MS (M+H)+ 505.3. The crude products were used in the subsequent step without purification.

Step B: A solution of 5-(5-chloro-1-(4-fluorophenyl)pentyl)-N-(4-(4-(difluoromethyl)-1H-imidazol-1-yl)-3-methoxyphenyl)-1H-1,2,4-triazol-3-amine (808 mg, 1.600 mmol), sodium iodide (1.20 g, 8.00 mmol), and diisoprolylethylamine (0.559 mL, 3.20 mmol) in acetone (20 mL) was heated in a sealed vessel at 100° C. for 4 h. The reaction was concentrated in vacuo. The crude product was purified using reverse phase preparatory-HPLC (MeOH/water/TFA) to afford 77 mg (8% yield) of the titled compound. LC-MS (M+H)+ 469.33. $^1$H NMR (500 MHz, chloroform-d) δ ppm 10.28 (s, 1 H) 8.16 (s, 1 H) 7.45 (s, 1 H) 7.34 (d, J=1.83 Hz, 1H) 7.16-7.25 (m, 2 H) 7.04-7.16 (m, 4 H) 6.89 (t, J=55.09 Hz, 1H) 4.54 (dd, J=7.63, 2.14 Hz, 1 H) 4.35-4.46 (m, 1 H) 4.19-4.31 (m, 1 H) 3.90 (s, 3H) 2.32-2.49 (m, 1 H) 2.09-2.23 (m, 1 H) 1.91-2.05 (m, 4 H).

EXAMPLE 44

N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine

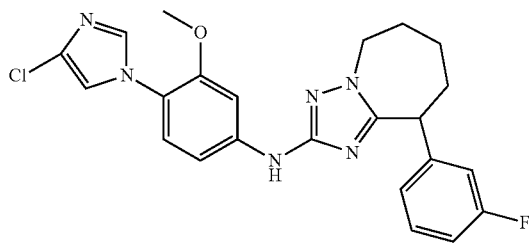 [SMILES: COc1cc(Nc2nc3n(n2)CCCCC3c2cccc(F)c2)ccc1-n1cnc(Cl)c1]

Step A: Methyl 4-(4-chloro-1H-imidazol-1-yl)-3-methoxyphenylcarbamimidothioate, hydroiodide (1.5 g, 5.05 mmol, from preparation A) and 6-chloro-2-(3-fluorophenyl)hexanoic acid (1.237 g, 5.05 mmol, from preparation AO) were coupled and then reacted with hydrazine (0.636 mL, 20.25 mmol) using a procedure analogous to Step A of Example 13. The crude product, 5-(5-chloro-1-(3-fluorophenyl)pentyl)-N-(4-(4-chloro-1H-imidazol-1-yl)-3-methoxyphenyl)-1H-1,2,4-triazol-3-amine (2.78 g, 100% yield), was used in the subsequent step without purification. LC-MS (M+H)+ 489.2.

Step B: A solution of 5-(5-chloro-1-(3-fluorophenyl)pentyl)-N-(4-(4-chloro-1H-imidazol-1-yl)-3-methoxyphenyl)-1H-1,2,4-triazol-3-amine (2.47 g, 5.05 mmol), sodium iodide (3.78 g, 25.2 mmol), and diisoprolylethylamine (1.76 mL, 10.1 mmol) in acetone (40 mL) was heated in a sealed vessel at 100° C. for 2 h. The reaction was concentrated in vacuo. The crude product was purified using silica gel column chromatography (0-35% EtOAc/chloroform, linear gradient) to afford 360 mg of an off-white solid. The solid was recrystallized from EtOH to afford 25 mg of the titled compound. The mother liquor was purified using reverse phase preparatory-HPLC (MeOH/water/TFA) to provide 362 mg (15% yield) of the trifluoroacetic acid salt of the titled compound. Analytical data for the free base: LC-MS (M+H)+ 453.3. $^1$H NMR (500 MHz, chloroform-d) δ ppm 7.50 (d, J=1.53 Hz, 1 H) 7.41 (d, J=2.14 Hz, 1 H) 7.31 (td, J=7.93, 6.10 Hz, 1 H) 7.08 (d, J=8.55 Hz, 1 H) 6.86-7.03 (m, 4 H) 6.81 (dd, J=8.39, 2.29 Hz, 1 H) 6.59 (s, 1H) 4.29 (dd, J=8.70, 2.29 Hz, 1 H) 4.15-4.25 (m, 2 H) 3.78 (s, 3H) 2.04-2.29 (m, 2 H) 1.75-2.03 (m, 4 H).

EXAMPLE 45 AND EXAMPLE 46

(S)—N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine

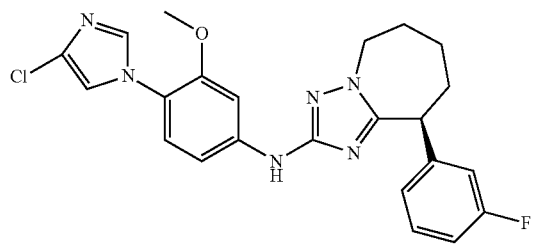

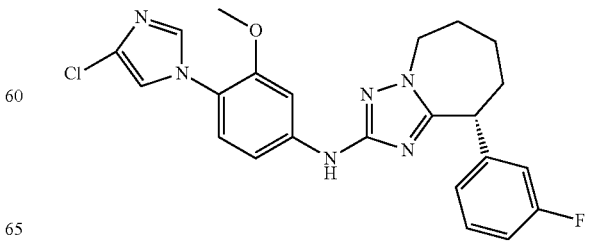

Step A: A racemic mixture of N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine, TFA (360 mg, 0.635 mmol, from Example 44) was purified using chiral supercritical fluid chromatography (SFC) to afford 157 mg of peak A (example 45) and 147 mg of peak B (example 46). SFC Method: Chiralpak AD-H (30×250 mm, 5 uM), 30% methanol (0.1% diethylamine) in $CO_2$, 35° C., 70 mL/min, absorbance 268 nm, $t_R$ (peak A) 21.8 min, $t_R$ (peak B) 28.9 min. The absolute stereochemistry of individual enantiomers (examples 39 and 40) was not determined. LC-MS and $^1$H NMR analytical data for the separated enantiomers was identical to the racemate (example 44).

EXAMPLE 47

9-(4-fluorophenyl)-N-(3-methoxy-4-(6-methylpyridazin-4-yl)phenyl)-6,7,8,9-tetrahydro-5H-[1,2,4]triazolo[1,5-a]azepin-2-amine

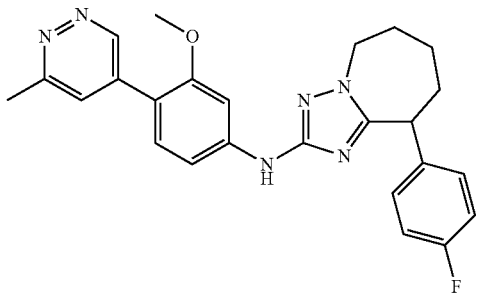 [SMILES: COc1cc(Nc2nc3n(n2)CCCCC3c2ccc(F)cc2)ccc1-c1cnnc(C)c1]

Step A: 1-Hydroxybenzotriazole hydrate (184 mg, 0.20 mmol), 1-ethyl-3-(3-dimethylaminopropyl)carbodiimide hydrochloride (223 mg, 1.163 mmol, from preparation L), and N-ethyldiisopropylamine (0.7 mL, 4.01 mmol) were sequentially added to a solution of 6-chloro-2-(4-fluorophenyl)hexanoic acid (233 mg, 0.952 mmol, from preparation AH) in dichloromethane (5 mL). The resulting mixture was stirred at rt for 10 min, then methyl 3-methoxy-4-(6-methylpyridazin-4-yl)phenylcarbamimidothioate hydroiodide (346 mg, 0.831 mmol) was added. After 3 h, the reaction mixture was concentrated to dryness and the residue was purified using silica gel column chromatography (0-100% EtOAc/$CH_2Cl_2$, linear gradient) to afford methyl N'-6-chloro-2-(4-fluorophenyl)hexanoyl-N-(3-methoxy-4-(6-methylpyridazin-4-yl)phenyl)carbamimidothioate (190 mg, 0.369 mmol, 44.4% yield). LC-MS (M+H)$^+$ 515.4.

Step B: Hydrazine (0.05 mL, 1.593 mmol) was added to a solution of methyl N'-6-chloro-2-(4-fluorophenyl)hexanoyl-N-(3-methoxy-4-(6-methylpyridazin-4-yl)phenyl)carbamimidothioate (190 mg, 0.369 mmol) in DMF (5 mL). The reaction mixture was stirred at rt for 5 hr and concentrated in vacuo. The crude product was purified using silica gel column chromatography (0-10% methanol/$CH_2Cl_2$, linear gradient) to afford 3-(5-chloro-1-(4-fluorophenyl)pentyl)-N-(3-methoxy-4-(6-methylpyridazin-4-yl)phenyl)-1H-1,2,4-triazol-5-amine (102 mg, 0.212 mmol, 58% yield). LC-MS (M+H)$^+$ 481.4.

Step C: A mixture of 3-(5-chloro-1-(4-fluorophenyl)pentyl)-N-(3-methoxy-4-(6-methylpyridazin-4-yl)phenyl)-1H-1,2,4-triazol-5-amine (102 mg, 0.212 mmol), potassium carbonate (117 mg, 0.848 mmol), and potassium iodide (70.4 mg, 0.424 mmol) in DMF (5 mL) was heated at 55° C. for 5 hrs. The solvent was removed in vacuo. The crude product was purified using silica gel column chromatography (0-10% MeOH/$CH_2Cl_2$, linear gradient) to afford 36 mg (36% yield) of the titled compound as a solid. LC-MS (M+H)$^+$ 455.3. $^1$H NMR (500 MHz, methanol-$d_4$) δ ppm 9.19 (s, 1 H) 7.68 (s, 1 H) 7.45 (s, 1 H) 7.33 (d, J=8.55 Hz, 1 H) 7.20 (dd, J=8.09, 5.65 Hz, 2 H) 7.00-7.10 (m, 3 H) 4.34 (d, J=8.24 Hz, 1 H) 4.14-4.30 (m, 2 H) 3.77 (s, 3 H) 2.64 (s, 3 H) 2.11-2.26 (m, 1 H) 1.71-2.08 (m, 5 H).

EXAMPLE 48

N-(4-(4-chloro-1H-imidazol-1-yl)-3,5-difluorophenyl)-9-(4-fluorophenyl)-6,7,8,9-tetrahydro-5H-[1,2,4]triazolo[1,5-a]azepin-2-amine

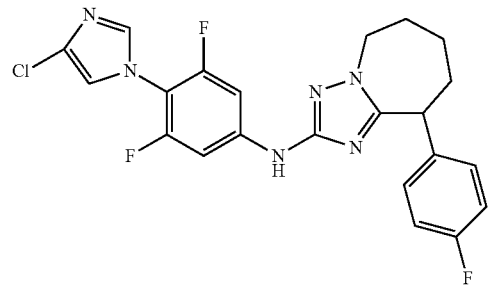 [SMILES: Fc1ccc(C2CCCCn3nc(Nc4cc(F)c(-n5cnc(Cl)c5)c(F)c4)nc32)cc1]

Step A: Methyl 4-(4-chloro-1H-imidazol-1-yl)-3,5-difluorophenylcarbamimidothioate hydroiodide (0.306 g, 0.711 mmol, from preparation J) and 6-chloro-2-(4-fluorophenyl)hexanoic acid (0.226 g, 0.924 mmol, from preparation AH) were coupled using a procedure analogous to Step A of Example 47. The crude product was purified using silica gel column chromatography (0-100% EtOAc/$CH_2Cl_2$, linear gradient) to afford methyl N-4-(4-chloro-1H-imidazol-1-yl)-3,5-difluorophenyl-N'-(6-chloro-2-(4-fluorophenyl)hexanoyl)carbamimidothioate (55 mg, 0.104 mmol, 15% yield). LC-MS (M+H)$^+$ 529.2.

Step B: Hydrazine (0.003 mL, 0.104 mmol) was added to a solution of methyl N'-6-chloro-2-(4-fluorophenyl)hexanoyl-N-(3-methoxy-4-(6-methylpyridazin-4-yl)phenyl)carbamimidothioate (55 mg, 0.104 mmol) in DMF (2 mL). The reaction mixture was stirred at rt for 5 hr and concentrated in vacuo. The crude product was purified using silica gel column chromatography (0-10% methanol/$CH_2Cl_2$, linear gradient) to afford 3-(5-chloro-1-(4-fluorophenyl)pentyl)-N-(4-(4-chloro-1H-imidazol-1-yl)-3,5-difluorophenyl)-1H-1,2,4-triazol-5-amine (43 mg, 0.087 mmol, 84% yield). LC-MS (M+H)$^+$ 495.2.

Step C: A mixture of 3-(5-chloro-1-(4-fluorophenyl)pentyl)-N-(4-(4-chloro-1H-imidazol-1-yl)-3,5-difluorophenyl)-1H-1,2,4-triazol-5-amine (40 mg, 0.081 mmol), potassium carbonate (11.2 mg, 0.081 mmol), and potassium iodide (13.4 mg, 0.081 mmol) in DMF (2 mL) was heated at 55° C. for 5 hrs. The solvent was removed in vacuo. The crude product was purified using silica gel column chromatography (0-10% MeOH/$CH_2Cl_2$, linear gradient) to afford 28 mg (72% yield) of the titled compound as a solid. LC-MS (M+H)$^+$ 459.2. $^1$H NMR (500 MHz, chloroform-d) δ ppm 7.49 (s, 1 H) 7.19 (d, J=10.38 Hz, 2 H) 7.14 (dd, J=8.55, 5.49 Hz, 2 H) 7.06 (t, J=8.55 Hz, 2 H) 7.00 (s, 1 H) 4.18-4.33 (m, 3 H) 2.15-2.28 (m, 1H) 1.78-2.15 (m, 5 H).

EXAMPLE 49

N-(4-(4-chloro-1H-imidazol-1-yl)-3-fluoro-5-methoxyphenyl)-9-(4-fluorophenyl)-6,7,8,9-tetrahydro-5H-[1,2,4]triazolo[1,5-a]azepin-2-amine

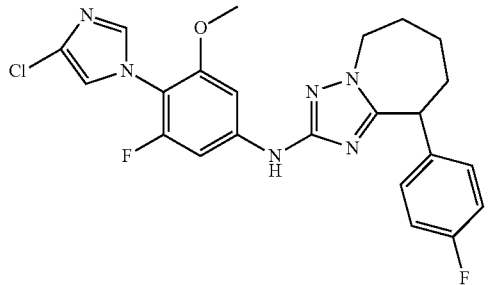 [SMILES: COc1cc(Nc2nc3n(n2)CCCCC3c2ccc(F)cc2)cc(F)c1-n1cnc(Cl)c1]

Step A: Methyl 4-(4-chloro-1H-imidazol-1-yl)-3-fluoro-5-methoxyphenylcarbamimidothioate hydroiodide (180 mg, 0.407 mmol, from preparation M) and 6-chloro-2-(4-fluorophenyl)hexanoic acid (119 mg, 0.488 mmol, from preparation AH) were coupled using a procedure analogous to Step A of Example 47. The crude product was purified using silica gel column chromatography (0-100% EtOAc/hexanes, linear gradient) to afford methyl N-4-(4-chloro-1H-imidazol-1-yl)-3-fluoro-5-methoxyphenyl-N'-(6-chloro-2-(4-fluorophenyl)hexanoyl)carbamimidothioate (130 mg, 0.240 mmol, 59.0% yield). LC-MS (M+H)+ 529.2.

Step B: Hydrazine (0.024 mL, 0.780 mmol) was added to a solution of methyl N-4-(4-chloro-1H-imidazol-1-yl)-3-fluoro-5-methoxyphenyl-N'-(6-chloro-2-(4-fluorophenyl)hexanoyl)carbamimidothioate (130 mg, 0.240 mmol) in DMF (3 mL). The reaction mixture was stirred at rt for 1 hr and concentrated in vacuo. The crude product was used in the next step without purification. LC-MS (M+H)+ 507.2.

Step C: A mixture of 5-(5-chloro-1-(4-fluorophenyl)pentyl)-N-(4-(4-chloro-1H-imidazol-1-yl)-3-fluoro-5-methoxyphenyl)-1H-1,2,4-triazol-3-amine (120 mg, 0.237 mmol), potassium carbonate (98 mg, 0.710 tunnel) and potassium iodide (58.9 mg, 0.355 mmol) in DMF (5 mL) was heated at 60° C. for 16 hrs. The solvent was removed in vacuo. The crude product was purified using silica gel column chromatography (0-100% EtOAc/CH$_2$Cl$_2$, linear gradient) to afford 72 mg (65% yield) of the titled compound as a solid. LC-MS (M+H)+ 471.2. $^1$H NMR (500 MHz, chloroform-d) δ ppm 7.41 (s, 1 H) 7.13 (dd, J=8.39, 5.34 Hz, 2 H) 7.03-7.06 (m, 3 H) 6.91 (s, 1 H) 6.89 (dd, J=11.90, 2.14 Hz, 1 H) 4.28 (d, J=7.32 Hz, 1 H) 4.23 (t, J=4.88 Hz, 2 H) 3.72 (s, 3 H) 2.15-2.26 (m, 1 H) 2.05-2.11 (m, 1 H) 1.79-2.03 (m, 4 H).

EXAMPLE 50

N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine

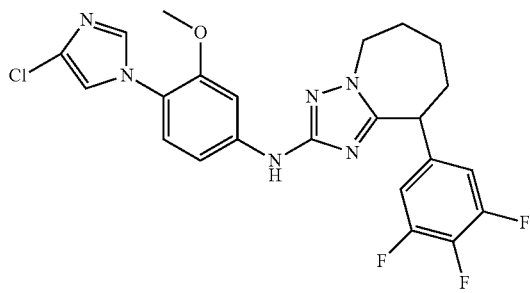 [SMILES: COc1cc(Nc2nc3n(n2)CCCCC3c2cc(F)c(F)c(F)c2)ccc1-n1cnc(Cl)c1]

Step A: Methyl 4-(4-chloro-1H-imidazol-1-yl)-3-methoxyphenylcarbamimidothioate (1.5 g, 5.05 mmol, from preparation A) and 6-chloro-2-(3,4,5-trifluorophenyl)hexanoic acid (1.419 g, 5.05 mmol, from preparation AN) were coupled and then reacted with hydrazine (0.635 mL, 20.23 mmol) using a procedure analogous to Step A of Example 13. The crude product, 5-(5-chloro-1-(3,4,5-trifluorophenyl)pentyl)-N-(4-(4-chloro-1H-imidazol-1-yl)-3-methoxyphenyl)-1H-1,2,4-triazol-3-amine (2.77 g, 100% yield), was used in the subsequent step without purification. LC-MS (M+H)+ 525.3.

Step B: A solution of 5-(5-chloro-1-(3,4,5-trifluorophenyl)pentyl)-N-(4-(4-chloro-1H-imidazol-1-yl)-3-methoxyphenyl)-1H-1,2,4-triazol-3-amine (2.66 g, 5.06 mmol), sodium iodide (3.79 g, 25.3 mmol), and diisoproplyethylamine (1.77 mL, 10.1 mmol) in acetone (40 mL) was heated in a sealed vessel at 100° C. for 2 h. The reaction was concentrated in vacuo. The crude product was purified using silica gel column chromatography (35-50% EtOAc/chloroform, linear gradient) to afford 420 mg (17% yield) of the titled compound as a pale yellow solid. The solid was recrystallized from EtOH to afford an analytical sample. LC-MS (M+H)+ 489.2. $^1$H NMR (500 MHz, chloroform-d) δ ppm 7.52 (d, J=1.53 Hz, 1 H) 7.39 (d, J=2.14 Hz, 1H) 7.11 (d, J=8.55 Hz, 1 H) 7.03 (d, J=1.22 Hz, 1H) 6.79-6.92 (m, 3 H) 6.59 (s, 1 H) 4.24-4.35 (m, 1 H) 4.10-4.24 (m, 2 H) 3.82 (s, 3H) 1.94-2.20 (m, 4 H) 1.78-1.94 (m, 2 H).

EXAMPLE 51 AND EXAMPLE 52

(S)—N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine

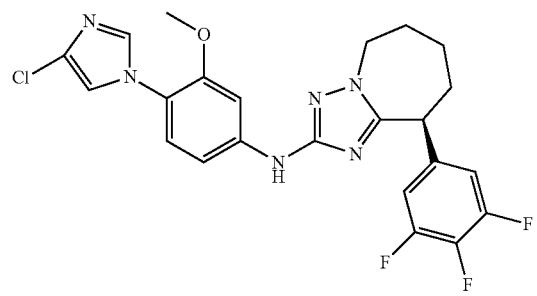

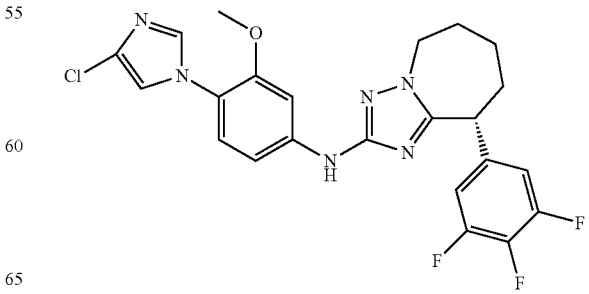

Step A: A racemic mixture of N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine (120 mg, from Example 50) was purified using chiral supercritical fluid chromatography (SFC) to afford 33 mg of peak A (Example 51) and 42 mg of peak B (Example 52). SFC Method: Chiralpak AD-H (30×250 mm, 5 uM), 25% methanol (0.1% diethylamine) in $CO_2$, 35° C., 70 mL/min, absorbance 268 nm, $t_R$ (peak A) 30.9 min, $t_R$ (peak B) 33.5 min. The absolute stereochemistry of individual enantiomers (examples 51 and 52) was not determined. LC-MS and $^1$H NMR analytical data for the separated enantiomers was identical to the racemate (Example 50).

EXAMPLE 53

N-(4-(4-chloro-1H-imidazol-1-yl)-3-methoxyphenyl)-9-(3-chlorophenyl)-6,7,8,9-tetrahydro-5H-[1,2,4]triazolo azepin-2-amine

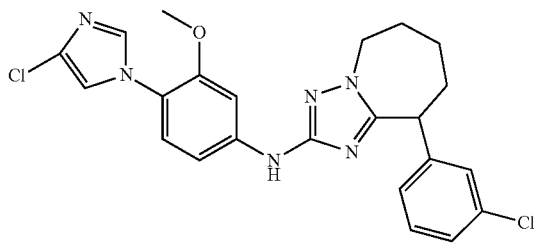 [SMILES: COc1cc(Nc2nc3n(n2)CCCCC3c2cccc(Cl)c2)ccc1-n1cnc(Cl)c1]

Step A: Methyl 4-(4-chloro-1H-imidazol-1-yl)-3-methoxyphenylcarbamimidothioate (1.5 g, 5.05 mmol, from preparation A) and 6-chloro-2-(3-chlorophenyl)hexanoic acid (1.320 g, 5.05 mmol, from preparation AP) were coupled and then reacted with hydrazine (0.635 mL, 20.23 mmol) using a procedure analogous to Step A of Example 13. The crude product, 5-(5-chloro-1-(3-chlorophenyl)pentyl)-N-(4-(4-chloro-1H-imidazol-1-yl)-3-methoxyphenyl)-1H-1,2,4-triazol-3-amine (2.78 g, 100% yield), was used in the subsequent step without purification. LC-MS (M+H)$^+$ 507.2.

Step B: A solution of 5-(5-chloro-1-(3-chlorophenyl)pentyl)-N-(4-(4-chloro-1H-imidazol-1-yl)-3-methoxyphenyl)-1H-1,2,4-triazol-3-amine (3.79 g, 25.3 mmol), sodium iodide (3.79 g, 25.3 mmol), and diisoproplylethylamine (1.77 mL, 10.1 mmol) in acetone (40 mL) was heated in a sealed vessel at 100° C. for 2 h. The reaction was concentrated in vacuo. The crude product was purified using silica gel column chromatography (0-35% EtOAc/chloroform, linear gradient) to afford 689 mg (28% yield) of the titled compound as a pale yellow solid. The solid was recrystallized from EtOH to afford an analytical sample. LC-MS (M+H)$^+$ 469.2. $^1$H NMR (500 MHz, chloroform-d) δ ppm 7.51 (d, J=1.22 Hz, 1 H) 7.43 (d, J=2.14 Hz, 1 H) 7.27-7.34 (m, 2 H) 7.20 (s, 1 H) 7.05-7.13 (m, 2 H) 7.02 (d, J=1.53 Hz, 1 H) 6.83 (dd, J=8.55, 2.44 Hz, 1H) 6.66 (s, 1H) 4.27 (dd, J=8.85, 2.44 Hz, 1H) 4.24 (dd, J=5.95, 4.12 Hz, 2 H) 3.79 (s, 3 H) 2.17-2.30 (m, 1 H) 2.06-2.15 (m, 1 H) 1.79-2.06 (m, 4 H).

EXAMPLE 54 AND EXAMPLE 55

(S)—N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine

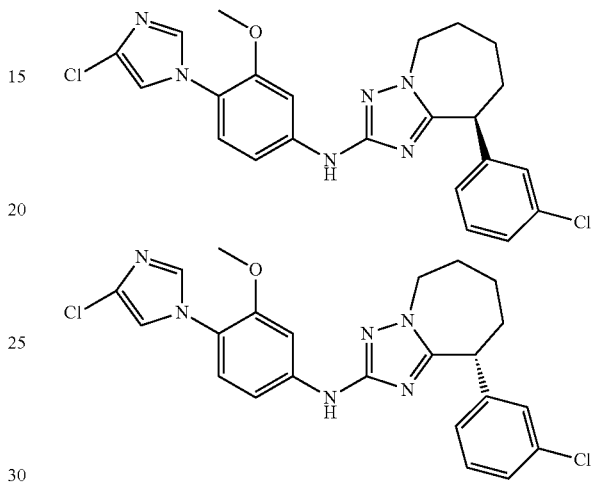

Step A: A racemic mixture of N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine, TFA salt (336 mg, 0.576 mmol, from Example 53) was purified using chiral supercritical fluid chromatography (SFC) to afford 37 mg of peak A (example 54) and 42 mg of peak B (example 55). SFC Method: Chiralpak AD-H (30×250 mm, 5 uM), 40% methanol (0.1% diethylamine) in $CO_2$, 35° C., 70 mL/min, absorbance 268 nm, $t_R$. (peak A) 19.8 min, $t_R$ (peak B) 32.2 min. The absolute stereochemistry of individual enantiomers (examples 54 and 55) was not determined. LC-MS and $^1$H NMR analytical data for the separated enantiomers was identical to the racemate (see Example 53).

EXAMPLE 56

N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine

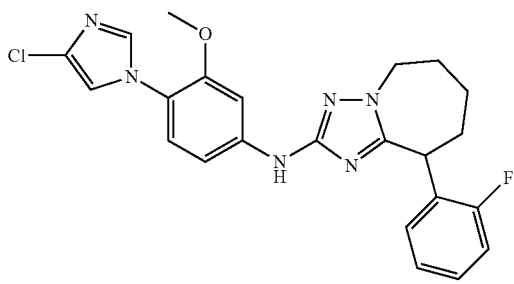 [SMILES: COc1cc(Nc2nc3n(n2)CCCCC3c2ccccc2F)ccc1-n1cnc(Cl)c1]

Step A: Methyl 4-(4-chloro-1H-imidazol-1-yl)-3-methoxyphenylcarbamimidothioate (1.5 g, 5.05 mmol, from preparation A) and 6-chloro-2-(2-fluorophenyl)hexanoic acid (1.24 g, 5.05 mmol, from preparation AQ) were coupled and then reacted with hydrazine (0.635 mL, 20.2 mmol) using a procedure analogous to Step A of Example 13. The crude product, 5-(5-chloro-1-(2-fluorophenyl)pentyl)-N-(4-(4-chloro-1H-imidazol-1-yl)-3-methoxyphenyl)-1H-1,2,4-triazol-3-amine (2.68 g, 100% yield), was used in the subsequent step without purification. LC-MS (M+H)$^+$ 489.2.

Step B: A solution of 5-(5-chloro-1-(2-fluorophenyl)pentyl)-N-(4-(4-chloro-1H-imidazol-1-yl)-3-methoxyphenyl)-1H-1,2,4-triazol-3-amine (2.47 g, 5.05 mmol), sodium iodide (3.79 g, 25.3 mmol), and diisoproplylethylamine (1.77 mL, 10.1 mmol) in acetone (40 mL) was heated in a sealed vessel at 100° C. for 2 h. The reaction was concentrated in vacuo. The crude product was purified using silica gel column chromatography (0-35% EtOAc/chloroform, linear gradient) to afford 234 mg (10% yield) of the titled compound as a pale yellow solid. The solid was recrystallized from EtOH to afford an analytical sample. LC-MS (M+H)$^+$ 453.3. $^1$H NMR (500 MHz, chloroform-d) δ ppm 7.50 (d, J=1.53 Hz, 1 H) 7.44 (d, J=2.14 Hz, 1 H) 7.27-7.34 (m, 1 H) 7.21-7.26 (m, 1 H) 7.16 (t, J=7.17 Hz, 1 H) 7.04-7.13 (m, 2 H) 7.01 (d, J=1.53 Hz, 1 H) 6.76 (dd, J=8.39, 2.29 Hz, 1 H) 6.60 (s, 1 H) 4.38-4.48 (m, 2 H) 4.22 (dd, J=14.50, 9.92 Hz, 1 H) 3.74 (s, 3H) 2.00-2.27 (m, 4H) 1.79-1.94 (m, 2 H).

EXAMPLE 57

4-(2-(4-(4-chloro-1H-imidazol-1-yl)-3-methoxyphenylamino)-6,7,8,9-tetrahydro-5H-[1,2,4]triazolo[1,5-a]azepin-9-yl)benzonitrile

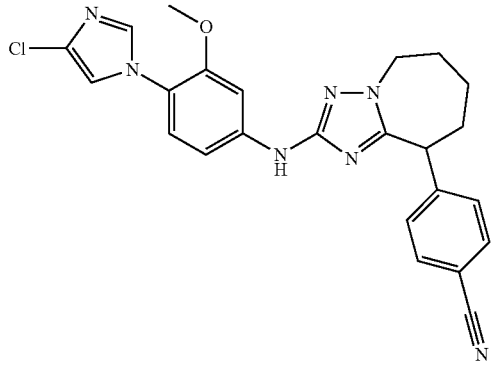 [SMILES: COc1cc(Nc2nc3n(n2)CCCCC3c2ccc(C#N)cc2)ccc1-n1cnc(Cl)c1]

Step A: Methyl 4-(4-chloro-1H-imidazol-1-yl)-3-methoxyphenylcarbamimidothioate, hydroiodide (1.0 g, 2.36 mmol, from preparation A) and 6-chloro-2-(4-cyanophenyl)hexanoic acid (0.741 g, 2.94 mmol, from preparation AU) were coupled [N-methylmorpholine (1.29 mL, 11.8 mmol) was substituted for N,N-diisopropylethylamine] and then reacted with hydrazine (0.370 mL, 11.8 mmol) using a procedure analogous to Step A of Example 13. After aqueous workup, 4-(5-chloro-1-(3-(4-(4-chloro-1H-imidazol-1-yl)-3-methoxyphenylamino)-1H-1,2,4-triazol-5-yl)pentyl)benzonitrile was obtained. The crude product was used in the subsequent step without purification. LC-MS (M+H)$^+$ 496.2.

Step B: A solution of 4-(5-chloro-1-(3-(4-(4-chloro-1H-imidazol-1-yl)-3-methoxyphenylamino)-1H-1,2,4-triazol-5-yl)pentyl)benzonitrile (1.17 g, 2.36 mmol), sodium iodide (1.77 g, 11.8 mmol), and diisoproplylethylamine (0.411 mL, 2.35 mmol) in acetone (10 mL) was heated in a sealed vessel at 100° C. for 12 h. The reaction was concentrated in vacuo. The crude product was purified using silica gel column chromatography (50% EtOAc/chloroform, linear gradient) to afford 430 mg of solid. The solid was recrystallized from EtOH to afford 269 mg (24% yield) of the titled compound. LC-MS (M+H)$^+$ 460.4. $^1$H NMR (500 MHz, DMSO-d$_6$) δ ppm 9.38 (s, 1 H), 7.84 (m, J=8.5 Hz, 2 H), 7.73 (d, J=1.2 Hz, 1 H), 7.52 (m, J=8.2 Hz, 2 H), 7.47 (d, J=2.1 Hz, 1 H), 7.41 (d, J=1.5 Hz, 1 H), 7.19 (d, J=8.9 Hz, 1H), 7.04 (dd, J=8.7, 2.3 Hz, 1H), 4.44 (d, J=10.7 Hz, 1 H), 4.26-4.38 (m, 1H), 4.16-4.26 (m, 1 H), 3.67 (s, 3 H), 2.05-2.21 (m, 1 H), 1.90-2.00 (m, 3 H), 1.76-1.90 (m, 1H), 1.60-1.75 (m, 1 H).

EXAMPLE 58 AND EXAMPLE 59

(S)—N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine

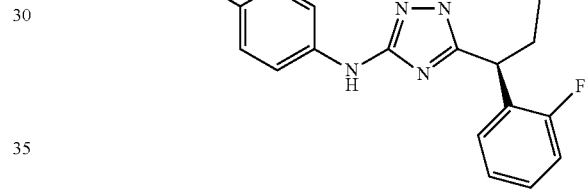

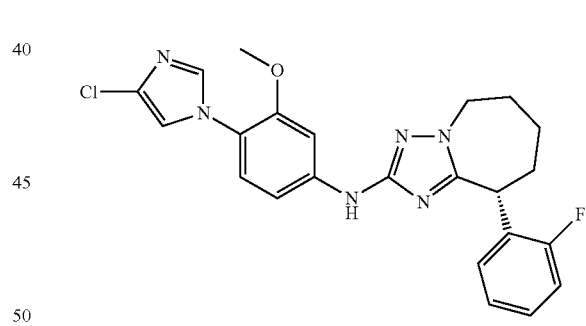

Step A: A racemic mixture of N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine (190 mg, from Example 56) was purified using chiral supercritical fluid chromatography (SFC) to afford 88 mg of peak A (example 58) and 87 mg of peak B (example 59). SFC Method: Chiralpak AD-H (30×250 mm, 5 uM), 35% methanol (0.1% diethylamine) in CO$_2$, 35° C., 70 mL/min, absorbance 268 nm, t$_R$ (peak A) 19.8 min, t$_R$ (peak B) 32.2 min. The absolute stereochemistry of individual enantiomers (examples 58 and 59) was not determined. LC-MS and $^1$H NMR analytical data for the separated enantiomers was identical to racemate (see Example 56).

EXAMPLE 60

9-(4-fluorophenyl)-N-(3-methoxy-4-(3-methyl-1,2,4-oxadiazol-5-yl)phenyl)-6,7,8,9-tetrahydro-5H-[1,2,4]triazolo[1,5-a]azepin-2-amine

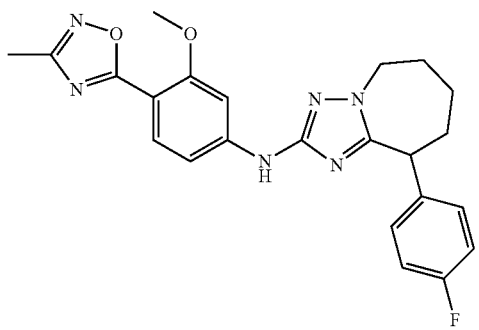 [SMILES: COc1cc(Nc2nc3n(n2)CCCCC3c2ccc(F)cc2)ccc1-c1nc(C)no1]

Step A: Methyl 3-methoxy-4-(3-methyl-1,2,4-oxadiazol-5-yl)phenylcarbamimidothioate, hydroiodide (1.11 g, 2.73 mmol, from preparation I) and 6-chloro-2-(4-fluorophenyl)hexanoic acid (1.00 g, 4.10 mmol, from preparation AH) were coupled using a procedure analogous to Step A of Example 47. The crude reaction was poured into water and extracted with EtOAc. The organic layer was washed with brine, dried over sodium sulfate and concentrated in vacuo to afford methyl N'-6-chloro-2-(4-fluorophenyl)hexanoyl-N-(3-methoxy-4-(3-methyl-1,2,4-oxadiazol-5-yl)phenyl)carbamimidothioate. The crude product was used in the subsequent step without purification. LC-MS (M+H)+ 505.2.

Step B: Hydrazine (0.157 ml, 5.0 mmol) was added to a solution of methyl N'-6-chloro-2-(4-fluorophenyl)hexanoyl-N-(3-methoxy-4-(3-methyl-1,2,4-oxadiazol-5-yl)phenyl)carbamimidothioate (600 mg, 1.188 mmol) in DMF (10 mL). The reaction mixture was stirred at rt for 1 hr and concentrated in vacuo. The crude product was concentrated to afford 5-(5-chloro-1-(4-fluorophenyl)pentyl)-N-(3-methoxy-4-(3-methyl-1,2,4-oxadiazol-5-yl)phenyl)-1H-1,2,4-triazol-3-amine. The crude product was used in the subsequent step without purification.

Step C: A mixture of 5-(5-chloro-1-(4-fluorophenyl)pentyl)-N-(3-methoxy-4-(3-methyl-1,2,4-oxadiazol-5-yl)phenyl)-1H-1,2,4-triazol-3-amine (559 mg, 1.188 mmol), potassium carbonate (657 mg, 4.75 mmol), and potassium iodide (394 mg, 2.376 mmol) in DMF (8 mL) was heated at 55° C. for 16 hrs. The solvent was removed in vacuo. The crude product was purified using reverse phase preparatory-HPLC (Column: Phenomenex Luna C18 30×100 mm, Solvent A=10 mM Ammonium Acetate in 95:5 water/ACN, Solvent B=10 mM Ammonium Acetate in 5:95 water/ACN, Flow rate: 40 ml/min, 30-85% B, 25 min) to afford 9-(4-fluorophenyl)-N-(3-methoxy-4-(3-methyl-1,2,4-oxadiazol-5-yl)phenyl)-6,7,8,9-tetrahydro-5H-[1,2,4]triazolo[1,5-a]azepin-2-amine (82 mg, 0.189 mmol, 16% yield). LC-MS (M+H)+ 435.3. $^1$H NMR (400 MHz, methanol-$d_4$) δ ppm 7.83 (d, J=8.56 Hz, 1 H) 7.56 (d, J=2.01 Hz, 1 H) 7.19-7.28 (m, 2 H) 7.08 (t, J=8.81 Hz, 2 H) 6.99 (dd, J=8.56, 2.01 Hz, 1 H) 4.17-4.43 (m, 3 H) 3.85 (s, 3 H) 2.39 (s, 3 H) 2.17-2.31 (m, 1 H) 2.01-2.11 (m, 1 H) 1.78-1.98 (m, 4 H).

EXAMPLE 61

9-(4-fluorophenyl)-N-(3-methoxy-4-(3-methylisoxazol-5-yl)phenyl)-6,7,8,9-tetrahydro-5H-[1,2,4]triazolo[1,5-a]azepin-2-amine

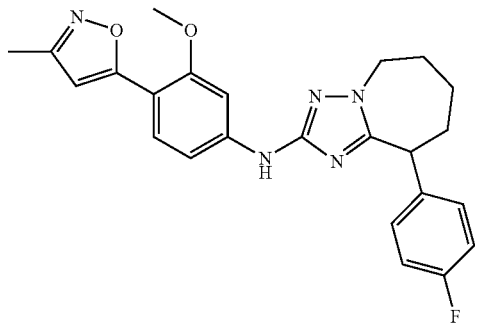 [SMILES: COc1cc(Nc2nc3n(n2)CCCCC3c2ccc(F)cc2)ccc1-c1cc(C)no1]

Step A: Methyl 3-methoxy-4-(3-methylisoxazol-5-yl)phenylcarbamimidothioate, hydroiodide (500 mg, 1.234 mmol, from preparation H) and 6-chloro-2-(4-fluorophenyl)hexanoic acid (453 mg, 1.851 mmol, from preparation AH) were coupled using a procedure analogous to Step A of Example 47. The crude reaction was poured into water and extracted with EtOAc. The organic layer was washed with brine, dried over sodium sulfate and concentrated in vacuo to afford methyl N'-6-chloro-2-(4-fluorophenyl)hexanoyl-N-(3-methoxy-4-(3-methylisoxazol-5-yl)phenyl)carbamimidothioate. The crude product was used in the subsequent step without purification. LC-MS (M+H)+ 504.3.

Step B: Hydrazine (0.163 ml, 5.2 mmol) was added to a solution of methyl N'-6-chloro-2-(4-fluorophenyl)hexanoyl-N-(3-methoxy-4-(3-methylisoxazol-5-yl)phenyl)carbamimidothioate (0.622 g, 1.234 mmol) in DMF (10 mL). The reaction mixture was stirred at rt for 1 hr and concentrated in vacuo. The crude product was concentrated to afford 5-(5-chloro-1-(4-fluorophenyl)pentyl)-N-(3-methoxy-4-(3-methylisoxazol-5-yl)phenyl)-1H-1,2,4-triazol-3-amine. The crude product was used in the subsequent step without purification. LC-MS (M+H)+ 4703.

Step C: A mixture of 5-(5-chloro-1-(4-fluorophenyl)pentyl)-N-(3-methoxy-4-(3-methylisoxazol-5-yl)phenyl)-1H-1,2,4-triazol-3-amine (580 mg, 1.234 mmol), potassium carbonate (682 mg, 4.94 mmol), and potassium iodide (410 mg, 2.468 mmol) in DMF (8 mL) was heated at 55° C. for 16 hrs. The solvent was removed in vacuo. The crude product was purified using reverse phase preparatory-HPLC (Column: Phenomenex Luna C18 30×100 mm, Solvent A=10 mM Ammonium Acetate in 95:5 water/ACN, Solvent B=10 mM Ammonium Acetate in 5:95 water/ACN. Flow rate: 40 ml/mM, 30-85% B, 25 min) to afford 9-(4-fluorophenyl)-N-(3-methoxy-4-(3-methylisoxazol-5-yl)phenyl)-6,7,8,9-tetrahydro-5H-[1,2,4]triazolo[1,5-a]azepin-2-amine (145 mg, 0.301 mmol, 24% yield). LC-MS (M+H)+ 434.3. $^1$H NMR (400 MHz, methanol-$d_4$) δ ppm 7.67 (d, J=8.56 Hz, 1 H) 7.49 (d, J=2.01 Hz, 1 H) 7.23 (dd, J=8.56, 5.29 Hz, 2H) 7.09 (t, J=8.69 Hz, 2 H) 6.99 (dd, J=8.56, 2.01 Hz, 1 H) 4.35-4.44 (m, 1H) 4.15-4.35 (m, 2 H) 3.87 (s, 3 H) 2.30 (s, 3 H) 2.19-2.28 (m, 1 H) 2.00-2.10 (m, 1 H) 1.72-1.94 (m, 4 H).

EXAMPLE 62 rel-(6R,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-6-ol 2,2,2-trifluoroacetate

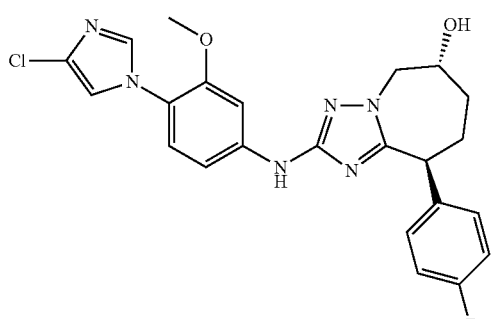

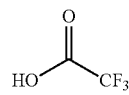

Step A: Borane tetrahydrofuran complex (1 M in THF) (309 μL, 0.309 mmol, 1 M in THF) was added dropwise over 2 min to a 0° C. solution of (Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine (63.23 mg, 0.140 mmol, from example 1). The reaction mixture was allowed to warm to rt and was then heated to reflux for 1 hr. The reaction mixture was cooled to 0° C. and aqueous sodium hydroxide solution (3 N) (71.6 μL, 0.215 mmol) was added followed by the dropwise addition of 30% aqueous hydrogen peroxide (71.6 μL, 0.701 mmol). The resulting mixture was allowed to warm to rt and stir for 3 h. The mixture was then diluted with EtOAc (2 mL) and washed with aqueous 1 N HCl (1 mL). The organic layer was dried over magnesium sulfate, filtered and concentrated in vacuo. The dark residue was determined by LCMS to contain a significant portion of unreacted starting material. The crude products were resubjected to the same reaction conditions; however, 5 equivalents of borane tetrahydrofuran complex were used. The reaction mixture from the second attempt was worked-up in a similar fashion. The crude material was purified by reverse phase preparatory HPLC (C18, 30×150 mm, acetonitrile/water/ammonium acetate) to afford multiple products diastereomeric with the desired molecular weight. The titled compound was isolated (2.3 mg, 3% yield) and the structure determined. Extensive NMR experiments supported a trans relationship of the hydroxyl group and the 4-fluorophenyl substituent. LC-MS (M+H)$^+$ 468.9. $^1$H NMR (500 MHz, chloroform-d) δ ppm 7.47-7.53 (1 H, m), 7.37 (1 H, d, J=2.14 Hz), 7.14 (2 H, dd, J=8.55, 5.19 Hz), 7.02-7.10 (3 H, m), 6.97-7.02 (1 H, m), 6.83 (1 H, dd, J=8.39, 2.29 Hz), 6.73 (1 H, s), 4.28 (3H, d, J=5.19 Hz), 3.99-4.08 (1 H, m), 3.74-3.81 (3 H, m), 2.24-2.36 (1H, m), 2.07-2.24 (2 H, m), 1.92-2.04 (1H, m).

EXAMPLE 63 rel-(6S,7R,9R)-2-(4-(4-chloro-1H-imidazol-1-yl)-3-methoxyphenylamino)-9-(4-fluorophenyl)-6,7,8,9-tetrahydro-5H-[1,2,4]triazolo azepine-6,7-diol 2,2,2-trifluoroacetate

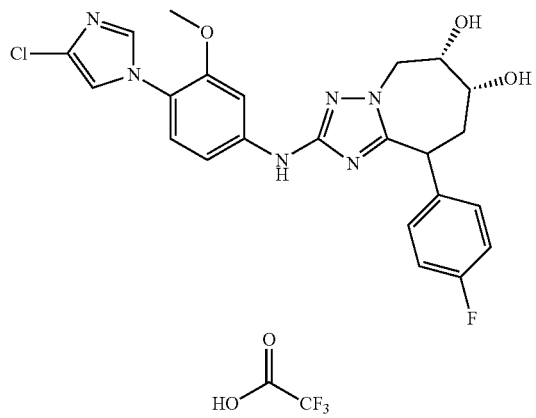

and

EXAMPLE 64 rel-(6S,7R,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepine-6,7-diol 2,2,2-trifluoroacetate

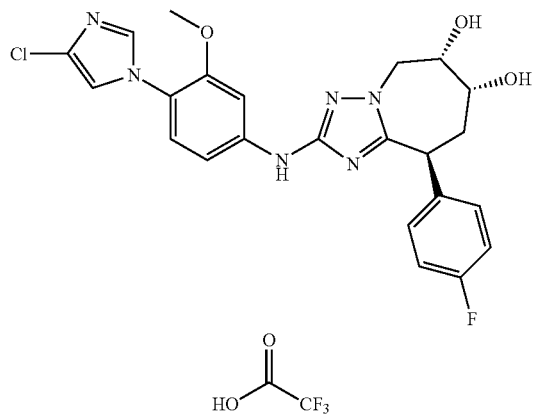

Step A: Water (94 μL), 4-methylmorpholine N-oxide (65.5 mg, 0.559 mmol), and osmium tetroxide (9.47 μL, 0.754 μmol) were sequentially added to a solution of (Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine (100 mg, 0.222 mmol, from example 1) in acetone (842 μL). The resulting mixture was stirred at rt for 18 h. The reaction mixture was diluted with EtOAc (10 mL) and washed with water (2×5 mL) and then brine. The organic layer was dried over MgSO$_4$, filtered, and concentrated in vacuo. The residue was purified using silica gel column chromatography (0-25% MOM/chloroform, linear gradient). The first major peak to elute which demonstrated a molecular ion consistent with the desired product was contaminated with impurities. Fractions that contained the second major peak were concentrated to afford 7.2 mg (7% yield) of example 63 as an off-white solid. The impure fractions of the first peak were repurified using reverse phase preparatory HPLC (C18, 30×150 mm, MeOH/water/TFA) to afford 12.5 mg (9% yield) of example 64. Extensive NMR experiments supported the relative stereochemical assignments of examples 63 and 64.

Data for example 63: LC-MS (M+H)$^+$ 485.1. $^1$H NMR (500 MHz, DMSO-d$_6$) δ ppm 9.31 (s, 1 H) 7.71 (s, 1 H) 7.48 (s, 1H) 7.39 (s, 1H) 7.36 (dd, J=8.24, 5.80 Hz, 2 H) 7.17 (t, J=9.31 Hz, 3 H) 7.01 (d, J=8.55 Hz, 1 H) 4.93 (t, J=5.49 Hz, 2 H) 4.30-4.45 (m, 1 H) 4.12-4.28 (m, 2 H) 4.02 (br. s., 1 H) 3.81-3.95 (m, 1H) 3.65 (s, 3 H) 2.21-2.34 (m, 1H) 1.73 (d, J=11.90 Hz, 1 H).

Data for example 64: LC-MS (M+H)$^+$ 485.2. $^1$H NMR (500 MHz, methanol-d$_4$) δ ppm 7.98 (d, J=1.22 Hz, 1 H) 7.56 (d, J=2.14 Hz, 1 H) 7.38 (d, J=1.53 Hz, 1 H) 7.30 (dd, J=8.55, 5.49 Hz, 2 H) 7.23 (d, J=8.55 Hz, 1 H) 7.11 (t, J=8.70 Hz, 2 H) 7.03 (dd, J=8.55, 2.14 Hz, 1 H) 4.70 (s, 1 H) 4.62 (dd, J=14.50, 8.70 Hz, 1 H) 3.98-4.09 (m, 2H) 3.92 (d, J=8.55 Hz, 1H) 3.81 (s, 3 H) 2.26-2.46 (m, 2 H).

EXAMPLE 65 rel-(6R,9R)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-6-ol 2,2,2-trifluoroacetate

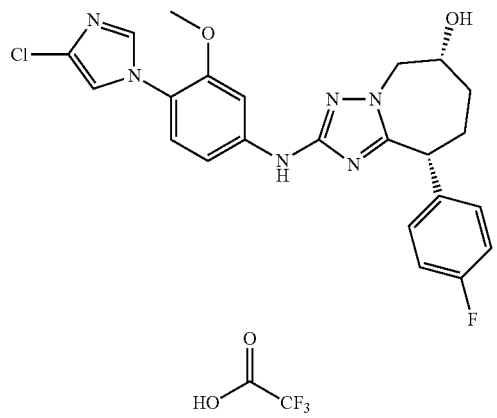

and

EXAMPLE 66 rel-(7S,9R)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-7-ol 2,2,2-trifluoroacetate

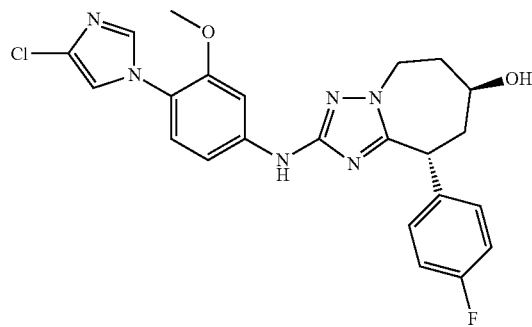

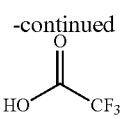

Step A: 9-Borabicyclo[3.3.1]nonane dimer (386 mg, 1.597 mmol) was added to a 0° C. solution of (Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine (144 mg, 0.319 mmol, from example 1) in THF (1.3 mL). The reaction mixture was allowed to warm to rt. The mixture was subsequently heated at reflux for 1 hr, then chilled in a 0° C. ice-water bath. A mixture of aqueous sodium hydroxide (3 N) (160 μL, 0.479 mmol) and aqueous 30% hydrogen peroxide (163 μL, 1.597 mmol) was slowly added. The resulting mixture was allowed to warm to rt and stir for 3 hr. The crude reaction was diluted with EtOAc (10 mL) and washed with water (5 mL). The organic layer was washed with brine (5 mL), dried over MgSO$_4$, filtered, and concentrated in vacuo. The crude product was purified using silica gel column chromatography (EtOAc/hexanes) to afford 30 mg of a mixture of product diastereomers. Further purification using reverse phase preparatory HPLC (C18, 30×150 mm, MeOH/water/TFA, isocratic 45%) afforded 5.0 mg (3% yield) of example 65, 1.3 mg (1% yield) of example 66, and 6.2 mg (3% yield) of example 62 all as tan solids. Extensive NMR experiments supported the relative stereochemical assignments of examples 65 and 66.

Data for example 65: LC-MS (M+H)$^+$ 469.2. $^1$H NMR (500 MHz, methanol-d$_4$) δ ppm 7.81 (s, 1 H) 7.53 (d, J=2.44 Hz, 0.1 H) 7.23-7.32 (m, 3 H) 7.19 (d, J=8.55 Hz, 1 H) 7.10 (t, J=8.70 Hz, 2 H) 7.02 (dd, J=8.70, 2.29 Hz, 1 H) 4.33-4.44 (m, 2 H) 4.19 (dd, J=14.34, 7.63 Hz, 1 H) 4.05 (t, J=6.71 Hz, 1 H) 3.79 (s, 3 H) 2.41-2.55 (m, 1 H) 1.87-2.14 (m, 3 H).

Data for example 66: LC-MS (M+H)$^+$ 469.2. $^1$H NMR (500 MHz, methanol-d$_4$) δ ppm 7.71 (s, 1H) 7.54 (d, J=2.44 Hz, 1H) 7.22-7.33 (m, 3H) 7.19 (d, J=8.55 Hz, 1H) 7.11 (t, J=8.70 Hz, 2H) 7.01 (dd, J=8.55, 2.14 Hz, 1H) 4.66-4.75 (m, 1 H) 4.48-4.60 (m, 1 H) 4.03-4.20 (m, 2 H) 3.79 (s, 3 H) 2.41-2.54 (m, 1 H) 2.04-2.16 (m, 3 H).

EXAMPLE 67

N-(3-methoxy-4-(3-methyl-1H-1,2,4-triazol-1-yl)phenyl)-4-phenyl-4,5,6,7-tetrahydrobenzo[d]thiazol-2-amine

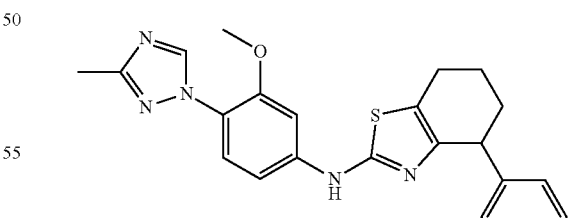

Step A: A mixture of 2-bromo-6-phenylcyclohexanone (84 mg, 0.332 mmol, from preparation AAA) and 1-(3-methoxy-4-(3-methyl-1H-1,2,4-triazol-1-yl)phenyl)thiourea (87 mg, 0.332 mmol, from step 4 of preparation F) was heated in ethanol (0.55 mL) at 80° C. for 3 h. The crude reaction was diluted with EtOAc and washed with saturated sodium bicarbonate solution. The organic layer was concentrated in vacuo.

The crude product was purified using preparatory TLC (60% acetone/hexanes) to give 54 mg (39% yield) of the titled compound as a white solid. LC-MS (M+H)+ 418.0. ¹H NMR (400 MHz, chloroform-d) δ ppm 8.44 (s, 1 H) 7.49 (dd, J=5.41, 3.15 Hz, 2 H) 7.23-7.35 (m, 2 H) 7.12-7.21 (m, 3 H) 6.60 (dd, J=8.56, 2.27 Hz, 1H) 3.98-4.08 (m, 1 H) 3.49 (s, 3 H) 2.66-2.85 (m, 2 H) 2.46 (s, 3 H) 2.17-2.26 (m, 1 H) 1.92-2.05 (m, 1 H) 1.78-1.91 (m, 2 H).

EXAMPLE 68

N-(4-(4-chloro-1H-imidazol-1-yl)-3-methoxyphenyl)-4-phenyl-4,5,6,7-tetrahydrobenzo[d]thiazol-2-amine

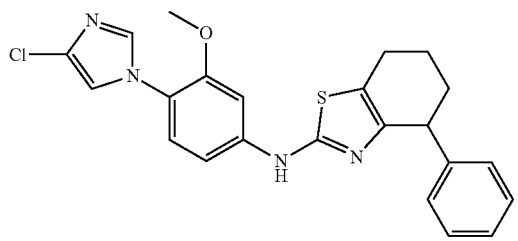

Step A: A mixture of 2-bromo-6-phenylcyclohexanone (89 mg, 0.352 mmol, from preparation AAA) and 1-(4-(4-chloro-1H-imidazol-1-yl)-3-methoxyphenyl)thiourea (99 mg, 0.352 mmol, from step 4 of preparation A) was heated in ethanol (0.60 mL) at 80° C. for 3 h. The crude reaction was diluted with EtOAc and washed with saturated sodium bicarbonate solution. The organic layer was concentrated in vacuo. The crude product was purified using preparatory TLC (60% acetone/hexanes) to give 42 mg (26% yield) of the titled compound as a white solid. LC-MS (M+H)+ 437.0. ¹H NMR (400 MHz, chloroform-d) δ ppm 7.50 (d, J=1.51 Hz, 1 H) 7.45 (d, J=2.52 Hz, 1 H) 7.28-7.36 (m, 2 H) 7.14-7.23 (m, 3H) 7.08 (d, J=8.31 Hz, 1 H) 7.00 (d, J=1.51 Hz, 1 H) 6.60 (dd, J=8.44, 2.39 Hz, 1 H) 4.05 (t, J=6.30 Hz, 1H) 3.47 (s, 3 H) 2.68-2.89 (m, 2 H) 2.20-2.28 (m, 1 H) 1.98 (dd, J=7.30, 5.29 Hz, 1 H) 1.78-1.93 (m, 2 H).

EXAMPLE 69 AND EXAMPLE 70

(S)—N-(4-(4-chloro-1H-imidazol-1-yl)-3-methoxyphenyl)-4-phenyl-4,5,6,7-tetrahydrobenzo[d]thiazol-2-amine and (R)—N-(4-(4-chloro-1H-imidazol-1-yl)-3-methoxyphenyl)-4-phenyl-4,5,6,7-tetrahydrobenzo[d]thiazol-2-amine

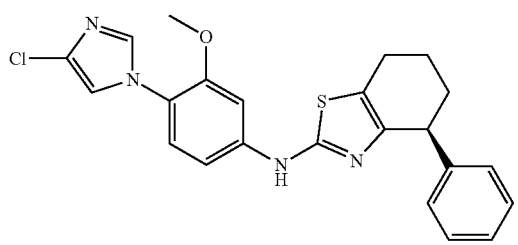

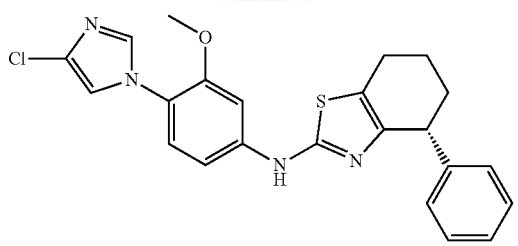

Step A: A racemic mixture of N-(4-(4-chloro-1H-imidazol-1-yl)-3-methoxyphenyl)-4-phenyl-4,5,6,7-tetrahydrobenzo[d]thiazol-2-amine (from Example 68) was purified using chiral supercritical fluid chromatography (SFC) to afford 11 mg of peak A (example 69) and 12 mg of peak B (example 70). SFC Method: Chiralpak AD-H (30×250 mm, 5 uM), 30% methanol (0.1% diethylamine) in CO₂, 35° C., 70 mL/min, absorbance 312 nm, $t_R$ (peak A) 12.0 min, $t_R$ (peak B) 16.3 min. The absolute stereochemistry of individual enantiomers (examples 69 and 70) was not determined. LC-MS for the separated enantiomers was identical to racemate (see example 68).

EXAMPLE 71

N-(3-methoxy-4-(4-methyl-1H-imidazol-1-yl)phenyl)-4-phenyl-4,5,6,7-tetrahydrobenzo[d]thiazol-2-amine 2,2,2-trifluoroacetate

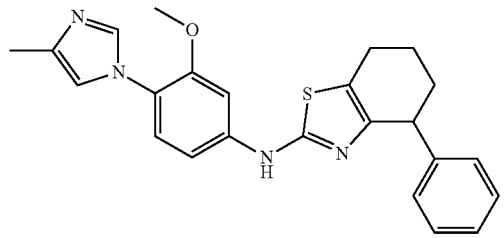 [SMILES: COc1cc(Nc2nc3c(s2)CCCC3c2ccccc2)ccc1-n1cnc(C)n1]

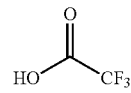

Step A: A mixture of 2-bromo-6-phenylcyclohexanone (85 mg, 0.335 mmol, from preparation AAA) and 1-(3-methoxy-4-(4-methyl-1H-imidazol-1-yl)phenyl)thiourea (80 mg, 0.305 mmol, from step 4 of preparation D) was heated in ethanol (1.5 mL) at 80° C. for 16 h. The crude reaction products were purified using Preparatory HPLC (Solvent A=10% MeOH-90% water-0.1% TFA, Solvent B=90% MeOH-10% water-0.1% TFA. Column: Phenomenex Luna 30×100 mm, S10, flow rate: 40 ml/min, 40-95% B, 35 min) to afford 93 mg (43% yield) of the titled compound as a clear oil. LC-MS (M+H)+ 417.2.

EXAMPLE 72

N-(3-methoxy-4-(2-methylpyridin-4-yl)phenyl)-4-phenyl-4,5,6,7-tetrahydrobenzo[d]thiazol-2-amine 2,2,2-trifluoroacetate

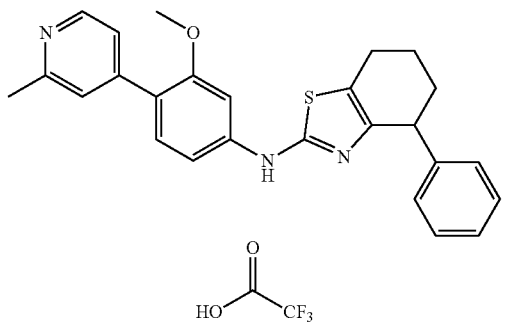

Step A: A mixture of 2-bromo-6-phenylcyclohexanone (85 mg, 0.335 mmol, from preparation AAA) and 1-(4-bromo-3-methoxyphenyl)thiourea (200 mg, 0.766 mmol, from preparation P) was heated in ethanol (2.5 mL) at 80° C. for 16 h. The crude reaction products were purified using Preparatory HPLC (Solvent A=10% MeOH-90% water-0.1% TFA, Solvent B=90% MeOH-10% water-0.1% TFA. Column: Phenomenex Luna 30×100 mm, S10, flow rate: 40 ml/min, 45-100% B, 30 min) to afford N-(4-bromo-3-methoxyphenyl)-4-phenyl-4,5,6,7-tetrahydrobenzo[d]thiazol-2-amine, TFA (156 mg, 0.265 mmol, 35% yield). LC-MS $(M+H)^+$ 417.1.

Step B: A mixture of N-(4-bromo-3-methoxyphenyl)-4-phenyl-4,5,6,7-tetrahydrobenzo[d]thiazol-2-amine, TFA (70 mg, 0.13 mmol), 2-methylpyridin-4-ylboronic acid (36 mg, 0.26 mmol), tetrakis(triphenylphosphine)palladium(0) (7.6 mg, 6.6 µmol) and $Cs_2CO_3$ (172 mg, 0.529 mmol) in DME (994 µL)/water (328 µL) was heated at 100° C. for 18 h. The crude reaction products were purified using preparatory HPLC (Solvent A=10% MeOH-90% water-0.1% TFA, Solvent B=90% MeOH-10% water-0.1% TFA. Column: Phenomenex Luna 30×100 mm, S10, flow rate: 40 ml/min, 40-100% B, 40 min) to afford 30 mg (35% yield) of the titled compound as a yellow oil. LC-MS $(M+H)^+$ 428.2.

EXAMPLE 73

N-(4-(4-chloro-1H-imidazol-1-yl)-3-methoxyphenyl)-4-methyl-4-phenyl-4,5,6,7-tetrahydrobenzo[d]thiazol-2-amine 2,2,2-trifluoroacetate

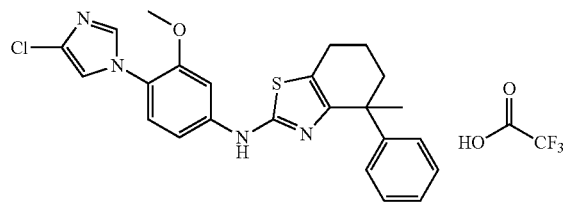

Step A: A mixture of 6-bromo-2-methyl-2-phenylcyclohexanone (177 mg, 0.664 mmol, from preparation AAB) and 1-(4-(4-chloro-1H-imidazol-1-yl)-3-methoxyphenyl)thiourea (134 mg, 0.474 mmol, from step 4 of preparation A) was heated in ethanol (2.5 mL) at 80° C. for 16 h. The crude reaction products were purified using Preparatory HPLC (Solvent A=10% MeOH-90% water-0.1% TFA, Solvent B=90% MeOH-10% water-0.1% TFA. Column: Phenomenex Luna 30×100 mm, S10, flow rate: 40 ml/min, 45-100% B, 15117 min) to afford 176 mg (49% yield) of the titled compound. LC-MS $(M+H)^+$ 451.2.

EXAMPLE 74

N-(4-(4-chloro-1H-imidazol-1-yl)-3-methoxyphenyl)-4-(4-fluorophenyl)-5,7-dihydro-4H-spiro[benzo[d]thiazole-6,2'-[1,3]dioxolan]-2-amine

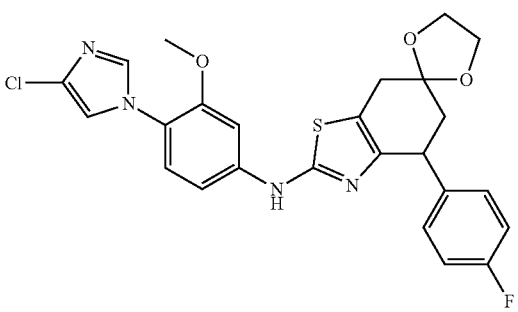 [SMILES: COc1cc(Nc2nc3c(s2)CC2(CC3c3ccc(F)cc3)OCCO2)ccc1-n1cnc(Cl)c1]

Step A: A mixture of 7-bromo-9-(4-fluorophenyl)-1,4-dioxaspiro[4.5]decan-8-on (50 mg, 0.177 mmol, preparation AAC) and 1-(4-(4-chloro-1H-imidazol-1-yl)-3-methoxyphenyl)thiourea (91 mg, 0.276 mmol, from step 4 of preparation A) was heated in ethanol (0.25 mL) at 80° C. for 45 min. The crude reaction was diluted with EtOAc and washed with saturated sodium bicarbonate solution. The organic layer was concentrated in vacuo. The crude product was purified using preparatory TLC (50% acetone/hexanes) to give 54 mg (57% yield) of the titled compound as a white solid. LC-MS $(M+H)^+$ 513.2. $^1$H NMR (400 MHz, chloroform-d) δ ppm 7.49 (dd, J=11.21, 1.89 Hz, 2 H) 7.15-7.24 (m, 2 H) 7.08 (d, J=8.31 Hz, 1 H) 6.93-7.04 (m, 3 H) 6.58 (dd, J=8.56, 2.27 Hz, 1 H) 4.16-4.33 (m, 1H) 3.89-4.15 (m, 4H) 3.49 (s, 3 H) 3.13 (dd, J=16.37, 3.02 Hz, 1 H) 2.82-2.98 (m, 1H) 1.98-2.32 (m, 2 H).

EXAMPLE 75

2-(4-(4-chloro-1H-imidazol-1-yl)-3-methoxyphenylamino)-4-(4-fluorophenyl)-4,5-dihydrobenzo[d]thiazol-6(7H)-one

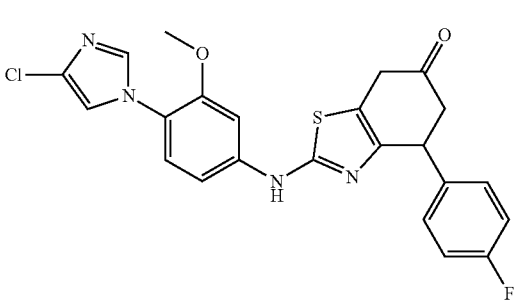 [SMILES: COc1cc(Nc2nc3c(s2)CC(=O)CC3c2ccc(F)cc2)ccc1-n1cnc(Cl)c1]

Step A: A mixture of N-(4-(4-chloro-1H-imidazol-1-yl)-3-methoxyphenyl)-4-(4-fluorophenyl)-5,7-dihydro-4H-spiro[benzo[d]thiazole-6,2'-[1,3]dioxolan]-2-amine (54 mg, 0.105 mmol, example 74), aqueous 1.0 M HCl (0.16 mL), and acetone (0.13 mL) was heated at reflux for 24 h. Partial conversion of the starting material to the desired product was evident by LCMS analysis of a crude aliquot. An additional portion of aqueous 1.0 M HCl (0.20 mL) was added and the acetone was removed in vacuo. The resulting mixture was heated at 75° C. for an additional 24 h. The crude reaction was quenched with saturated sodium bicarbonate solution and extracted with EtOAc. The organic layer was concentrated in vacuo. The crude product was purified using preparatory TLC (50% acetone/hexanes) to give 22 mg (43% yield) of the titled compound as an oil. LC-MS (M+H)$^+$ 469.2. $^1$H NMR (400 MHz, chloroform-d) δ ppm 7.54 (d, J=1.51 Hz, 1 H) 7.46 (d, J=2.52 Hz, 1 H) 7.09-7.20 (m, 3 H) 6.94-7.07 (m, 3 H) 6.77 (dd, J=8.44, 2.39 Hz, 1 H) 4.46 (t, J=6.42 Hz, 1 H) 3.63-3.67 (m, 2 H) 3.62 (s, 3 H) 3.08 (dd, J=14.35, 6.55 Hz, 1 H) 2.86 (dd, J=14.23, 6.42 Hz, 1 H).

EXAMPLE 76

2-(4-(4-chloro-1H-imidazol-1-yl)-3-methoxyphenylamino)-4-(4-fluorophenyl)-4,5,6,7-tetrahydrobenzo[d]thiazol-6-ol

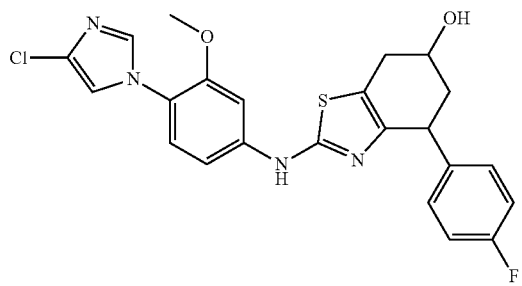

Step A: A mixture of 2-(4-(4-chloro-1H-imidazol-1-yl)-3-methoxyphenylamino)-4-(4-fluorophenyl)-4,5-dihydrobenzo[d]thiazol-6(7H)-one (5.0 mg, 0.011 mmol, from example 75), sodium borohydride (1.2 mg, 0.032 mmol), and methanol (0.050 mL) were stirred at rt for 1 h. The crude reaction was quenched with brine solution and extracted with EtOAc. The organic layer was concentrated in vacuo to afford 4.0 mg (76% yield) of the titled compound as a brown oil. LC-MS (M+H)$^+$ 471.2. $^1$H NMR (400 MHz, methanol-d$_4$) δ ppm 7.82 (d, J=2.01 Hz, 1 H) 7.63 (d, J=1.51 Hz, 1H) 7.33 (s, 1 H) 7.17-7.24 (m, 3 H) 7.13 (d, J=8.56 Hz, 1 H) 7.02 (t, J=8.81 Hz, 2 H) 6.64 (dd, J=8.56, 2.27 Hz, 1 H) 4.00-4.23 (m, 3 H) 3.33 (s, 3 H) 3.04 (dd, J=15.23, 5.41 Hz, 1 H) 2.70 (ddd, J=15.30, 9.76, 3.15 Hz, 1 H) 2.29-2.42 (m, 1 H).

EXAMPLE 77

N2-(4-(4-chloro-1H-imidazol-1-yl)-3-methoxyphenyl)-4-(4-fluorophenyl)-4,5,6,7-tetrahydrobenzo[d]thiazole-2,6-diamine

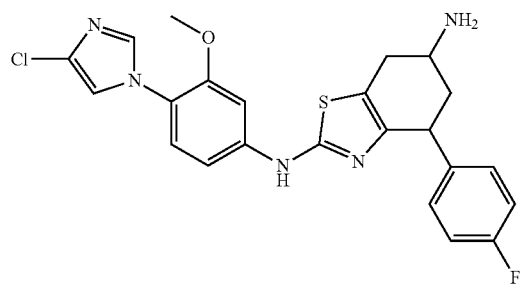 [SMILES: COc1cc(Nc2nc3c(s2)CC(O)CC3c2ccc(F)cc2)ccc1-n1cnc(Cl)c1]

Step A: Ammonium acetate (123 mg, 1.599 mmol) and sodium borohydride (46.9 mg, 0.746 mmol) were added to a solution of 2-(4-(4-chloro-1H-imidazol-1-yl)-3-methoxyphenylamino)-4-(4-fluorophenyl)-4,5-dihydrobenzo[d]thiazol-6(7H)-one (50 mg, 0.107 mmol, from example 75) in MeOH (1.1 mL). The mixture was heated at 65° C. for 20 hours. Several drops of aqueous 1 M HCl were added to the reaction mixture to decompose the excess borohydride reagent. The solvent was removed in vacuo. The residue was made basic with 1N NaOH solution and extracted with dichloromethane. The crude product was purified using preparatory HPLC (Column: Phenomenex Luna C18 30×100 mm, Solvent A=10 mM Ammonium Acetate in 95:5 water/ACN, Solvent B=10 mM Ammonium Acetate in 5:95 water/ACN, flow rate: 40 ml/min, 30-80% B, 18 min) to afford N2-(4-(4-chloro-1H-imidazol-1-yl)-3-methoxyphenyl)-4-(4-fluorophenyl)-4,5,6,7-tetrahydrobenzo[d]thiazole-2,6-diamine (21 mg, 0.040 mmol, 37.7% yield) as a white solid. LC-MS (M+H)$^+$ 470.2. $^1$H NMR (400 MHz, methanol-d$_4$) δ ppm 7.82 (d, J=2.52 Hz, 1 H) 7.63 (d, J=1.51 Hz, 1H) 7.33 (s, 1 H) 7.17-7.24 (m, 3 H) 7.13 (d, J=8.56 Hz, 1 H) 6.97-7.06 (m, 2 H) 6.64 (dd, J=8.56, 2.27 Hz, 1H) 4.00-4.23 (m, 3H) 3.31 (s, 3 H) 2.99-3.09 (m, 1 H) 2.70 (ddd, J=15.23, 9.69, 3.27 Hz, 1 H) 2.30-2.41 (m, 1 H).

EXAMPLE 78

N2-(4-(4-chloro-1H-imidazol-1-yl)-3-methoxyphenyl)-4-(4-fluorophenyl)-N6,N6-dimethyl-4,5,6,7-tetrahydrobenzo[d]thiazole-2,6-diamine

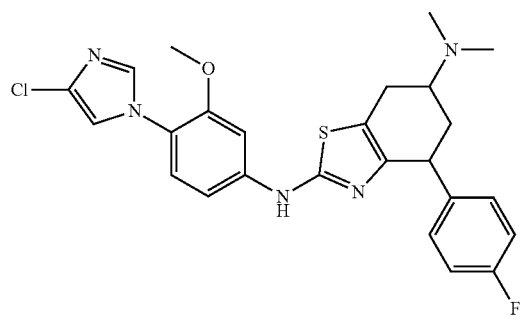 [SMILES: COc1cc(Nc2nc3c(s2)CC(N(C)C)CC3c2ccc(F)cc2)ccc1-n1cnc(Cl)c1]

Step A: Sodium cyanoborohydride (14.53 mg, 0.231 mmol) and formaldehyde (16.15 μL, 0.217 mmol) were added to a solution of N2-(4-(4-chloro-1H-imidazol-1-yl)-3-methoxyphenyl)-4-(4-fluorophenyl)-4,5,6,7-tetrahydrobenzo[d]thiazole-2,6-diamine (18 mg, 0.038 mmol, from example 78) in MeOH (0.4 mL). The mixture was stirred at rt for 20 hours. The crude reaction mixture was purified using preparatory HPLC (Column: Phenomenex Luna C18 30×100 mm, Solvent A=10 mM Ammonium Acetate in 95:5 water/ACN, Solvent B=10 mM Ammonium Acetate in 5:95 water/ACN. Flow rate: 40 ml/min, 30-95% B, 20 min to afford 10 mg (47% yield) of the titled compound as a white solid. LC-MS (M+H)+ 498.3.

EXAMPLE 79

N2-(4-(4-chloro-1H-imidazol-1-yl)-3-methoxyphenyl)-4-(4-fluorophenyl)-N-6-methyl-4,5,6,7-tetrahydrobenzo[d]thiazole-2,6-diamine

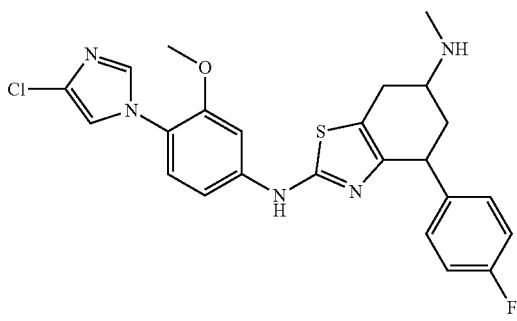 [SMILES: CNC1Cc2sc(Nc3ccc(-n4cnc(Cl)c4)c(OC)c3)nc2C(c2ccc(F)cc2)C1]

Step A: Sodium cyanoborohydride (37 mg, 0.59 mmol) and methylamine (170 μL, 0.34 mmol) were added to a solution of 2-(4-(4-chloro-1H-imidazol-1-yl)-3-methoxyphenylamino)-4-(4-fluorophenyl)-4,5-dihydrobenzo[d]thiazol-6(7H)-one (50 mg, 0.107 mmol, from example 75) in MeOH (1.1 mL). The mixture was stirred at rt for 4 hours. The crude reaction mixture was purified using preparatory HPLC (Column: Phenomenex Luna C18 30×100 mm, Solvent A=10 mM Ammonium Acetate in 95:5 water/ACN, Solvent B=10 mM Ammonium Acetate in 5:95 water/ACN. Flow rate: 40 ml/mM, 30-95% B, 20 min to afford 5.0 mg (9% yield) of N2-(4-(4-chloro-1H-imidazol-1-yl)-3-methoxyphenyl)-4-(4-fluorophenyl)-N6-methyl-4,5,6,7-tetrahydrobenzo[d]thiazole-2,6-diamine. LC-MS (M+H)+ 484.2.

EXAMPLE 80

4-benzyl-N-(4-(4-chloro-1H-imidazol-1-yl)-3-methoxyphenyl)-4,5,6,7-tetrahydrobenzo[d]thiazol-2-amine 2,2,2-trifluoroacetate

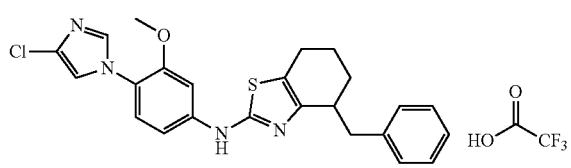

Step A: A mixture of 2-benzyl-6-bromocyclohexanone (213 mg, 0.7965 mmol, from preparation AAD) and 1-(4-(4-chloro-1H-imidazol-1-yl)-3-methoxyphenyl)thiourea (161 mg, 0.5689 mmol, from step 4 of preparation A) was heated in ethanol (2.5 mL) at 80° C. for 16 h. The crude reaction products were purified using Preparatory HPLC (Solvent A=10% MeOH-90% water-0.1% TFA, Solvent B=90% MeOH-10% water-0.1% TFA. Column: Phenomenex Luna 30×100 min, 510, Flow rate: 40 ml/min, 50-100% B, 17/20 min) to afford 25 mg (6% yield) of the titled compound. LC-MS (M+H)+ 451.2.

EXAMPLE 81

2-(3-methoxy-4-(3-methyl-1H-1,2,4-triazol-1-yl)phenylamino)-4-phenyl-4,5,6,7-tetrahydrobenzo[d]thiazol-4-ol

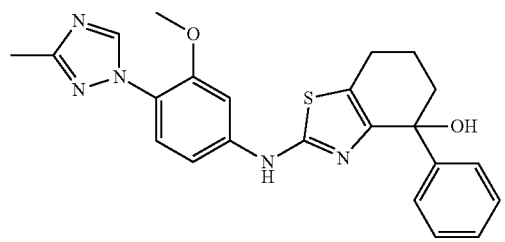

Step A: A mixture of 3-bromocyclohexane-1,2dione (158 mg, 0.827 mmol, from preparation AAE) and 1-(3-methoxy-4-(3-methyl-1H-1,2,4-triazol-1-yl)phenyl)thiourea (109 mg, 0.414 mmol, from step 4 of preparation F) was heated in ethanol (1.4 mL) at 80° C. for 12 h. The crude reaction was diluted with EtOAc and washed with saturated sodium bicarbonate solution. The organic layer was concentrated in vacuo. The crude product was purified using preparatory TLC (80% acetone/hexanes) to afford 2-(3-methoxy-4-(3-methyl-1H-1,2,4-triazol-1-yl)phenylamino)-6,7-dihydrobenzo[d]thiazol-4(5H)-one (64 mg, 44% yield) as a yellow solid. LC-MS (M+H)+ 356.3. ¹H NMR (400 MHz, chloroform-d) δ ppm 8.55 (s, 1 H) 7.68 (d, J=8.56 Hz, 1 H) 7.31 (d, J=2.27 Hz, 1 H) 6.96 (dd, J=8.56, 2.52 Hz, 1 H) 3.95 (s, 3H) 3.00 (t, J=6.04 Hz, 2 H) 2.59-2.68 (m, 2 H) 2.45-2.52 (m, 3H) 2.20-2.31 (m, 2H).

Step B: Phenylmagnesium bromide (1.0 M in THF, 0.118 mL, 0.118 mmol) was added to a rt solution of 2-(3-methoxy-4-(3-methyl-1H-1,2,4-triazol-1-yl)phenylamino)-6,7-dihydrobenzo[d]thiazol-4(5H)-one (14 mg, 0.039 mmol) in diethyl ether (0.13 mL). The reaction was quenched with saturated ammonium chloride and extracted with EtOAc. The organic layer was concentrated in vacuo. The crude product was purified using preparatory TLC (60% acetone/hexanes) to afford 10 mg (53% yield) of the titled compound as a oil. LC-MS (M+H)+ 434.3.

EXAMPLE 82

N2-(3-methoxy-4-(3-methyl-1H-1,2,4-triazol-1-yl)phenyl)-4-phenyl-4,5,6,7-tetrahydrobenzo[d]thiazole-2,4-diamine

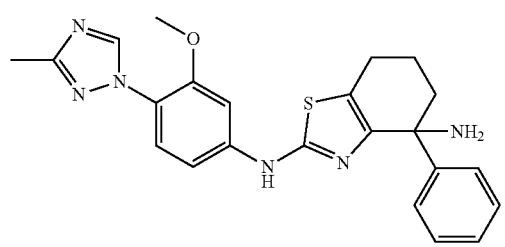 [SMILES: COc1cc(Nc2nc3c(s2)CCCC3(O)c2ccccc2)ccc1-n1cnc(C)n1]

Step A: Sodium azide (4.5 mg, 0.069 mml) and trifluoroacetic acid were sequentially added to a solution of 2-(4-(4-chloro-1H-imidazol-1-yl)-3-methoxyphenylamino)-4-phenyl-4,5,6,7-tetrahydrobenzo[d]thiazol-4-ol (10 mg, 0.023 mmol, from example 81) in chloroform (0.1 mL). After stirring 4 h at rt, the reaction was diluted with chloroform and washed with saturated sodium bicarbonate solution. The organic layer was concentrated in vacuo to afford 4-azido-N-(4-(4-chloro-1H-imidazol-1-yl)-3-methoxyphenyl)-4-phenyl-4,5,6,7-tetrahydrobenzo[d]thiazol-2-amine (6 mg, 57% yield). LC-MS (M+H)$^+$ 459.33.

Step B: A small spatula tip of lithium aluminum hydride was added to a stirred solution of 4-azido-N-(4-(4-chloro-1H-imidazol-1-yl)-3-methoxyphenyl)-4-phenyl-4,5,6,7-tetrahydrobenzo[d]thiazol-2-amine (10 mg, 0.022 mmol) in THF (0.22 mL). The reaction mixture was stirred for 2 h at rt. A crystal of sodium sulfate hydrate was added followed by diethyl ether (5 mL). Anhydrous sodium sulfate was added and the resulting mixture stirred for 30 min. The solvent was removed in vacuo. The crude product was purified using preparatory TLC (90%/9%/1%, dichloromethane/methanol/ammonium hydroxide) to afford 6 mg (60% yield) of the titled compound as a oil. $^1$H NMR (400 MHz, chloroform-d) δ ppm 8.47 (s, 1 H) 7.56 (d, J=8.56 Hz, 1 H) 7.46 (d, J=2.27 Hz, 1 H) 7.34-7.41 (m, 2 H) 7.27-7.34 (m, 2 H) 7.15-7.25 (m, 1 H) 6.72 (dd, J=8.56, 2.52 Hz, 1H) 3.63 (s, 3 H) 2.70-2.81 (m, 2 H) 2.41-2.53 (m, 3 H) 2.11-2.22 (m, 1 H) 1.75-2.02 (m, 3 H).

EXAMPLE 83

N2-(4-(4-chloro-1H-imidazol-1-yl)-3-methoxyphenyl)-N4-(4-chlorobenzyl)-4-phenyl-4,5,6,7-tetrahydrobenzo[d]thiazole-2,4-diamine

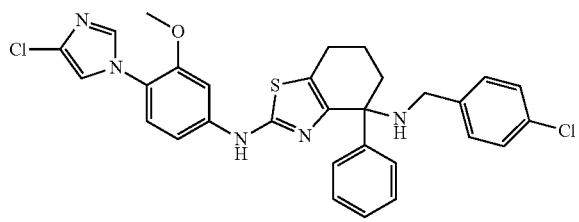 [SMILES: COc1cc(Nc2nc3c(s2)CCCC3(NCc2ccc(Cl)cc2)c2ccccc2)ccc1-n1cnc(Cl)c1]

Step A: A mixture of 4-chlorobenzaldehyde (6.8 mg, 0.049 mmol), N2-(3-methoxy-4-(3-methyl-1H-1,2,4-triazol-1-yl)phenyl)-4-phenyl-4,5,6,7-tetrahydrobenzo[d]thiazole-2,4-diamine (7.0 mg, 0.016 mmol), sodium triacetoxyborohydride (10 mg, 0.049 mmol), and acetic acid (5.0 uL, 0.081 mmol) in THF (0.1 mL) was stirred at rt for 12 h. The solvent was removed in vacuo. The crude product was purified using preparatory TLC (90%/9%/1%, dichloromethane/methanol/ammonium hydroxide) to afford 2 mg (20% yield) of the titled compound as a oil. $^1$H NMR (400 MHz, chloroform-d) δ ppm 8.48 (s, 1 H) 7.60 (d, J=8.56 Hz, 1 H) 7.29-7.37 (m, 9 H) 7.22-7.26 (m, 2H) 4.69 (s, 2H) 3.63 (s, 3 H) 2.67-2.79 (m, 2 H) 2.48 (s, 3 H) 2.14-2.28 (m, 1 H) 1.84-1.99 (m, 1 H) 1.57-1.76 (m, 2 H).

EXAMPLE 84

N-(4-(4-chloro-1H-imidazol-1-yl)-3-methoxyphenyl)-4-(4-fluorophenyl)-6,6-dimethoxy-4,5,6,7-tetrahydrobenzo[d]thiazol-2-amine

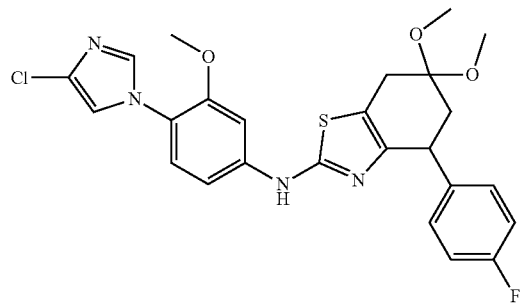 [SMILES: COc1cc(Nc2nc3c(s2)CC(OC)(OC)CC3c2ccc(F)cc2)ccc1-n1cnc(Cl)c1]

Step A: A solution of N-(4-(4-chloro-1H-imidazol-1-yl)-3-methoxyphenyl)-4-(4-fluorophenyl)-5,7-dihydro-4H-spiro[benzo[d]thiazole-6,2'-[1,3]dioxolan]-2-amine (569 mg, 1.109 mmol) in acetone (7.9 mL)/water (1.6 mL)/70% HClO$_4$ (1.6 mL) was stirred at 50° C. overnight. The crude product was purified using preparatory HPLC (Column: Phenomenex Luna C18 30×100 mm, Solvent A=10 mM ammonium acetate in 95:5 water/ACN, Solvent B=10 mM Ammonium Acetate in 5:95 water/ACN. Flow rate: 40 ml/min, 30-100% B, 15 min) to afford 273 mg (47% yield) of 2-(4-(4-chloro-1H-imidazol-1-yl)-3-methoxyphenylamino)-4-(4-fluorophenyl)-4,5-dihydrobenzo[d]thiazol-6(7H)-one and 120 mg (19% yield) of the titled compound as a yellow solid. Data for example 83: LC-MS (M+H)$^+$ 515.2. $^1$H NMR (400 MHz, methanol-d$_4$) δ ppm 7.82 (d, J=2.27 Hz, 1 H) 7.64 (d, J=1.51 Hz, 1 H) 7.19-7.27 (m, 2 H) 7.18 (d, J=1.51 Hz, 1 H) 7.13 (d, J=8.56 Hz, 1H) 6.96-7.06 (m, 2 H) 6.66 (dd, J=8.56, 2.27 Hz, 1 H) 3.95-4.05 (m, 1 H) 3.33 (s, 3H) 3.31 (s, 3 H) 3.25 (s, 3 H) 3.12 (dt, J=16.12, 2.01 Hz, 1 H) 2.92 (dd, J=16.12, 3.02 Hz, 1 H) 2.48 (ddd, J=13.79, 5.73, 2.39 Hz, 1H).

EXAMPLE 85

N-(4-(4-chloro-1H-imidazol-1-yl)-3-methoxyphenyl)-4-(4-fluorophenyl)-5,6,7,8-tetrahydro-4H-cyclohepta[d]thiazol-2-amine 2,2,2-trifluoroacetate

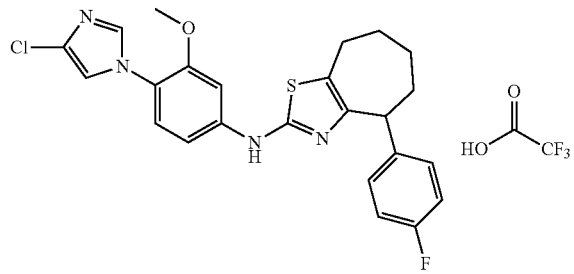

Step A: A mixture of 2-bromo-7-(4-fluorophenyl)cycloheptanone (207 mg, 0.727 mmol, from preparation AAF) and 1-(4-(4-chloro-1H-imidazol-1-yl)-3-methoxyphenyl)thiourea (206 mg, 0.727 mmol, from step 4 of preparation A) was heated in ethanol (1.8 mL) at 80° C. for 16 h. The crude reaction products were purified using Prep-HPLC (Solvent A=10% MeOH-90% water-0.1% TFA, Solvent B=90% MeOH-10% water-0.1% TFA. Column: Phenomenex Luna 30×100 mm, S10, Flow rate: 40 ml/min, 50-100% B, 20 min) to afford 175 mg (31% yield) of the titled compound. LC-MS (M+H)$^+$ 469.0. $^1$H NMR (400 MHz, chloroform-d) δ ppm 8.04 (br. s., 1 H) 7.34 (d, J=8.56 Hz, 1H) 7.15 (s, 1H) 6.98-7.13 (m, 6 H) 4.43 (t, J=4.66 Hz, 1H) 3.92 (s, 3 H) 2.68-2.90 (m, 2 H) 2.15-2.29 (m, 1 H) 1.96-2.13 (m, 2 H) 1.76-1.90 (m, 1 H) 1.51-1.76 (m, 2 H).

EXAMPLE 86

N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine

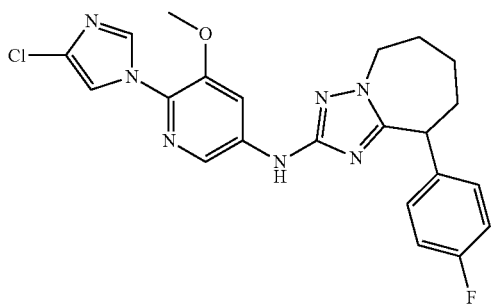 [SMILES: COc1cc(Nc2nc3n(n2)CCCCC3c2ccc(F)cc2)cnc1-n1cnc(Cl)c1]

Step A: Methyl 6-(4-chloro-1H-imidazol-1-yl)-5-methoxypyridin-3-ylcarbamimidothioate, hydroiodide (1.00 g, 2.349 mmol, from preparation O) and 6-chloro-2-(4-fluorophenyl)hexanoic acid (0.632 g, 2.58 mmol, from preparation AH) were coupled and then reacted with hydrazine (0.295 mL, 9.40 mmol) using a procedure analogous to Step A of Example 13. The crude product was purified using silica gel column chromatography (10-50, EtOAc/chloroform, linear gradient) to afford N-(5-(5-chloro-1-(4-fluorophenyl)pentyl)-1H-1,2,4-triazol-3-yl)-6-(4-chloro-1H-imidazol-1-yl)-5-methoxypyridin-3-amine (550 mg, 1.122 mmol, 47.7% yield). LC-MS (M+H)$^+$ 490.2. After purification the product was still contaminated with a significant portion of HOBt. The impure product was used for subsequent chemistry without further purification.

Step B: A solution of N-(5-(5-chloro-1-(4-fluorophenyl)pentyl)-1H-1,2,4-triazol-3-yl)-6-(4-chloro-1H-imidazol-1-yl)-5-methoxypyridin-3-amine (550 mg, 1.122 mmol, contaminated with HOBt), sodium iodide (841 mg, 5.61 mmol), and diisoproplylethylamine (0.196 mL, 1.12 mmol) in acetone (10 mL) was heated in a sealed vessel at 90° C. for 12 h. The reaction was concentrated in vacuo. The crude product was purified using silica gel column chromatography (10-100% EtOAc/chloroform, linear gradient) to afford N-(5-(5-(1H-benzo[d][1,2,3]triazol-1-yloxy)-1-(4-fluorophenyl)pentyl)-1H-1,2,4-triazol-3-yl)-6-(4-chloro-1H-imidazol-1-yl)-5-methoxypyridin-3-amine (644 mg, 1.093 mmol, 97% yield) as yellow oil which solidified upon standing at rt. LC-MS (M+H)$^+$ 589.3.

Step C: A microwave vial was charged with N-(5-(5-(1H-benzo[d][1,2,3]triazol-1-yloxy)-1-(4-fluorophenyl)pentyl)-1H-1,2,4-triazol-3-yl)-6-(4-chloro-1H-imidazol-1-yl)-5-methoxypyridin-3-amine (300 mg, 0.509 mmol), DIEA (0.089 mL, 0.509 mmol), and 2-butanone (5 mL). The mixture was heated in a microwave at 180° C. for 4 h. The reaction mixture was concentrated in vacuo. The crude product was purified using silica gel column chromatography (10-80% EtOAc/chloroform, linear gradient) to afford N-(6-(4-chloro-1H-imidazol-1-yl)-5-methoxypyridin-3-yl)-9-(4-fluorophenyl)-6,7,8,9-tetrahydro-5H-[1,2,4]triazolo[1,5-a]azepin-2-amine (13 mg, 0.029 mmol, 6% yield) as white solid. LC-MS (M+H)$^+$ 454.2. $^1$H NMR (500 MHz, chloroform-d) δ ppm 8.13 (d, J=1.53 Hz, 1 H) 8.03 (d, J=2.44 Hz, 1 H) 7.82 (d, J=2.44 Hz, 1 H) 7.58 (d, J=1.83 Hz, 1 H) 7.13-7.21 (m, 2H) 7.06 (t, J=8.70 Hz, 2H) 6.77 (s, 1 H) 4.16-4.34 (m, 3 H) 3.88 (s, 3 H) 1.78-2.28 (m, 6 H).

EXAMPLE 87 AND EXAMPLE 88

(S)—N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine and (R)—N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine

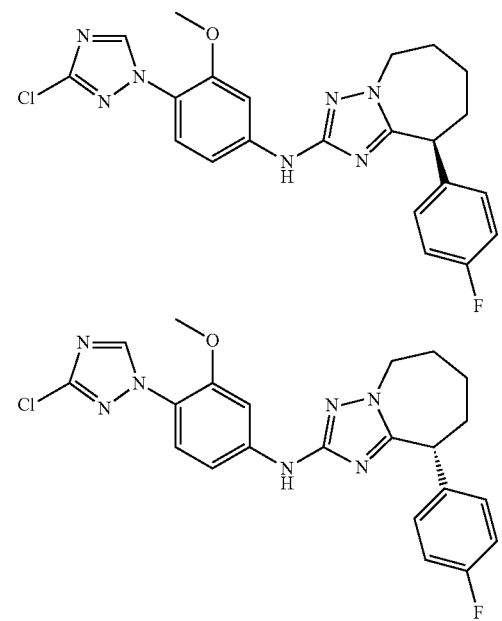

Step A: A racemic mixture of (S)—N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine (744 mg, from Example 33) was purified using chiral supercritical fluid chromatography (SFC) to afford 360 mg of peak A (example 87) and 360 mg of peak B (example 88). SFC Method: Chiralcel OJ-H (5×25 cm, 5 uM), 26% methanol in $CO_2$, 35° C., 250 mL/min, absorbance 215 nm, $t_R$ (peak A) 9.0 min, $t_R$ (peak B) 16.5 min. The absolute stereochemistry of individual enantiomers (examples 87 and 88) was not determined. $^1$H NMR analytical data for the separated enantiomers was identical. $^1$H NMR (500 MHz, chloroform-d) δ ppm 8.44-8.50 (m, 1 H) 7.47-7.57 (m, 2 H) 7.12-7.16 (m, 2 H)

7.00-7.08 (m, 2 H) 6.81 (dd, J=8.70, 2.29 Hz, 1 H) 6.73 (s, 1 H) 4.18-4.32 (m, 3H) 3.85 (s, 3 H) 1.77-2.30 (m, 6 H).

EXAMPLE 89

N-(4-(4-chloro-1H-imidazol-1-yl)-3-methoxyphenyl)-5-(4-fluorophenyl)-5,6,7,8-tetrahydro-[1,2,4]triazolo[1,5-a]pyridin-2-amine 2,2,2-trifluoroacetate

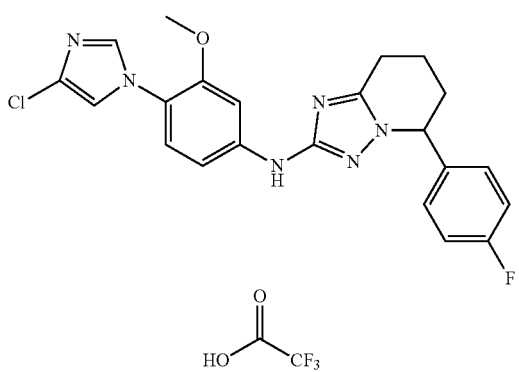

Step A: A mixture of 1-amino-6-(4-fluorophenyl)piperidin-2-one (25 mg, 0.120 mmol, from preparation AAG) and methyl 4-(4-chloro-1H-imidazol-1-yl)-3-methoxyphenylcarbamimidothioate hydroiodide (51.0 mg, 0.120 mmol, from preparation AH) in pyridine (1 mL) was stirred at 115° C. for 6 hrs. The pyridine was removed in vacuo. The residue was purified using reverse phase preparatory HPLC to afford 5 mg (9% yield) of the titled compound. LC-MS (M+H)+ 439.2. $^1$H NMR (500 MHz, chloroform-d) δ ppm 10.37 (br. s., 1H) 7.83 (br. s., 1 H) 7.25 (d, J=2.14 Hz, 1 H) 7.08-7.20 (m, 5 H) 7.04 (br. s., 1 H) 6.97 (dd, J=8.55, 2.14 Hz, 1H) 5.32-5.42 (m, 1 H) 3.62 (s, 3 H) 3.13-3.22 (m, 2 H) 2.47-2.59 (m, 1 H) 1.97-2.29 (m, 3H).

EXAMPLE 90

N-(4-(4-chloro-1H-imidazol-1-yl)-3-methoxyphenyl)-7-(4-fluorophenyl)-4,5,6,7-tetrahydropyrazolo[1,5-a]pyridin-2-amine

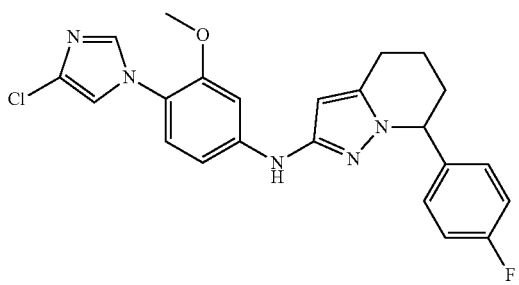 [SMILES: COc1cc(Nc2cc3n(n2)C(c2ccc(F)cc2)CCC3)ccc1-n1cnc(Cl)c1]

Step A: A mixture of 7-phenyl-4,5-dihydropyrazolo[1,5-a]pyridin-2-yl 1,1,2,2,3,3,4,4,4-nonafluorobutane-1-sulfonate (400 mg, 0.809 mmol, from AAH), 4-(4-chloro-1H-imidazol-1-yl)-3-methoxyaniline (362 mg, 1.618 mmol, from step 2 of preparation A), tris(dibenzylideneacetone)dipalladium (0) (29.6 mg, 0.032 mmol), 9,9-dimethyl-4,5-bis(diphenylphosphino)xanthene (70.2 mg, 0.121 mmol), and 1-methyl-2,3,4,6,7,8-hexahydro-1H-pyrimido[1,2-a]pyrimidine (372 mg, 2.428 mmol) in toluene (5 mL) was microwaved in a biotage chemistry microwave at 160° C. for 2 h. The crude reaction mixture was loaded directly on to silica gel and purified using silica gel column chromatography (0-80% EtOAc/hexanes) to afford N-(4-(4-chloro-1H-imidazol-1-yl)-3-methoxyphenyl)-7-phenyl-4,5-dihydropyrazolo[1,5-a]pyridin-2-amine (70 mg, 21% yield). LC-MS (M+H)+ 418.1. $^1$H NMR (500 MHz, chloroform-d) δ ppm 7.58 (dd, J=6.56, 1.37 Hz, 2 H) 7.49 (d, J=1.53 Hz, 1H) 7.43 (d, 0.1-2.44 Hz, 1 H) 7.34-7.40 (m, 3H) 7.02 (d, J=8.55 Hz, 1H) 6.99 (d, J=1.83 Hz, 1H) 6.53 (dd, J=8.55, 2.44 Hz, 1H) 6.31 (s, 1 H) 5.83 (s, 1 H) 5.47-5.52 (m, 1 H) 3.53 (s, 3 H) 2.96 (t, J=7.93 Hz, 2 H) 2.43-2.52 (m, 2H).

Step B: 10% Palladium on carbon (0.5 g) was carefully added to a solution of N-(4-(4-chloro-1H-imidazol-1-yl)-3-methoxyphenyl)-7-phenyl-4,5-dihydropyrazolo[1,5-a]pyridin-2-amine (40 mg, 0.096 mmol) in ethanol. The reaction vessel was repeatedly evacuated and flushed with hydrogen gas (double balloon). The mixture was stirred for 6 h. The vessel was flushed with nitrogen. The reaction contents were filtered through diatomaceous earth (Celite®). The plug and vessel were washed with fresh methanol. The filtrates were combined and concentrated in vacuo. The crude product was purified using silica gel column chromatography (0-5%, MeOH/CH$_2$Cl$_2$, linear gradient) to afford 20 mg (47% yield) of the titled compound. LC-MS (M+H)+ 420.1. $^1$H NMR (500 MHz, chloroform-d) δ ppm 7.46 (d, J=1.83 Hz, 1 H) 7.21-7.33 (m, 4 H) 6.93-7.06 (m, 5H) 6.52 (dd, J=8.55, 2.44 Hz, 1H) 6.27 (br. s., 1 H) 5.77 (s, 1 H) 5.30 (t, J=5.80 Hz, 1 H) 3.54 (s, 3 H) 2.76-3.00 (m, 2 H) 2.30-2.43 (m, 1 H) 2.01-2.15 (m, 1 H) 1.70-1.94 (m, 2 H).

EXAMPLE 91 rel-(6S,7R,9S)—N-(4-(4-chloro-1H-imidazol-1-yl)-3-methoxyphenyl)-6,7-difluoro-9-(4-fluorophenyl)-6,7,8,9-tetrahydro-5H-[1,2,4]triazolo[1,5-a]azepin-2-amine 2,2,2-trifluoroacetate

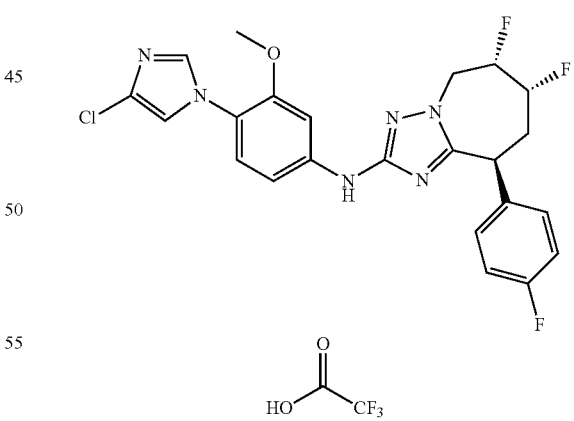

Step A: To a stirred solution of (6R,7S,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepine-6,7-diol (78036-064-02) (200 mg, 0.412 mmol) in dichloromethane (412 µL) was added [bis(2-methoxyethyl)amino]sulfur trifluoride (167 µL, 0.907 mmol). The resulting mixture was heated at reflux overnight. After cooling to rt, the reaction was diluted with dichloromethane (10 mL), washed with water (10 mL), dried (MgSO$_4$) filtered, and concentrated in vacuo. The crude residue was purified using reverse phase preparatory HPLC(C18, 30×150 mm, MeOH/water/TFA) to afford the titled compound (10.0 mg, 0.017 mmol, 4.0% yield) as a white solid. LC-MS (M+H)$^+$ 489.1. $^1$H NMR (400 MHz, DMSO-d$_6$) δ ppm 2.28-2.41 (m, 1 H) 2.59-2.74 (m, 1 H) 3.71 (s, 3H) 4.37 (t, J=15.49 Hz, 1 H) 4.68 (d, J=8.81 Hz, 1 H) 4.78 (dd, J=13.98, 9.69 Hz, 1 H) 5.03-5.26 (m, 2H) 7.07 (dd, J=8.56, 2.27 Hz, 1 H) 7.21 (dt, J=8.81, 4.41 Hz, 3 H) 7.34 (dd, J=8.56, 5.54 Hz, 2 H) 7.42 (d, J=1.51 Hz, 1 H) 7.48 (d, J=2.27 Hz, 1H) 7.73 (d, J=1.51 Hz, 1 H) 9.50 (s, 1H).

EXAMPLE 92

2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-9-ol

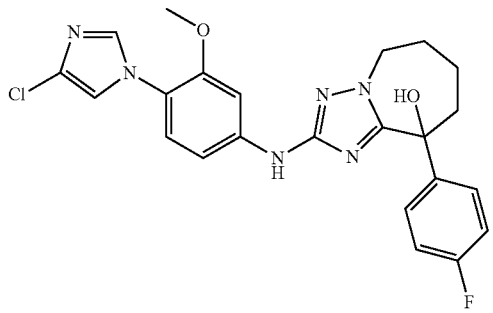

Step A: To a stirred solution of 2-(4-chlorobutyl)-1,3-dithiane-2-carboxylic acid (200 mg, 0.785 mmol, from preparation AS) in dichloromethane (4 mL) was added 1H-benzo[d][1,2,3]triazol-1-ol hydrate (144 mg, 0.942 mmol), N1-((ethylimino)methylene)-N3,N3-dimethylpropane-1,3-diamine hydrochloride (166 mg, 0.863 mmol) and diisopropylethylamine (0.411 mL, 2.36 mmol). After 15 min, methyl 4-(4-chloro-1H-imidazol-1-yl)-3-methoxyphenyl-carbamimidothioate hydroiodide (367 mg, 0.863 mmol, from preparation A) was added. The mixture was stirred at rt for 16 h. The solvent was removed in vacuo. The crude residue was purified using silica gel column chromatography (80% EtOAc/hexanes) to afford methyl N-4-(4-chloro-1H-imidazol-1-yl)-3-methoxyphenyl-N'-(2-(4-chlorobutyl)-1,3-dithiane-2-carbonyl)carbamimidothioate (350 mg, 0.656 mmol, 84% yield). LC-MS (M+H)$^+$ 533.0.

Step B: To a solution of methyl N-4-(4-chloro-1H-imidazol-1-yl)-3-methoxyphenyl-N'-(2-(4-chlorobutyl)-1,3-dithiane-2-carbonyl)carbamimidothioate (210 mg, 0.394 mmol) in DMF (2 mL) was added anhydrous hydrazine (0.025 mL, 0.787 mmol). The mixture was stirred at rt for 2 h and at 70° C. for 1.5 h. Acetic acid (5 drops) was added and the resulting mixture stirred at 80° C. for 5 h. The reaction mixture was concentrated in vacuo. The crude residue was purified using silica gel column chromatography (0-100 EtOAc/hexanes, linear gradient) to afford N-(4-(4-chloro-1H-imidazol-1-yl)-3-methoxyphenyl)-5-(2-(4-chlorobutyl)-1,3-dithian-2-yl)-1H-1,2,4-triazol-3-amine (120 mg, 0.240 mmol, 61% yield). LC-MS (M+H)$^+$ 499.1.

Step C: To a solution of N-(4-(4-chloro-1H-imidazol-1-yl)-3-methoxyphenyl)-5-(2-(4-chlorobutyl)-1,3-dithian-2-yl)-1H-1,2,4-triazol-3-amine (110 mg, 0.220 mmol) in DMF (3 mL) was added potassium carbonate (122 mg, 0.881 mmol) and potassium iodide (73.1 mg, 0.440 mmol). The mixture was stirred at 72° C. for 5 h. The mixture was concentrated in vacuo. The residue was purified using silica gel column chromatography (0-80% EtOAc/hexanes, linear gradient) to afford N-(4-(4-chloro-1H-imidazol-1-yl)-3-methoxyphenyl)-5,6,7,8-tetrahydrospiro[[1,2,4]triazolo[1,5-a]azepine-9,2'-[1,3]dithian]-2-amine (90 mg, 0.185 mmol, 84% yield). LC-MS (M+H)$^+$=463.1.

Step D: To a suspension of N-(4-(4-chloro-1H-imidazol-1-yl)-3-methoxyphenyl)-5,6,7,8-tetrahydrospiro[[1,2,4]triazolo[1,5-a]azepine-9,2'-[1,3]dithian]-2-amine (80 mg, 0.173 mmol) in acetonitrile (1.5 mL) and water (0.4 mL) was added calcium carbonate (51.9 mg, 0.518 mmol) and mercury(II) chloride (141 mg, 0.518 mmol). The mixture was stirred at 80° C. for 5 h and at 100° C. for 6 h. The crude reaction was diluted with EtOAc (150 mL) and washed with aqueous solution of ammonium acetate. The organic layer was dried over sodium sulfate, filtered, and concentrated in vacuo to afford 2-(4-(4-chloro-1H-imidazol-1-yl)-3-methoxyphenylamino)-7,8-dihydro-5H-[1,2,4]triazolo[1,5-a]azepin-9(6H)-one (28 mg, 0.075 mmol, 44% yield). LC-MS (M+H)$^+$ =373.1. The crude product was used in the next step without purification.

Step E: To a suspension of 2-(4-(4-chloro-1H-imidazol-1-yl)-3-methoxyphenylamino)-7,8-dihydro-5H-[1,2,4]triazolo[1,5-a]azepin-9(6H)-one (28 mg, 0.075 mmol) in THF (0.5 mL) was added (4-fluorophenyl)magnesium bromide/THF (0.188 mL, 0.188 mmol) at −20° C. under nitrogen. After warming from −20° C. to rt, the mixture was stirred for 16 h. An additional portion of (4-fluorophenyl)magnesium bromide/THF (0.225 mL, 0.225 mmol) was added. The rxn was stirred an additional 3 h at rt, then 4 h at 60° C. The reaction mixture was concentrated in vacuo. The crude residue was dissolved in dichloromethane (2 mL). The solution was washed with water (1 mL) and then loaded onto silica gel. The crude product was purified using silica gel column chromatography (0-80% EtOAc/hexanes). The fractions containing product were combined and concentrated. The residue was repurified using reverse phase preparatory HPLC (AcCN/water/ammonium acetate) to afford the titled compound (3.4 mg, 7.25 μmol, 9.7% yield). LC-MS (M+H)$^+$=469.1. $^1$H NMR (500 MHz, chloroform-d) δ ppm 1.43-1.52 (m, 1 H) 1.82-1.95 (m, 2 H) 1.99-2.10 (m, 1 H) 2.11-2.21 (m, 1 H) 2.59 (ddd, J=14.34, 6.41, 2.14 Hz, 1 H) 3.85 (s, 3 H) 3.86-3.93 (m, 1 H) 4.43 (ddd, J=11.60, 2.90, 2.59 Hz, 1 H) 6.77 (s, 1 H) 6.95 (dd, J=8.39, 2.29 Hz, 1 H) 7.02-7.09 (m, 3 H) 7.09-7.17 (m, 3 H) 7.39 (d, J=2.14 Hz, 1 H) 7.53 (d, J=1.22 Hz, 1 H).

EXAMPLE 93

N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine

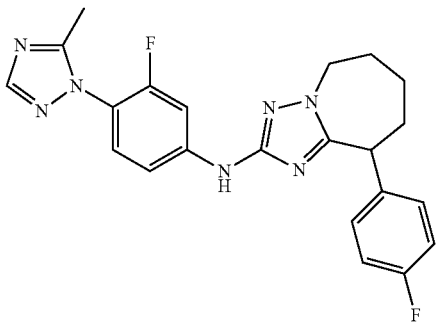 [SMILES: Cc1ncnn1-c1ccc(Nc2nc3n(n2)CCCCC3c2ccc(F)cc2)cc1F]

Step A: Methyl 3-fluoro-4-(5-methyl-1H-1,2,4-triazol-1-yl)phenylcarbamimidothioate, hydroiodide (0.739 g, 2.79 mmol, from preparation C) and 6-chloro-2-(4-fluorophenyl)hexanoic acid (0.750 g, 3.07 mmol, from preparation AE) were coupled and then reacted with hydrazine (0.350 mL, 11.2 mmol) using a procedure analogous to Step A of Example 13. The crude products were purified using silica gel chromatography (0-95% ethyl acetate/chloroform) to afford 5-(5-chloro-1-(4-fluorophenyl)pentyl)-N-(3-fluoro-4-(5-methyl-1H-1,2,4-triazol-1-yl)phenyl)-1H-1,2,4-triazol-3-amine (230 mg, 0.502 mmol, 18% yield) as a viscous oil. LC-MS (M+H)+ 458.2.

Step B: A solution of 5-(5-chloro-1-(4-fluorophenyl)pentyl)-N-(3-fluoro-4-(5-methyl-1H-1,2,4-triazol-1-yl)phenyl)-1H-1,2,4-triazol-3-amine (230 mg, 0.502 mmol), sodium iodide (376 mg, 2.51 mmol), and diisoproplyethylamine (0.088 mL, 0.50 mmol) in acetone (10 mL) was heated in a sealed vessel at 100° C. for 2 h. The reaction was concentrated in vacuo. The crude product was purified using silica gel column chromatography (10-80% EtOAc/chloroform, linear gradient) to afford 67 mg (30% yield) of the titled compound as a pink solid. LC-MS (M+H)+ 422.3. $^1$H NMR (500 MHz, chloroform-d) δ ppm 7.93 (s, 1H) 7.65 (dd, J=12.51, 2.44 Hz, 1H) 721-7.24 (m, 1H) 7.09-7.16 (m, 2H) 6.99-7.08 (m, 3H) 6.90 (s, 1H) 4.21-4.31 (m, 3H) 2.37 (s, 3H) 2.15-2.26 (m, 1H) 2.03-2.12 (m, 1H) 1.81-2.01 (m, 4H).

EXAMPLE 94 AND EXAMPLE 95

(S)—N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine and (R)—N-(3-fluoro-4-(5-methyl-1H-1,2,4-triazol-1-yl)phenyl)-9-(4-fluorophenyl)-6,7,8,9-tetrahydro-5H-[1,2,4]triazolo azepin-2-amine

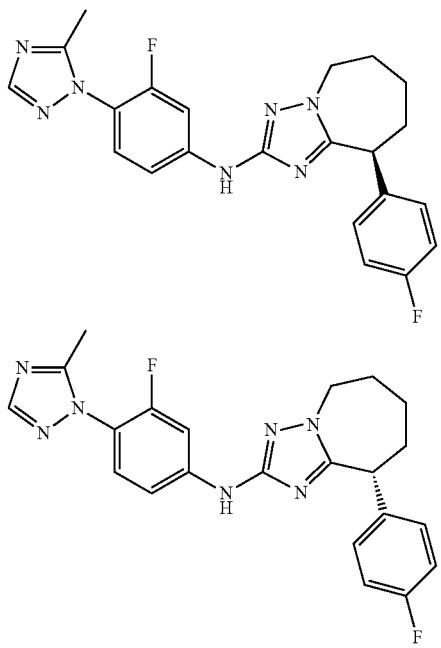

Step A: A racemic mixture of N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine (75 mg from Example 93) was purified using chiral supercritical fluid chromatography (SFC) to afford 35 mg of peak A (first to elute, Example 94) and 35 mg of peak B (second to elute, Example 95). SFC Method: Chiralpak OJ-H (30×250 mm, 5 uM), 15% methanol (0.1% diethylamine) in CO$_2$, 35° C., 70 mL/min, absorbance 268 nm, t$_R$ (peak A) 7.5 min, t$_R$ (peak B) 9.8 min. The absolute stereochemistry of individual enantiomers (examples 94 and 95) was not determined. LC-MS and $^1$H NMR analytical data for the separated enantiomers was identical to the racemate (see Example 93).

EXAMPLE 96

N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

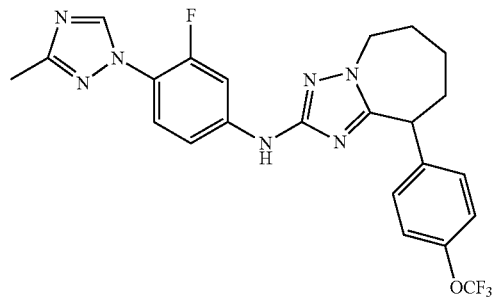 [SMILES: Cc1ncn(-c2ccc(Nc3nc4n(n3)CCCCC4c3ccc(OC(F)(F)F)cc3)cc2F)n1]

Step A: Methyl 3-fluoro-4-(3-methyl-1H-1,2,4-triazol-1-yl)phenylcarbamimidothioate, hydroiodide (2.30 g, 5.58 mmol, from preparation Q) and 6-chloro-2-(4-(trifluoromethoxy)phenyl)hexanoic acid (2.00 g, 6.43 mmol, from preparation AI) were coupled were coupled [N-methylmorpholine (3.22 mL, 29.2 mmol) was substituted for N,N-diisopropylethylamine] and then reacted with hydrazine (0.920 mL, 29.3 mmol) using a procedure analogous to Step A of Example 13. The crude product, 5-(5-chloro-1-(4-(trifluoromethoxy)phenyl)pentyl)-N-(3-fluoro-4-(3-methyl-1H-1,2,4-triazol-1-yl)phenyl)-1H-1,2,4-triazol-3-amine, was used in the next step without purification. LC-MS (M+H)+ 524.3.

Step B: A solution of 5-(5-chloro-1-(4-(trifluoromethoxy)phenyl)pentyl)-N-(3-fluoro-4-(3-methyl-1H-1,2,4-triazol-1-yl)phenyl)-1H-1,2,4-triazol-3-amine (3.07 g, 5.85 mmol), sodium iodide (4.38 g, 29.3 mmol), and diisoproplyethylamine (5.11 mL, 29.3 mmol) in acetone (100 mL) was heated in a sealed vessel at 100° C. for 12 h. The reaction was concentrated in vacuo. Water (250 mL) was added and the mixture was extracted with EtOAc (2×250 mL). The combined organic layers were washed with brine (50 mL), dried (MgSO$_4$), filtered, and concentrated in vacuo. Ethanol (50 mL) was added to the residue. The mixture was stirred at rt for 30 min. The solid was collected by vacuum filtration to afford 630 mg (21% yield) of the titled compound as an off-white solid. LC-MS (M+H)+ 488.5. $^1$H NMR (500 MHz, CHLOROFORM-d) δ ppm 8.39 (d, J=2.4 Hz, 1 H), 7.68 (dd, J=14.0, 2.4 Hz, 1 H), 7.61 (t, J=8.5 Hz, 1 H), 7.17-7.26 (m, 4H), 7.02 (dd, J=89, 2.4 Hz, 1 H), 6.78 (s, 1H), 4.31 (dd, J=8.5, 2.4 Hz, 1 H), 4.26 (t, J=4.9 Hz, 2 H), 2.50 (s, 3 H), 2.17-2.29 (m, 1H), 2.06-2.16 (m, 1H), 1.86-2.03 (m, 4H).

EXAMPLE 97 AND EXAMPLE 98

(S)—N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine and (R)—N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

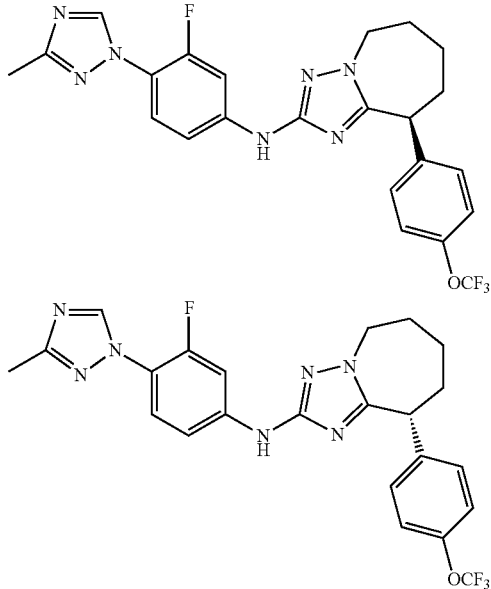

Step A: A racemic mixture of N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine (300 mg from Example 96) was purified using chiral supercritical fluid chromatography (SFC) to afford 134 mg of peak A (first to elute, example 97) and 132 mg of peak B (second to elute, example 98). SFC Method: Chiralpak OJ-H (30×150 mm, 5 uM), 15% methanol (0.1% diethylamine) in $CO_2$, 85 mL/min, absorbance 268 nm. The absolute stereochemistry of individual enantiomers (examples 97 and 98) was not determined. LC-MS and $^1$H NMR analytical data for the separated enantiomers was identical to the racemate (see Example 96).

EXAMPLE 99

N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

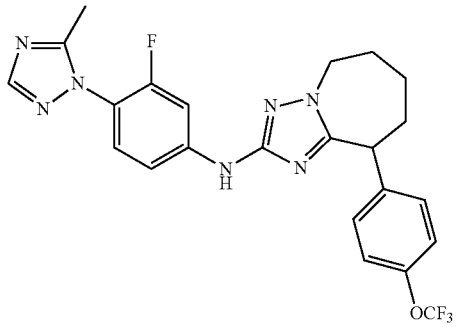 [SMILES: Cc1ncnn1-c1ccc(Nc2nc3n(n2)CCCCC3c2ccc(OC(F)(F)F)cc2)cc1F]

Step A: Methyl 3-fluoro-4-(5-methyl-1H-1,2,4-triazol-1-yl)phenylcarbamimidothioate, hydroiodide (1.50 g, 3.81 mmol, from preparation C) and 6-chloro-2-(4-(trifluoromethoxy)phenyl)hexanoic acid (1.48 g, 4.77 mmol, from preparation AI) were coupled [N-methylmorpholine (2.10 mL, 19.1 mmol) was substituted for N,N-diisopropylethylamine] and then reacted with hydrazine (0.60 mL, 19 mmol) using a procedure analogous to Step A of Example 13. After an aqueous workup, the crude product, 5-(5-chloro-1-(4-(trifluoromethoxy)phenyl)pentyl)-N-(3-fluoro-4-(5-methyl-1H-1,2,4-triazol-1-yl)phenyl)-1H-1,2,4-triazol-3-amine, was used in the next step without purification. LC-MS (M+H)$^+$ 524.1.

Step B: A solution of 5-(5-chloro-1-(4-(trifluoromethoxy)phenyl)pentyl)-N-(3-fluoro-4-(5-methyl-1H-1,2,4-triazol-1-yl)phenyl)-1H-1,2,4-triazol-3-amine (2.00 g, 3.81 mmol), sodium iodide (2.90 g, 19.1 mmol), and diisoproplylethylamine (3.33 mL, 19.1 mmol) in acetone (25 mL) was heated in a sealed vessel at 100° C. for 6 h. The reaction was concentrated in vacuo. Water (250 mL) was added and the mixture was extracted with EtOAc (2×250 mL). The combined organic layers were washed with brine (50 mL), dried ($MgSO_4$), filtered, and concentrated in vacuo. The crude product was purified using silica gel column chromatography (70% EtOAc/chloroform) to afford 350 mg (19% yield) of the titled compound as a white solid. LC-MS (M+H)$^+$ 488.1. $^1$H NMR (500 MHz, CHLOROFORM-d) δ ppm 7.96 (s, 1 H), 7.68 (dd, J=12.7, 2.3 Hz, 1 H), 7.26-7.29 (m, 1 H), 7.19-7.25 (m, 4 H), 7.04 (dd, J=8.9, 2.1 Hz, 1H), 6.87 (s, 1 H), 4.31 (dd, J=8.9, 2.4 Hz, 1 H), 4.27 (t, J=5.0 Hz, 2 H), 2.39 (s, 3 H), 2.17-2.29 (m, 1 H), 2.06-2.16 (m, 1 H), 1.84-2.04 (m, 4 H).

EXAMPLE 100 AND EXAMPLE 101

(S)—N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine and (R)—N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

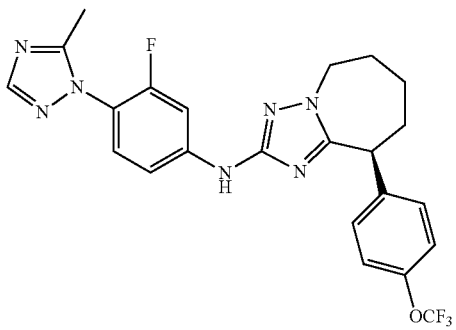

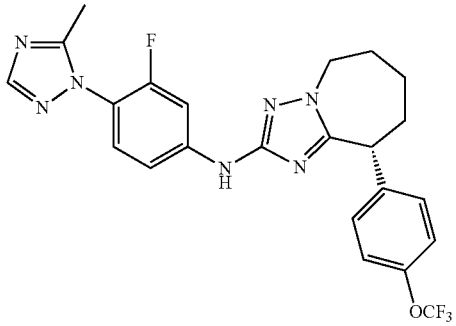

Step A: A racemic mixture of N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine (350 mg from Example 99) was purified using chiral supercritical fluid chromatography (SFC) to afford 165 mg of peak A (first to elute, Example 100) and 167 mg of peak B (second to elute, Example 101). SFC Method: Chiralpak AD-H (30×250 mm, 5 uM), 20% methanol (0.1% diethylamine) in $CO_2$, 70 mL/min, absorbance 268 nm, $t_R$ (peak A) 11.9 min, $t_R$ (peak B) 16.9 min. The absolute stereochemistry of individual enantiomers (examples 100 and 101) was not determined. LC-MS and $^1$H NMR analytical data for the separated enantiomers was identical to the racemate (see Example 99).

EXAMPLE 102

N-(4-(4-chloro-1H-imidazol-1-yl)-3-methoxyphenyl)-9-(4-isopropoxyphenyl)-6,7,8,9-tetrahydro-5H-[1,2,4]triazolo azepin-2-amine

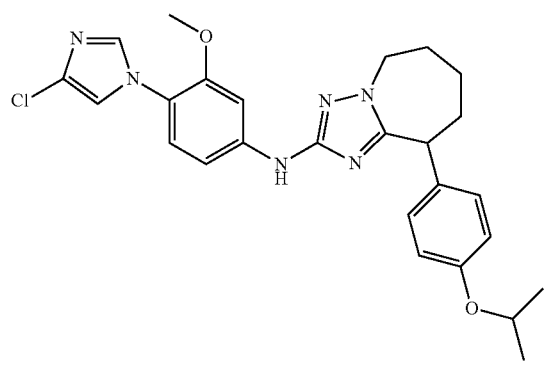 [SMILES: COc1cc(Nc2nc3n(n2)CCCCC3c2ccc(OC(C)C)cc2)ccc1-n1cnc(Cl)c1]

Step A: Methyl 4-(4-chloro-1H-imidazol-1-yl)-3-methoxyphenylcarbamimidothioate, hydroiodide (1.50 g, 3.53 mmol, from preparation A) and 6-chloro-2-(4-isopropoxyphenyl)hexanoic acid (1.26 g, 4.42 mmol, from preparation AV) were coupled [N-methylmorpholine (2.00 mL, 17.7 mmol) was substituted for N,N-diisopropylethylamine] and then reacted with hydrazine (0.556 mL, 17.7 mmol) using a procedure analogous to Step A of Example 13. The crude products were purified using silica gel chromatography (50% ethyl acetate/chloroform) to afford 5-(5-chloro-1-(4-isopropoxyphenyl)pentyl)-N-(4-(4-chloro-1H-imidazol-1-yl)-3-methoxyphenyl)-1H-1,2,4-triazol-3-amine (805 mg, 1.52 mmol, 43% yield) as an off-white solid. LC-MS (M+H)$^+$ 529.3.

Step B: A solution of 5-(5-chloro-1-(4-isopropoxyphenyl)pentyl)-N-(4-(4-chloro-1H-imidazol-1-yl)-3-methoxyphenyl)-1H-1,2,4-triazol-3-amine (780 mg, 1.47 mmol), sodium iodide (1.10 g, 7.37 mmol), and diisoproplylethylamine (0.257 mL, 1.47 mmol) in acetone (25 mL) was heated in a sealed vessel at 100° C. for 4 h. The reaction was concentrated in vacuo. The crude product was purified using silica gel column chromatography (50% EtOAc/chloroform) to afford 200 mg (27% yield) of the titled compound as an off-white solid. LC-MS (M+H)$^+$ 493.3. $^1$H NMR (500 MHz, CHLOROFORM-d) δ ppm 7.51 (d, J=1.5 Hz, 1 H), 7.44 (d, J=2.4 Hz, 1 H), 6.99-7.12 (m, 4 H), 6.87 (d, J=8.9 Hz, 2 H), 6.83 (dd, J=8.4, 2.3 Hz, 1H), 6.69 (s, 1 H), 4.53 (dt, J=12.0, 6.1 Hz, 1H), 4.28 (dd, J=8.5, 1.8 Hz, 1 H), 4.16-4.26 (m, 2 H), 3.80 (s, 3H), 2.17-2.31 (m, 1 H), 2.03-2.15 (m, 1H), 1.82-2.02 (m, 4 H), 1.35 (d, J=6.1 Hz, 6 H).

EXAMPLE 103 AND EXAMPLE 104

(S)—N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine

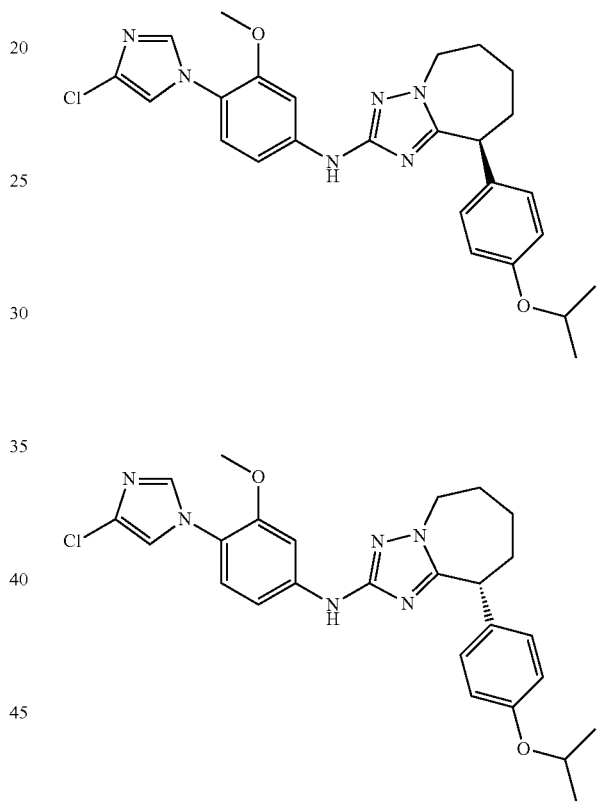

Step A: A racemic mixture of N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine (118 mg from Example 102) was purified using chiral supercritical fluid chromatography (SFC) to afford 37 mg of peak A (first to elute, Example 103) and 39 mg of peak B (second to elute, Example 104). SFC Method: Chiralpak OJ-H (30×250 mm, 5 uM), 25% methanol (0.1% diethylamine) in $CO_2$, 70 mL/min, absorbance 268 nm, $t_R$ (peak A) 18.5 min, $t_R$ (peak B) 35.6 min. The absolute stereochemistry of individual enantiomers (examples 103 and 104) was not determined. LC-MS and $^1$H NMR analytical data for the separated enantiomers was identical to the racemate (see Example 102).

EXAMPLE 105

N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine

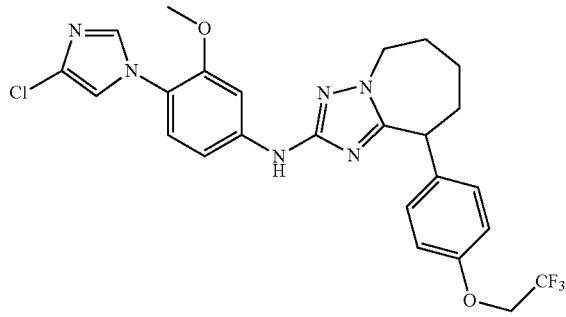 [SMILES: COc1cc(Nc2nc3n(n2)CCCCC3c2ccc(OCC(F)(F)F)cc2)ccc1-n1cnc(Cl)c1]

Step A: Methyl 4-(4-chloro-1H-imidazol-1-yl)-3-methoxyphenylcarbamimidothioate, hydroiodide (1.50 g, 3.53 mmol, from preparation A) and 6-chloro-2-(4-(2,2,2-trifluoroethoxy)phenyl)hexanoic acid (1.43 g, 4.42 mmol, from preparation AW) were coupled [N-methylmorpholine (2.00 mL, 17.7 mmol) was substituted for N,N-diisopropylethylamine] and then reacted with hydrazine (0.556 mL, 17.7 mmol) using a procedure analogous to Step A of Example 13. After an aqueous workup, 5-(5-chloro-1-(4-(2,2,2-trifluoroethoxy)phenyl)pentyl)-N-(4-(4-chloro-1H-imidazol-1-yl)-3-methoxyphenyl)-1H-1,2,4-triazol-3-amine was obtained as a brown foamy solid. LC-MS (M+H)+ 569.3. The crude product was used in the next step without purification.

Step B: A solution of 5-(5-chloro-1-(4-(2,2,2-trifluoroethoxy)phenyl)pentyl)-N-(4-(4-chloro-1H-imidazol-1-yl)-3-methoxyphenyl)-1H-1,2,4-triazol-3-amine (2.02 g, 3.54 mmol), sodium iodide (2.65 g, 17.7 mmol), and diisoproplylethylamine (0.618 mL, 3.54 mmol) in acetone (25 mL) was heated in a sealed vessel at 100° C. for 4 h. The reaction was concentrated in vacuo. The crude product was purified using silica gel column chromatography (50% EtOAc/chloroform) to afford 281 mg (15% yield) of the titled compound as an off-white solid. LC-MS (M+H)+ 533.2. $^1$H NMR (500 MHz, CHLOROFORM-d) δ ppm 7.51 (d, J=1.5 Hz, 1H), 7.41 (d, J=2.4 Hz, 1 H), 7.14 (m, J=8.9 Hz, 2 H), 7.09 (d, J=8.5 Hz, 1 H), 7.02 (d, J=1.5 Hz, 1 H), 6.95 (m, J=8.9 Hz, 2 H), 6.84 (dd, J=8.5, 2.1 Hz, 1 H), 6.66 (s, 1 H), 4.36 (q, J=8.1 Hz, 2 H), 4.20-4.27 (m, 3 H), 3.80 (s, 3 H), 2.16-2.29 (m, 1H), 2.05-2.13 (m, 1 H), 1.92-2.03 (m, 2 H), 1.83-1.90 (m, 2 H).

EXAMPLE 106 AND EXAMPLE 107

(S)—N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine

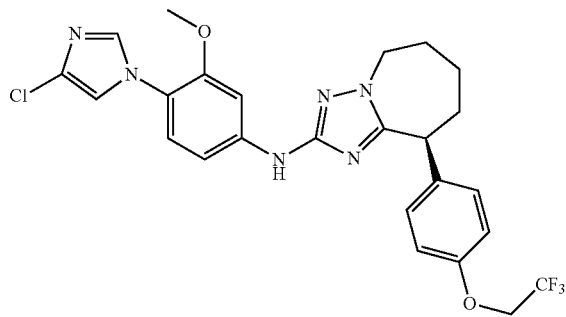

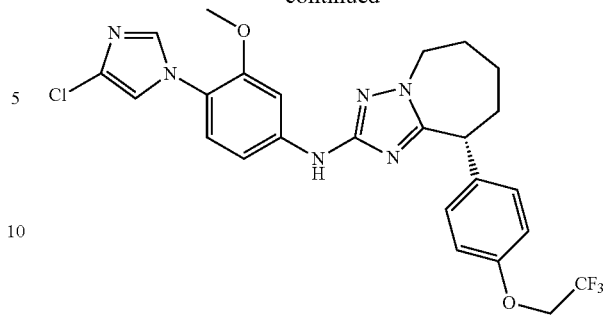

Step A: A racemic mixture of N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine (200 mg from Example 105) was purified using chiral supercritical fluid chromatography (SFC) to afford 81 mg of peak A (first to elute, Example 106) and 85 mg of peak B (second to elute, Example 107). SFC Method: Chiralpak OJ-H (30×250 mm, 5 uM), 20% methanol (0.1% diethylamine) in $CO_2$, 70 mL/min, absorbance 268 nm, $t_R$ (peak A) 9.8 min, $t_R$ (peak B) 14.9 min. The absolute stereochemistry of individual enantiomers (examples 106 and 107) was not determined LC-MS and $^1$H NMR analytical data for the separated enantiomers was identical to the racemate (see Example 105).

EXAMPLE 108

N-(3,5-difluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

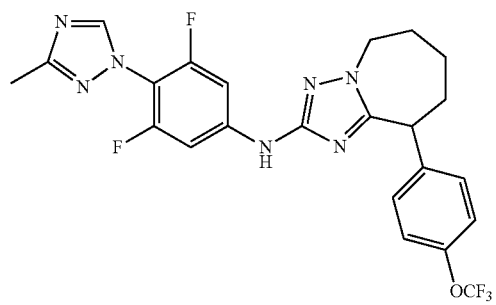

Step A: Methyl 3,5-difluoro-4-(3-methyl-1H-1,2,4-triazol-1-yl)phenylcarbamimidothioate, hydroiodide (0.942 g, 2.92 mmol, from preparation R) and 6-chloro-2-(4-(trifluoromethoxy)phenyl)hexanoic acid (0.890 g, 2.86 mmol, from preparation AI) were coupled [N-methylmorpholine (0.1.26 mL, 11.0 mmol) was substituted for N,N-diisopropylethylamine] and then reacted with hydrazine (0.360 mL, 11.5 mmol) using a procedure analogous to Step A of Example 13. After an aqueous workup, crude 5-(5-chloro-1-(4-(trifluoromethoxy)phenyl)pentyl)-N-(3,5-difluoro-4-(3-methyl-1H-1,2,4-triazol-1-yl)phenyl)-1H-1,2,4-triazol-3-amine was obtained as a brown solid. The crude product was used in the next step without purification. LC-MS (M+H)+ 542.1.

Step B: A solution of 5-(5-chloro-1-(4-(trifluoromethoxy)phenyl)pentyl)-N-(3,5-difluoro-4-(3-methyl-1H-1,2,4-triazol-1-yl)phenyl)-1H-1,2,4-triazol-3-amine (1.24 g, 2.30 mmol), sodium iodide (1.72 g, 11.5 mmol), and diisopropylethylamine (2.00 mL, 11.5 mmol) in acetone (50 mL) was heated in a sealed vessel at 100° C. for 6 h. The reaction was concentrated in vacuo. The crude product was purified using silica gel column chromatography (70% EtOAc/chloroform) to afford 400 mg of the titled compound. The solid was recrystallized from EtOAc/Hex to afford 230 mg (19% yield) of the titled compound as a crystalline white solid. LC-MS (M+H)$^+$ 506.1. $^1$H NMR (500 MHz, CHLOROFORM-d) δ ppm 8.11 (1H, s), 7.13-7.23 (6H, m), 6.92 (1 H, s), 4.22-4.33 (3 H, m), 2.49 (3 H, s), 2.15-2.27 (1 H, m), 2.05-2.13 (1H, m), 1.92-2.01 (2 H, m, J=14.8, 9.8, 7.2, 7.2 Hz), 1.82-1.90 (2 H, m).

EXAMPLE 109

9-(4-(2,2-difluoroethoxy)phenyl)-N-(4-(3,5-dimethyl-1H-1,2,4-triazol-1-yl)-3-fluorophenyl)-6,7,8,9-tetrahydro-5H-[1,2,4]triazolo[1,5-a]azepin-2-amine 2,2,2-trifluoroacetate

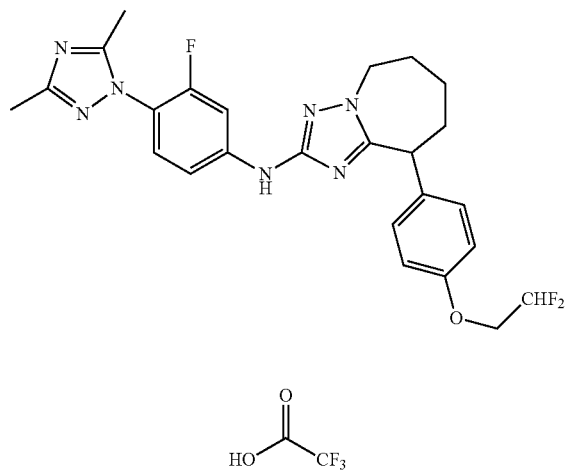 [SMILES: Cc1nc(C)n(-c2ccc(Nc3nc4n(n3)CCCCC4c3ccc(OCC(F)F)cc3)cc2F)n1 ; O=C(O)C(F)(F)F]

Step A: Methyl 4-(3,5-dimethyl-1H-1,2,4-triazol-1-yl)-3-fluorophenylcarbamimidothioate, hydroiodide (600 mg, 1.47 mmol, from preparation T) and 6-chloro-2-(4-(2,2-difluoroethoxy)phenyl)hexanoic acid (475 mg, 1.55 mmol, from preparation AX) were coupled [N-methylmorpholine (0.810 mL, 7.37 mmol) was substituted for N,N-diisopropylethylamine] and then reacted with hydrazine (0.231 mL, 7.37 mmol) using a procedure analogous to Step A of Example 13. After an aqueous workup, crude 5-(5-chloro-1-(4-(2,2-difluoroethoxy)phenyl)pentyl)-N-(4-(3,5-dimethyl-1H-1,2,4-triazol-1-yl)-3-fluorophenyl)-1H-1,2,4-triazol-3-amine was obtained as a brown gummy oil. LC-MS (M+H)$^+$ 534.4.

Step B: A solution of 5-(5-chloro-1-(4-(2,2-difluoroethoxy)phenyl)pentyl)-N-(4-(3,5-dimethyl-1H-1,2,4-triazol-1-yl)-3-fluorophenyl)-1H-1,2,4-triazol-3-amine (787 mg, 1.47 mmol), sodium iodide (1.10 g, 7.37 mmol), and diisopropylethylamine (1.29 mL, 7.37 mmol) in acetone (30 mL) was heated in a sealed vessel at 100° C. for 3 h. The reaction was concentrated in vacuo. After an aqueous workup, the crude organic concentrate was purified using reverse phase preparatory HPLC (MeOH/water/TFA) to afford 145 mg (16% yield) of the titled compound as the TFA salt. LC-MS (M+H)$^+$ 498.3. $^1$H NMR (500 MHz, CHLOROFORM-d) d ppm 9.45 (1 H, br. s.), 7.69 (1 H, dd, J=12.5, 2.1 Hz), 7.29 (1H, t, J=8.5 Hz), 7.18 (1 H, d, J=8.5 Hz), 7.04 (2 H, d, J=8.5 Hz), 6.93 (2 H, d, J=8.5 Hz), 6.08 (1 H, tt, J=55.1, 4.1 Hz), 4.40 (1 H, d, J=7.9 Hz), 4.30-4.37 (1 H, m), 4.21-4.30 (1 H, m), 4.17 (2 H, td, J=13.0, 4.1 Hz), 2.45 (3H, s), 2.42 (3 H, s), 2.25-2.35 (1 H, m), 2.06-2.17 (1 H, m), 1.84-2.04 (4 H, m).

EXAMPLE 110

N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

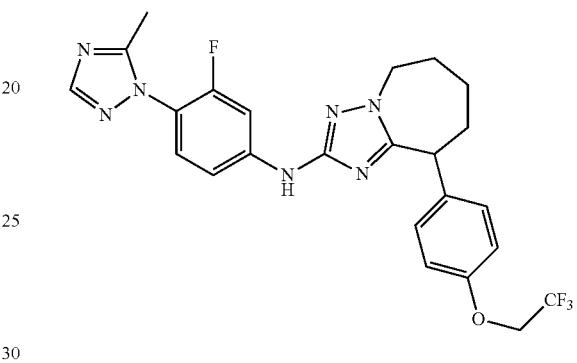

Step A: Methyl 3-fluoro-4-(5-methyl-1H-1,2,4-triazol-1-yl)phenylcarbamimidothioate, hydroiodide (1.50 g, 3.81 mmol, from preparation C) and 6-chloro-2-(4-(2,2,2-trifluoroethoxy)phenyl)hexanoic acid (1.30 g, 4.00 mmol, from preparation AW) were coupled [N-methylmorpholine (2.10 mL, 19.1 mmol) was substituted for N,N-diisopropylethylamine] and then reacted with hydrazine (0.598 mL, 19.1 mmol) using a procedure analogous to Step A of Example 13. After an aqueous workup, 5-(5-chloro-1-(4-(2,2,2-trifluoroethoxy)phenyl)pentyl)-N-(3-fluoro-4-(5-methyl-1H-1,2,4-triazol-1-yl)phenyl)-1H-1,2,4-triazol-3-amine (2.11 g, 3.92 mmol, quantitative yield) was obtained as a brown foamy solid. The crude product was used in the next step without purification. LC-MS (M+H)$^+$ 538.4.

Step B: A solution of 5-(5-chloro-1-(4-(2,2,2-trifluoroethoxy)phenyl)pentyl)-N-(3-fluoro-4-(5-methyl-1H-1,2,4-triazol-1-yl)phenyl)-1H-1,2,4-triazol-3-amine (2.11 g, 3.92 mmol), sodium iodide (2.94 g, 19.6 mmol), and diisoproplylethylamine (0.685 mL, 3.92 mmol) in acetone (30 mL) was heated in a sealed vessel at 100° C. for 12 h. The reaction was concentrated in vacuo. The crude product was purified using silica gel column chromatography (50% EtOAc/chloroform) to afford 770 mg (38% yield) of the titled compound as an off-white solid. This material was recrystallized from EtOH (20 mL) to afford 424 mg (22% yield) of the titled compound as a crystalline white solid. LC-MS (M+H)$^+$ 502.5. $^1$H NMR (500 MHz, CHLOROFORM-d) δ ppm 7.96 (s, 1 H), 7.67 (dd, J=12.8, 2.4 Hz, 1H), 7.24 (t, J=8.5 Hz, 1 H), 7.13 (d, J=8.9 Hz, 2 H), 7.02 (dd, J=9.2, 2.1 Hz, 1 H), 7.00 (s, 1 H), 6.93-6.98 (m, 2H), 4.36 (q, J=8.2 Hz, 2 H), 4.29 (dd, J=8.5, 2.1 Hz, 1 H), 4.22-4.27 (m, 2 H), 2.40 (s, 3 H), 2.17-2.30 (m, 1 H), 2.04-2.13 (m, 1 H), 1.82-2.02 (m, 4 H).

EXAMPLE 111 AND EXAMPLE 112

(S)—N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine and (R)—N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

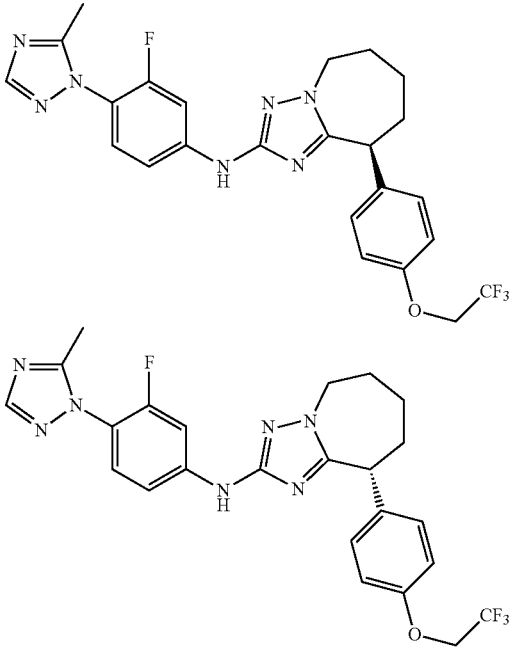

Step A: A racemic mixture of N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine (250 mg from Example 110) was purified using chiral supercritical fluid chromatography (SFC) to afford 115 mg of peak A (first to elute, example 111) and 117 mg of peak 13 (second to elute, example 112). SFC Method: Chiralpak OJ-H (20×250 mm, 5 uM), 20% methanol (0.1% diethylamine) in $CO_2$, 70 mL/min, absorbance 268 nm. The absolute stereochemistry of individual enantiomers (examples 111 and 112) was not determined. LC-MS and $^1$H NMR analytical data for the separated enantiomers was identical to the racemate (see Example 110).

EXAMPLE 113

N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

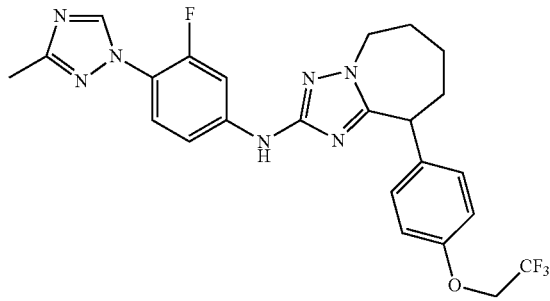 [SMILES: Cc1ncn(-c2ccc(Nc3nc4n(n3)CCCCC4c3ccc(OCC(F)(F)F)cc3)cc2F)n1]

Step A: Methyl 3-fluoro-4-(3-methyl-1H-1,2,4-triazol-1-yl)phenylcarbamimidothioate, hydroiodide (0.750 g, 1.91 mmol, from preparation Q) and 6-chloro-2-(4-(2,2,2-trifluoroethoxy)phenyl)hexanoic acid (0.650 g, 2.00 mmol, from preparation AW) were coupled [N-methylmorpholine (1.05 mL, 9.54 mmol) was substituted for N,N-diisopropylethylamine] and then reacted with hydrazine (0.300 mL, 9.54 mmol) using a procedure analogous to Step A of Example 13. After an aqueous workup, 5-(5-chloro-1-(4-(2,2,2-trifluoroethoxy)phenyl)pentyl)-N-(5-fluoro-4-(3-methyl-1H-1,2,4-triazol-1-yl)phenyl)-1H-1,2,4-triazol-3-amine was obtained as a brown solid. The crude product was used in the next step without purification. LC-MS (M+H)$^+$ 538.5.

Step B: A solution of 5-(5-chloro-1-(4-(2,2,2-trifluoroethoxy)phenyl)pentyl)-N-(5-fluoro-4-(3-methyl-1H-1,2,4-triazol-1-yl)phenyl)-1H-1,2,4-triazol-3-amine (1.03 g, 1.91 mmol), sodium iodide (1.43 g, 9.54 mmol), and diisoproplylethylamine (0.1.67 mL, 9.54 mmol) in acetone (10 mL) was heated in a sealed vessel at 100° C. for 4 h. The reaction was concentrated in vacuo. The crude product was purified using silica gel column chromatography (50% EtOAc/chloroform) to afford 480 mg (48% yield) of the titled compound as an off-white solid. This material was recrystallized from EtOH to afford 225 mg (23% yield) of the titled compound as a crystalline white solid, LC-MS (M+H)$^+$ 502.4. $^1$H NMR (500 MHz, CHLOROFORM-d) δ ppm 8.39 (d, J=2.1 Hz, 1 H), 7.69 (dd, J=13.7, 2.1 Hz, 1 H), 7.60 (t, J=8.7 Hz, 1 H), 7.13 (d, J=8.2 Hz, 2 H), 7.01 (d, J=8.9 Hz, 1H), 6.95 (d, J=8.5 Hz, 2H), 6.80 (s, 1 H), 4.36 (q, J=8.2 Hz, 2 H), 4.28 (d, J=7.3 Hz, 1 H), 4.21-4.26 (m, 2 H), 2.50 (s, 3 H), 2.17-2.28 (m, 1 H), 2.04-2.14 (m, 1 H), 1.84-2.03 (m, 4 H).

EXAMPLE 114 AND EXAMPLE 115

(S)—N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine and (R)—N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

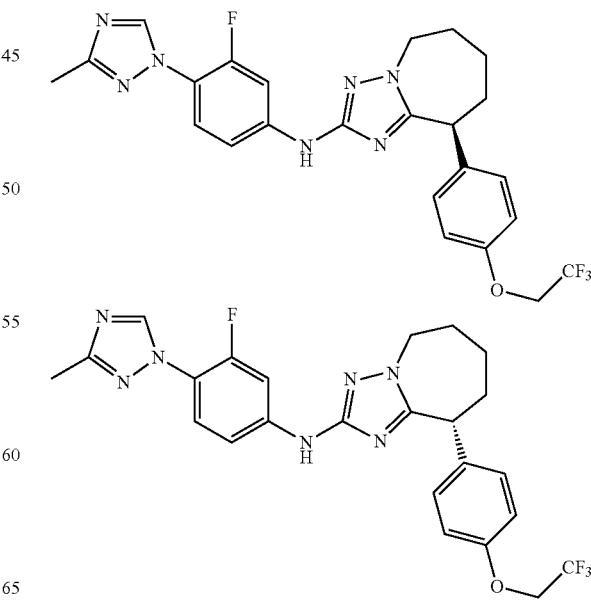

Step A: A racemic mixture of N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine (186 mg from Example 113) was purified using chiral supercritical fluid chromatography (SFC) to afford 89 mg of peak A (first to elute, example 114) and 89 mg of peak B (second to elute, example 115). SFC Method: Chiralpak OJ-H (20×250 mm, 5 uM), 25% methanol (0.1% diethylamine) in $CO_2$, 50 mL/min, absorbance 220 nm. The absolute stereochemistry of individual enantiomers (examples 114 and 115) was not determined. LC-MS and $^1$H NMR analytical data for the separated enantiomers was identical to the racemate (see Example 113).

EXAMPLE 116

N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

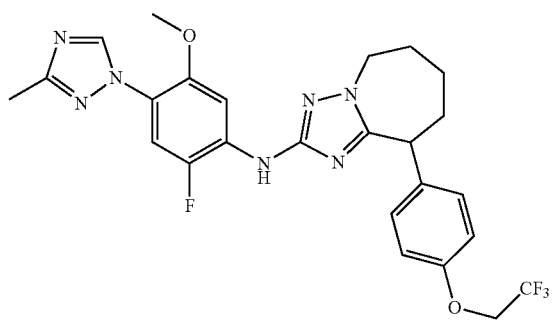 [SMILES: COc1cc(Nc2nc3n(n2)CCCCC3c2ccc(OCC(F)(F)F)cc2)c(F)cc1-n1cnc(C)n1]

Step A: Methyl 2-fluoro-5-methoxy-4-(3-methyl-1H-1,2,4-triazol-1-yl)phenylcarbamimidothioate, hydroiodide (1.50 g, 3.54 mmol, from preparation B) and 6-chloro-2-(4-(2,2,2-trifluoroethoxy)phenyl)hexanoic acid (1.21 g, 3.72 mmol, from preparation AW) were coupled [N-methylmorpholine (1.95 mL, 17.7 mmol) was substituted for N,N-diisopropylethylamine] and then reacted with hydrazine (0.560 mL, 17.7 mmol) using a procedure analogous to Step A of Example 13. After an aqueous workup, 5-(5-chloro-1-(4-(2,2,2-trifluoroethoxy)phenyl)pentyl)-N-(2-fluoro-5-methoxy-4-(3-methyl-1H-1,2,4-triazol-1-yl)phenyl)-1H-1,2,4-triazol-3-amine was obtained as a brown foamy solid. The crude product was used in the next step without purification. LC-MS (M+H)$^+$ 568.5.

Step B: A solution of 5-(5-chloro-1-(4-(2,2,2-trifluoroethoxy)phenyl)pentyl)-N-(2-fluoro-5-methoxy-4-(3-methyl-1H-1,2,4-triazol-1-yl)phenyl)-1H-1,2,4-triazol-3-amine (2.01 g, 3.54 mmol), sodium iodide (2.65 g, 17.7 mmol), and diisoproplylethylamine (1.55 mL, 8.85 mmol) in acetone (10 mL) was heated in a sealed vessel at 100° C. for 4 h. The reaction was concentrated in vacuo. The crude product was purified using silica gel column chromatography (50% EtOAc/chloroform) to afford 474 mg (25% yield) of the titled compound as an off-white solid. LC-MS (M+H)$^+$ 532.5. $^1$H NMR (500 MHz, CHLOROFORM-d) δ ppm 8.55 (s, 1 H), 8.11 (d, J=7.6 Hz, 1 H), 7.47 (d, J=11.6 Hz, 1 H), 7.16 (d, J=8.5 Hz, 2 H), 6.95 (d, J=8.5 Hz, 2 H), 6.86 (d, J=3.4 Hz, 1 H), 4.36 (q, J=8.2 Hz, 2 H), 4.17-4.26 (m, 3 H), 3.83 (s, 3 H), 2.47 (s, 3 H), 2.15-2.28 (m, 1 H), 1.93-2.13 (m, 3 H), 1.80-1.93 (m, 2 H).

EXAMPLE 117 AND EXAMPLE 118

(S)—N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo azepin-2-amine and (R)—N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine

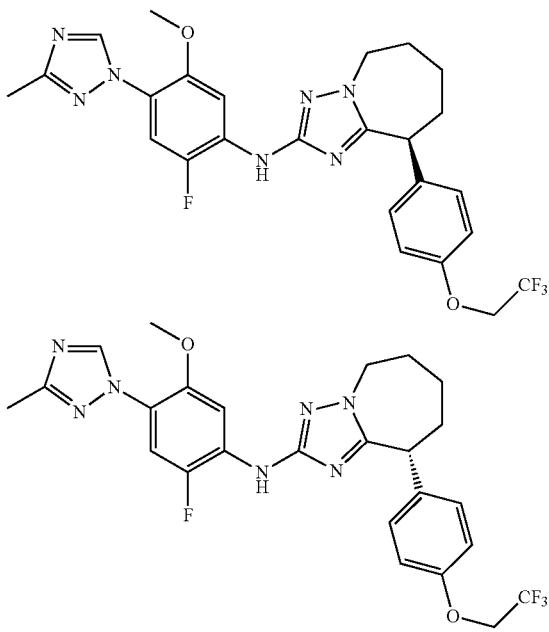

Step A: A racemic mixture of N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine (205 mg from Example 116) was purified using chiral supercritical fluid chromatography (SFC) to afford 79 mg of peak A (first to elute, example 117) and 79 mg of peak B (second to elute, example 118). SFC Method: Chiralpak AD-H (20×150 mm, 5 uM), 15% methanol (0.1% diethylamine) in $CO_2$, 50 mL/min, absorbance 220 nm. The absolute stereochemistry of individual enantiomers (examples 117 and 118) was not determined. LC-MS and $^1$H NMR analytical data for the separated enantiomers was identical to the racemate (see Example 116).

EXAMPLE 119

9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine

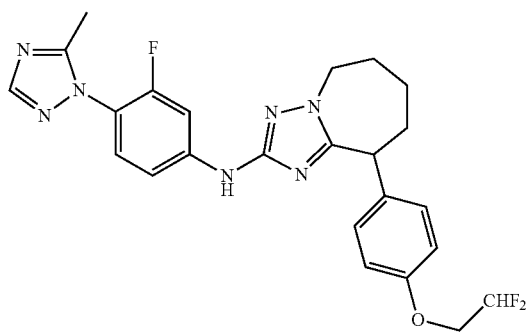 [SMILES: Cc1ncnn1-c1ccc(Nc2nc3n(n2)CCCCC3c2ccc(OCC(F)F)cc2)cc1F]

Step A: Methyl 3-fluoro-4-(5-methyl-1H-1,2,4-triazol-1-yl)phenylcarbamimidothioate, hydroiodide (1.22 g, 3.10 mmol, from preparation C) and 6-chloro-2-(4-(2,2-difluoroethoxy)phenyl)hexanoic acid (1.0 g, 3.26 mmol, from preparation AX) were coupled [N-methylmorpholine (1.71 mL, 15.5 mmol) was substituted for N,N-diisopropylethylamine] and then reacted with hydrazine (0.490 mL, 15.5 mmol) using a procedure analogous to Step A of Example 13. After an aqueous workup, 5-(5-chloro-1-(4-(2,2-difluoroethoxy)phenyl)pentyl)-N-(3-fluoro-4-(5-methyl-1H-1,2,4-triazol-1-yl)phenyl)-1H-1,2,4-triazol-3-amine was obtained as a brown solid. The crude product was used in the next step without purification. LC-MS (M+H)+ 520.5.

Step B: A solution of -(5-chloro-1-(4-(2,2-difluoroethoxy)phenyl)pentyl)-N-(3-fluoro-4-(5-methyl-1H-1,2,4-triazol-1-yl)phenyl)-1H-1,2,4-triazol-3-amine (1.98 g, 3.81 mmol), sodium iodide (2.86 g, 19.1 mmol), and diisoproplylethylamine (3.33 mL, 19.1 mmol) in acetone (30 mL) was heated in a sealed vessel at 100° C. for 18 h. The reaction was concentrated in vacuo. The crude product was purified using silica gel column chromatography (50% EtOAc/chloroform). The purified product was recrystallized from ethanol to afford 294 mg (16% yield) of the titled compound as a crystalline white solid. LC-MS (M+H)+ 484.3. $^1$H NMR (500 MHz, CHLOROFORM-d) δ ppm 7.93 (s, 1 H), 7.66 (dd, J=12.5, 2.4 Hz, 1 H), 7.21-7.25 (m, 1 H), 7.09 (d, J=8.5 Hz, 2 H), 7.01 (dd, J=8.2, 2.1 Hz, 1 H), 6.88-6.94 (m, 3 H), 6.07 (tt, J=55.2, 4.3, 4.1 Hz, 1 H), 4.27 (dd, J=8.5, 2.1 Hz, 1 H), 4.23 (dt, J=6.8, 3.5 Hz, 2 H), 4.17 (td, J=13.0, 4.1 Hz, 2 H), 2.37 (s, 3 H), 2.15-2.27 (m, 1 H), 2.02-2.12 (m, 1 H), 1.80-2.00 (m, 4 H).

EXAMPLE 120 AND EXAMPLE 121

(S)-9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine and (R)-9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine

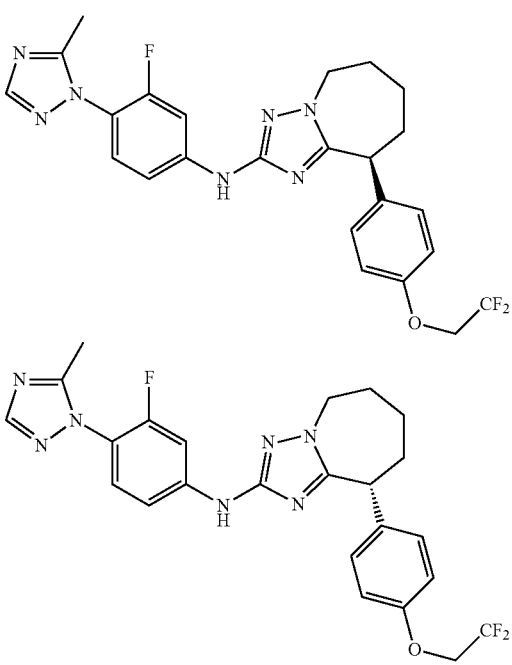

Step A: A racemic mixture of 9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine (250 mg from Example 119) was purified using chiral supercritical fluid chromatography (SFC) to afford 115 mg of peak A (first to elute, example 120) and 117 mg of peak B (second to elute, example 121). SFC Method: Chiralcel OJ-H (30×150 mm, 5 uM), 30% methanol (0.1% diethylamine) in $CO_2$, 50 mL/min, absorbance 220 nm. The absolute stereochemistry of individual enantiomers (examples 120 and 121) was not determined. LC-MS and $^1$H NMR analytical data for the separated enantiomers was identical to the racemate (see Example 119).

EXAMPLE 122

N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine 2,2,2-trifluoroacetate

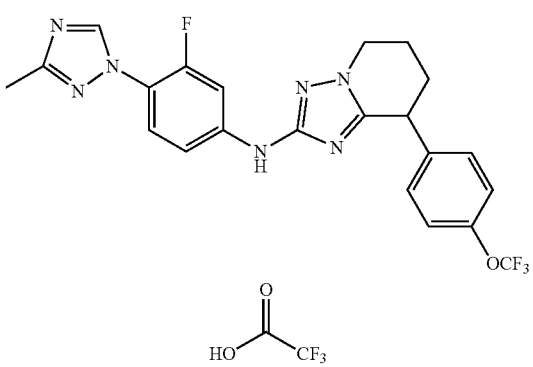

Step A: Methyl 3-fluoro-4-(3-methyl-1H-1,2,4-triazol-1-yl)phenylcarbamimidothioate, hydroiodide (0.578 g, 1.471 mmol), from preparation Q) and 5-chloro-2-(4-(trifluoromethoxy)phenyl)pentanoic acid (0.480 g, 1.62 mmol, from preparation AAK) were coupled [N-methylmorpholine (0.81 mL, 7.36 mmol) was substituted for N,N-diisopropylethylamine] and then reacted with hydrazine (0.185 mL, 5.88 mmol) using a procedure analogous to Step A of Example 13. After an aqueous workup, 5-(4-chloro-1-(4-(trifluoromethoxy)phenyl)butyl)-N-(3-fluoro-4-(3-methyl-1H-1,2,4-triazol-1-yl)phenyl)-1H-1,2,4-triazol-3-amine was obtained as a brown residue. The crude product was used in the next step without purification. LC-MS (M+H)+ 510.1.

Step B: A solution of 5-(4-chloro-1-(4-(trifluoromethoxy)phenyl)butyl)-N-(3-fluoro-4-(3-methyl-1H-1,2,4-triazol-1-yl)phenyl)-1H-1,2,4-triazol-3-amine (0.150 g, 1.47 mmol), sodium iodide (1.10 g, 7.35 mmol), and diisoproplylethylamine (0.514 mL, 2.94 mmol) in acetone (5 mL) was heated in a sealed vessel at 100° C. for 4 h. The reaction was concentrated in vacuo. The crude product was purified using reverse phase preparatory HPLC (MeOH/water/trifluoroacetic acid) to afford the titled compound as the TFA salt (190 mg, 21% yield). LC-MS (M+H)+ 474.1. $^1$H NMR (500 MHz, MeOD) δ ppm 8.80 (1 H, s), 7.75 (1 H, dd, J=13.7, 2.4 Hz), 7.52-7.64 (1 H, m), 7.23-7.39 (5 H, m), 4.36 (1 H, t, J=6.9 Hz), 4.19-4.29 (2 H, m), 2.47 (3 H, s), 2.34-2.43 (1 H, m), 2.08-2.26 (2 H, m), 1.98-2.09 (1 H, m).

EXAMPLE 123 AND EXAMPLE 124

(S)—N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine and (R)—N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine

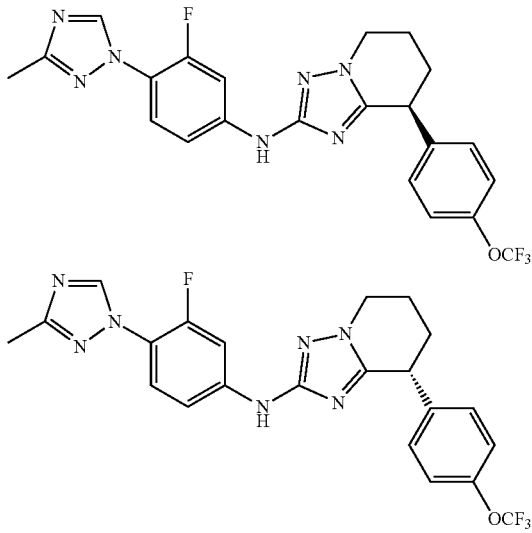

Step A: A racemic mixture of N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine trifluoroacetate (151 mg from Example 122) was purified using chiral supercritical fluid chromatography (SFC) to afford 63 mg of peak A (first to elute, example 123) and 61.3 mg of peak B (second to elute, example 124). SFC Method: Chiralpak AD-H (4.6×250 mm, 5 uM), 35% methanol (0.1% diethylamine) in $CO_2$, 2.0 mL/min, absorbance 268 nm. The absolute stereochemistry of individual enantiomers (examples 123 and 124) was not determined. LC-MS and $^1$H NMR analytical data for the separated enantiomers was identical to the racemate (see Example 122).

EXAMPLE 125 AND EXAMPLE 126

(S)—N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine

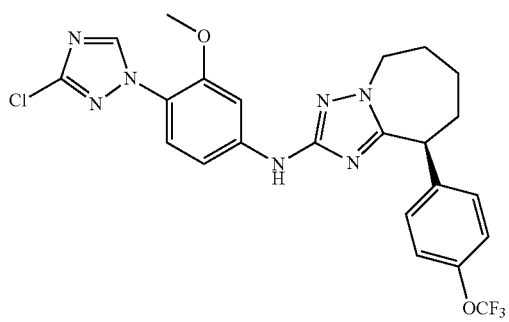

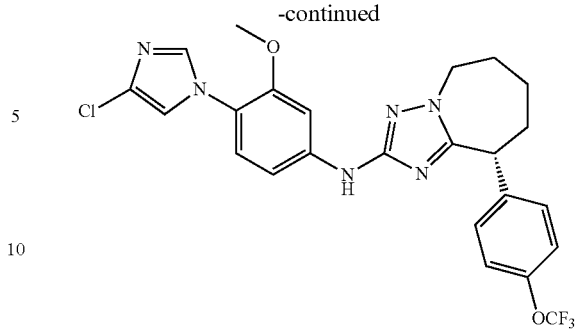

Step A: A racemic mixture of N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine (253 mg from Example 31) was purified using chiral supercritical fluid chromatography (SFC) to afford 112 mg of peak A (first to elute, example 125) and 104 mg of peak B (second to elute, example 126). SEC Method: Chiralpak OJ-H (4.6×250 mm, 5 uM), 25% methanol (0.1% diethylamine) in $CO_2$, 2.0 mL/min, absorbance 268 nm. The absolute stereochemistry of individual enantiomers (examples 125 and 126) was not determined. LC-MS and $^1$H NMR analytical data for the separated enantiomers was identical to the racemate (see Example 31).

EXAMPLE 127

9-(4-(difluoromethoxy)phenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine 2,2,2-trifluoroacetate

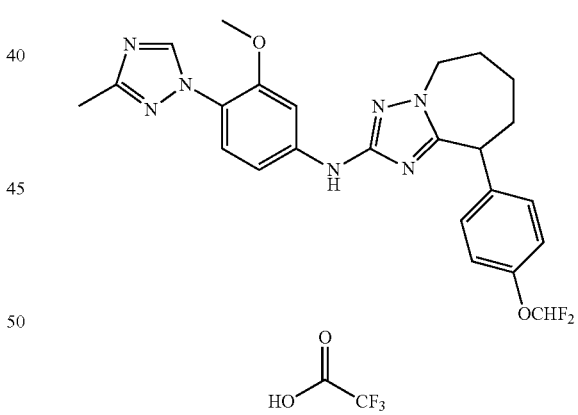

Step A: Methyl 3-methoxy-4-(3-methyl-1H-1,2,4-triazol-1-yl)phenylcarbamimidothioate, hydroiodide (0.250 g, 0.617 mmol), from preparation F) and 6-chloro-2-(4-(difluoromethoxy)phenyl)hexanoic acid (0.271 g, 0.925 mmol, from preparation AZ) were coupled and then reacted with hydrazine (0.078 mL, 2.47 mmol) using a procedure analogous to Step A of Example 13. After an aqueous workup, 5-(5-chloro-1-(4-(difluoromethoxy)phenyl)pentyl)-N-(3-methoxy-4-(3-methyl-1H-1,2,4-triazol-1-yl)phenyl)-1H-1,2,4-triazol-3-amine was obtained as a brown residue. The crude product was used in the next step without purification. LC-MS (M+H)$^+$ 518.2.

Step B: A solution of 5-(5-chloro-1-(4-(difluoromethoxy) phenyl)pentyl)-N-(3-methoxy-4-(3-methyl-1H-1,2,4-triazol-1-yl)phenyl)-1H-1,2,4-triazol-3-amine (0.320 g, 0.618 mmol), sodium iodide (0.463 g, 3.09 mmol), and diisoproplylethylamine (0.216 mL, 1.24 mmol) in acetone (4 mL) was heated in a sealed vessel at 100° C. for 2 h. The reaction was concentrated in vacuo. The crude product was purified using reverse phase preparatory HPLC (MeOH/water/trifluoroacetic acid) to afford the titled compound as the TFA salt (22 mg, 6% yield). LC-MS (M+H)+ 482.2. $^1$H NMR (500 MHz, CHLOROFORM-d) δ ppm 10.13 (1 H, br. s.), 8.98 (1 H, s), 7.64 (1 H, d, J=8.9 Hz), 7.37 (1 H, d, J=2.1 Hz), 7.16 (3 H, d, J=8.5 Hz), 7.06-7.12 (2 H, m), 6.31-6.70 (1H, m), 4.49 (1 H, d, J=5.8 Hz), 4.39 (1 H, d, J=14.3 Hz), 4.27 (1 H, br. s.), 3.90-3.98 (3 H, m), 2.56 (3 H, s), 2.36 (1 H, br. s.), 2.17 (1 H, br. s.), 1.96 (4 H, br. s.).

EXAMPLE 128

9-(3-fluoro-4-(trifluoromethoxy)phenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine 2,2,2-trifluoroacetate

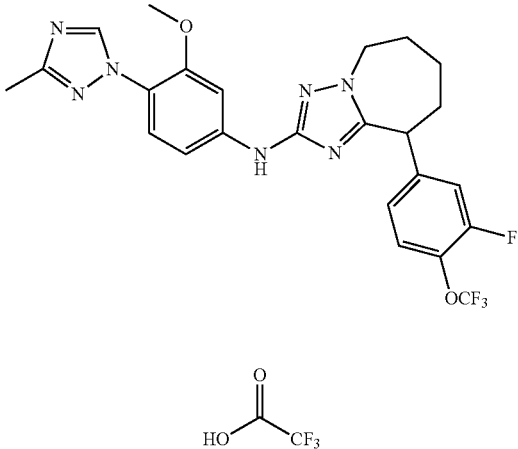 [SMILES: COc1cc(Nc2nc3n(n2)CCCCC3c2ccc(OC(F)(F)F)c(F)c2)ccc1-n1cnc(C)n1 ; O=C(O)C(F)(F)F]

Step A: Methyl 3-methoxy-4-(3-methyl-1H-1,2,4-triazol-1-yl)phenylcarbamimidothioate, hydroiodide (0.250 g, 0.617 mmol), from preparation F) and 6-chloro-2-(3-fluoro-4-(trifluoromethoxy)phenyl)hexanoic acid (0.304 g, 0.925 mmol, from preparation AY) were coupled and then reacted with hydrazine (0.078 mL, 2.47 mmol) using a procedure analogous to Step A of Example 13. After an aqueous workup, 5-(5-chloro-1-(3-fluoro-4-(trifluoromethoxy)phenyl)pentyl)-N-(3-methoxy-4-(3-methyl-1H-1,2,4-triazol-1-yl)phenyl)-1H-1,2,4-triazol-3-amine was obtained as a brown residue. The crude product was used in the next step without purification. LC-MS (M+H)+ 554.1.

Step B: A solution of 5-(5-chloro-1-(3-fluoro-4-(trifluoromethoxy)-phenyl)pentyl)-N-(3-methoxy-4-(3-methyl-1H-1,2,4-triazol-1-yl)phenyl)-1H-1,2,4-triazol-3-amine (0.342 g, 0.617 mmol), sodium iodide (0.463 g, 3.09 mmol), and diisoproplylethylamine (0.216 mL, 1.24 mmol) in acetone (4 mL) was heated in a sealed vessel at 100° C. for 4 h. The reaction was concentrated in vacuo. The crude product was purified using reverse phase preparatory HPLC (MeOH/water/trifluoroacetic acid) to afford the titled compound as the TFA salt (91.7 mg, 22% yield). LC-MS (M+H)+ 518.2. $^1$H NMR (500 MHz, CHLOROFORM-d) δ ppm 1.88-2.05 (m, 4 H) 2.17 (d, J=4.88 Hz, 1 H) 2.24-2.36 (m, 1 H) 2.56 (s, 3 H) 3.93 (s, 3 H) 4.23-4.31 (m, 1 H) 4.32-4.39 (m, 1 H) 4.41 (dd, J=8.24, 2.14 Hz, 1 H) 6.91 (d, J=8.55 Hz, 1 H) 6.98-7.05 (m, 1H) 7.09 (dd, J=8.55, 2.14 Hz, 1 H) 7.33 (t, J=8.09 Hz, 1H) 7.37-7.43 (m, 1 H) 7.40 (d, J=2.14 Hz, 1 H) 7.63 (d, J=8.55 Hz, 1 H) 8.95 (s, 1 H).

EXAMPLE 129

N-(3-methoxy-4-(3-methyl-1H-1,2,4-triazol-1-yl) phenyl)-9-(4-(methylsulfonyl)phenyl)-6,7,8,9-tetrahydro-5H-[1,2,4]-triazolo[1,5-a]azepin-2-amine 2,2,2-trifluoroacetate

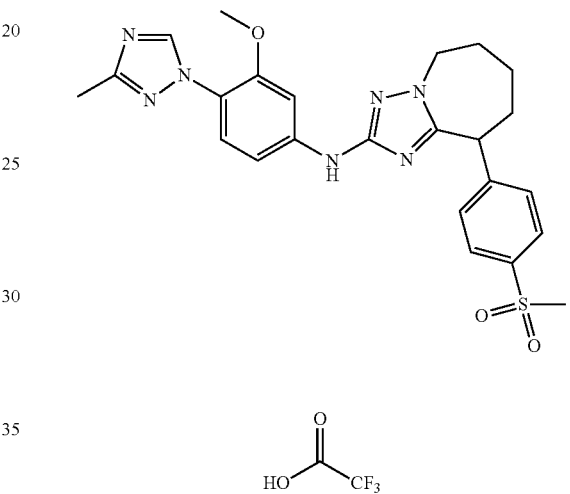

Step A: Methyl 3-methoxy-4-(3-methyl-1H-1,2,4-triazol-1-yl)phenylcarbamimidothioate, hydroiodide (0.250 g, 0.617 mmol), from preparation F) and 6-chloro-2-(4-(methylsulfonyl)phenyl)hexanoic acid (0.282 g, 0.925 mmol, from preparation AAL) were coupled and then reacted with hydrazine (0.077 mL, 2.47 mmol) using a procedure analogous to Step A of Example 13. After an aqueous workup, 5-(5-chloro-1-(4-(methylsulfonyl)phenyl)pentyl)-N-(3-methoxy-4-(3-methyl-1H-1,2,4-triazol-1-yl)phenyl)-1H-1,2,4-triazol-3-amine was obtained as a brown residue. The crude product was used in the next step without purification. LC-MS (M+H)+ 530.1.

Step B: A solution of 5-(5-chloro-1-(4-(methylsulfonyl) phenyl)pentyl)-N-(3-methoxy-4-(3-methyl-1H-1,2,4-triazol-1-yl)phenyl)-1H-1,2,4-triazol-3-amine (0.327 g, 0.617 mmol), sodium iodide (0.462 g, 3.08 mmol), and diisoproplylethylamine (0.215 mL, 1.23 mmol) in acetone (4 mL) was heated in a sealed vessel at 100° C. for 4 h. The reaction was concentrated in vacuo. The crude product was purified using reverse phase preparatory HPLC (MeOH/water/trifluoroacetic acid) to afford the titled compound as the TFA salt (115 mg, 29% yield). LC-MS (M+H)+ 494.1. $^1$H NMR (500 MHz, CHLOROFORM-d) δ ppm 9.81 (1 H, br. s.), 9.04 (1H, s), 8.02 (2H, d, J=8.2 Hz), 7.68 (1 H, d, J=8.9 Hz), 7.35-7.44 (3 H, m), 7.16 (1 H, dd, J=8.7, 2.3 Hz), 4.50-4.59 (1 H, m), 4.38-4.46 (1 H, m), 4.29-4.38 (1 H, m), 3.98 (3 H, s), 3.11 (3

H, s), 2.60 (3 H, s), 2.40 (1 H, dd, J=14.6, 8.2 Hz), 2.21 (1 H, d, J=15.0 Hz), 2.02 (4 H, d, J=7.9 Hz).

EXAMPLE 130

N-(3-methoxy-4-(3-methyl-1H-1,2,4-triazol-1-yl) phenyl)-9-(4-(trifluoromethylsulfonyl)phenyl)-6,7,8, 9-tetrahydro-5H-[1,2,4]triazolo[1,5-a]azepin-2-amine 2,2,2-trifluoroacetate

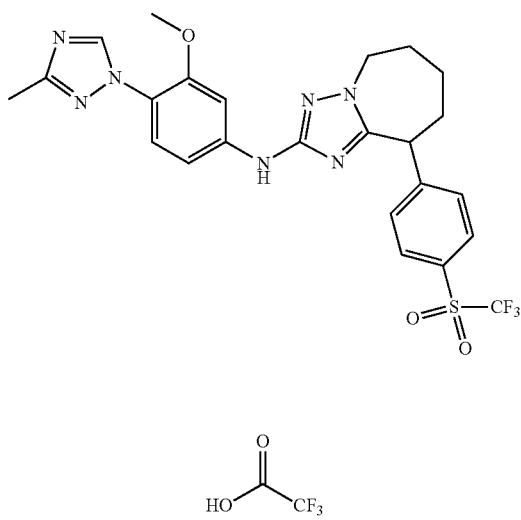

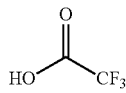

Step A: Methyl 3-methoxy-4-(3-methyl-1H-1,2,4-triazol-1-yl)phenylcarbamimidothioate, hydroiodide (0.250 g, 0.617 mmol), from preparation F) and 6-chloro-2-(4-(trifluoromethylsulfonyl)phenyl)hexanoic acid (0.221 g, 0.617 mmol, from preparation AAM) were coupled [N-methylmorpholine (0.339 mL, 3.08 mmol) was substituted for N,N-diisopropylethylamine] and then reacted with hydrazine (0.069 mL, 2.21 mmol) using a procedure analogous to Step A of Example 13. After an aqueous workup, 5-(5-chloro-1-(4-(trifluoromethylsulfonyl)phenyl)pentyl)-N-(3-methoxy-4-(3-methyl-1H-1,2,4-triazol-1-yl)phenyl)-1H-1,2,4-triazol-3-amine was obtained as a brown residue. The crude product was used in the next step without purification. LC-MS (M+H)+ 584.0.

Step B: A solution of 5-(5-chloro-1-(4-(trifluoromethylsulfonyl)-phenyl)pentyl)-N-(3-methoxy-4-(3-methyl-1H-1, 2,4-triazol-1-yl)phenyl)-1H-1,2,4-triazol-3-amine (0.322 g, 0.551 mmol), sodium iodide (0.413 g, 2.76 mmol), and diisopropylethylamine (0.193 mL, 1.01 mmol) in acetone (4 mL) was heated in a sealed vessel at 100° C. for 4 h. The reaction was concentrated in vacuo. The crude product was purified using reverse phase preparatory HPLC (MeOH/water/trifluoroacetic acid) to afford the titled compound as the TFA salt (83.7 mg, 21% yield). LC-MS (M+H)+ 548.1. $^1$H NMR (500 MHz, CHLOROFORM-d) δ ppm 8.89 (1 H, s), 8.26 (1 H, br. s.), 8.09 (2 H, d, J=8.5 Hz), 7.63 (1 H, d, J=8.9 Hz), 7.52 (2 H, d, J=8.2 Hz), 7.43 (1 H, d, J=2.4 Hz), 7.03 (1 H, dd, J=8.7, 2.3 Hz), 4.49 (1 H, dd, J=8.9, 2.4 Hz), 4.29-4.38 (2 H, m), 3.93 (3 H, s), 2.57 (3 H, s), 2.30-2.40 (1 H, m), 2.16-2.25 (1 H, m), 1.91-2.08 (4 H, m).

EXAMPLE 131

N-(4-(4-chloro-1H-imidazol-1-yl)-3-methoxyphenyl)-9-(4-ethoxyphenyl)-6,7,8,9-tetrahydro-5H-[1,2,4]triazolo[1,5-a]azepin-2-amine 2,2,2-trifluoroacetate

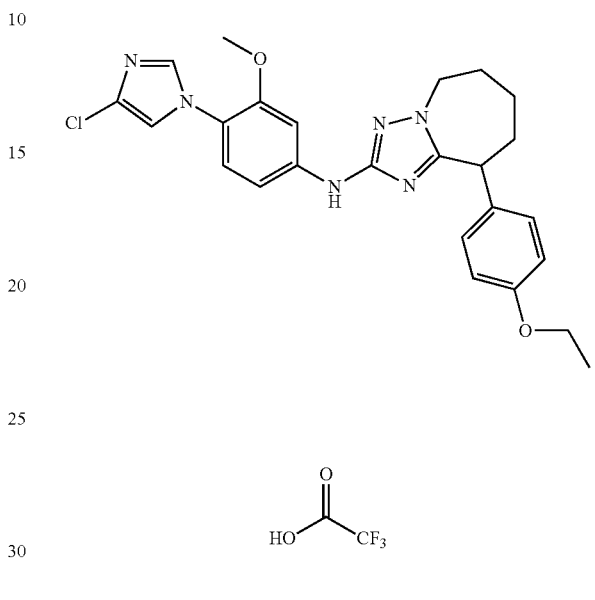

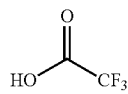

Step A: Methyl 4-(4-chloro-1H-imidazol-1-yl)-3-methoxyphenylcarbamimidothioate, hydroiodide (0.500 g, 1.18 mmol), from preparation A) and 6-chloro-2-(4-ethoxyphenyl)hexanoic acid (0.351 g, 1.30 mmol, from preparation AAN) were coupled [N-methylmorpholine (0.647 mL, 5.89 mmol) was substituted for N,N-diisopropylethylamine] and then reacted with hydrazine (0.148 mL, 4.71 mmol) using a procedure analogous to Step A of Example 13. After an aqueous workup, 5-(5-chloro-1-(4-ethoxyphenyl)pentyl)-N-(4-(4-chloro-1H-imidazol-1-yl)-3-methoxyphenyl)-1H-1,2,4-triazol-3-amine was obtained as a brown residue. The crude product was used in the next step without purification. LC-MS (M+H)+ 515.1.

Step B: A solution of 5-(5-chloro-1-(4-ethoxyphenyl)pentyl)-N-(4-(4-chloro-1H-imidazol-1-yl)-3-methoxyphenyl)-1H-1,2,4-triazol-3-amine (0.607 g, 1.18 mmol), sodium iodide (0.883 g, 5.89 mmol), and diisoproplylethylamine (0.411 mL, 2.36 mmol) in acetone (10 mL) was heated in a sealed vessel at 100° C. for 2 h. The reaction was concentrated in vacuo. The crude product was purified using reverse phase preparatory HPLC (MeOH/water/trifluoroacetic acid) to afford the titled compound as the TFA salt (110 mg, 15% yield). LC-MS (M+H)+ 479.2. $^1$H NMR (500 MHz, CHLOROFORM-d) δ ppm 9.88 (1 H, br. s.), 7.66 (1 H, s), 7.34 (1 H, d, J=2.1 Hz), 7.11-7.21 (2 H, m), 7.07 (1 H, s), 6.96-7.01 (2 H, m), 6.89-6.95 (2 H, m), 4.54 (1 H, d, J=5.2 Hz), 4.34-4.44 (1 H, m), 4.21 (1 H, dd, J=14.3, 7.9 Hz), 4.05 (2 H, q, J=7.0 Hz), 3.88 (3 H, s), 2.35-2.47 (1 H, m), 2.06-2.15 (1H, m), 1.88-1.99 (4 H, m), 1.44 (3 H, t, J=6.9 Hz).

EXAMPLE 132

9-(4-ethoxyphenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine 2,2,2-trifluoroacetate

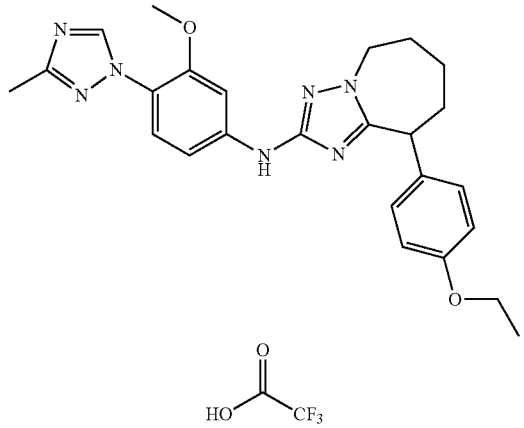

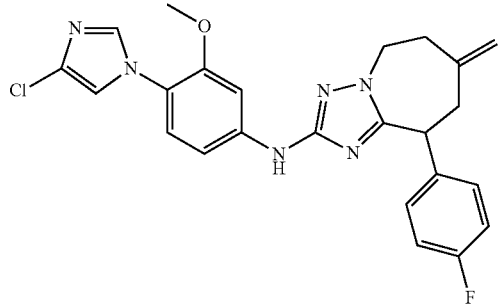

Step A: Methyl 3-methoxy-4-(3-methyl-1H-1,2,4-triazol-1-yl)phenylcarbamimidothioate, hydroiodide (0.500 g, 1.23 mmol), from preparation F) and 6-chloro-2-(4-ethoxyphenyl)hexanoic acid (0.367 g, 1.36 mmol, from preparation AAN) were coupled [N-methylmorpholine (0.678 mL, 6.17 mmol) was substituted for N,N-diisopropylethylamine] and then reacted with hydrazine (0.155 mL, 4.94 mmol) using a procedure analogous to Step A of Example 13. After an aqueous workup, 5-(5-chloro-1-(4-ethoxyphenyl)pentyl)-N-(3-methoxy-4-(3-methyl-1H-1,2,4-triazol-1-yl)phenyl)-1H-1,2,4-triazol-3-amine was obtained as a brown residue. The crude product was used in the next step without purification. LC-MS (M+H)$^+$ 496.2.

Step B: A solution of 5-(5-chloro-1-(4-ethoxyphenyl)pentyl)-N-(3-methoxy-4-(3-methyl-1H-1,2,4-triazol-1-yl)phenyl)-1H-1,2,4-triazol-3-amine (0.612 g, 1.23 mmol), sodium iodide (0.925 g, 6.17 mmol), and diisoproplylethylamine (0.431 mL, 2.47 mmol) in acetone (5 mL) was heated in a sealed vessel at 100° C. for 2 h. The reaction was concentrated in vacuo. The crude product was purified using reverse phase preparatory HPLC (MeOH/water/trifluoroacetic acid) to afford the titled compound as the TFA salt (57.5 mg, 8% yield). LC-MS (M+H)$^+$ 460.2. $^1$H NMR (500 MHz, CHLOROFORM-d) δ ppm 8.61 (1 H, s), 7.59 (1 H, d, J=8.9 Hz), 7.43 (1 H, d, J=2.1 Hz), 7.07 (1 H, dd, J=8.7, 2.3 Hz), 7.01 (2 H, d, J=8.5 Hz), 6.88-6.94 (2 H, m), 4.44-4.48 (1 H, m), 4.36 (1 H, d, J=15.3 Hz), 4.16-4.24 (1 H, m), 4.05 (2 H, q, J=7.0 Hz), 3.91 (3 H, s), 2.51-2.54 (3 H, m), 2.37 (1 H, dd, J=15.7, 7.8 Hz), 2.06-2.13 (1 H, m), 2.05-2.14 (1 H, m), 1.89-1.97 (4 H, m), 1.42-1.46 (3 H, m).

EXAMPLE 133

N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine 2,2,2-trifluoroacetate

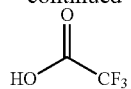

Step A: Methyl 4-(4-chloro-1H-imidazol-1-yl)-3-methoxyphenyl-carbamimidothioate, hydroiodide (0.750 g, 1.77 mmol), from preparation A) and 6-chloro-2-(4-fluorophenyl)-4-methylenehexanoic acid (0.499 g, 1.94 mmol, from preparation AAI) were coupled [N-methylmorpholine (0.971 mL, 8.83 mmol) was substituted for N,N-diisopropylethylamine] and then reacted with hydrazine (0.222 mL, 7.07 mmol) using a procedure analogous to Step A of Example 13. After an aqueous workup, 5-(5-chloro-1-(4-ethoxyphenyl)pentyl)-N-(4-(4-chloro-1H-imidazol-1-yl)-3-methoxyphenyl)-1H-1,2,4-triazol-3-amine was obtained as a brown residue. The crude product was used in the next step without purification. LC-MS (M+H)$^+$ 501.2.

Step B: A solution of 5-(5-chloro-1-(4-fluorophenyl)-3-methylenepentyl)-N-(4-(4-chloro-1H-imidazol-1-yl)-3-methoxyphenyl)-1H-1,2,4-triazol-3-amine (0.100 g, 0.199 mmol), sodium iodide (0.149 g, 0.997 mmol), and diisoproplylethylamine (0.070 mL, 0.399 mmol) in acetone (2 mL) was heated in a sealed vessel at 100° C. for 2 h. The reaction was concentrated in vacuo. The crude product was purified using reverse phase preparatory HPLC (MeOH/water/trifluoroacetic acid) to afford the titled compound as the TFA salt (13.1 mg, 11% yield). LC-MS (M+H)$^+$ 465.1. $^1$H NMR (500 MHz, CHLOROFORM-d) δ ppm 9.35 (1 H, br. s.), 7.74 (1 H, d, J=1.5 Hz), 7.32 (1 H, d, J=2.4 Hz), 7.13-7.19 (3 H, m), 7.03-7.13 (4 H, m), 4.98-5.09 (2 H, m), 4.48 (1 H, dd, J=8.2, 3.7 Hz), 4.29-4.43 (2 H, m), 3.87 (3 H, s), 2.98 (1 H, dd, J=14.0, 8.2 Hz), 2.83-2.91 (1 H, m), 2.62-2.74 (2 H, m).

EXAMPLE 134 AND EXAMPLE 135

(S)—N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine

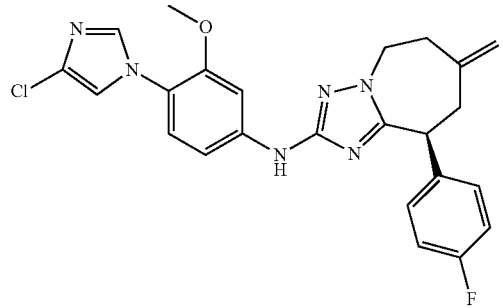

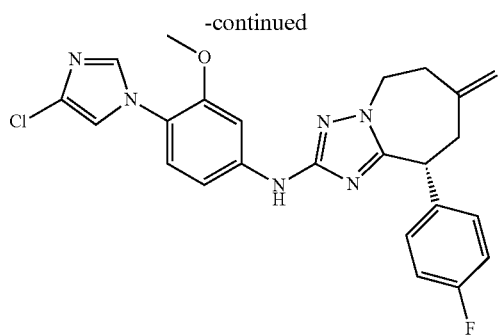

Step A: A racemic mixture of N-(4-(4-chloro-1H-imidazol-1-yl)-3-methoxyphenyl)-9-(4-fluorophenyl)-7-methylene-6,7,8,9-tetrahydro-5H [1,2,4]triazolo[1,5-a]azepin-2-amine (540 mg from Example 133) was purified using chiral supercritical fluid chromatography (SFC) to afford 216 mg of peak A (first to elute, example 134) and 219 mg of peak B (second to elute, example 135). SFC Method: Chiralpak OJ-H (4.6×250 mm, 5 uM), 30% methanol (0.1% diethylamine) in $CO_2$, 2.0 mL/min, absorbance 268 nm. The absolute stereochemistry of individual enantiomers (examples 134 and 135) was not determined. LC-MS and $^1$H NMR analytical data for the separated enantiomers was identical to the racemate (see Example 133).

EXAMPLE 136

N-(4-(4-chloro-1H-imidazol-1-yl)-3-methoxyphenyl)-9-(4-fluorophenyl)-7-methyl-6,7,8,9-tetrahydro-5H-[1,2,4]triazolo[1,5-a]azepin-2-amine

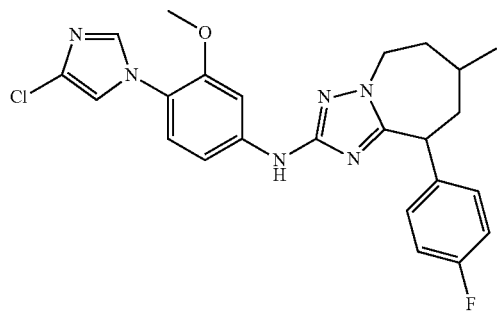 [SMILES: COc1cc(Nc2nc3n(n2)CCC(C)CC3c2ccc(F)cc2)ccc1-n1cnc(Cl)c1]

Step A: N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine (65 mg, 0.140 mmol, from example 133) was dissolved in ethanol (5 mL), flushed with nitrogen, and chilled to 0° C. Platinum on sulfided carbon (136 mg, 0.140 mmol) was added and the flask was repeated evacuated and flushed with hydrogen gas (balloon). The reaction mixture was stirred under an atmosphere of hydrogen gas at rt for 16 h. The reaction mixture was purged with nitrogen, filtered over celite. The celite was washed with methanol and the combined filtrates were concentrated in vacuo. The crude product was purified using reverse phase preparatory HPLC (AcCN/water/ammonium acetate) to afford the titled compound as a mixture of diasteromers (51.6 mg, 74% yield). LC-MS (M+H)$^+$ 467.2. $^1$H NMR (500 MHz, CHLOROFORM-d, mixture of diastereomers) δ ppm 7.53 (1 H, dd, J=16.2, 1.5 Hz), 7.41 (1 H, t, J=2.1 Hz), 7.29-7.34 (1 H, m), 6.95-7.16 (5 H, m), 6.71-6.79 (1 H, m), 4.62 (1 H, br. s.), 3.96-4.16 (1 H, m), 3.73-3.88 (3 H, m), 2.00-2.10 (2 H, m), 1.91 (1 H, dd, J=14.2, 6.6 Hz), 1.71-1.85 (1 H, m), 1.50-1.68 (2 H, m), 1.09 (3 H, dd, J=16.9, 6.6 Hz).

EXAMPLE 137

2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one 2,2,2-trifluoroacetate

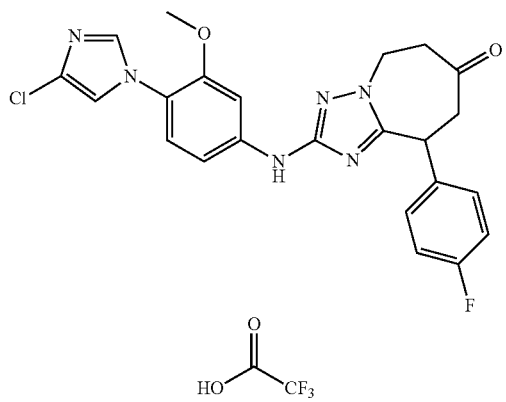

Step A: A solution of sodium periodate (138 mg, 0.645 mmol) in water (5.0 mL) was added over a 10 min period, via pipet, to a vigorously stirred solution of the N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine (100 mg, 0.215 mmol, from example 133) and osmium tetroxide (5.47 mg, 0.022 mmol) in THF (5.0 mL). The reaction was stirred for 1 h and then diluted with water (150 mL)/brine (100 mL) and extracted with ethyl acetate (3×). The combined organic layers were washed with brine, dried over sodium sulfate, and concentrated in vacuo. The crude product was purified using reverse phase preparatory HPLC (MeOH/water/trifluoroacetic acid) to afford the titled compound as the TFA salt (60 mg, 47% yield). LC-MS (M+H)$^+$ 467.1. $^1$H NMR (500 MHz, CHLOROFORM-d) δ ppm 9.24 (1 H, br. s.), 8.12 (1 H, d, J=1.5 Hz), 7.33 (1 H, d, J=2.1 Hz), 7.19-7.24 (1 H, m), 7.07-7.18 (5 H, m), 4.71 (1H, dd, J=8.5, 4.0 Hz), 4.54-4.64 (1 H, m), 4.45-4.54 (1 H, m), 3.90 (3 H, s), 3.44 (1 H, dd, J=14.3, 8.5 Hz), 3.16 (1 H, dd, J=14.3, 4.0 Hz), 2.89-3.06 (2 H, m).

EXAMPLE 138

(E)-2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one O-methyl oxime 2,2,2-trifluoroacetate

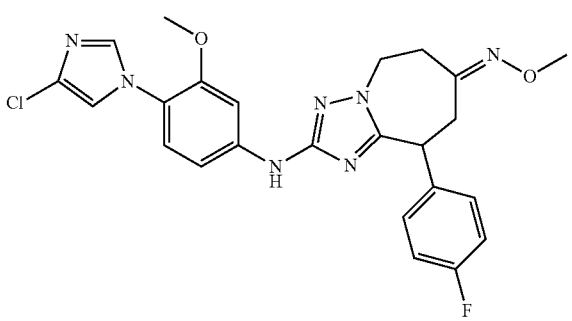

-continued

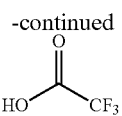

Step A: To a solution of 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from example 137) in ethanol (1.1 mL) was added methoxylamine hydrochloride (35.8 mg, 0.428 mmol) and DIPEA (112 µL, 0.643 mmol). The resulting mixture was stirred at rt for 16 h. The reaction mixture was diluted with EtOAc (10 mL), washed with water (5 mL), brine (5 mL), dried over Mg SO$_4$, filtered and concentrated in vacuo. The crude product was purified using reverse phase preparatory HPLC (MeOH/water/trifluoroacetic acid) to afford the TFA salt of the titled compound as a mixture of E/Z isomers (76.7 mg, 56% yield). LC-MS (M+H)$^+$ 496.2. $^1$H NMR (500 MHz, CHLOROFORM-d) δ ppm 9.52-9.79 (1 H, m), 8.02 (1 H, s), 7.25-7.36 (1 H, m), 7.05-7.25 (7 H, m), 4.46-4.73 (3 H, m), 3.81-3.97 (6 H, m), 2.95-3.24 (3 H, m), 2.84 (1 H, t, J=5.8 Hz).

EXAMPLE 139

N-(4-(4-chloro-1H-imidazol-1-yl)-3-methoxyphenyl)-7,7-difluoro-9-(4-fluorophenyl)-6,7,8,9-tetrahydro-5H-[1,2,4]triazolo[1,5-a]azepin-2-amine 2,2,2-trifluoroacetate

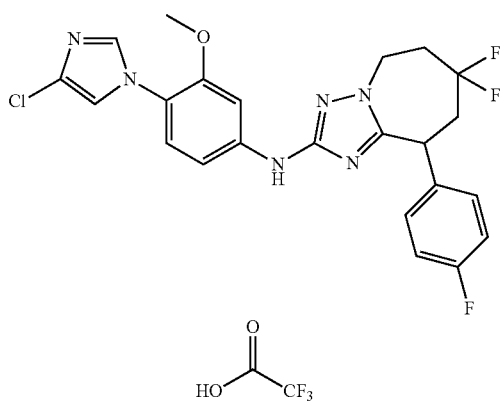

Step A: To a 10 mL round bottomed flask was added 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from Example 137). The vessel was purged with nitrogen. DCM (1 mL) was added and the solution was cooled to 0° C. DAST (0.071 mL, 0.535 mmol) was added and the stirred reaction mixture was allowed to slowly warm to ambient temperature. After 18 h, saturated aqueous NaHCO$_3$ (200 mL) was carefully added, and the mixture was extracted with EtOAc (300 mL). The organics were washed with brine (100 mL), dried over sodium sulfate, filtered, and concentrated in vacuo. The crude product was purified using reverse phase preparatory HPLC (MeOH/water/trifluoroacetic acid) to afford the titled compound (8.2 mg, 6% yield) as a TFA salt. LC-MS (M+H)$^+$ 489.2. $^1$H NMR (500 MHz, CHLOROFORM-d) δ ppm 9.14 (1 H, br. s.), 8.11 (1 H, s), 7.03-7.45 (7 H, m), 4.59 (1 H, br. s.), 4.26-4.46 (2 H, m), 3.87 (3 H, s), 2.29-2.84 (4 H, m).

EXAMPLE 140

N2-(4-(4-chloro-1H-imidazol-1-yl)-3-methoxyphenyl)-9-(4-fluorophenyl)-N-7-methyl-6,7,8,9-tetrahydro-5H-[1,2,4]triazolo[1,5-a]azepine-2,7-diamine 2,2,2-trifluoroacetate

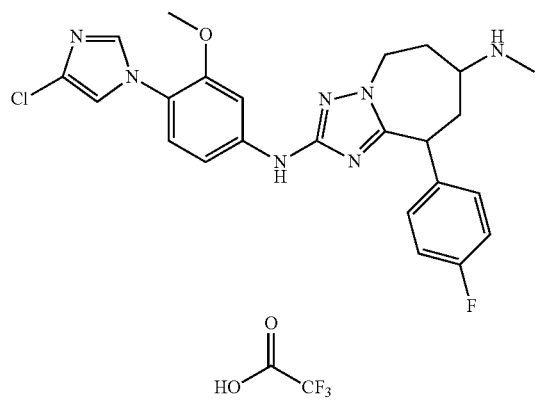

Step A: 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from example 137) was added to a mixture of methanamine (66.5 mg, 2.14 mmol), and sodium cyanoborohydride (857 µL, 0.857 mmol) in ethanol (1.1 mL). The mixture was stirred at rt for 16 h and then concentrated in vacuo. The crude product was purified using reverse phase preparatory HPLC (MeOH/water/trifluoroacetic acid) to afford the titled compound (65.2 mg, 49% yield) as a TFA salt. LC MS (M+H)$^+$ 482.1. $^1$H NMR (500 MHz, MeOD) δ ppm 7.90 (1 H, s), 7.53 (1 H, d, J=2.1 Hz), 7.35 (1 H, s), 7.23-7.30 (1 H, m), 7.09-7.21 (5 H, m), 4.61 (1 H, ddd, J=15.0, 6.0, 2.1 Hz), 3.97-4.06 (3 H, m), 3.82-3.91 (3 H, m), 2.94 (1 H, dd, J=13.9, 6.0 Hz), 2.71-2.78 (3H, m), 2.38 (1 H, br. s.), 2.24 (1 H, ddd, J=14.3, 11.4, 3.1 Hz), 1.94-2.07 (1 H, m).

EXAMPLE 141

N2-(4-(4-chloro-1H-imidazol-1-yl)-3-methoxyphenyl)-9-(4-fluorophenyl)-N7,N7-dimethyl-6,7,8,9-tetrahydro-5H-[1,2,4]triazolo[1,5-a]azepine-2,7-diamine

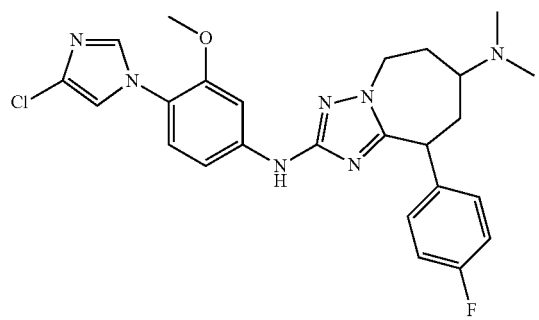

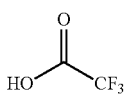

Step A: 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from example 137) was added to a mixture of dimethylamine (2M in THF, 1.07 mL, 2.14 mmol), and sodium cyanoborohydride (1.0 M in THF, 857 μL, 0.857 mmol) in ethanol (1.1 mL). The mixture was stirred at rt for 16 h and then concentrated in vacuo. The crude product was purified using reverse phase preparatory HPLC (MeOH/water/trifluoroacetic acid) to afford the titled compound (59.5 mg, 43% yield) as a TFA salt. LC-MS (M+H)$^+$ 496.2. $^1$H NMR (500 MHz, CHLOROFORM-d) δ ppm 7.90-7.99 (1 H, m), 7.32-7.39 (1 H, m), 7.19-7.25 (1 H, m), 7.09-7.17 (4 H, m), 6.91-7.04 (2 H, m), 4.99 (1 H, br. s.), 4.70 (1 H, ddd, J=15.2, 5.3, 2.4 Hz), 4.03 (1 H, dd, J=14.2, 12.1 Hz), 3.86-3.97 (3 H, m), 3.39-3.55 (1 H, m), 3.03 (1 H, dd, J=13.9, 5.6 Hz), 2.74-2.88 (6 H, m), 2.52 (1 H, br, s.), 2.17-2.33 (1 H, m), 1.97-2.13 (1 H, m), 1.37-1.51 (1 H, m).

EXAMPLE 142

7-(azetidin-1-yl)-N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine

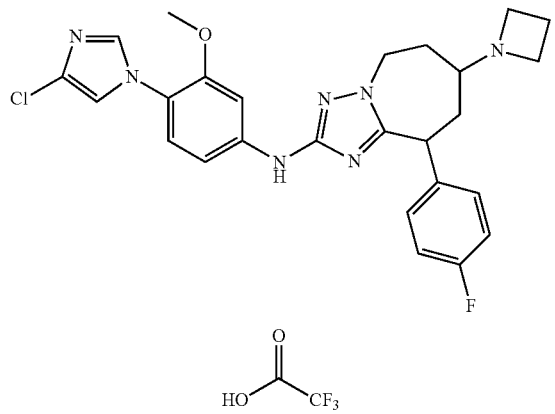

Step A: 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (50 mg, 0.107 mmol, from example 137) was added to a mixture of azetidine (6.11 mg, 0.107 mmol), and sodium cyanoborohydride (1.0M in THF, 428 μL, 0.428 mmol) in ethanol (0.535 mL). The mixture was stirred at rt for 16 h and then concentrated in vacuo. The crude product was purified using reverse phase preparatory HPLC (MeOH/water/trifluoroacetic acid) to afford the titled compound (18.7 mg, 27% yield) as a TFA salt. LC-MS (M+H)$^+$ 508.3. $^1$H NMR (500 MHz, CHLOROFORM-d) δ ppm 8.63 (1 H, d, J=3.7 Hz), 7.89-7.98 (1 H, m), 7.31-7.38 (1 H, m), 7.07-7.22 (5 H, m), 7.01 (2 H, dd, J=8.5, 4.9 Hz), 4.92 (2 H, d, J=4.6 Hz), 4.64-4.77 (1 H, m), 4.42 (2 H, br. s.), 3.98-4.10 (1 H, m), 3.66-3.97 (5 H, m), 2.58-2.90 (2 H, m), 2.14-2.44 (4 H, m).

EXAMPLE 143

N-(4-(4-chloro-1H-imidazol-1-yl)-3-methoxyphenyl)-9-(4-fluorophenyl)-7-(pyrrolidin-1-yl)-6,7,8,9-tetrahydro-5H-[1,2,4]triazolo[1,5-a]azepin-2-amine

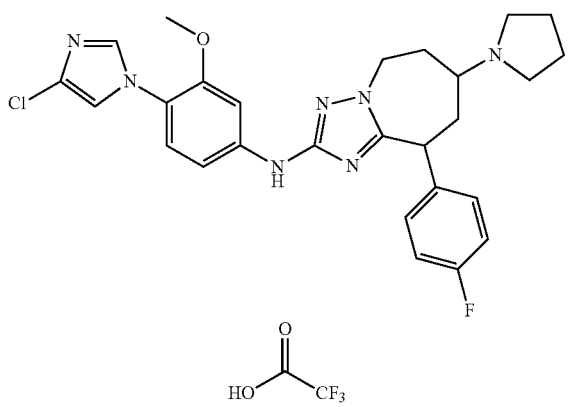

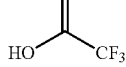

Step A: 2-(4-(4-Chloro-1H-imidazol-1-yl)-3-methoxyphenylamino)-9-(4-fluorophenyl)-8,9-dihydro-5H-[1,2,4]triazolo[1,5-a]azepin-7(6H)-one (50 mg, 0.107 mmol, from example 137) was added to a mixture of pyrrolidine (7.62 mg, 0.107 mmol), and sodium cyanoborohydride (1.0 M in THF, 428 μL, 0.428 mmol) in ethanol (0.535 mL). The mixture was stirred at rt for 48 h and then concentrated in vacuo. The crude product was purified using reverse phase preparatory HPLC (MeOH/water/trifluoroacetic acid) to afford the titled compound (24.8 mg, 35% yield) as a TFA salt. LC-MS (M+H)$^+$ 522.4. $^1$H NMR (500 MHz, CHLOROFORM-d) δ ppm 7.80 (1 H, d, J=1.5 Hz), 7.35 (1 H, d, J=2.1 Hz), 6.98-7.22 (7 H, m), 4.96 (1 H, br. s.), 4.65-4.74 (1 H, m), 3.97-4.09 (1 H, m), 3.78-3.97 (5 H, m), 3.38 (1 H, br. s.), 2.92-3.02 (1 H, m), 2.84 (2 H, d, J=4.9 Hz), 2.36-2.53 (2 H, m), 2.03-2.31 (5 H, m).

EXAMPLE 144

N-(4-(4-chloro-1H-imidazol-1-yl)-3-methoxyphenyl)-9-(4-fluorophenyl)-5,6,8,9-tetrahydrospiro[[1,2,4]triazolo[1,5-a]azepine-7,2'-[1,3]dioxolan]-2-amine 2,2,2-trifluoroacetate

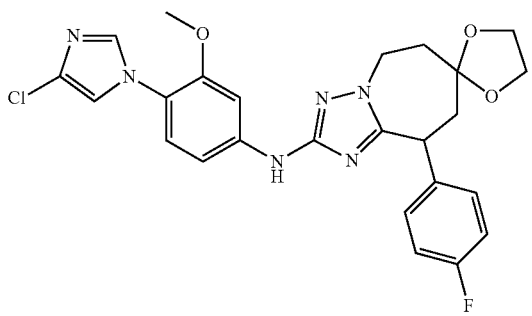

-continued

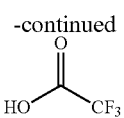

Step A: A solution of 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (84 mg, 0.180 mmol, from example 137) in benzene (1 mL) was treated with ethylene glycol (0.011 mL, 0.198 mmol), and 4-methylbenzenesulfonic acid, hydrate (34.2 mg, 0.180 mmol). The mixture was heated to reflux using a Dean-Stark trap for 6 h, the mixture was cooled to room temperature and quenched with saturated sodium bicarbonate and extracted with ethyl acetate. The aqueous phase was extracted twice more with ethyl acetate and the combined organic layers were combined and washed with brine, dried over sodium sulfate and concentrated in vacuo. The crude product was purified using reverse phase preparatory HPLC (MeOH/water/trifluoroacetic acid) to afford the titled compound (39.4 mg, 34% yield) as a TFA salt. LC-MS (M+H)$^+$ 511.3. $^1$H NMR (500 MHz, CHLOROFORM-d) δ ppm 7.75 (1 H, br. s.), 7.30-7.33 (1 H, m), 7.25-7.29 (2 H, m), 7.09-7.17 (3 H, m), 7.06 (1 H, br. s.), 7.02 (1 H, dd, J=8.5, 2.4 Hz), 4.45-4.54 (1 H, m), 4.32-4.42 (2 H, m), 4.02-4.11 (4 H, m), 3.83 (3 H, s), 2.32-2.40 (1 H, m), 2.23 (1 H, d, J=13.7 Hz), 2.08-2.19 (2 H, m).

EXAMPLE 145

N-(4-(4-chloro-1H-imidazol-1-yl)-3-methoxyphenyl)-9-(4-fluorophenyl)-7,7-dimethoxy-6,7,8,9-tetrahydro-5H-[1,2,4]triazolo[1,5-a]azepin-2-amine

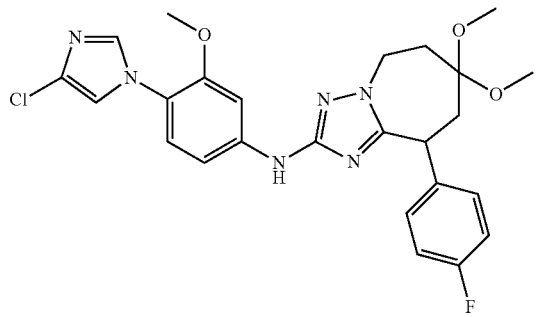 [SMILES: COc1cc(Nc2nc3n(n2)CCC(OC)(OC)CC3c2ccc(F)cc2)ccc1-n1cnc(Cl)c1]

Step A: To a stirred solution of 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (200 mg, 0.428 mmol, from example 137) in MeOH (2 mL) was added trimethyl orthoformate (0.469 mL, 4.28 mmol) followed by Ts-OH (8.15 mg, 0.043 mmol). The reaction mixture was stirred at room temperature for 16 h. The reaction was concentrated in vacuo. The crude product was purified using reverse phase preparatory HPLC (AcCN/water/ammonium acetate) to afford the titled compound (104 mg, 46% yield). LC-MS (M+H)$^+$ 513.3. $^1$H NMR (500 MHz, CHLOROFORM-d) δ ppm 7.51 (1 H, d, J=1.5 Hz), 7.40 (1 H, d, J=2.4 Hz), 7.31-7.35 (2 H, m), 7.06-7.14 (3 H, m), 7.02 (1 H, d, J=1.5 Hz), 6.78 (1 H, dd, J=8.5, 2.4 Hz), 6.59 (1 H, s), 4.39 (1 H, ddd, J=14.7, 5.9, 2.3 Hz), 4.20-4.28 (1 H, m), 4.11-4.17 (1 H, m), 3.76 (3 H, s), 3.29 (3 H, s), 3.26 (3 H, s), 2.35-2.43 (2 H, m), 2.05-2.12 (1 H, m), 1.89 (1 H, ddd, J=14.5, 11.9, 2.3 Hz).

EXAMPLE 146

2-(4-(4-chloro-1H-imidazol-1-yl)-3-methoxyphenylamino)-7-ethyl-9-(4-fluorophenyl)-6,7,8,9-tetrahydro-5H-[1,2,4]triazolo[1,5-a]azepin-7-ol

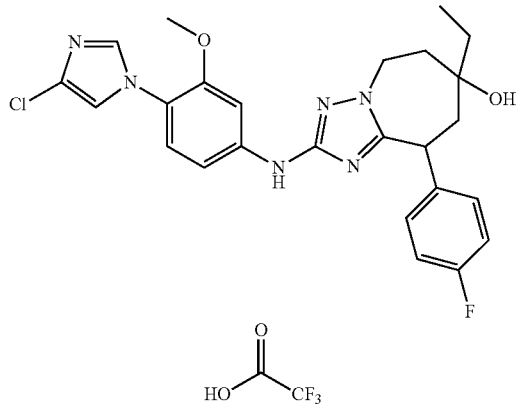

Step A: A 25 mL round bottom flask was charged with copper (I) iodide (8.16 mg, 0.043 mmol) in THF (1 mL), and cooled to 0° C. A solution of ethylmagnesium bromide (0.714 mL, 2.142 mmol, 3 M in Et$_2$O) was added dropwise to the stirred solution and stirred for 20 min. To this was added 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from example 137) in THF (1 mL) and the reaction was stirred at 0° C. for an additional 2 h and then slowly warmed to rt and stirred for 16 h. The reaction mixture was quenched slowly with saturated ammonium chloride, and the aqueous layer was extracted with EtOAc (×3). The combined organic layers were then washed with brine (100 mL), dried over sodium sulfate and concentrated in vacuo. The crude product was purified using reverse phase preparatory HPLC (MeOH/water/trifluoroacetic acid) to afford the titled compound (14.2 mg, 10% yield) as a TFA salt. LC-MS (M+H)$^+$ 497.2. $^1$H NMR (500 MHz, CHLOROFORM-d) δ ppm 8.14 (1 H, br. s.), 7.45-7.97 (2 H, m), 7.05-7.20 (6 H, m), 4.63-4.77 (2 H, m), 4.36-4.49 (1 H, m), 3.88 (3 H, s), 1.88-2.35 (4 H, m), 1.71 (2 H, q, J=7.4 Hz), 1.24-1.51 (1 H, m), 1.03 (3 H, t, J=7.5 Hz).

EXAMPLE 147 rel-(7R,9R)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol 2,2,2-trifluoroacetate

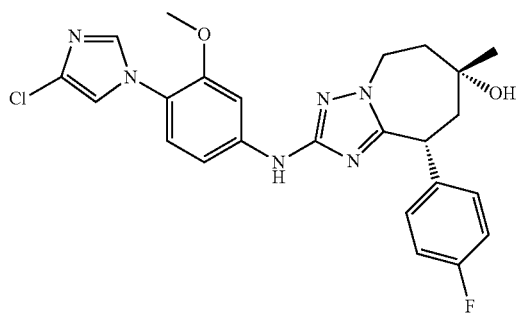

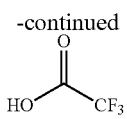

Step A: A 25 mL round bottom flask was charged with copper (I) iodide (8.16 mg, 0.043 mmol) in THF (1 mL), and cooled to 0° C. A solution of methylmagnesium bromide (1.53 mL, 2.142 mmol, 1.4 M in THF) was added dropwise to the stirred solution and stirred for 20 min. To solution of methyl cuprate was added 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (100 mg, 0.214 mmol, from example 137) in THF (1 mL) and the reaction was stirred at 0° C. for an additional 2 h. The resulting mixture was quenched slowly with saturated ammonium chloride, and the aqueous layer was washed with EtOAc (×3). The combined organic layers were then washed with brine (100 mL), dried over sodium sulfate and concentrated in vacuo. The crude product was purified using reverse phase preparatory HPLC (MeOH/water/trifluoroacetic acid) to afford the titled compound (21.6 mg, 17% yield) as a TFA salt. LC-MS (M+H)$^+$ 483.2. $^1$H NMR (500 MHz, CHLOROFORM-d) δ ppm 10.36 (1 H, br. s.), 9.30 (1 H, br. s.), 8.05 (1 H, s), 7.22-7.33 (2 H, m), 7.08-7.20 (6 H, m), 4.62-4.76 (2 H, m), 4.34-4.46 (1 H, m), 3.82-3.92 (3 H, m), 2.16-2.34 (2 H, m), 2.04-2.14 (1 H, m), 1.92-2.04 (1 H, m), 1.43-1.53 (3 H, m).

EXAMPLE 148 AND EXAMPLE 149

(7R,9R)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol 2,2,2-trifluoroacetate and (7S,9R)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol

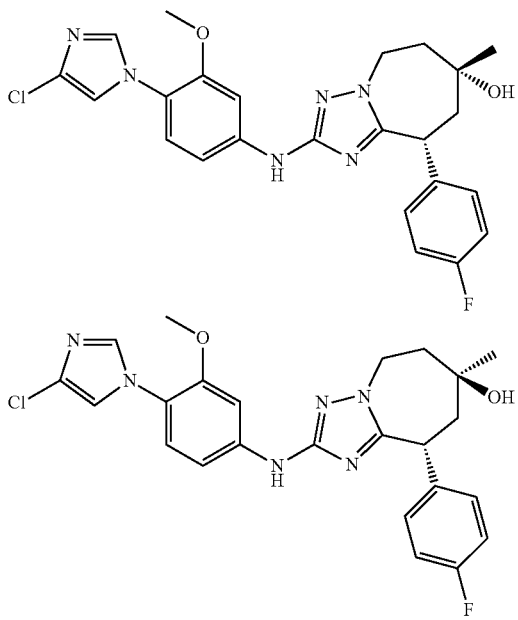

Step A: A solution of sodium periodate (276 mg, 1.29 mmol) in water (5.0 mL) was added over a 10 min period to a vigorously stirred solution of the (R)—N-(4-(4-chloro-1H-imidazol-1-yl)-3-methoxyphenyl)-9-(4-fluorophenyl)-methylene-6,7,8,9-tetrahydro-5H-[1,2,4]triazolo[1,5-a]azepin-2-amine (200 mg, 0.430 mmol, from example 134) and osmium tetroxide (10.9 mg, 0.043 mmol) in THF (5.0 mL). The reaction was stirred for 1 h and then diluted with water (150 mL)/brine (100 mL) and extracted with ethyl acetate (3×). The combined organic layers were washed with brine, dried over sodium sulfate, and concentrated in vacuo to afford (R)-2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (192 mg, 77% yield). LC-MS (M+H)$^+$ 467.1.

Step B: A 25 mL round bottom flask was charged with copper (I) iodide (15.7 mg, 0.082 mmol) in THF (2 mL), and cooled to 0° C. A solution of methyl magnesium bromide (2.94 mL, 4.11 mmol) was added dropwise. The resulting mixture was stirred for 20 min. To the solution of methyl caprate was added (R)-2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (192 mg, 0.411 mmol) in THF (1 mL). The resulting mixture was stirred at 0° C. for 2 h. The reaction was quenched with saturated ammonium chloride. The aqueous solution extracted with EtOAc (×3). The combined organic layers were then washed with brine (100 mL), dried over sodium sulfate, and concentrated in vacuo. The crude product was purified using silica-gel column chromatography (50-100% EtOAc/Chloroform, flow=25 mL/min, linear gradient) to afford diastereomer A (Example 149, first to elute) and 36.2 mg of diastereomer B (Example 148, second to elute). Diastereomer A (first to elute) was repurified using reverse phase preparatory HPLC (MeOH/water/trifluoroacetic acid) to afford 33.2 mg of Example 149 as the TINA salt. Data for Example 148: LC-MS (M+H)$^+$ 483.3. $^1$H NMR (500 MHz, CHLOROFORM-d) δ ppm 7.52 (1 H, d, J=1.5 Hz), 7.39 (1 H, d, J=2.4 Hz), 7.21-7.26 (2 H, m), 7.06-7.12 (3 H, m), 7.03 (1 H, d, J=1.5 Hz), 6.81 (1 H, dd, J=8.4, 2.3 Hz), 6.60 (1 H, s), 4.51 (1 H, ddd, J=14.9, 8.2, 2.0 Hz), 4.15-4.22 (1 H, m), 4.05 (1 H, d, J=11.0 Hz), 3.77 (3 H, s), 2.42 (1 H, dd, J=13.6, 11.4 Hz), 2.10-2.17 (2 H, m), 2.02-2.10 (1 H, m), 1.58 (3 H, s), 1.54 (1 H, s). Data for Example 149: LC-MS (M+H)$^+$ 483.3. $^1$H NMR (500 MHz, CHLOROFORM-d) δ ppm 7.80 (1H, s), 7.26-7.31 (3 H, m), 7.10-7.17 (3 H, m), 7.05-7.10 (2 H, m), 4.62-4.70 (2 H, m), 4.37 (1 H, ddd, J=14.7, 5.1, 2.4 Hz), 3.85 (3 H, s), 2.14-2.30 (2H, m), 2.03-2.11 (1 H, m), 1.92-2.01 (1 H, m), 1.48 (3 H, s).

EXAMPLE 150 AND EXAMPLE 151 rel-(7R,9R)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol 2,2,2-trifluoroacetate and rel-(7S,9R)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol 2,2,2-trifluoroacetate

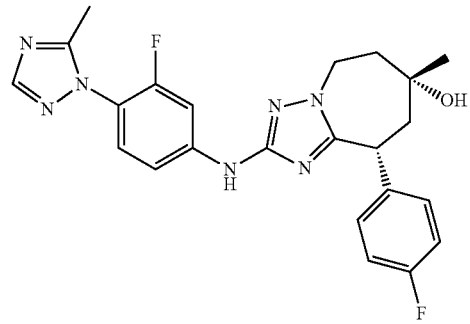

-continued

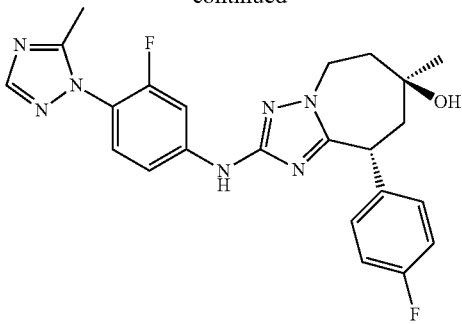

Step A: Methyl N'-3-fluoro-4-(5-methyl-1H-1,2,4-triazol-1-yl)phenylcarbamimidothioate hydroiodide (2.78 g, 7.08 mmol, from preparation C) and 6-chloro-2-(4-fluorophenyl)-4-methylenehexanoic acid (2.00 g, 7.79 mmol, from preparation AAI) were coupled [N-methylmorpholine (3.89 mL, 35.4 mmol) was substituted for N,N-diisopropylethylamine] and then reacted with hydrazine (0.889 mL, 28.3 mmol) using a procedure analogous to Step A of Example 13. After an aqueous workup, 5-(5-chloro-1-(4-fluorophenyl)-3-methylenepentyl)-N-(3-fluoro-4-(5-methyl-1H-1,2,4-triazol-1-yl)phenyl)-1H-1,2,4-triazol-3-amine was isolated as a brown residue. The crude product was used in the next step without purification. LC-MS (M+H)+ 470.1.

Step B: A solution of 5-(5-chloro-1-(4-fluorophenyl)-3-methylenepentyl)-N-(3-fluoro-4-(5-methyl-1H-1,2,4-triazol-1-yl)phenyl)-1H-1,2,4-triazol-3-amine (3.33 g, 7.09 mmol), sodium iodide (5.31 g, 35.4 mmol), and diisoproplylethylamine (2.48 mL, 14.2 mmol) in acetone (50 mL) was heated in a sealed vessel at 100° C. for 1 h. The reaction was concentrated in vacuo. The crude product was purified using silica gel column chromatography (50-100% EtOAc/chloroform). The fractions containing product were combined and concentrated to afford N-(3-fluoro-4-(5-methyl-1H-1,2,4-triazol-1-yl)phenyl)-9-(4-fluorophenyl)-7-methylene-6,7,8,9-tetrahydro-5H-[1,2,4]triazolo[1,5-a]azepin-2-amine (2.0 g, 52% yield). LC-MS (M+H)+ 434.1.

Step C: A solution of sodium periodate (2.78 g, 13.0 mmol) in water (10 mL) was added over a 10 min period via pipet to a vigorously stirred solution of the N-(3-fluoro-4-(5-methyl-1H-1,2,4-triazol-1-yl)phenyl)-9-(4-fluorophenyl)-7-methylene-6,7,8,9-tetrahydro-5H-[1,2,4]triazolo[1,5-a]azepin-2-amine (1.88 g, 4.34 mmol) and osmium tetroxide (110 mg, 0.43 mmol) in THF (10.0 mL). The reaction was stirred for 1 h and then diluted with water (150 mL)/brine (100 mL) and extracted with ethyl acetate (3×). The combined organic layers were washed with brine, dried over sodium sulfate, and concentrated in vacuo to afford 2-(3-fluoro-4-(5-methyl-1H-1,2,4-triazol-1-yl)phenylamino)-9-(4-fluorophenyl)-8,9-dihydro-5H-[1,2,4]triazolo[1,5-a]azepin-7(6H)-one (1.47 g, 78% yield). The crude product was used in the next step without further purification. LC-MS (M+H)+ 436.3. 1H NMR (500 MHz, CHLOROFORM-d) δ ppm 7.98 (1 H, s), 7.70 (1 H, dd, J=12.5, 2.1 Hz), 7.27-7.34 (1 H, m), 6.96-7.21 (5 H, m), 4.62 (1 H, dd, J=8.9, 3.7 Hz), 4.41-4.56 (2 H, m), 3.36 (1 H, dd, J=14.2, 9.0 Hz), 3.11 (1 H, dd, J=14.2, 3.8 Hz), 2.83-3.01 (2 H, m), 2.40 (3 H, s).

Step D: A 25 mL round bottom flask was charged with copper (I) iodide (35.0 mg, 0.184 mmol) in THF (5 mL), and cooled to 0° C. A solution of methyl magnesium bromide (6.56 mL, 9.19 mmol) was added dropwise to the stirred solution and stirred for 20 min. To this was added 2-(3-fluoro-4-(5-methyl-1H-1,2,4-triazol-1-yl)phenylamino)-9-(4-fluorophenyl)-8,9-dihydro-5H-[1,2,4]triazolo[1,5-a]azepin-7(6H)-one (400 mg, 0.919 mmol) in THF (1 mL) and the reaction was stirred at 0° C. for an additional 2 h. The reaction mixture was quenched slowly with saturated ammonium chloride and diluted with EtOAc. The organic layer was collected and washed with H2O (100 mL), aq sat. NaHCO3 solution (100 mL), brine (100 mL), dried over sodium sulfate and concentrated in vacuo. The crude product was purified using reverse phase preparatory HPLC (Mead/water/trifluoroacetic acid) to afford (7R,9S)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol, TFA (42.9 mg, 0.072 mmol, 8% yield, Example 151, first isomer to elute) and (7S,9S)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol, TFA (37.3 mg, 0.063 mmol, 6.82% yield, Example 150, second isomer to elute). Data for Example 150: LC-MS (M+H)+ 452.3. 1H NMR (500 MHz, CHLOROFORM-d) δ ppm 10.57 (1 H, s), 8.27 (1 H, s), 7.73 (1 H, dd, J=12.5, 2.1 Hz), 7.23-7.38 (4 H, m), 7.09-7.18 (2 H, m), 4.65-4.75 (2 H, m), 4.40-4.49 (1 H, m), 2.59 (3 H, s), 2.24-2.32 (1 H, m), 2.17-2.24 (1 H, m), 2.08 (1 H, d, J=4.3 Hz), 1.93-2.04 (1 H, m), 1.50 (3 H, s). Data for Example 151: LC-MS (M+H)+ 452.3. 1H NMR (500 MHz, CHLOROFORM-d) δ ppm 8.14 (1 H, s), 7.72 (1 H, dd, J=12.4, 2.3 Hz), 7.31-7.37 (2 H, m), 7.24 (1 H, dd, J=8.5, 2.4 Hz), 7.08-7.20 (4 H, m), 4.64 (1 H, ddd, J=14.9, 8.2, 2.6 Hz), 4.34 (1 H, ddd, J=15.0, 7.4, 2.6 Hz), 4.21 (1 H, dd, J=10.1, 1.8 Hz), 4.00 (1 H, s), 2.50-2.59 (4 H, m), 2.09-2.27 (3 H, m), 1.52 (3 H, s).

EXAMPLE 152 AND EXAMPLE 153 rel-(7R,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol 2,2,2-trifluoroacetate and rel-(7S,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol 2,2,2-trifluoroacetate

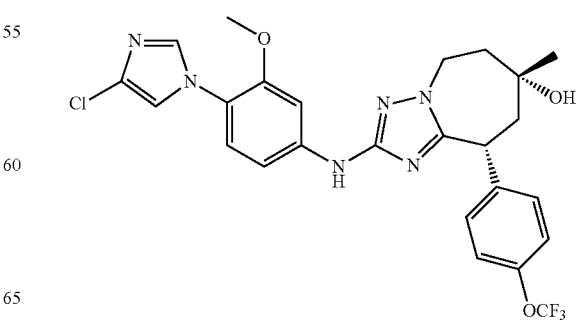

-continued

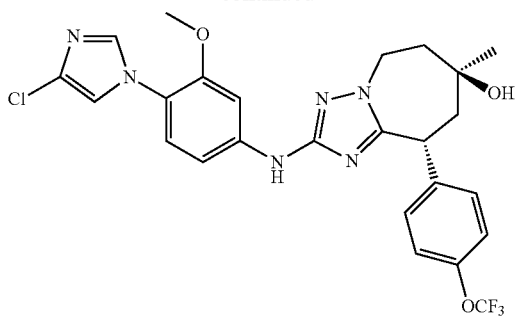

Step A: 2-(4-(4-Chloro-1H-imidazol-1-yl)-3-methoxyphenylamino)-9-(4-(trifluoromethoxy)phenyl)-8,9-dihydro-5H-[1,2,4]triazolo[1,5-a]azepin-7(6H)-one was prepared from methyl 4-(4-chloro-1H-imidazol-1-yl)-3-methoxyphenylcarbamimidothioate, hydroiodide (Preparation A) and 6-chloro-4-methylene-2-(4-(trifluoromethoxy)phenyl)hexanoic acid (Preparation AAJ) following the combined methods and procedures outlined in Examples 133 and 137.

Step B: A 25 mL round bottom flask was charged with copper (I) iodide (53.1 mg, 0.279 mmol) in THF (5 mL), and cooled to 0° C. A solution of methyl magnesium bromide (9.96 mL, 14.0 mmol) was added. The resulting mixture was stirred for 20 min. To the solution of methyl cuprate was added 2-(4-(4-chloro-1H-imidazol-1-yl)-3-methoxyphenylamino)-9-(4-(trifluoromethoxy)phenyl)-8,9-dihydro-5H-[1,2,4]triazolo[1,5-a]azepin-7(6H)-one (743 mg, 1.39 mmol) in THF (1 mL). The mixture was stirred at 0° C. for 2 h. The reaction mixture was quenched with saturated ammonium chloride and diluted with EtOAc. The organic layer was collected and washed sequentially with H$_2$O (100 mL), aq sat. NaHCO$_3$ solution (100 mL), and brine (100 mL). The organic layer was dried over sodium sulfate and concentrated in vacuo. The crude product was purified using reverse phase preparatory HPLC (MeOH/water/trifluoroacetic acid) to afford rel-(7R,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol (43 mg, 4% yield, Example 152, first isomer to elute) and rel-(7S,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol (39.6 mg, 4% yield, Example 153, second isomer to elute). Data for Example 152: LC-MS (M+H)$^+$ 549.3. $^1$H NMR (500 MHz, CHLOROFORM-d) δ ppm 10.09 (1 H, br. s.), 8.02 (1 H, d, J=1.5 Hz), 7.26-7.38 (5 H, m), 7.08-7.20 (3 H, m), 4.63-4.75 (2 H, m), 4.40 (1 H, ddd, J=14.9, 5.1, 2.3 Hz), 3.86 (3 H, s), 2.23-2.31 (1 H, m), 2.14-2.21 (1 H, m), 2.05-2.12 (1 H, m), 1.94-2.03 (1 H, m), 1.48 (3 H, s). Data for Example 153: LC-MS (M+H)$^+$ 549.3. $^1$H NMR (500 MHz, CHLOROFORM-d) δ ppm 7.76 (1 H, s), 7.32 (1 H, d, J=2.4 Hz), 7.22-7.30 (5 H, m), 7.15 (1 H, d, J=8.5 Hz), 7.02-7.09 (2 H, m), 4.60 (1 H, ddd, J=14.7, 8.3, 2.6 Hz), 4.30 (1 H, ddd, J=14.9, 7.4, 2.4 Hz), 4.21 (1 H, dd, J=10.1, 1.8 Hz), 3.83-3.87 (3 H, m), 2.54 (1 H, dd, J=14.3, 10.4 Hz), 2.11-2.22 (3 H, m), 1.52 (3 H, s).

EXAMPLE 154 AND EXAMPLE 155 rel-(7R,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol 2,2,2-trifluoroacetate and rel-(7S,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol 2,2,2-trifluoroacetate

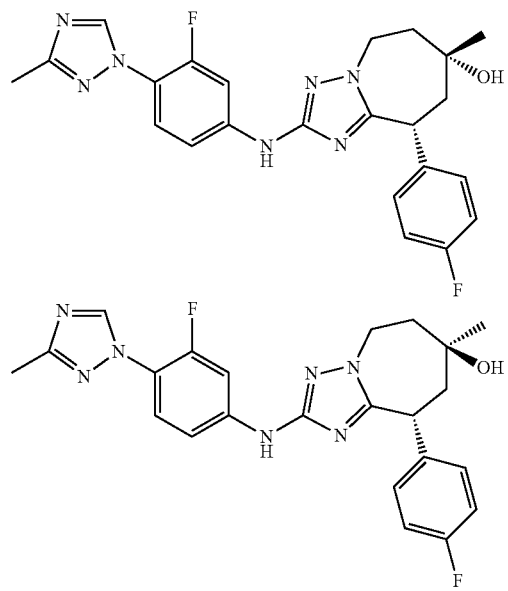

Step A: 2-(3-Fluoro-4-(3-methyl-1H-1,2,4-triazol-1-yl)phenylamino)-9-(4-fluorophenyl)-8,9-dihydro-5H-[1,2,4]triazolo[1,5-a]azepin-7(6H)-one was prepared from methyl 3-fluoro-4-(3-methyl-1H-1,2,4-triazol-1-yl)phenylcarbamimidothioate, hydroiodide (Preparation Q) and 6-chloro-2-(4-fluorophenyl)-4-methylenehexanoic acid (Preparation AAI) following the combined methods and procedures outlined in Examples 133 and 137.

Step B: A 25 mL round bottom flask was charged with copper (I) iodide (26.2 mg, 0.138 mmol) in THF (4 mL), and cooled to 0° C. A solution of methyl magnesium bromide (4.92 mL, 6.89 mmol) was added dropwise. The mixture was stirred for 20 min. To the solution of methyl cuprate was added 2-(3-fluoro-4-(3-methyl-1H-1,2,4-triazol-1-yl)phenylamino)-9-(4-fluorophenyl)-8,9-dihydro-5H-[1,2,4]triazolo[1,5-a]azepin-7(6H)-one (300 mg, 0.689 mmol) in THF (1 mL). The mixture was stirred at 0° C. for 2 h. The reaction mixture was quenched with saturated ammonium chloride and diluted with EtOAc. The organic layer was sequentially washed with H$_2$O (100 mL), aq sat. NaHCO$_3$ solution (100 mL), and brine (100 mL). The organic layer was dried over sodium sulfate and concentrated in vacuo. The crude product was purified using reverse phase preparatory HPLC (MeOH/water/trifluoroacetic acid) to afford (7S,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol (21 mg, 7% yield, Example 155, first to elute) and (7R,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol (43.7 mg, 11% yield, Example 154). Data for Example 153: LC-MS (M+H)⁺ 452.2. ¹H NMR (500 MHz, CHLOROFORM-d) δ ppm 9.71 (1 H, br. s.), 8.55 (1 H, br. s.), 7.59-7.68 (2 H, m), 7.21-7.28 (2 H, m), 7.06-7.18 (3 H, m), 4.58-4.67 (2 H, m), 4.39 (1 H, ddd, J=14.8, 5.0, 2.4 Hz), 2.50 (3 H, s), 2.17-2.26 (1 H, m), 2.10-2.16 (1 H, m), 1.99-2.07 (1 H, m), 1.89-1.98 (1 H, m), 1.44 (3 H, s). Data for Example 153: LC-MS (M+H)⁺ 452.2. ¹H NMR (500 MHz, CHLOROFORM-d) δ ppm 8.40 (1 H, d, J=2.4 Hz), 7.58-7.69 (2 H, m), 7.21 (2 H, dd, J=8.5, 5.2 Hz), 7.16 (1 H, s), 7.07-7.13 (2 H, m), 7.03 (1 H, dd, J=8.9, 2.1 Hz), 4.54 (1 H, ddd, J=14.8, 8.4, 2.1 Hz), 4.22 (1 H, ddd, J=14.9, 8.8, 1.7 Hz), 4.03-4.11 (1 H, m), 2.51 (3 H, s), 2.42 (1 H, dd, J=14.0, 10.7 Hz), 2.02-2.17 (4 H, m), 1.51 (3 H, s).

EXAMPLE 156 AND EXAMPLE 157 rel-(7R,9R)-2-(3-fluoro-4-(5-methyl-1H-1,2,4-triazol-1-yl)phenylamino)-9-(4-fluorophenyl)-6,7,8,9-tetrahydro-5H-[1,2,4]triazolo[1,5-a]azepin-7-ol 2,2,2-trifluoroacetate and rel-(7S,9R)-2-(3-fluoro-4-(5-methyl-1H-1,2,4-triazol-1-yl)phenylamino)-9-(4-fluorophenyl)-6,7,8,9-tetrahydro-5H-[1,2,4]triazolo[1,5-a]azepin-7-ol 2,2,2-trifluoroacetate

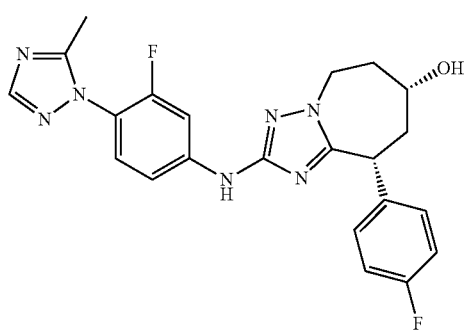

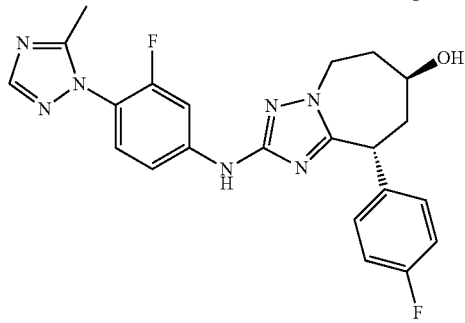

Step A: To a stirred solution of 2-(3-fluoro-4-(5-methyl-1H-1,2,4-triazol-1-yl)phenylamino)-9-(4-fluorophenyl)-8,9-dihydro-5H-[1,2,4]triazolo[1,5-a]azepin-7(6H)-one (500 mg, 1.15 mmol, from Example 150, Step C) in MeOH (2 mL) was added sodium borohydride (87 mg, 2.30 mmol). The resulting mixture was stirred at room temperature for 16 h. The reaction was cooled to 0° C. and quenched with saturated ammonium chloride. The aqueous layer was extracted with ethyl acetate (3×). The combined organic layers were washed with saturated sodium chloride, dried over sodium sulfate, filtered, and concentrated in vacuo. The crude product was purified using reverse phase preparatory HPLC (MeOH/water/trifluoroacetic acid) to afford Example 156 (21 mg, 6.62% yield) and Example 157 (43.7 mg, 10.99% yield). Data for Example 156: LC-MS (M+H)⁺ 438.3. ¹H NMR (500 MHz, MeOD) δ ppm 8.32 (1 H, s), 7.70 (1 H, dd, J=13.1, 2.4 Hz), 7.32-7.47 (3 H, m), 7.26 (1 H, dd, J=8.9, 1.8 Hz), 7.03-7.16 (2 H, m), 4.45-4.58 (1 H, m), 4.16-4.29 (2 H, m), 3.99-4.12 (1 H, m, J=10.3, 10.3, 3.7, 3.5 Hz), 2.47 (3 H, s), 2.24-2.39 (2 H, m), 1.92-2.11 (1 H, m), 1.65-1.85 (1 H, m). Data for Example 157: LC-MS (M+H)⁺ 438.3. ¹H NMR (500 MHz, MeOD) δ ppm 8.24 (1 H, s), 7.74 (1 H, dd, J=13.3, 2.3 Hz), 7.38 (1 H, t, J=8.5 Hz), 7.25-7.33 (3 H, m), 7.08-7.15 (2 H, m), 4.71-4.76 (1 H, m), 4.60 (1 H, ddd, J=14.8, 9.5, 1.7 Hz), 4.10-4.18 (2 H, m), 2.43-2.54 (4 H, m), 2.05-2.15 (2 H, m), 1.96-2.04 (1 H, m).

EXAMPLE 158

N-(3-fluoro-4-(3-methyl-1H-1,2,4-triazol-1-yl)phenyl)-9-(4-fluorophenyl)-5,6,8,9-tetrahydrospiro[[1,2,4]triazolo[1,5-a]azepine-7,2'-[1,3]dioxolan]-2-amine 2,2,2-trifluoroacetate

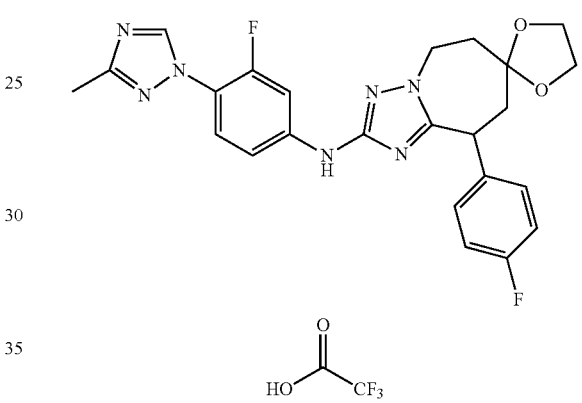

Step A: Step A: 2-(3-Fluoro-4-(3-methyl-1H-1,2,4-triazol-1-yl)phenylamino)-9-(4-fluorophenyl)-8,9-dihydro-5H-[1,2,4]triazolo[1,5-a]azepin-7(6H)-one was prepared from methyl 3-fluoro-4-(3-methyl-1H-1,2,4-triazol-1-yl)phenylcarbamimidothioate, hydroiodide (Preparation Q) and 6-chloro-2-(4-fluorophenyl)-4-methylenehexanoic acid (Preparation AAI) following the combined methods and procedures outlined in Examples 133 and 137.

Step B: A solution of 2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one (84 mg, 0.18 mmol) in benzene (1 mL) was treated with ethylene glycol (0.011 mL, 0.20 mmol), and 4-methylbenzenesulfonic acid, H₂O (34 mg, 0.18 mmol). The mixture was heated to reflux using a Dean-Stark trap. After 6 h, the mixture was cooled to rt and quenched with saturated sodium bicarbonate. The aqueous layer was extracted with ethyl acetate (3×). The combined organic layers were washed with brine, dried over sodium sulfate, and concentrated in vacuo. The crude product was purified using reverse phase preparatory HPLC (MeOH/water/trifluoroacetic acid) to afford the titled compound (39.4 mg, 34% yield). LC-MS (M+H)⁺ 511.3. ¹H NMR (500 MHz, CHLOROFORM-d) δ ppm 7.75 (1 H, br. s.), 7.30-7.33 (1 H, m), 7.25-7.29 (2 H, m), 7.09-7.17 (3 H, m), 7.06 (1 H, br. s.), 7.02 (1 H, dd, J=8.5, 2.4 Hz), 4.45-4.54 (1 H, m), 4.32-4.42 (2 H, m), 4.02-4.11 (4 H, m), 3.83 (3 H, s), 2.32-2.40 (1 H, m), 2.23 (1 H, d, J=13.7 Hz), 2.08-2.19 (2 H, m).

EXAMPLE 159

N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine 2,2,2-trifluoroacetate

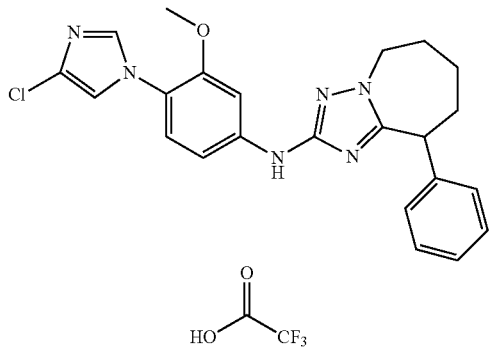

Step A: Step A: Methyl 4-(4-chloro-1H-imidazol-1-yl)-3-methoxyphenylcarbamimidothioate, hydroiodide (0.500 g, 1.18 mmol), from preparation A) and 6-chloro-2-phenylhexanoic acid (0.294 g, 1.30 mmol, from preparation AAO) were coupled [N-methylmorpholine (0.647 mL, 5.89 mmol) was substituted for N,N-diisopropylethylamine] and then reacted with hydrazine (0.148 mL, 4.71 mmol) using a procedure analogous to Step A of Example 13. After an aqueous workup, 5-(5-chloro-1-phenylpentyl)-N-(4-(4-chloro-1H-imidazol-1-yl)-3-methoxyphenyl)-1H-1,2,4-triazol-3-amine was obtained as a brown residue. The crude product was used in the next step without purification. LC-MS (M+H)+ 471.3.

Step B: A solution of 5-(5-chloro-1-phenylpentyl)-N-(4-(4-chloro-1H-imidazol-1-yl)-3-methoxyphenyl)-1H-1,2,4-triazol-3-amine (0.555 g, 1.18 mmol), sodium iodide (0.882 g, 5.89 mmol), and diisoproplyethylamine (0.411 mL, 2.36 mmol) in acetone (10 mL) was heated in a sealed vessel at 100° C. for 2 h. The reaction was concentrated in vacuo. The crude product was purified using reverse phase preparatory HPLC (MeOH/water/trifluoroacetic acid) to afford the titled compound as the TFA salt (84.4 mg, 13% yield). LC-MS (M+H)+ 435.2. $^1$H NMR (500 MHz, CHLOROFORM-d) δ ppm 9.98 (1 H, br. s.), 7.72 (1 H, s), 7.31-7.46 (4 H, m), 7.14-7.21 (2 H, m), 7.04-7.11 (3 H, m), 4.61-4.67 (1 H, m), 4.44 (1 H, dd, J=14.6, 6.4 Hz), 4.15-4.24 (1 H, m), 3.89 (3 H, s), 2.46-2.56 (1 H, m), 2.13 (1 H, d, J=14.6 Hz), 1.85-2.03 (4 H, m).

EXAMPLE 160

N-(3-fluoro-4-(5-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine

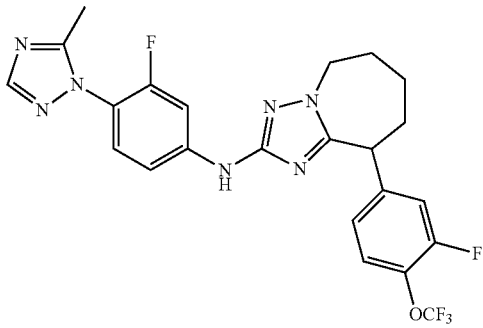 [SMILES: Cc1ncnn1-c1ccc(Nc2nc3n(n2)CCCCC3c2ccc(OC(F)(F)F)c(F)c2)cc1F]

Step A: 3-Fluoro-4-(5-methyl-1H-1,2,4-triazol-1-yl)phenylcarbamimidothioate, hydroiodide (0.330 g, 0.839 mmol, from preparation C) and 6-chloro-2-(3-fluoro-4-(trifluoromethoxy)phenyl)hexanoic acid (0.345 g, 1.05 mmol, from preparation AY) were coupled [N-methylmorpholine (0.461 mL, 4.20 mmol) was substituted for N,N-diisopropylethylamine] and then reacted with hydrazine (0.132 mL, 4.20 mmol) using a procedure analogous to Step A of Example 13. After an aqueous workup, the crude product, 5-(5-chloro-1-(3-fluoro-4-(trifluoromethoxy)phenyl)pentyl)-N-(3-fluoro-4-(5-methyl-1H-1,2,4-triazol-1-yl)phenyl)-1H-1,2,4-triazol-3-amine was obtained as a brown solid. LC-MS (M+H)+ 542.1. The crude product was used in the next step without purification.

Step B: A solution of 5-(5-chloro-1-(3-fluoro-4-(trifluoromethoxy)phenyl)pentyl)-N-(3-fluoro-4-(5-methyl-1H-1,2,4-triazol-1-yl)phenyl)-1H-1,2,4-triazol-3-amine (455 mg, 0.839 mmol), sodium iodide (0.629 g, 4.20 mmol), and diisoproplylethylamine (0.733 mL, 4.20 mmol) in acetone (10 mL) was heated in a sealed vessel at 100° C. for 6 h. The reaction was concentrated in vacuo. The crude product was purified using silica gel column chromatography (70% EtOAc/chloroform) to afford 140 mg of a solid. The solid was recrystallized from EtOAC/hexanes to afford 70 mg (16% yield) of the titled compound as a white crystalline solid. LC-MS (M+H)+ 506.1. $^1$H NMR (500 MHz, CHLOROFORM-d) δ ppm 7.94 (s, 1 H), 7.66 (dd, J=12.7, 2.3 Hz, 1 H), 7.26-7.34 (m, 2 H), 7.06 (dd, J=11.0, 1.8 Hz, 1 H), 7.03 (dd, J=8.7, 1.7 Hz, 1 H), 6.96 (d, J=8.5 Hz, 1 H), 6.78 (s, 1 H), 4.17-4.35 (m, 3 H), 2.38 (s, 3 H), 2.06-2.18 (m, 2 H), 1.93-2.05 (m, 2 H), 1.79-1.93 (m, 2 H).

EXAMPLE 161

N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine

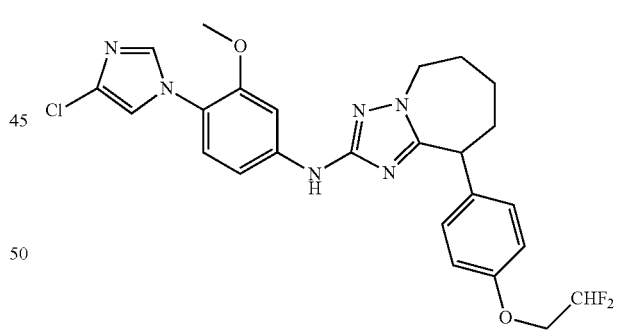

Step A: Methyl 4-(4-chloro-1H-imidazol-1-yl)-3-methoxyphenylcarbamimidothioate, hydroiodide (1.108 g, 2.61 mmol, from preparation A) and 6-chloro-2-(4-(2,2-difluoroethoxy)phenyl)hexanoic acid (1.0 g, 3.26 mmol, from preparation AX) were coupled [N-methylmorpholine (1.43 mL, 13.0 mmol) was substituted for N,N-diisopropylethylamine] and then reacted with hydrazine (0.410 mL, 13.1 mmol) using a procedure analogous to Step A of Example 13. After an aqueous workup, 5-(5-chloro-1-(4-(2,2-difluoroethoxy)phenyl)pentyl)-N-(4-(4-chloro-1H-imidazol-1-yl)-3-methoxyphenyl)-1H-1,2,4-triazol-3-amine was obtained as a brown solid. The crude product was used in the next step without purification. LC-MS (M+H)+ 551.5.

Step B: A solution of 5-(5-chloro-1-(4-(2,2-difluoroethoxy)phenyl)pentyl)-N-(4-(4-chloro-1H-imidazol-1-yl)-3-methoxyphenyl)-1H-1,2,4-triazol-3-amine (1.44 g, 2.61 mmol, sodium iodide (1.96 g, 13.1 mmol), and diisoproplylethylamine (2.28 mL, 13.1 mmol) in acetone (30 mL) was heated in a sealed vessel at 100° C. for 16 h. The reaction was concentrated in vacuo. The crude product was purified using silica gel column chromatography (50% EtOAc/chloroform). The purified product was recrystallized from EtOAc/hexane to afford 279 mg (20% yield) of the titled compound as an off-white crystalline white solid. LC-MS (M+H)$^+$ 515.3. $^1$H NMR (500 MHz, CHLOROFORM-d) δ ppm 7.51 (d, J=1.5 Hz, 1 H), 7.42 (d, J=2.4 Hz, 1 H), 7.12 (d, J=8.9 Hz, 2 H), 7.09 (d, J=8.5 Hz, 1 H), 7.02 (d, J=1.5 Hz, 1 H), 6.92 (d, J=8.5 Hz, 2 H), 6.84 (dd, J=8.4, 2.3 Hz, 1 H), 6.67 (s, 1 H), 6.10 (tt, J=55.1, 4.1 Hz, 1 H), 4.26 (d, J=8.5 Hz, 1 H), 4.15-4.25 (m, 4 H), 3.80 (s, 3 H), 2.16-2.30 (m, 1 H), 2.05-2.13 (m, 1 H), 1.83-2.02 (m, 4 H).

EXAMPLE 162 AND EXAMPLE 163

(S)—N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine and (R)—N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine

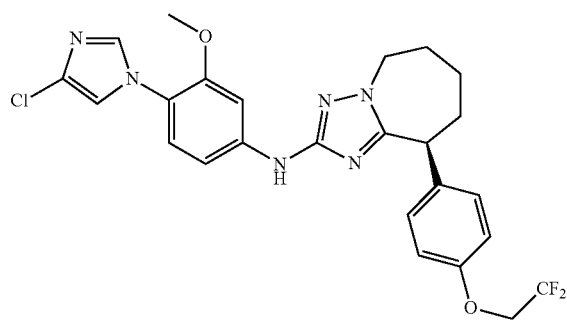

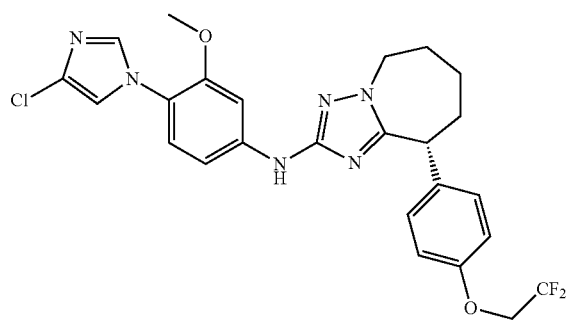

Step A: A racemic mixture of N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine (230 mg from Example 161) was purified using chiral supercritical fluid chromatography (SFC) to afford 97 mg of peak A (first to elute, example 162) and 107 mg of peak B (second to elute, example 163). SFC Method: Chiralcel OJ-H (30×200 mm, 5 uM), 40% methanol (0.1% diethylamine) in $CO_2$, 50 mL/min, absorbance 220 nm. The absolute stereochemistry of individual enantiomers (examples 162 and 163) was not determined. LC-MS and $^1$H NMR analytical data for the separated enantiomers was identical to the racemate (see Example 161).

EXAMPLE 164

N-(3-fluoro-4-(3-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine

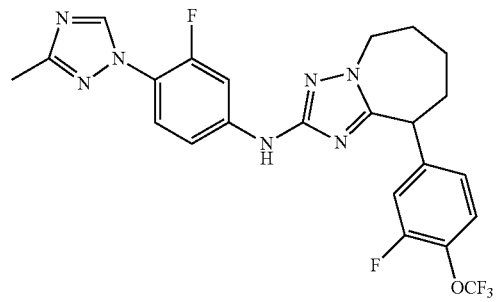 [SMILES: Cc1ncn(-c2ccc(Nc3nc4n(n3)CCCCC4c3ccc(OC(F)(F)F)c(F)c3)cc2F)n1]

Step A: Methyl 3-fluoro-4-(3-methyl-1H-1,2,4-triazol-1-yl)phenylcarbamimidothioate, hydroiodide (0.718 g, 1.83 mmol, from preparation Q) and 6-chloro-2-(3-fluoro-4-(trifluoromethoxy)phenyl)hexanoic acid (0.750 g, 2.28 mmol from preparation AY) were coupled [N-methylmorpholine (1.00 mL, 9.13 mmol) was substituted for N,N-diisopropylethylamine] and then reacted with hydrazine (0.286 mL, 9.13 mmol) using a procedure analogous to Step A of Example 13. After an aqueous workup, 5-(5-chloro-1-(3-fluoro-4-(trifluoromethoxy)phenyl)pentyl)-N-(3-fluoro-4-(3-methyl-1H-1,2,4-triazol-1-yl)phenyl)-1H-1,2,4-thiazol-3-amine was obtained as a brown solid. The crude product was used in the next step without purification. LC-MS (M+H)$^+$ 542.1.

Step B: A solution of 5-(5-chloro-1-(3-fluoro-4-(trifluoromethoxy)phenyl)pentyl)-N-(3-fluoro-4-(3-methyl-1H-1,2,4-triazol-1-yl)phenyl)-1H-1,2,4-triazol-3-amine (989 mg, 1.83 mmol), sodium iodide (1.37 g, 9.13 mmol), and diisopropylethylamine (1.60 mL, 9.13 mmol) in acetone (25 mL) was heated in a sealed vessel at 100° C. for 6 h. The reaction was concentrated in vacuo. The crude product was purified using silica gel column chromatography (70% EtOAc/chloroform). The purified product was recrystallized from EtOAc/hexane to afford 211 mg (22% yield) of the titled compound as a white solid. LC-MS (M+H)$^+$ 506.1. $^1$H NMR (500 MHz, CHLOROFORM-d) δ ppm 8.40 (1 H, d, J=2.4 Hz), 7.68 (1 H, dd, J=13.9, 2.3 Hz), 7.62 (1 H, t, J=8.7 Hz), 7.31 (1 H, t, J=8.1 Hz), 7.08 (1 H, dd, J=11.0, 2.1 Hz), 7.03 (1 H, dd, J=8.9, 2.4 Hz), 6.98 (1 H, d, J=8.5 Hz), 6.68 (1 H, s), 4.20-4.33 (3 H, m), 2.50 (3 H, s), 2.08-2.22 (2 H, m), 1.94-2.06 (2 H, m), 1.84-1.93 (2 H, m).

EXAMPLE 165 AND EXAMPLE 166

(S)—N-(3-fluoro-4-(3-methyl-1H-1,2,4-triazol-1-yl)
phenyl)-9-(3-fluoro-4-(trifluoromethoxy)phenyl)-6,
7,8,9-tetrahydro-5H-[1,2,4]triazolo[1,5-a]azepin-2-
amine and (R)—N-(3-fluoro-4-(3-methyl-1H-1,2,4-
triazol-1-yl)phenyl)-9-(3-fluoro-4-(trifluoromethoxy)
phenyl)-6,7,8,9-tetrahydro-5H-[1,2,4]triazolo[1,5-a]
azepin-2-amine

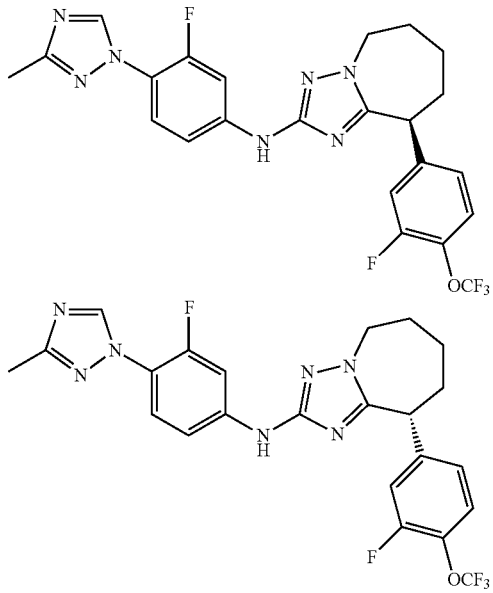

Step A: A racemic mixture of N-(3-fluoro-4-(3-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine (180 mg from Example 164) was purified using chiral supercritical fluid chromatography (SFC) to afford 78 mg of peak A (first to elute, example 165) and 77 mg of peak B (second to elute, example 166). SFC Method: Chiralcel IA (20×150 mm, 5 uM), 40% methanol (0.1% diethylamine) in CO$_2$, 60 mL/min, absorbance 220 nm. The absolute stereochemistry of individual enantiomers (examples 165 and 166) was not determined. LC-MS and $^1$H NMR analytical data for the separated enantiomers was identical to the racemate (see Example 164).

EXAMPLE 167

N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

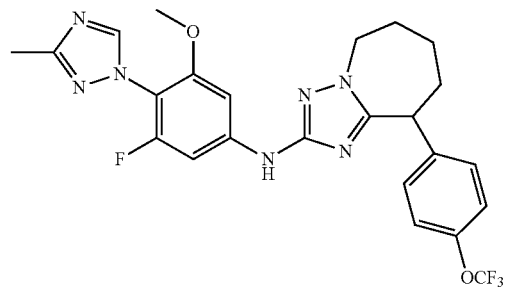 [SMILES: COc1cc(Nc2nc3n(n2)CCCCC3c2ccc(OC(F)(F)F)cc2)cc(F)c1-n1cnc(C)n1]

Step A: Methyl 3-fluoro-5-methoxy-4-(3-methyl-1H-1,2,4-triazol-1-yl)phenylcarbamimidothioate, hydroiodide (0.575 g, 1.36 mmol, from preparation 5) and 6-chloro-2-(4-(trifluoromethoxy)phenyl)hexanoic acid (0.528 g, 1.70 mmol, from preparation AI) were coupled [N-methylmorpholine (0.747 mL, 6.79 mmol) was substituted for N,N-diisopropylethylamine] and then reacted with hydrazine (0.213 mL, 6.80 mmol) using a procedure analogous to Step A of Example 13. After an aqueous workup, 5-(5-chloro-1-(4-(trifluoromethoxy)phenyl)pentyl)-N-(3-fluoro-5-methoxy-4-(3-methyl-1H-1,2,4-triazol-1-yl)phenyl)-1H-1,2,4-triazol-3-amine was obtained as a brown solid. The crude product was used in the next step without purification. LC-MS (M+H)$^+$ 554.2.

Step B: A solution of 5-(5-chloro-1-(4-(trifluoromethoxy)phenyl)pentyl)-N-(3-fluoro-5-methoxy-4-(3-methyl-1H-1,2,4-triazol-1-yl)phenyl)-1H-1,2,4-triazol-3-amine (753 mg, 1.36 mmol), sodium iodide (1.02 g, 6.80 mmol), and diisopropylethylamine (1.19 mL, 6.80 mmol) in acetone (30 mL) was heated in a sealed vessel at 100° C. for 6 h. The reaction was concentrated in vacuo. The crude product was purified using silica gel column chromatography (50% EtOAc/chloroform) to afford 321 mg (44% yield) of the titled compound as a white solid. LC-MS (M+H)$^+$ 518.3. $^1$H NMR (500 MHz, CHLOROFORM-d) δ ppm 8.02 (s, 1 H), 7.20 (s, 4 H), 6.90-6.96 (m, 2 H), 6.73 (s, 1 H), 4.17-4.34 (m, 3 H), 3.72 (s, 3 H), 2.47 (s, 3 H), 2.13-2.26 (m, 1 H), 2.05-2.13 (m, 1 H), 1.92-2.04 (m, 2 H), 1.82-1.92 (m, 2 H).

EXAMPLE 168 AND EXAMPLE 169

(S)—N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine and (R)—N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

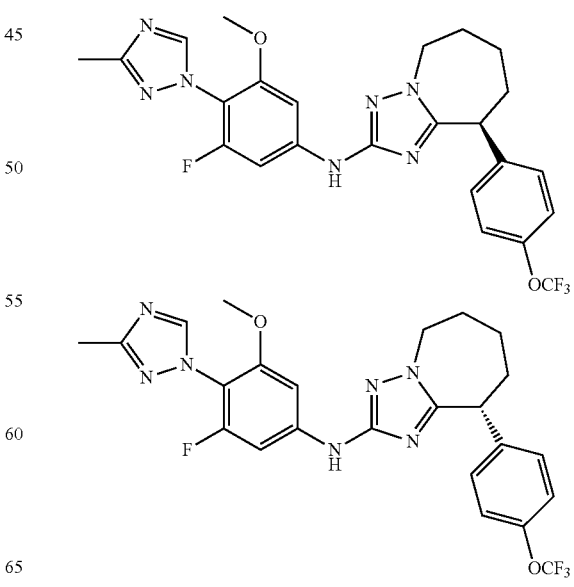

Step A: A racemic mixture of N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine (290 mg from Example 167) was purified using chiral supercritical fluid chromatography (SFC) to afford 132 mg of peak A (first to elute, example 169) and 131 mg of peak B (second to elute, example 170). SEC Method: Chiralcel IA (20×150 mm, 5 uM), 40% methanol (0.1% diethylamine) in $CO_2$, 80 mL/min, absorbance 220 nm. The absolute stereochemistry of individual enantiomers (examples 169 and 170) was not determined. LC-MS and $^1H$ NMR analytical data for the separated enantiomers was identical to the racemate (see Example 168).

EXAMPLE 170

9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine

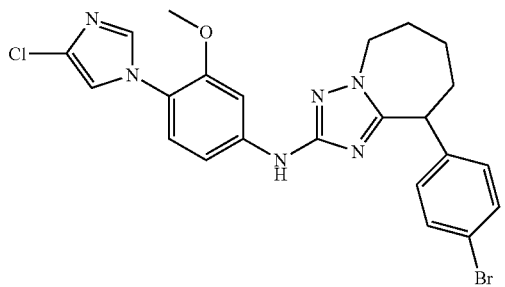 [SMILES: COc1cc(Nc2nc3n(n2)CCCCC3c2ccc(Br)cc2)ccc1-n1cnc(Cl)c1]

Step A: Methyl 4-(4-chloro-1H-imidazol-1-yl)-3-methoxyphenylcarbamimidothioate, hydroiodide (4.0 g, 9.42 mmol, from preparation A) and 2-(4-bromophenyl)-6-chlorohexanoic acid (3.60 g, 11.77 mmol, from preparation AT) were coupled [N-methylmorpholine (5.18 mL, 47.1 mmol) was substituted for N,N-diisopropylethylamine] and then reacted with hydrazine (1.48 mL, 47.1 mmol) using a procedure analogous to Step A of Example 13. After an aqueous workup, crude 5-(1-(4-bromophenyl)-5-chloropentyl)-N-(4-(4-chloro-1H-imidazol-1-yl)-3-methoxyphenyl)-1H-1,2,4-triazol-3-amine (2.43 g, 4.42 mmol, 46.9% yield) was obtained as a brown foamy solid The crude product was used in next step without purification. LC-MS (M+H)$^+$ 551.2.

Step B: A solution of 5-(1-(4-bromophenyl)-5-chloropentyl)-N-(4-(4-chloro-1H-imidazol-1-yl)-3-methoxyphenyl)-1H-1,2,4-triazol-3-amine (2.5 g, 4.54 mmol), sodium iodide (3.40 g, 22.7 mmol), and diisopropylethylamine (0.793 mL, 4.54 mmol) in acetone (10 mL) was heated in a sealed vessel at 100° C. for 12 h. The reaction was concentrated in vacuo. The crude product was purified using silica gel column chromatography (50% EtOAc/chloroform) to afford 475 mg (19% yield) of the titled compound as an off-white solid. LC-MS (M+H)$^+$ 515.1. $^1H$ NMR (500 MHz, CHLOROFORM-d) δ ppm 7.45-7.47 (m, 3 H), 7.40 (d, J=2.1 Hz, 1 H), 7.04-7.10 (m, 3 H), 7.00 (d, J=1.5 Hz, 1 H), 6.79 (dd, J=8.5, 2.4 Hz, 1 H), 6.64 (s, 1 H), 4.15-4.27 (m, 3 H), 3.76 (s, 3 H), 2.14-2.21 (m, 1 H), 1.91-2.10 (m, 3 H), 1.80-1.91 (m, 2 H).

EXAMPLE 171

9-(4-(1H-pyrazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine 2,2,2-trifluoroacetate

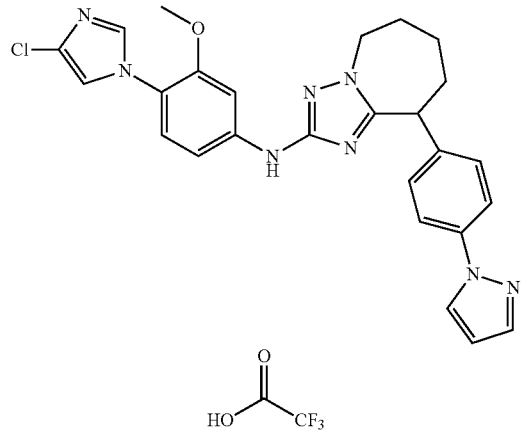

Step A: A vessel charged with a mixture of 9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine (100 mg, 0.195 mmol, from Example 170), copper(I) iodide (7.41 mg, 0.039 mmol), cesium carbonate (127 mg, 0.389 mmol), and 1H-pyrazole (18.55 mg, 0.272 mmol) was flushed with nitrogen. DMF (1.0 mL) was added, the vessel was sealed, and the resulting mixture was stirred at rt for 30 min. The mixture was heated at 120° C. for 16 h. The mixture was cooled to rt and diluted with EtOAc. The solids were removed by filtration through a pad of silica gel. The silica gel was rinsed with EtOAc. The combined filtrates were concentrated in vacuo. The residue was dissolved in MeOH and purified using reverse phase preparatory HPLC (MeOH/water/TFA) to afford the titled compound as its TFA salt (31 mg, 0.049 mmol, 25% yield) as an off white solid. LC-MS (M+H)$^+$ 501.3. $^1H$ NMR (500 MHz, CHLOROFORM-d) δ ppm 9.46 (br. s., 1 H), 7.94 (d, J=2.4 Hz, 1 H), 7.72-739 (m, 3 H), 7.68 (br. s., 1 H), 7.33 (d, J=-2.1 Hz, 1 H), 7.20 (d, J=8.5 Hz, 2 H), 7.14-7.18 (m, 1 H), 7.08-7.12 (m, 1 H), 7.07 (br. s., 1 H), 6.50 (t, J=2.0 Hz, 1 H), 4.56 (d, J=5.8 Hz, 1 H), 4.34-4.45 (m, 1 H), 4.21-4.26 (m, 1 H), 3.86 (s, 3 H), 2.37-2.55 (m, 1 H), 2.12-2.23 (m, 1 H), 1.88-2.04 (m, 4 H).

EXAMPLE 172

9-(4-(1H-1,2,4-triazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine 2,2,2-trifluoroacetate

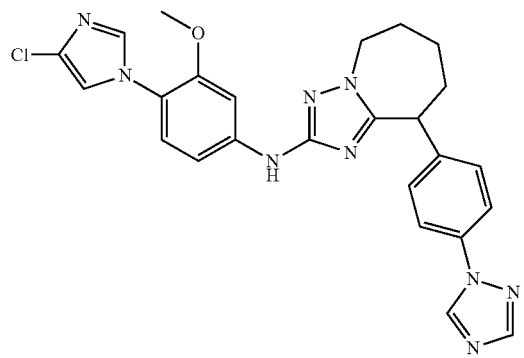

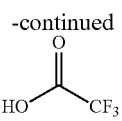

Step A: The titled compound (29 mg, 24% yield) was prepared via copper catalyzed coupling of 9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine (100 mg, 0.195 mmol, from Example 170) and 1H-1,2,4-triazole (33.6 mg, 0.487 mmol) following a method analogous to the procedure described in Example 171. LC-MS (M+H)+ 502.3. ¹H NMR (500 MHz, CHLOROFORM-d) δ ppm 9.40 (br. s., 1 H), 8.61 (s, 1 H), 8.15 (s, 1 H), 7.66-7.81 (m, 3 H), 7.29-7.36 (m, 3 H), 7.13-7.20 (m, 1 H), 7.08-7.13 (m, 1 H), 7.07 (s, 1 H), 4.47-4.56 (m, 1 H), 4.27-4.43 (m, 2 H), 3.86 (s, 3 H), 2.33-2.50 (m, 1 H), 2.22 (dd, J=14.5, 7.8 Hz, 1 H), 1.90-2.10 (m, 4 H).

EXAMPLE 173

9-(4-(1H-imidazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine 2,2,2-trifluoroacetate

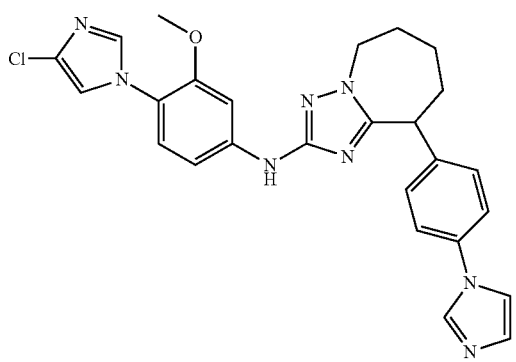

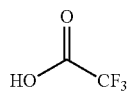

Step A: The titled compound (37 mg, 30% yield) was prepared via copper catalyzed coupling of 9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine (100 mg, 0.195 mmol, Example 170) and 1H-imidazole (33.1 mg, 0.487 mmol) following a method analogous to the procedure described in Example 171. LC-MS (M+H)+ 501.3. ¹H NMR (500 MHz, CHLOROFORM-d) δ ppm 8.55 (s, 1 H), 8.09 (d, J=7.6 Hz, 1 H), 7.48 (d, J=11.6 Hz, 1 H), 7.19-7.26 (m, 3 H), 6.84 (d, J=3.1 Hz, 1 H), 4.17-4.36 (m, 3 H), 3.81 (s, 3 H), 2.47 (s, 3 H), 2.16-2.24 (m, 1 H), 1.96-2.15 (m, 3 H), 1.78-1.94 (m, 2 H).

EXAMPLE 174

N-(4-(4-chloro-1H-imidazol-1-yl)-3-methoxyphenyl)-9-(4-(4-methyl-1H-pyrazol-1-yl)phenyl)-6,7,8,9-tetrahydro-5H-[1,2,4]triazolo[1,5-a]azepin-2-amine 2,2,2-trifluoroacetate

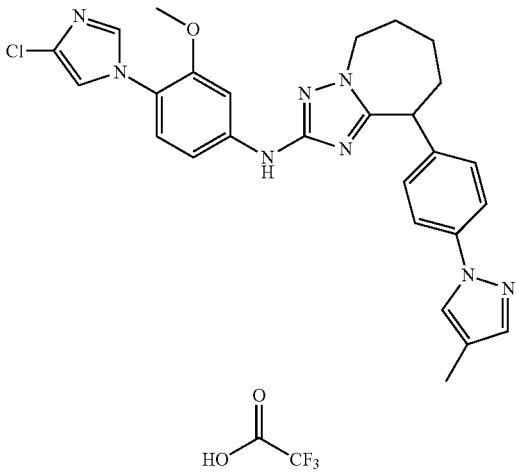

Step A: The titled compound (37 mg, 30% yield) was prepared via copper catalyzed coupling of 9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine (100 mg, 0.195 mmol, Example 170) and 4-methyl-1H-pyrazole (47.9 mg, 0.584 mmol) following a method analogous to the procedure described in Example 171. LC-MS (M+H)+ 515.5. ¹H NMR (500 MHz, DMSO-d₆) δ ppm 9.39 (br. s., 1 H), 8.25 (br. s., 1 H), 7.74 (br. s., 3 H), 7.46-7.59 (m, 2 H), 7.41 (br. s., 1 H), 7.36 (d, J=7.6 Hz, 2 H), 7.18 (d, J=8.2 Hz, 1 H), 7.04 (d, J=7.9 Hz, 1 H), 4.36 (d, J=9.8 Hz, 1 H), 4.17-4.32 (m, 2 H), 3.64 (br. s., 3 H), 2.12 (br. s., 4 H), 1.91-2.06 (m, 3 H), 1.78-1.91 (m, 1 H), 1.61-1.78 (m, 1 H).

EXAMPLE 175

N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

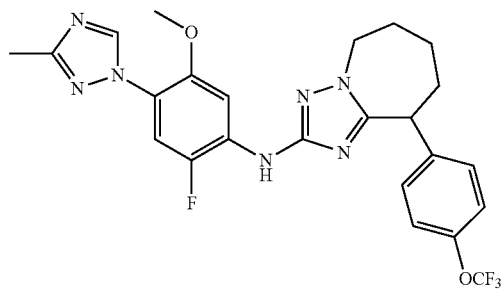 [SMILES: COc1cc(Nc2nc3n(n2)CCCCC3c2ccc(OC(F)(F)F)cc2)c(F)cc1-n1cnc(C)n1]

Step A: Allyl 2-fluoro-5-methoxy-4-(3-methyl-1H-1,2,4-triazol-1-yl)phenylcarbamimidothioate, hydrobromide (1.42 g, 3.54 mmol, from preparation U) and 6-chloro-2-(4-(trifluoromethoxy)phenyl)hexanoic acid (1.375 g, 4.43 mmol, from preparation AY) were coupled [N-methylmorpholine (2.00 mL, 17.7 mmol) was substituted for N,N-diisopropylethylamine] and then reacted with hydrazine (0.556 mL, 17.7 mmol) using a procedure analogous to Step A of Example 13. After purification by silica gel column chromatography, 5-(5-chloro-1-(4-(trifluoromethoxy)phenyl)pentyl)-N-(2-fluoro-5-methoxy-4-(3-methyl-1H-1,2,4-triazol-1-yl)phenyl)-1H-1,2,4-triazol-3-amine (570 mg, 1.03 mmol, 29% yield) as a foamy solid. LC-MS (M+H)$^+$ 554.3.

Step B: A solution of 5-(5-chloro-1-(4-(trifluoromethoxy)phenyl)pentyl)-N-(2-fluoro-5-methoxy-4-(3-methyl-1H-1,2,4-triazol-1-yl)phenyl)-1H-1,2,4-triazol-3-amine (820 mg, 1.480 mmol), sodium iodide (1.11 g, 7.40 mmol), and diisoproplylethylamine (0.256 mL, 1.48 mmol) in acetone (10 mL) was heated in a sealed vessel at 100° C. for 4 h. The reaction was concentrated in vacuo. The crude product was purified using silica gel column chromatography (50% EtOAc/chloroform) to afford 420 mg (52% yield) of the titled compound as an off-white solid. LC-MS (M+H)$^+$ 518.3. $^1$H NMR (500 MHz, CHLOROFORM-4) δ ppm 8.55 (s, 1 H), 8.09 (d, J=7.6 Hz, 1 H), 7.48 (d, J=11.6 Hz, 1 H), 7.19-7.26 (m, 4 H), 6.83 (d, J=3.4 Hz, 1 H), 4.18-4.35 (m, 3 H), 3.81 (s, 3 H), 2.47 (s, 3 H), 2.16-2.24 (m, 1 H), 1.96-2.15 (m, 3 H), 1.80-1.95 (m, 2 H).

EXAMPLE 176 AND EXAMPLE 177

(S)—N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine and (R)—N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine

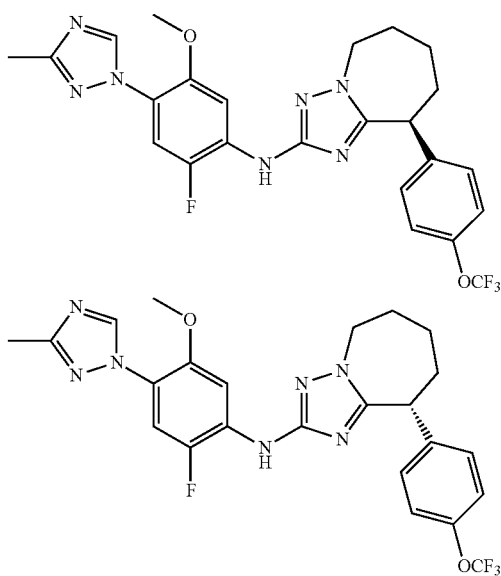

Step A: A racemic mixture of N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1, 5-a]azepin-2-amine (400 mg from Example 175) was purified using chiral supercritical fluid chromatography (SFC) to afford 184 mg of peak A (example 176) and 183 mg of peak B (example 177). SFC Method: Chiralpak AD-H (30×250 mm, 5 uM), 15% methanol (0.1% diethylamine) in CO$_2$, 70 mL/min, absorbance 268 nm, t (peak A) 10.5 min, t$_R$ (peak B) 13.9 min. The absolute stereochemistry of individual enantiomers (examples 179 and 180) was not determined. LC-MS and $^1$H NMR analytical data for the separated enantiomers was identical to the racemate (see Example 175).

BIOLOGICAL METHODS

Cellular assays for inhibition of Aβ1-40 and Aβ1-42 production

H4 cells stably transfected with APP751 containing the Swedish mutation (H4 APP751 SWE clone 8.20, developed at BMS) were maintained in log phase through twice weekly passage at a 1:20 split. For IC$_{50}$ determinations, 30 µl cells (1.5×10$^4$ cells/well) in DMEM media containing 0.0125% BSA (Sigma A8412) were plated directly into 384-well compound plates (Costar 3709) containing 0.1 µl serially diluted compound in DMSO. Following incubation for 19 h in 5% CO$_2$ at 37° C., plates were briefly centrifuged (1000 rpm, 5 min). A 10 µl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 µl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 µl of the mixture was added to the 10 µl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

TABLE 1

| Compound of Example | Activity Rating$^a$ | Compound of Example | Activity Rating$^a$ |
|---|---|---|---|
| 1 | +++ | 90 | 12 nM |
| 2 | 9 nM | 91 | +++ |
| 3 | +++ | 92 | 11 nM |
| 4 | ++ | 93 | ++ |
| 5 | ++ | 94 | ++ |
| 6 | ++ | 95 | ++ |
| 7 | ++ | 96 | +++ |
| 8 | ++ | 97 | 9 nM |
| 9 | 110 nM | 98 | ++ |
| 10 | ++ | 99 | ++ |
| 11 | 110 nM | 100 | +++ |
| 12 | 8 nM | 101 | ++ |
| 13 | ++ | 102 | +++ |
| 14 | 53 nM | 103 | +++ |
| 15 | + | 104 | ++ |
| 16 | +++ | 105 | ++ |
| 17 | +++ | 106 | 5 nM |

TABLE 1-continued

| Compound of Example | Activity Rating[a] | Compound of Example | Activity Rating[a] |
|---|---|---|---|
| 18 | ++ | 107 | ++ |
| 19 | +++ | 108 | ++ |
| 20 | +++ | 109 | 240 nM |
| 21 | +++ | 110 | ++ |
| 22 | +++ | 111 | +++ |
| 23 | +++ | 112 | ++ |
| 24 | +++ | 113 | ++ |
| 25 | ++ | 114 | ++ |
| 26 | ++ | 115 | ++ |
| 27 | ++ | 116 | ++ |
| 28 | ++ | 117 | ++ |
| 29 | ++ | 118 | 107 nM |
| 30 | 47 nM | 119 | ++ |
| 31 | +++ | 120 | ++ |
| 32 | +++ | 121 | + |
| 33 | 9 nM | 122 | ++ |
| 34 | ++ | 123 | + |
| 35 | +++ | 124 | ++ |
| 36 | +++ | 125 | +++ |
| 37 | +++ | 126 | ++ |
| 38 | +++ | 127 | ++ |
| 39 | +++ | 128 | ++ |
| 40 | ++ | 129 | 1000 nM |
| 41 | ++ | 130 | ++ |
| 42 | ++ | 131 | ++ |
| 43 | ++ | 132 | ++ |
| 44 | +++ | 133 | ++ |
| 45 | +++ | 134 | 3 nM |
| 46 | ++ | 135 | ++ |
| 47 | ++ | 136 | +++ |
| 48 | +++ | 137 | +++ |
| 49 | +++ | 138 | ++ |
| 50 | +++ | 139 | ++ |
| 51 | 4 nM | 140 | ++ |
| 52 | +++ | 141 | 70 nM |
| 53 | +++ | 142 | ++ |
| 54 | +++ | 143 | ++ |
| 55 | +++ | 144 | +++ |
| 56 | +++ | 145 | +++ |
| 57 | ++ | 146 | +++ |
| 58 | +++ | 147 | +++ |
| 59 | +++ | 148 | +++ |
| 60 | + | 149 | 2 nM |
| 61 | + | 150 | ++ |
| 62 | +++ | 151 | ++ |
| 63 | 140 nM | 152 | +++ |
| 64 | ++ | 153 | +++ |
| 65 | +++ | 154 | ++ |
| 66 | +++ | 155 | ++ |
| 67 | 19 nM | 156 | 122 nM |
| 68 | ++ | 157 | ++ |
| 69 | ++ | 158 | 16 nM |
| 70 | + | 159 | +++ |
| 71 | ++ | 160 | +++ |
| 72 | ++ | 161 | ++ |
| 73 | 140 nM | 162 | ++ |
| 74 | ++ | 163 | ++ |
| 75 | ++ | 164 | +++ |
| 76 | +++ | 165 | ++ |
| 77 | + | 166 | +++ |
| 78 | + | 167 | 44 nM |
| 79 | ++ | 168 | ++ |
| 80 | + | 169 | + |
| 81 | ++ | 170 | +++ |
| 82 | 190 nM | 171 | ++ |
| 83 | + | 172 | 64 nM |
| 84 | ++ | 173 | + |
| 85 | ++ | 174 | +++ |
| 86 | 6 nM | 175 | ++ |
| 87 | +++ | 176 | +++ |
| 88 | ++ | 177 | ++ |
| 89 | ++ | | |

[a] Activity based on Aβ42 cellular $IC_{50}$ values in H4 APP751 SWE clone 8.20.
+++ = <0.010 μM
++ = 0.010 – 0.100 μM
+ = 0.100 – 1.0 μM It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound selected from:
(Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine;
(S,Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine;
(R,Z)—N-(4-(4-chloro-1H-imidazol-1-yl)-3-methoxyphenyl)-9-(4-fluorophenyl)-8,9-dihydro-5H-[1,2,4]triazolo[1,5-a]azepin-2-amine;
(Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine;
(S,Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine;
(R,Z)-9-(4-fluorophenyl)-N-(3-methoxy-4-(3-methyl-1H-1,2,4-triazol-1-yl)phenyl)-8,9-dihydro-5H-[1,2,4]triazolo[1,5-a]azepin-2-amine;
9-(4-fluorophenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine 2,2,2-trifluoroacetate;
(Z)—N-(4-(4-chloro-1H-imidazol-1-yl)-3-methoxyphenyl)-9-(2,4-dichlorophenyl)-8,9-dihydro-5H-[1,2,4]triazolo[1,5-a]azepin-2-amine;
(Z)—N-(4-(4-chloro-1H-imidazol-1-yl)-3-methoxyphenyl)-9,9-dimethyl-8,9-dihydro-5H-[1,2,4]triazolo[1,5-a]azepin-2-amine 2,2,2-trifluoroacetate;
N-(4-(4-chloro-1H-imidazol-1-yl)-3-methoxyphenyl)-8-(4-fluorophenyl)-5,6,7,8-tetrahydro-[1,2,4]triazolo[1,5-a]pyridin-2-amine 2,2,2-trifluoroacetate;
2-(4-chloro-1H-imidazol-1-yl)-5-(8-(4-fluorophenyl)-5,6,7,8-tetrahydro-[1,2,4]triazolo[1,5-a]pyridin-2-ylamino)benzonitrile 2,2,2-trifluoroacetate;
N-(4-(4-chloro-1H-imidazol-1-yl)-3-methoxyphenyl)-8-(2,4-dichlorophenyl)-5,6,7,8-tetrahydro-[1,2,4]triazolo[1,5-a]pyridin-2-amine;
N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine;
(S)—N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine;
(R)—N-(3-fluoro-4-(5-methyl-1H-1,2,4-triazol-1-yl)phenyl)-8-(4-fluorophenyl)-5,6,7,8-tetrahydro-[1,2,4]triazolo[1,5-a]pyridin-2-amine;
N-(4-(4-Chloro-1H-imidazol-1-yl)-3-methoxyphenyl)-9-(4-fluorophenyl)-6,7,8,9-tetrahydro-5H-[1,2,4]triazolo[1,5-a]azepin-2-amine;
(S)—N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine;
(R)—N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(2,4-dichlorophenyl)-6,7,8,9-tetrahydro-5H-[1,2,4]triazolo[1,5-a]azepin-2-amine 2,2,2-trifluoroacetate;

(S)—N-(4-(4-chloro-1H-imidazol-1-yl)-3-methoxyphenyl)-9-(2,4-dichlorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(2,4-dichlorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine 2,2,2-trifluoroacetate;

(S)—N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(3,4-difluorophenyl)-6,7,8,9-tetrahydro-5H-[1,2,4]triazolo[1,5-a]azepin-2-amine;

N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine;

(S)—N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine;

(R)—N-(3-fluoro-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine;

N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine 2,2,2-trifluoroacetate;

(S)—N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine;

(R)—N-(2-fluoro-5-methoxy-4-(3-methyl-1H-1,2,4-triazol-1-yl)phenyl)-9-(4-fluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine 2,2,2-trifluoroacetate;

N-(4-(4-chloro-1H-imidazol-1-yl)-3-methoxyphenyl)-9-(4-chlorophenyl)-6,7,8,9-tetrahydro-5H-[1,2,4]triazolo[1,5-a]azepin-2-amine 2,2,2-trifluoroacetate;

N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine 2,2,2-trifluoroacetate;

9-(4-chlorophenyl)-N-(3-methoxy-4-(1-methyl-1H-pyrazol-4-yl)phenyl)-6,7,8,9-tetrahydro-5H-[1,2,4]triazolo[1,5-a]azepin-2-amine 2,2,2-trifluoroacetate;

N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine 2,2,2-trifluoroacetate;

(S)—N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(2,4-difluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(3,5-difluorophenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(3,5-difluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(3,5 difluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(6-chloropyridin-3-yl)-6,7,8,9-tetrahydro-5H-[1,2,4]triazolo[1,5-a]azepin-2-amine 2,2,2-trifluoroacetate;

N-(4-(4-chloro-1H-imidazol-1-yl)-3-methoxyphenyl)-9-(4-chloro-1H-pyrazol-1-yl)-6,7,8,9-tetrahydro-5H-[1,2,4]triazolo[1,5-a]azepin-2-amine 2,2,2-trifluoroacetate;

N-(4-(4-(difluoromethyl)-1H-imidazol-1-yl)-3-methoxyphenyl)-9-(4-fluorophenyl)-6,7,8,9-tetrahydro-5H-[1,2,4]triazolo[1,5-a]azepin-2-amine 2,2,2-trifluoroacetate;

N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(3-fluorophenyl)-6,7,8,9-tetrahydro-5H-[1,2,4]triazolo[1,5-a]azepin-2-amine;

9-(4-fluorophenyl)-N-(3-methoxy-4-(6-methylpyridazin-4-yl)phenyl)-6,7,8,9-tetrahydro-5H-[1,2,4]triazolo[1,5-a]azepin-2-amine;

N-(4-(4-chloro-1H-imidazol-1-yl)-3,5-difluorophenyl)-9-(4-fluorophenyl)-6,7,8,9-tetrahydro-5H-[1,2,4]triazolo[1,5-a]azepin-2-amine;

N-(4-(4-chloro-1H-imidazol-1-yl)-3-fluoro-5-methoxyphenyl)-9-(4-fluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(3-chlorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine;

4-(2-(4-(4-chloro-1H-imidazol-1-yl)-3-methoxyphenylamino)-6,7,8,9-tetrahydro-5H-[1,2,4]triazolo[1,5-a]azepin-9-yl)benzonitrile (S)—N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(2-fluorophenyl)-6,7,8,9-tetrahydro-5H-[1,2,4]triazolo[1,5-a]azepin-2-amine;

9-(4-fluorophenyl)-N-(3-methoxy-4-(3-methyl-1,2,4-oxadiazol-5-yl)phenyl)-6,7,8,9-tetrahydro-5H-[1,2,4]triazolo[1,5-a]azepin-2-amine;

9-(4-fluorophenyl)-N-(3-methoxy-4-(3-methylisoxazol-5-yl)phenyl)-6,7,8,9-tetrahydro-5H-[1,2,4]triazolo[1,5-a]azepin-2-amine;

rel-(6R,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-6-ol 2,2,2-trifluoroacetate;

rel-(6S,7R,9R)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepine-6,7-diol 2,2,2-trifluoroacetate;

rel-(6S,7R,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepine-6,7-diol 2,2,2-trifluoroacetate;

rel-(6R,9S)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-6-ol 2,2,2-trifluoroacetate;

rel-(7S,9R)-2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-7-ol 2,2,2-trifluoroacetate;

N-(4-(4-chloro-1H-imidazol-1-yl)-3-methoxyphenyl)-9-(3,4,5-trifluorophenyl)-6,7,8,9-tetrahydro-5H-[1,2,4]triazolo[1,5-a]azepin-2-amine;

(S)—N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine;

(R)—N-(4-(3-chloro-1H-1,2,4-triazol-1-yl)-3-methoxyphenyl)-9-(4-fluorophenyl)-6,7,8,9-tetrahydro-5H-[1,2,4]triazolo[1,5-a]azepin-2-amine;

N-(4-(4-chloro-1H-imidazol-1-yl)-3-methoxyphenyl)-5-(4-fluorophenyl)-5,6,7,8-tetrahydro-[1,2,4]triazolo[1,5-a]pyridin-2-amine 2,2,2-trifluoroacetate;

N-(4-(4-chloro-1H-imidazol-1-yl)-3-methoxyphenyl)-7-(4-fluorophenyl)-4,5,6,7-tetrahydropyrazolo[1,5-a]pyridin-2-amine;

rel-(6S,7R,9S)—N-(4-(4-chloro-1H-imidazol-1-yl)-3-methoxyphenyl)-6,7-difluoro-9-(4-fluorophenyl)-6,7,8,9-tetrahydro-5H-[1,2,4]triazolo[1,5-a]azepin-2-amine 2,2,2-trifluoroacetate; and 2-(4-(4-chloro-1H-imidazol-1-yl)-3-methoxyphenylamino)-9-(4-fluorophenyl)-6,7,8,9-tetrahydro-5H-[1,2,4]triazolo[1,5-a]azepin-9-ol;

N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine;

(S)—N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine;

(R)—N-(3-fluoro-4-(5-methyl-1H-1,2,4-triazol-1-yl)phenyl)-9-(4-fluorophenyl)-6,7,8,9-tetrahydro-5H-[1,2,4]triazolo[1,5-a]azepin-2-amine;

N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

(S)—N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

(R)—N-(3-fluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

(S)—N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

(R)—N-(3-fluoro-4-(5-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(4-isopropoxyphenyl)-6,7,8,9-tetrahydro-5H-[1,2,4]triazolo[1,5-a]azepin-2-amine;

N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine;

(S)—N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine;

(R)—N-(4-(4-chloro-1H-imidazol-1-yl)-3-methoxyphenyl)-9-(4-(2,2,2-trifluoroethoxy)phenyl)-6,7,8,9-tetrahydro-5H-[1,2,4]triazolo[1,5-a]azepin-2-amine;

N-(3,5-difluoro-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;

9-(4-(2,2-difluoroethoxy)phenyl)-N-(4-(3,5-dimethyl-1H-1,2,4-triazol-1-yl)-3-fluorophenyl)-6,7,8,9-tetrahydro-5H-[1,2,4]triazolo[1,5-a]azepin-2-amine 2,2,2-trifluoroacetate;

N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

(S)—N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

(R)—N-(3-fluoro-4-(5-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

(S)—N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

(R)—N-(3-fluoro-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

(S)—N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5a]azepin-2-amine;

(R)—N-(2-fluoro-5-methoxy-4-(3-methyl-1H-1,2,4-triazol-1-yl)phenyl)-9-(4-(2,2,2-trifluoroethoxy)phenyl)-6,7,8,9-tetrahydro-5H-[1,2,4]triazolo[1,5-a]azepin-2-amine;

9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine;

(S)-9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine;

(R)-9-(4-(2,2-difluoroethoxy)phenyl)-N-(3-fluoro-4-(5-methyl-1H-1,2,4-triazol-1-yl)phenyl)-6,7,8,9-tetrahydro-5H-[1,2,4]triazolo[1,5-a]azepin-2-amine;
N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine;
(S)—N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine;
(R)—N-(3-fluoro-4-(3-methyl-1H-1,2,4-triazol-1-yl)phenyl)-8-(4-(trifluoromethoxy)phenyl)-5,6,7,8-tetrahydro-[1,2,4]triazolo[1,5-a]pyridin-2-amine;
(S)—N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine;
(R)—N-(4-(4-chloro-1H-imidazol-1-yl)-3-methoxyphenyl)-9-(4-(trifluoromethoxy)phenyl)-6,7,8,9-tetrahydro-5H-[1,2,4]triazolo[1,5-a]azepin-2-amine;
9-(4-(difluoromethoxy)phenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine;
9-(4-(difluoromethoxy)phenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine;
N-(3-methoxy-4-(3-methyl-1H-1,2,4-triazol-1-yl)phenyl)-9-(4-(methylsulfonyl)phenyl)-6,7,8,9-tetrahydro-5H-[1,2,4]triazolo[1,5-a]azepin-2-amine;
N-(3-methoxy-4-(3-methyl-1H-1,2,4-triazol-1-yl)phenyl)-9-(4-(trifluoromethylsulfonyl)phenyl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-ethoxyphenyl)-6,7,8,9-tetrahydro-5H-[1,2,4]triazolo[1,5-a]azepin-2-amine;
9-(4-ethoxyphenyl)-N-(3-methoxy-4-(3-methyl-1H-1,2,4-triazol-1-yl)phenyl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine;
(S)—N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine;
(R)—N-(4-(4-chloro-1H-imidazol-1-yl)-3-methoxyphenyl)-9-(4-fluorophenyl)-7-methylene-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-fluorophenyl)-7-methyl-6,7,8,9-tetrahydro-5H-[1,2,4]triazolo[1,5-a]azepin-2-amine;
2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one;
2-(4-(4-chloro-1H-imidazol-1-yl)-3-methoxyphenylamino)-9-(4-fluorophenyl)-8,9-dihydro-5H-[1,2,4]triazolo[1,5-a]azepin-7(6H)-one O-methyl oxime;
N-(4-(4-chloro-1H-imidazol-1-yl)-3-methoxyphenyl)-7,7-difluoro-9-(4-fluorophenyl)-6,7,8,9-tetrahydro-5H-[1,2,4]triazolo[1,5-a]azepin-2-amine;
N2-(4-(4-chloro-1H-imidazol-1-yl)-3-methoxyphenyl)-9-(4-fluorophenyl)-N7-methyl-6,7,8,9-tetrahydro-5H-[1,2,4]triazolo[1,5-a]azepine-2,7-diamine;
N2-(4-(4-chloro-1H-imidazol-1-yl)-3-methoxyphenyl)-9-(4-fluorophenyl)-N7,N7-dimethyl-6,7,8,9-tetrahydro-5H-[1,2,4]triazolo[1,5-a]azepine-2,7-diamine;
7-(azetidin-1-yl)-N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-fluorophenyl)-7-(pyrrolidin-1-yl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-fluorophenyl)-5,6,8,9-tetrahydrospiro[[1,2,4]triazolo[1,5-a]azepine-7,2'-[1,3]dioxolan]-2-amine;
N-(4-(4-chloro-1H-imidazol-1-yl)-3-methoxyphenyl)-9-(4-fluorophenyl)-7,7-dimethoxy-6,7,8,9-tetrahydro-5H-[1,2,4]triazolo[1,5-a]azepin-2-amine;
2-(4-(4-chloro-1H-imidazol-1-yl)-3-methoxyphenylamino)-7-ethyl-9-(4-fluorophenyl)-6,7,8,9-tetrahydro-5H-[1,2,4]triazolo[1,5-a]azepin-7-ol;
rel-(7R,9R)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol;
(7R,9S)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol;
(7S,9S)-2-(4-(4-chloro-1H-imidazol-1-yl)-3-methoxyphenylamino)-9-(4-fluorophenyl)-7-methyl-6,7,8,9-tetrahydro-5H-[1,2,4]triazolo[1,5-a]azepin-7-ol;
rel-(7R,9R)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol;
rel-(7S,9R)-2-(3-fluoro-4-(5-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol;
rel-(7R,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol;
rel-(7S,9R)-2-(4-(4-chloro-1H-imidazol-1-yl)-3-methoxyphenylamino)-7-methyl-9-(4-(trifluoromethoxy)phenyl)-6,7,8,9-tetrahydro-5H-[1,2,4]triazolo[1,5-a]azepin-7-ol;
rel-(7R,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol;
rel-(7S,9R)-2-(3-fluoro-4-(3-methyl-1H-1,2,4-triazol-1-yl)phenylamino)-9-(4-fluorophenyl)-7-methyl-6,7,8,9-tetrahydro-5H-[1,2,4]triazolo[1,5-a]azepin-7-ol;
rel-(7R,9R)-2-(3-fluoro-4-(5-methyl-1H-1,2,4-triazol-1-yl)phenylamino)-9-(4-fluorophenyl)-6,7,8,9-tetrahydro-5H-[1,2,4]triazolo[1,5-a]azepin-7-ol;
rel-(7S,9R)-2-(3-fluoro-4-(5-methyl-1H-1,2,4-triazol-1-yl)phenylamino)-9-(4-fluorophenyl)-6,7,8,9-tetrahydro-5H-[1,2,4]triazolo[1,5-a]azepin-7-ol;
N-(3-fluoro-4-(3-methyl-1H-1,2,4-triazol-1-yl)phenyl)-9-(4-fluorophenyl)-5,6,8,9-tetrahydrospiro[[1,2,4]triazolo[1,5-a]azepine-7,2'-[1,3]dioxolan]-2-amine;
N-(4-(4-chloro-1H-imidazol-1-yl)-3-methoxyphenyl)-9-(4-fluorophenyl)-6,7,8,9-tetrahydro-5H-[1,2,4]triazolo[1,5-a]azepin-2-amine;
N-(3-fluoro-4-(5-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine;
(S)—N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine;
(R)—N-(4-(4-chloro-1H-imidazol-1-yl)-3-methoxyphenyl)-9-(4-(2,2-difluoroethoxy)phenyl)-6,7,8,9-tetrahydro-5H-[1,2,4]triazolo[1,5-a]azepin-2-amine;

N-(3-fluoro-4-(3-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine;
(S)—N-(3-fluoro-4-(3-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine;
(R)—N-(3-fluoro-4-(3-methyl-1H-1,2,4-triazol-1-yl)phenyl)-9-(3-fluoro-4-(trifluoromethoxy)phenyl)-6,7,8,9-tetrahydro-5H-[1,2,4]triazolo[1,5-a]azepin-2-amine;
N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;
(S)—N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;
(R)—N-(3-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;
9-(4-bromophenyl)-N-(4-(4-chloro-1H-imidazol-1-yl)-3-methoxyphenyl)-6,7,8,9-tetrahydro-5H-[1,2,4]triazolo[1,5-a]azepin-2-amine;
9-(4-(1H-pyrazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine;
9-(4-(1H-1,2,4-triazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine;
9-(4-(1H-imidazol-1-yl)phenyl)-N-(4-(4-chloro-1H-imidazol-1-yl)-3-methoxyphenyl)-6,7,8,9-tetrahydro-5H-[1,2,4]triazolo[1,5-a]azepin-2-amine;
N-(4-(4-chloro-1H-imidazol-1-yl)-3-methoxyphenyl)-9-(4-(4-methyl-1H-pyrazol-1-yl)phenyl)-6,7,8,9-tetrahydro-5H-[1,2,4]triazolo[1,5-a]azepin-2-amine;
N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;
(S)—N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine; and
(R)—N-(2-fluoro-5-methoxy-4-(3-methyl-1H-1,2,4-triazol-1-yl)phenyl)-9-(4-(trifluoromethoxy)phenyl)-6,7,8,9-tetrahydro-5H-[1,2,4]triazolo[1,5-a]azepin-2-amine;
or a pharmaceutically acceptable salt thereof.

2. A pharmaceutical composition for the treatment of disorders responsive to the reduction of µ-amyloid peptide production comprising a therapeutically effective amount of a compound of claim 1, or a pharmaceutically acceptable salt thereof, in association with a pharmaceutically acceptable carrier or diluent.

3. A method for the treatment of disorders responsive to the reduction of µ-amyloid peptide production in a mammal in need thereof, which comprises administering to said mammal a therapeutically effective amount of a compound of claim 1 or a pharmaceutically acceptable salt thereof.

4. A method of claim 3 wherein said disorder is selected from Alzheimer's disease (AD), Down syndrome, mild cognitive impairment (MCI), cerebral amyloid angiopathy (CAA), amyotrophic lateral sclerosis (ALS-D), and age-related macular degeneration.

5. A method of claim 4 wherein said disorder is selected from Alzheimer's Disease and Down Syndrome.

6. A method of claim 5 wherein said disorder is Alzheimer's Disease.

* * * * *